(12) United States Patent
Ordway et al.

(10) Patent No.: US 8,067,168 B2
(45) Date of Patent: Nov. 29, 2011

(54) GENE METHYLATION IN CANCER DIAGNOSIS

(75) Inventors: Jared Ordway, St. Louis, MO (US); Jeffrey A. Jeddeloh, Oakville, MO (US); Joseph Bedell, Chesterfield, MO (US)

(73) Assignee: Orion Genomics LLC, St. Louis, MO (US)

( * ) Notice: Subject to any disclaimer, the term of this patent is extended or adjusted under 35 U.S.C. 154(b) by 462 days.

(21) Appl. No.: 11/809,355

(22) Filed: May 30, 2007

(65) Prior Publication Data

US 2007/0298506 A1 Dec. 27, 2007

Related U.S. Application Data

(60) Provisional application No. 60/803,571, filed on May 31, 2006, provisional application No. 60/848,543, filed on Sep. 28, 2006.

(51) Int. Cl.
*C12Q 1/68* (2006.01)
*C12P 19/34* (2006.01)
*C07H 21/02* (2006.01)

(52) U.S. Cl. ............... 435/6.1; 435/91.2; 536/23.1

(58) Field of Classification Search .................. None
See application file for complete search history.

(56) References Cited

U.S. PATENT DOCUMENTS

2004/0234960 A1* 11/2004 Olek et al. .................... 435/6

FOREIGN PATENT DOCUMENTS

| WO | WO 02/00927 A2 | 1/2002 |
| WO | WO 02/18632 A2 | 3/2002 |
| WO | WO 2007/016668 A2 | 2/2007 |

OTHER PUBLICATIONS

GenBank Locus AF369786 'Homo sapiens growth hormone secretagogue receptor gene, complete cds, alternatively spliced' (Jul. 7, 2001), from www.ncbi.nlm.nih.gov, 5 printed pages.*
Juppner H. Bone (1995) vol. 17 No. 2 Supplement, pp. 39S-42S.*
GenBank Locus AC069523 "Homo sapiens 3 BAC RP11-1K20 (Roswell Park Cancer Institute Human BAC Library) complete sequence" (Aug. 30, 2002) from www.ncbi.nlm.nih.gov, pp. 1-31.*
Rein T. et al. Nucleic Acids Research (1998) vol. 26, No. 10, pp. 2255-2264.*
Gaytan F. et al. The Journal of Clinical Endocrinology & Metabolism (Mar. 2005) vol. 90, No. 3, pp. 1798-1804.*
Cmaeron E.E. et al Blood (Oct. 1, 1999) vol. 94, No. 7, p. 2445-2451.*
Costello, Josoph F. et al.; "Graded Methylation in the Promoter and BOdy of the $O^6$-Methylguanine DNA Methyltransferase (MGMT) Gene Correlates with MGMT Expression in Human Glioma Cells"; 1994, *The Journal of Biological Chemistry*, vol. 269, No. 25, pp. 17228-17237.
Widschwendter, Martin et al.; "Methylation and Silencing of the Retinoic Acid Receptor-β2 Gene in Breast Cancer"; 2000, *Journal of the National Cancer Institute*, vol. 92, No. 10, pp. 826-832.
Bae, Young Kyung et al.; "Hypermethylation in histologically distinct classes of breast cancer"; 2004, *Clinical Cancer Research: An Official Journal of the American Association for Cancer Research*, vol. 10, No. 18, pp. 5998-6005.
Makiyama, K. et al.; "Aberrant expression of HOX genes in human invasive breast carcinoma"; 2005, *Oncology Reports*, vol. 13, No. 4, pp. 673-679.
Yan, P.S. et al.; "Differential distribution of DNA methylation within the RASSF1A CpG island in breast cancer"; 2003, *Cancer Research*, vol. 63, No. 19, pp. 6178-6186.

* cited by examiner

*Primary Examiner* — Stephen Kapushoc
(74) *Attorney, Agent, or Firm* — Kilpatrick Townsend & Stockon LLP

(57) ABSTRACT

The present invention provides DNA biomarker sequences that are differentially methylated in samples from normal individuals and individuals with cancer. The invention further provides methods of identifying differentially methylated DNA biomarker sequences and their use in detecting and diagnosing cancer.

14 Claims, 18 Drawing Sheets

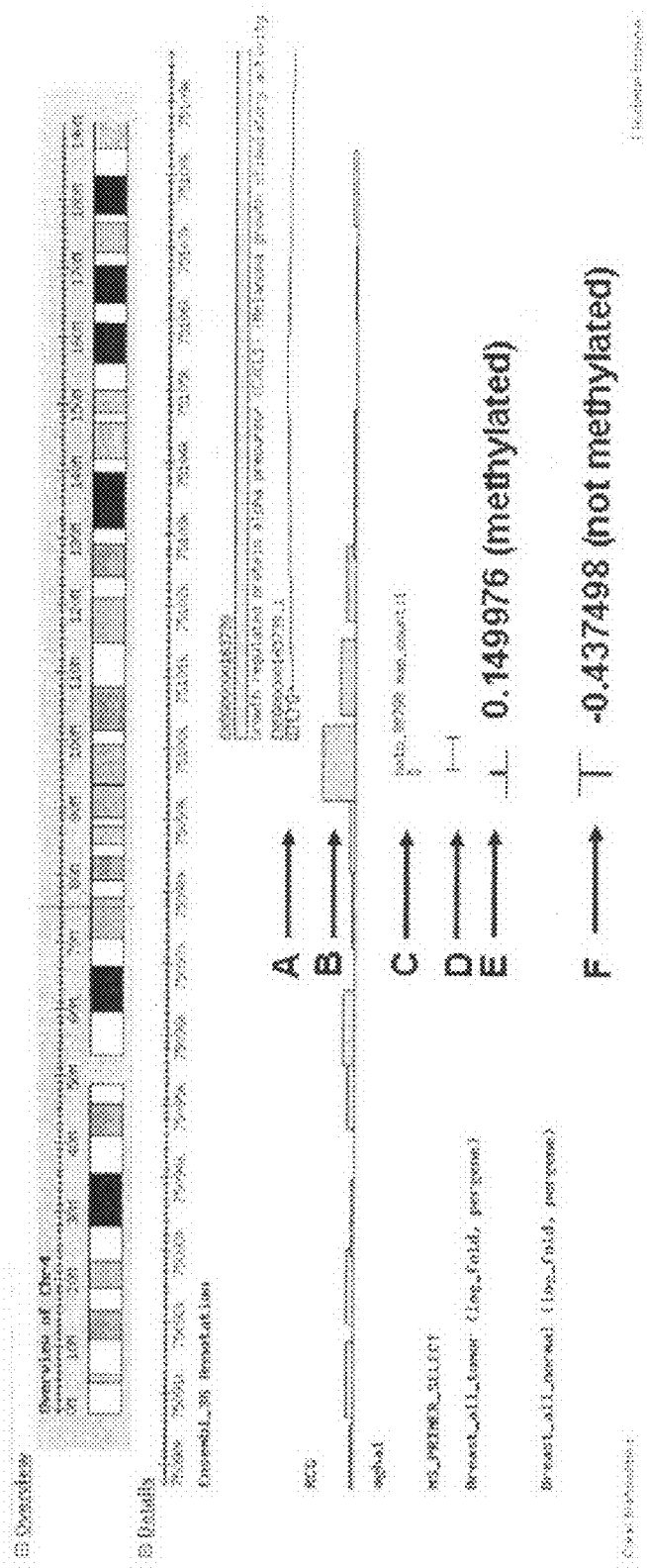
Figure 1. General overview of differential methylation screening experimental design.

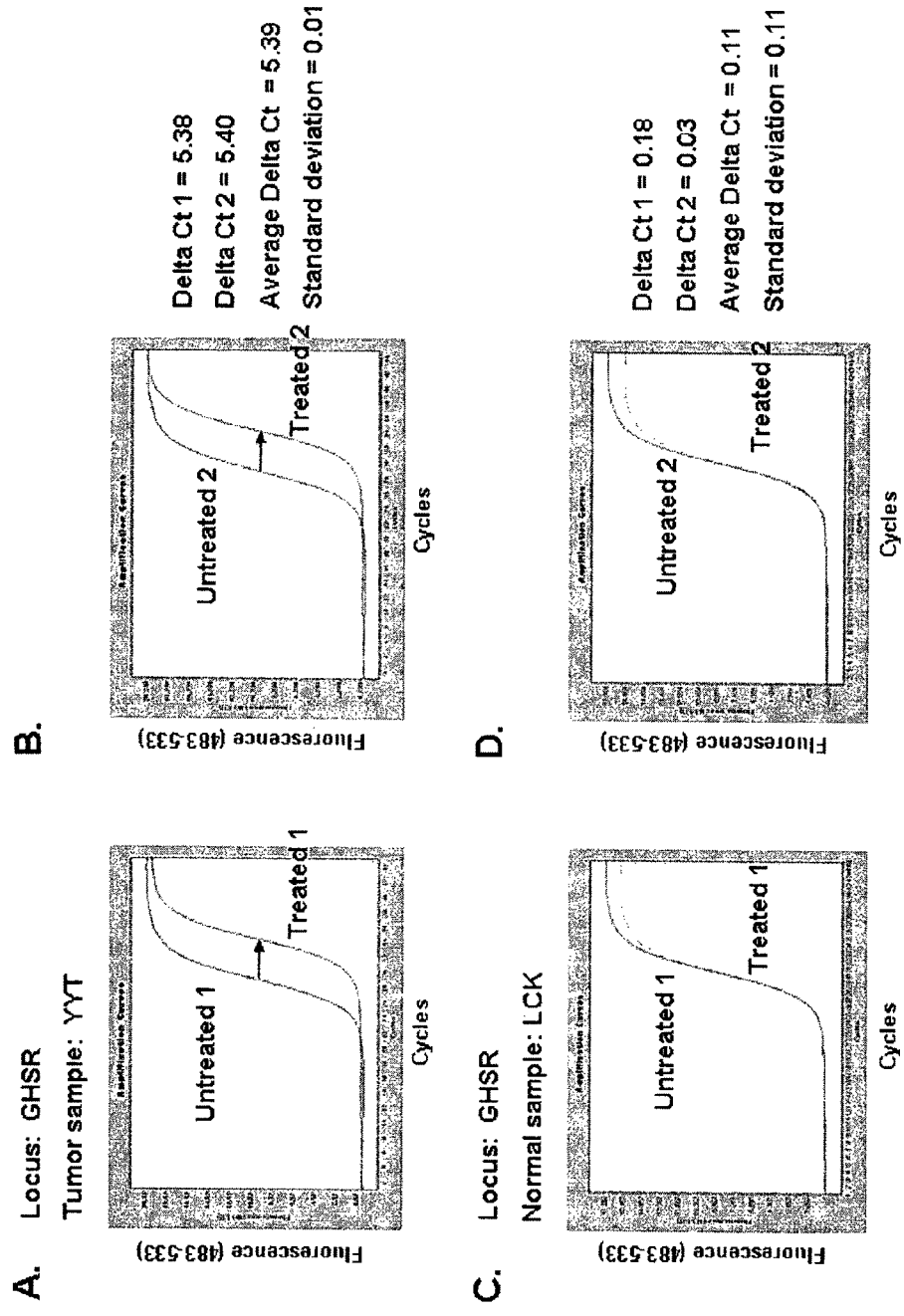
Figure 2. Example of McrBC-based real-time PCR strategy to monitor DNA methylation status.

Figure 3A. Verification of microarray DNA methylation predictions.

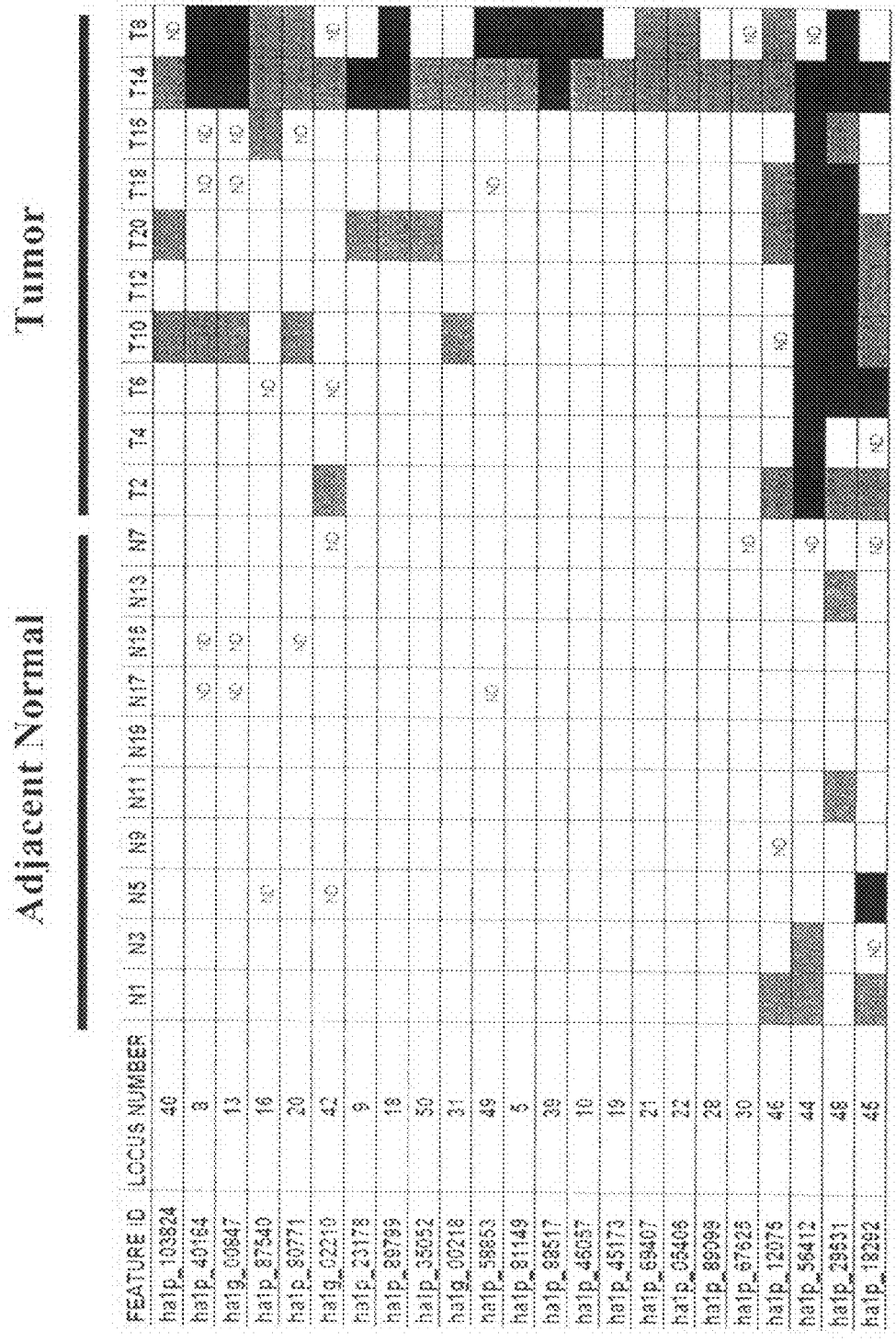
Figure 3B. Verification of microarray DNA methylation predictions.

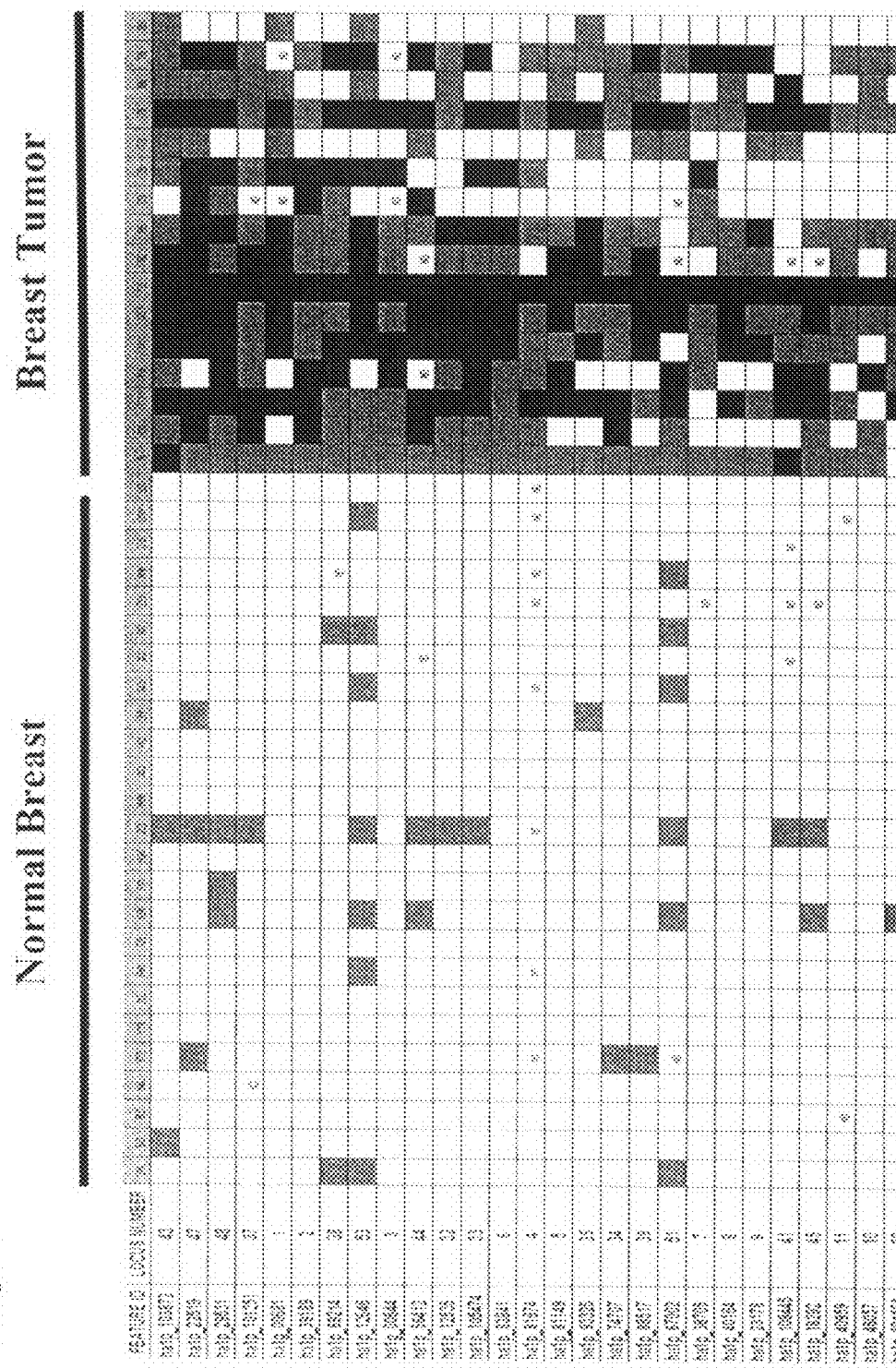
Figure 4A. Validation of DNA methylation differences in independent tumor and normal samples.

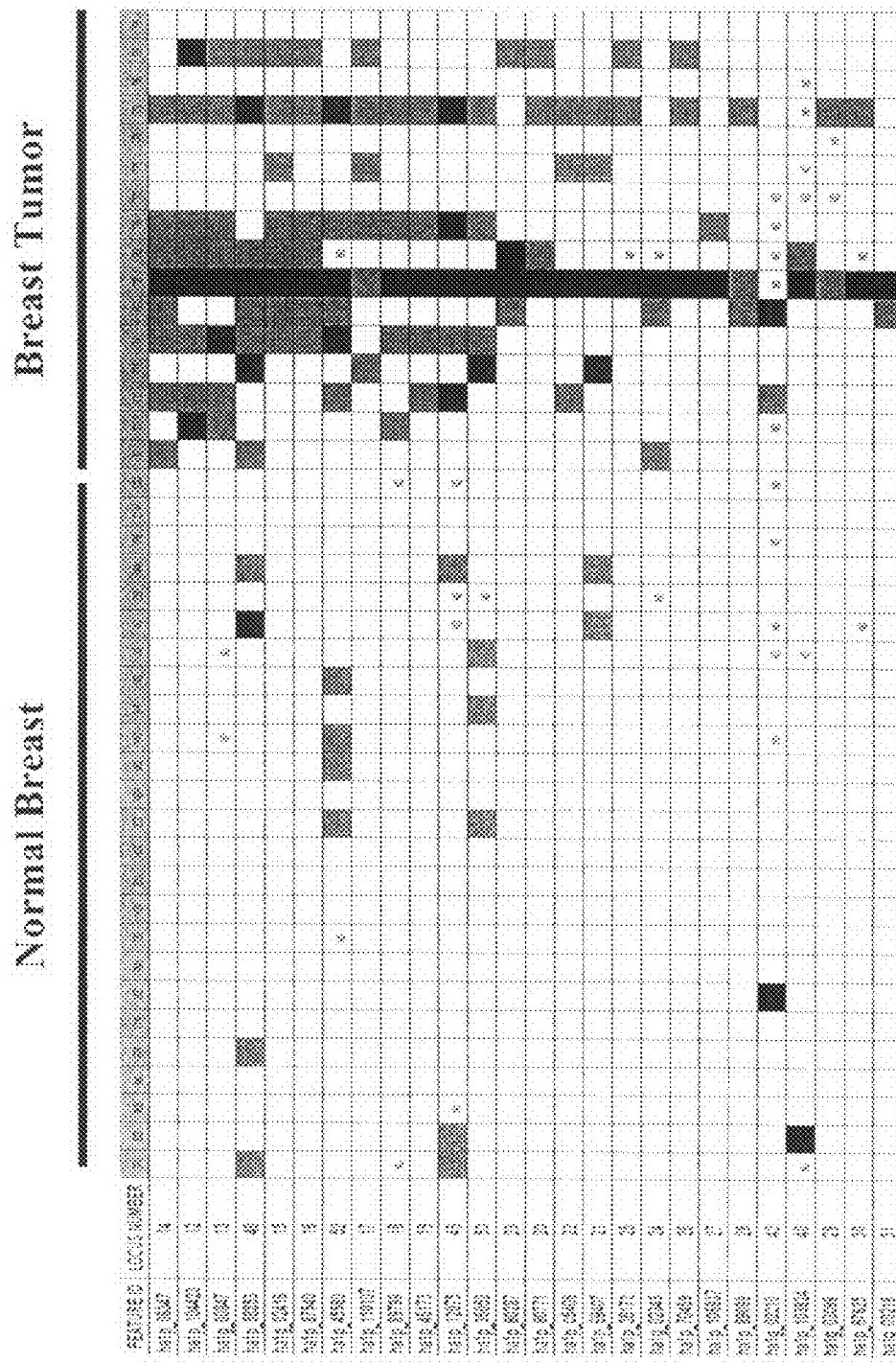
Figure 4B. Validation of DNA methylation differences in independent breast tumor and normal samples.

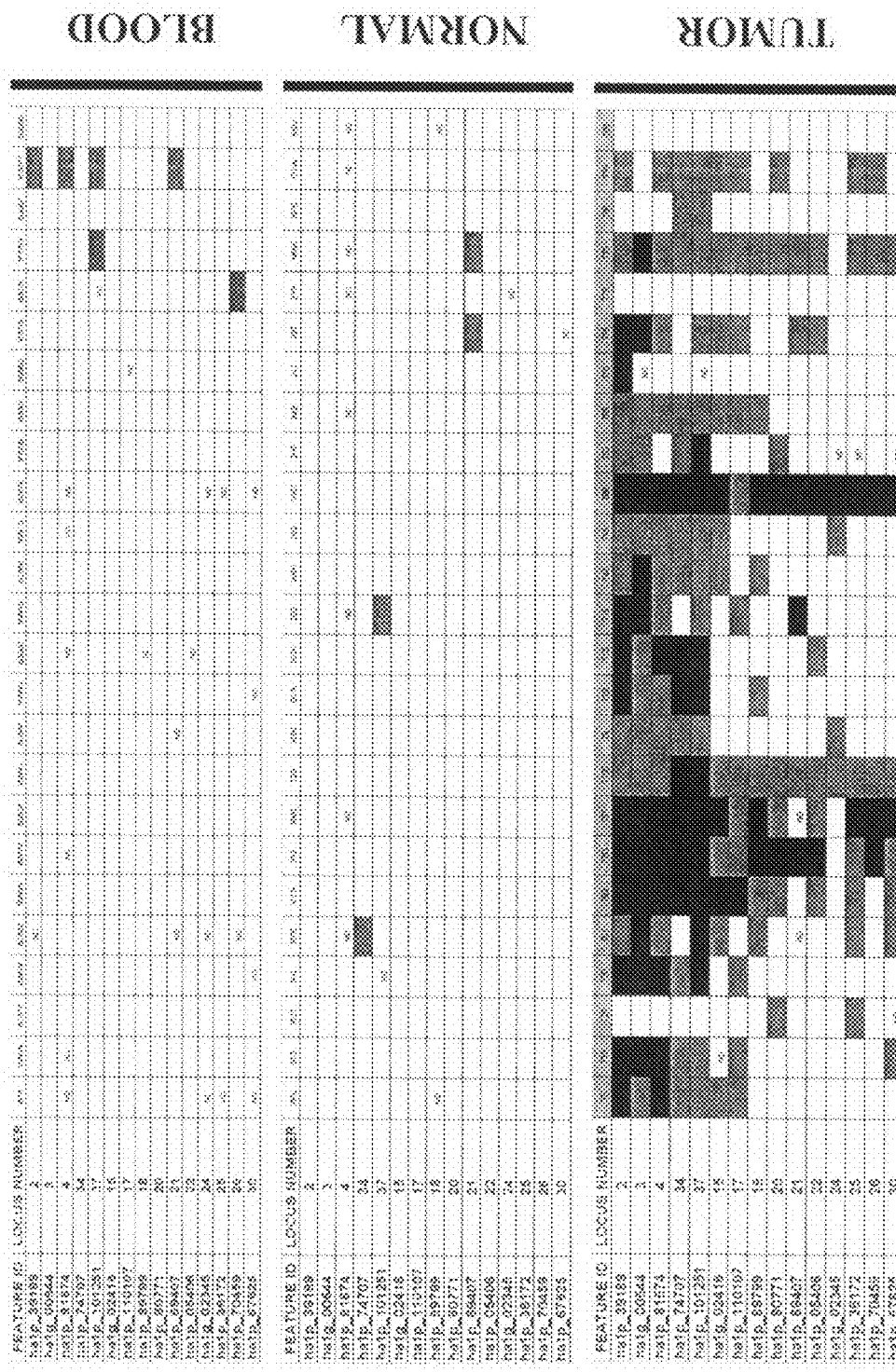
Figure 5. Validation of DNA methylation differences in a larger panel of breast tumor, normal breast and normal peripheral blood samples.

Figure 6. Demonstration of threshold adjustment for determining sensitivity and specificity.
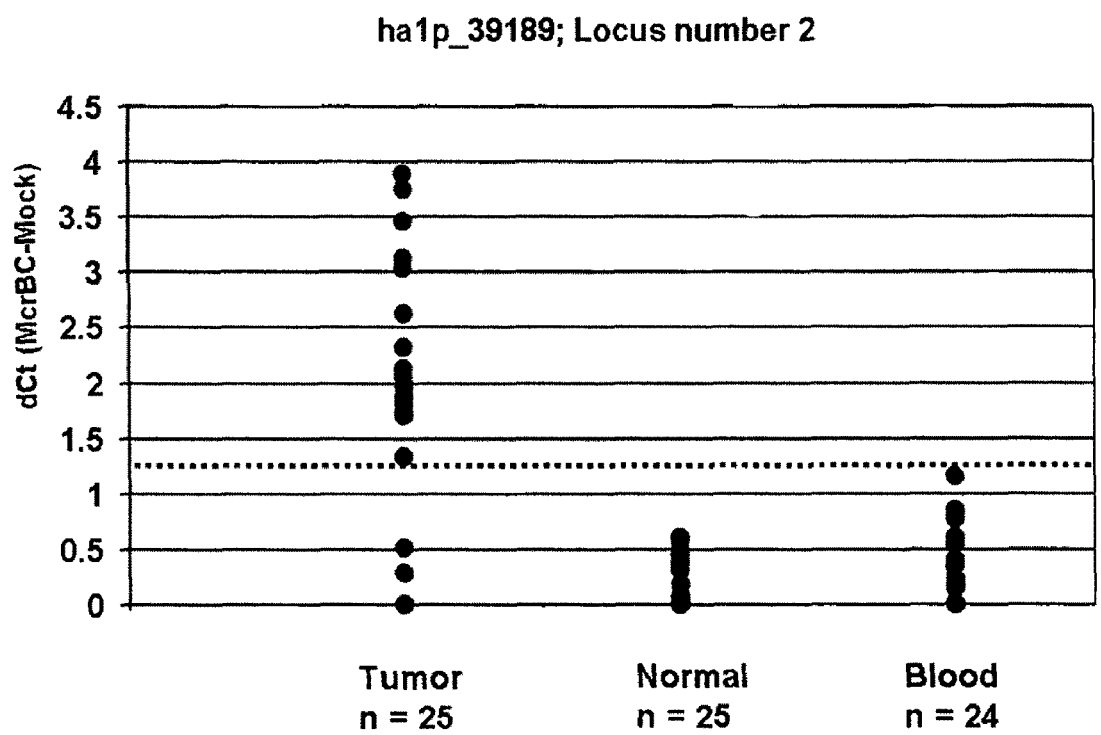

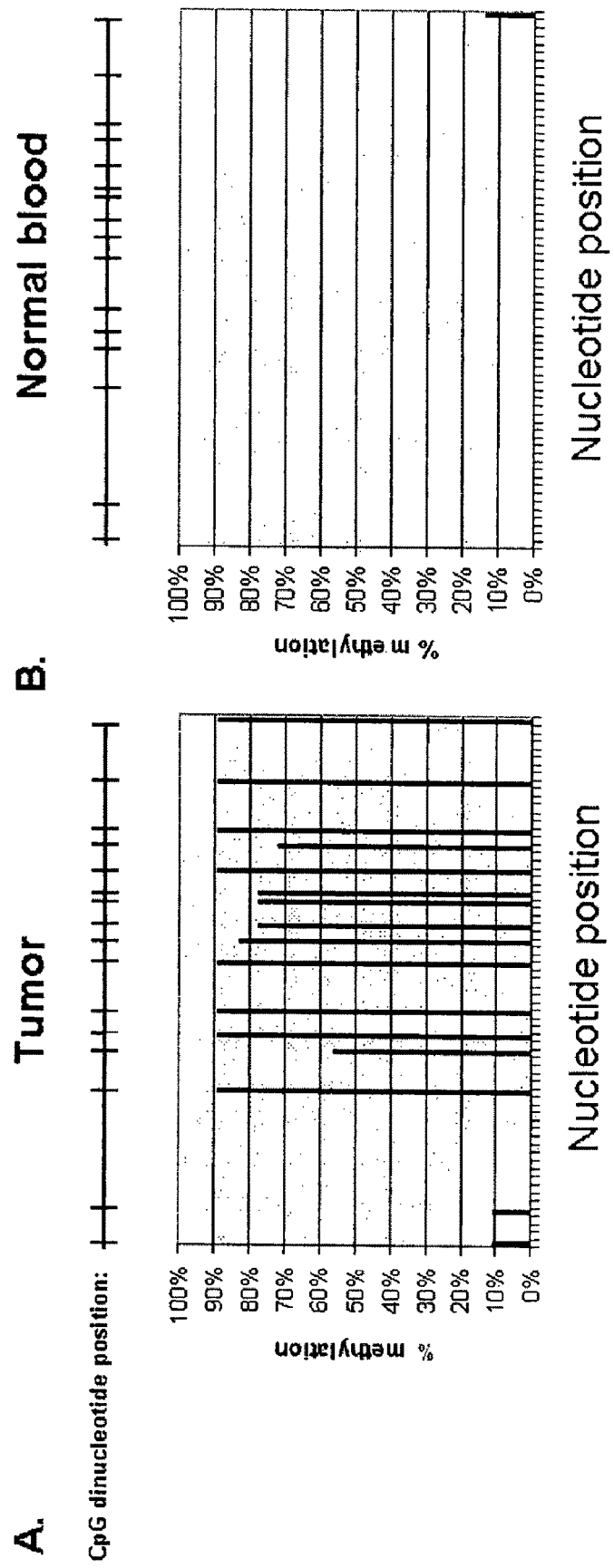
Figure 7. Bisulfite sequencing confirmation of differential DNA methylation.

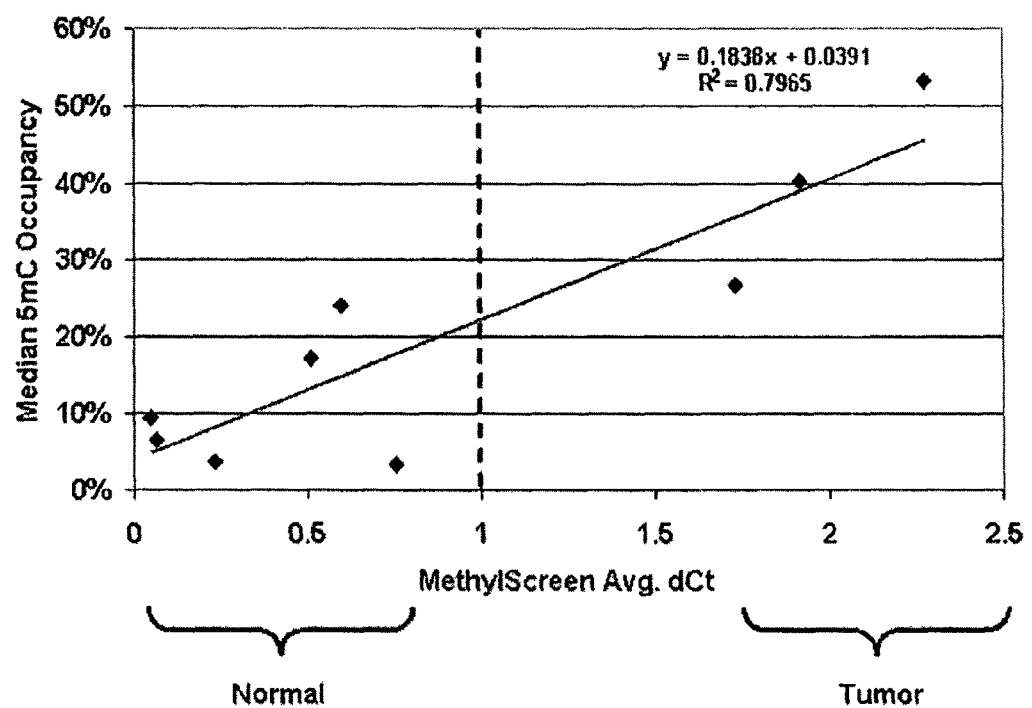
Figure 8. Correlation between qPCR based DNA methylation detection and 5-methylcytosine content measured by bisulfite sequencing.

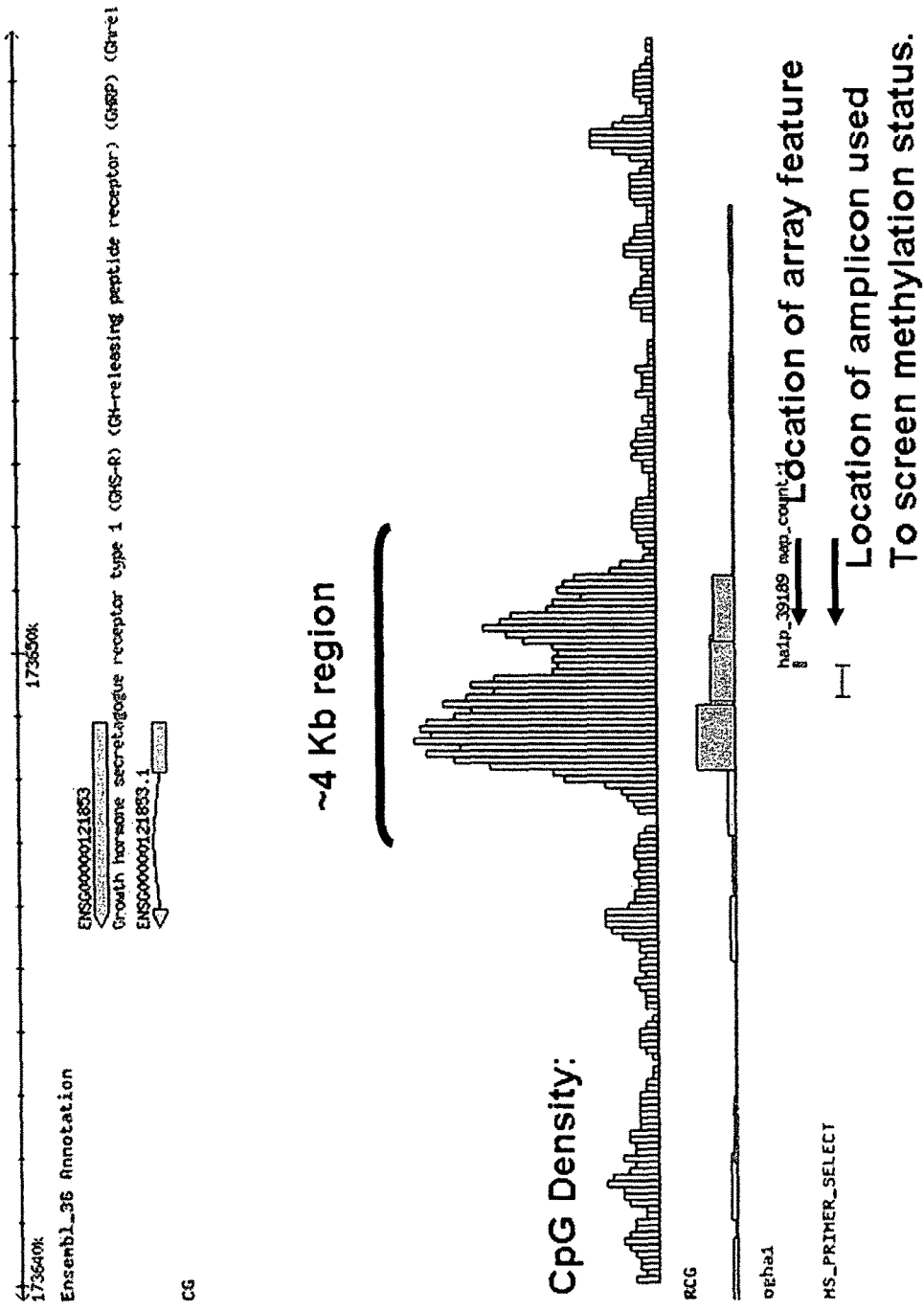
Figure 9. Example of selection of potential differentially methylated region.

Figure 10A. Detection of tumor-specific DNA methylation in Stage I breast tumors relative to Stage II-III breast tumors.
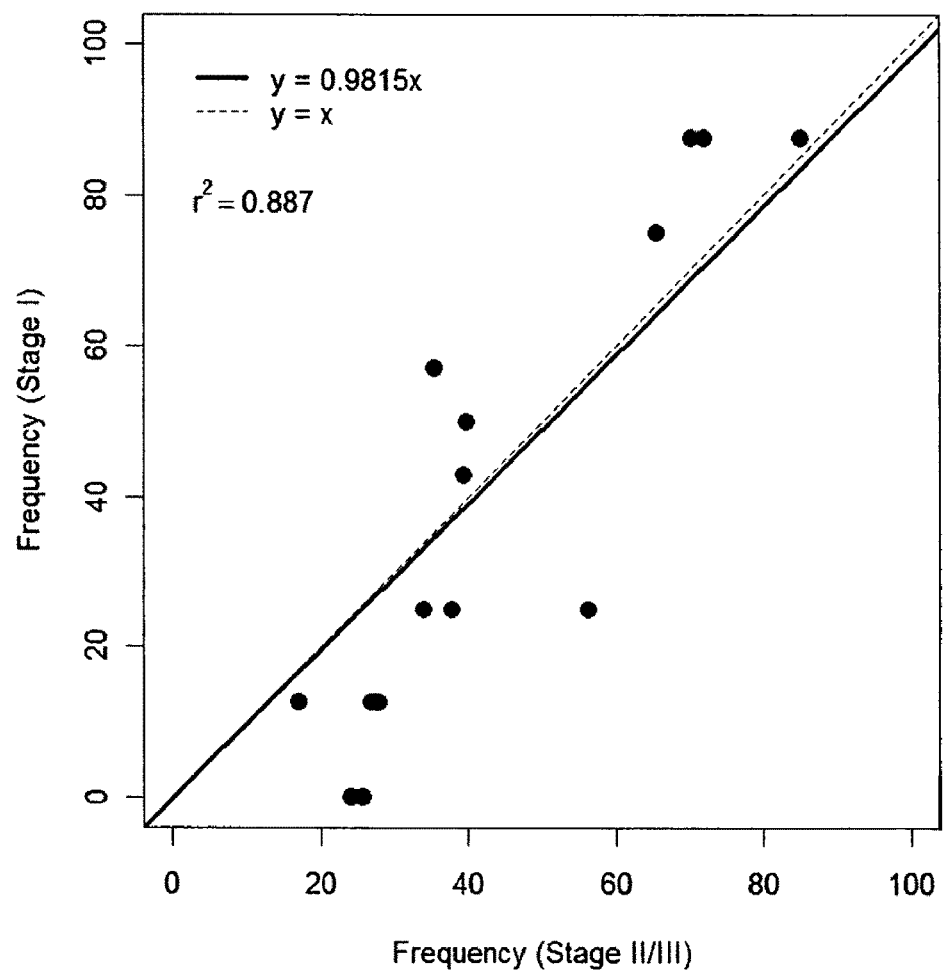

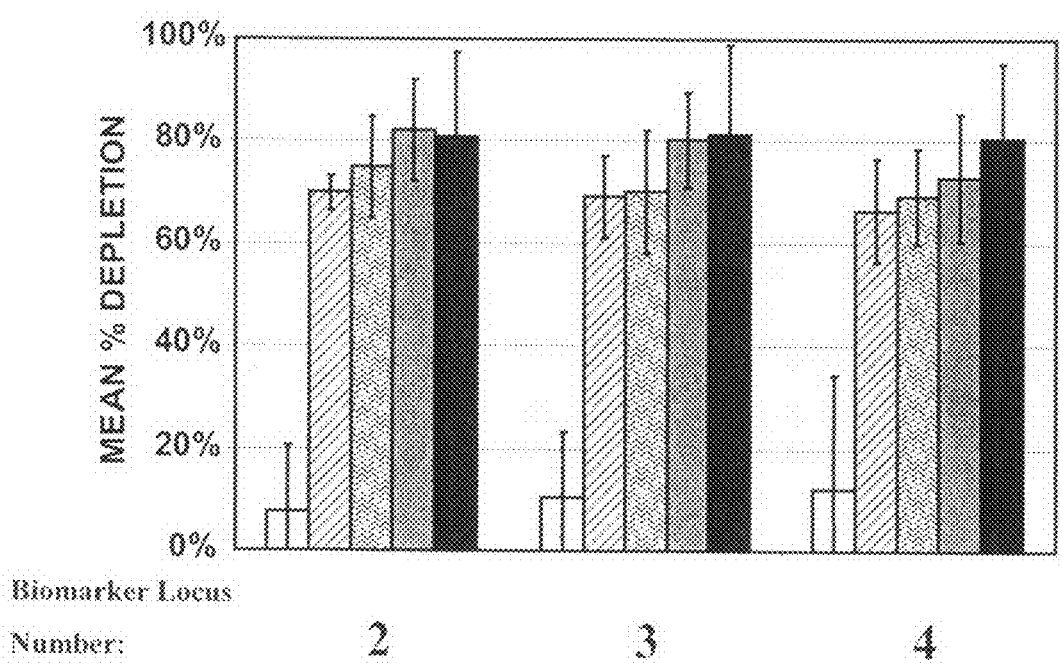
Figure 10B. Proportion of methylated molecules in normal breast and Stage I, II and III breast tumors.

Figure 11A. Examples of DNA methylation data for four selected biomarker loci.
Biomarker Locus Number: 2
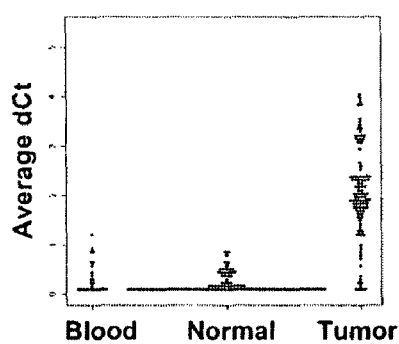
Biomarker Locus Number: 3
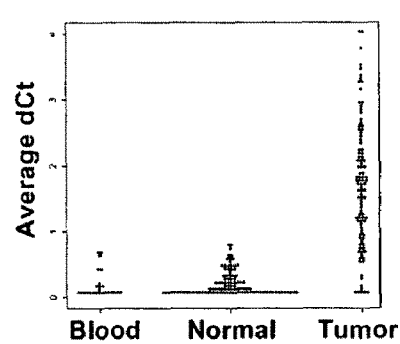
Biomarker Locus Number: 4
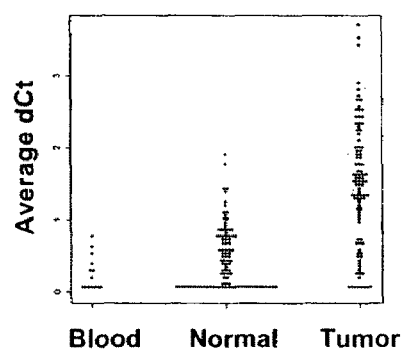
Biomarker Locus Number: 12
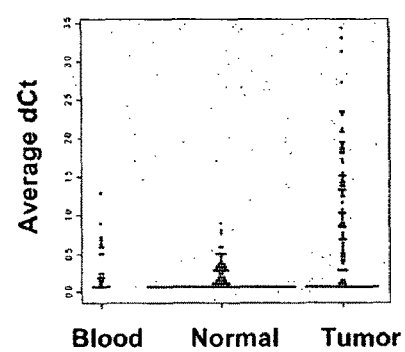

Figure 11B. ROC curve plots for loci shown in Figure 11A.
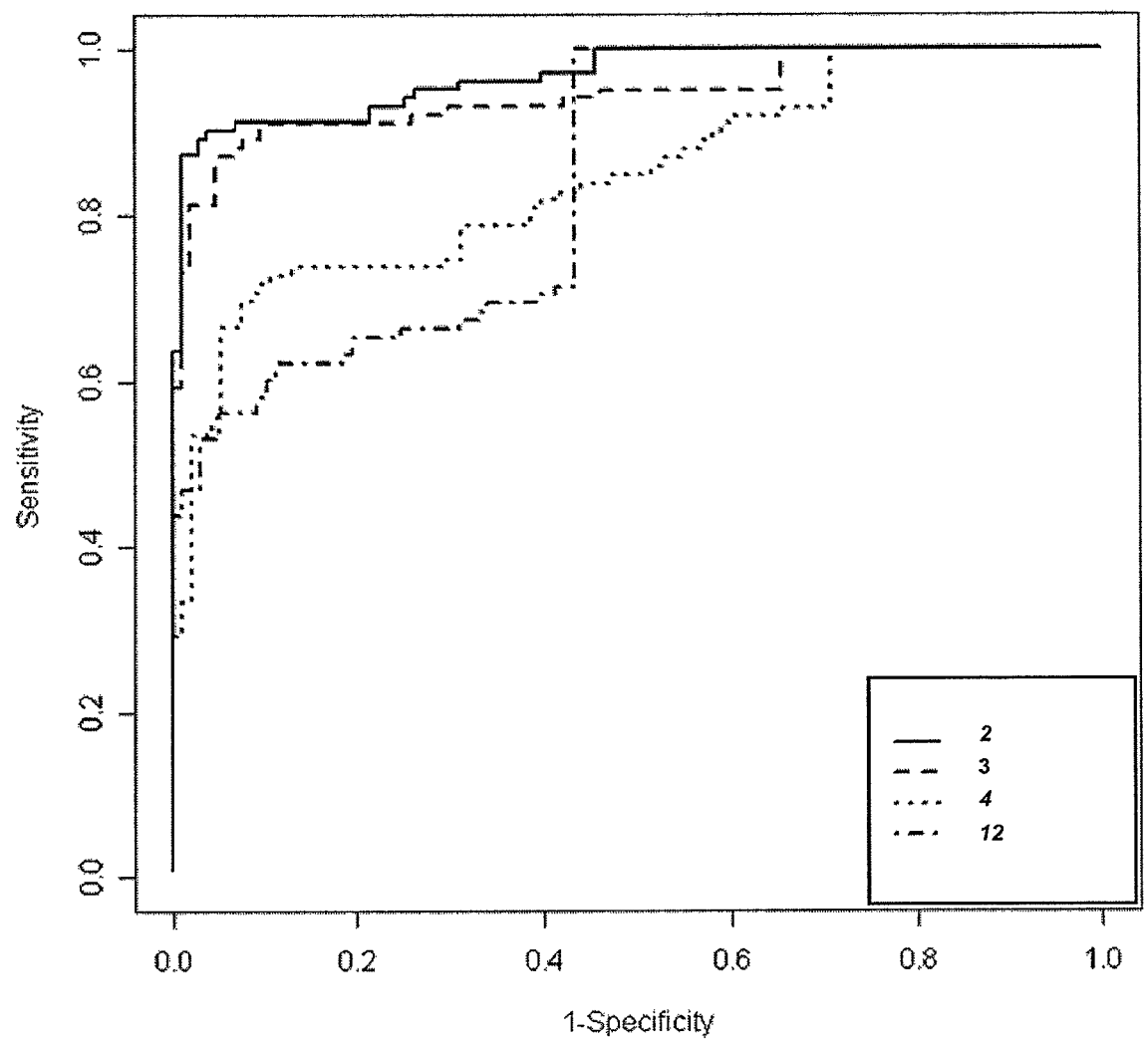

Figure 12. Analysis of DNA methylation by bisulfite sequencing.
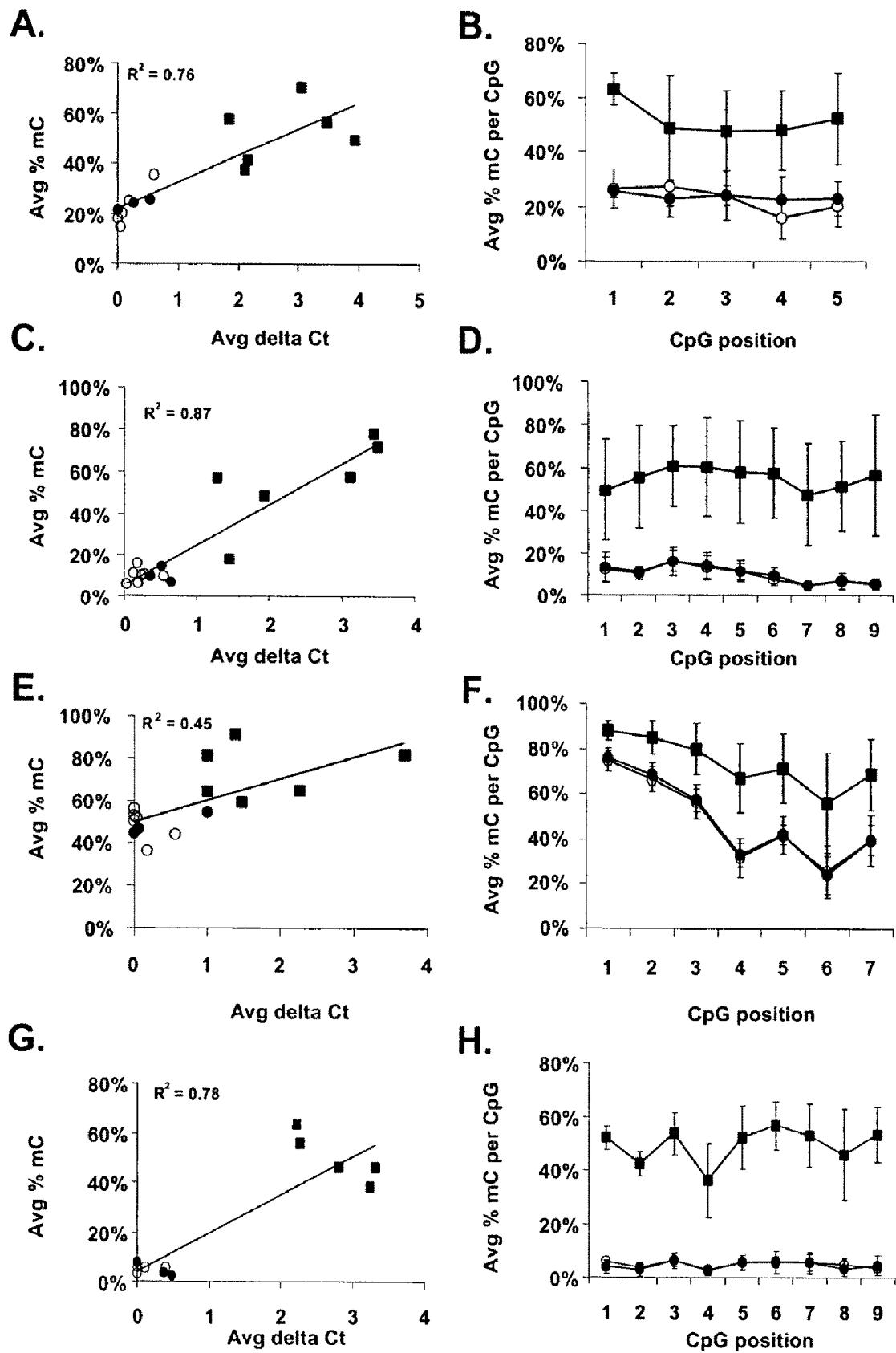

Figure 13. Hypermethylation is associated with decreased transcription.
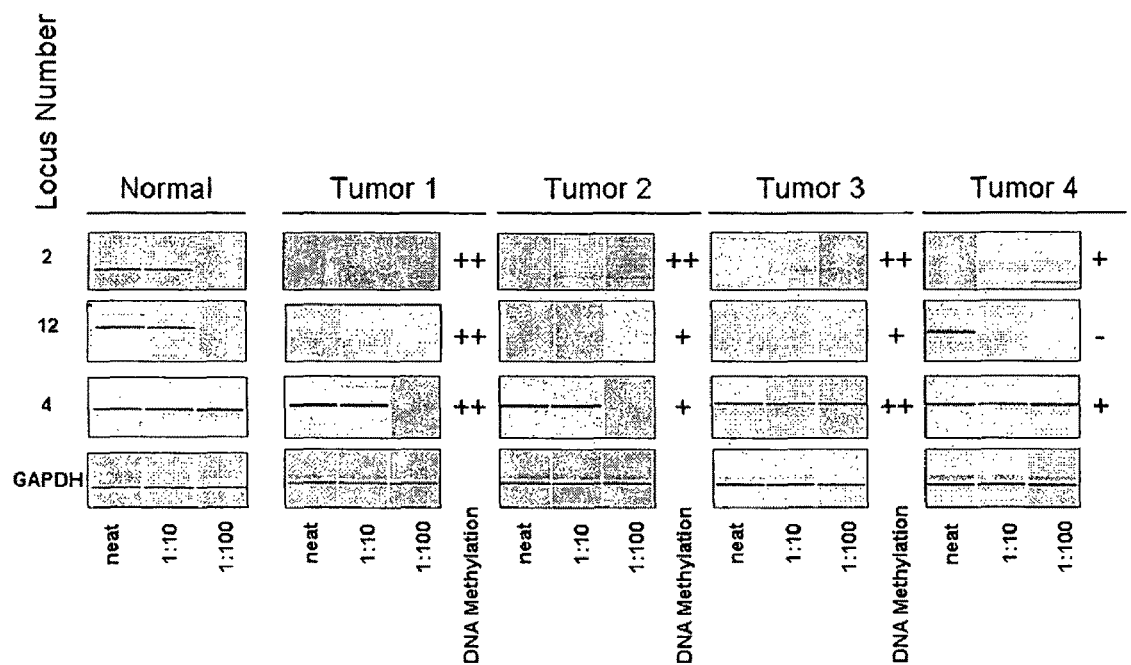

Figure 14. DNA methylation detection in fine needle aspirate specimens.
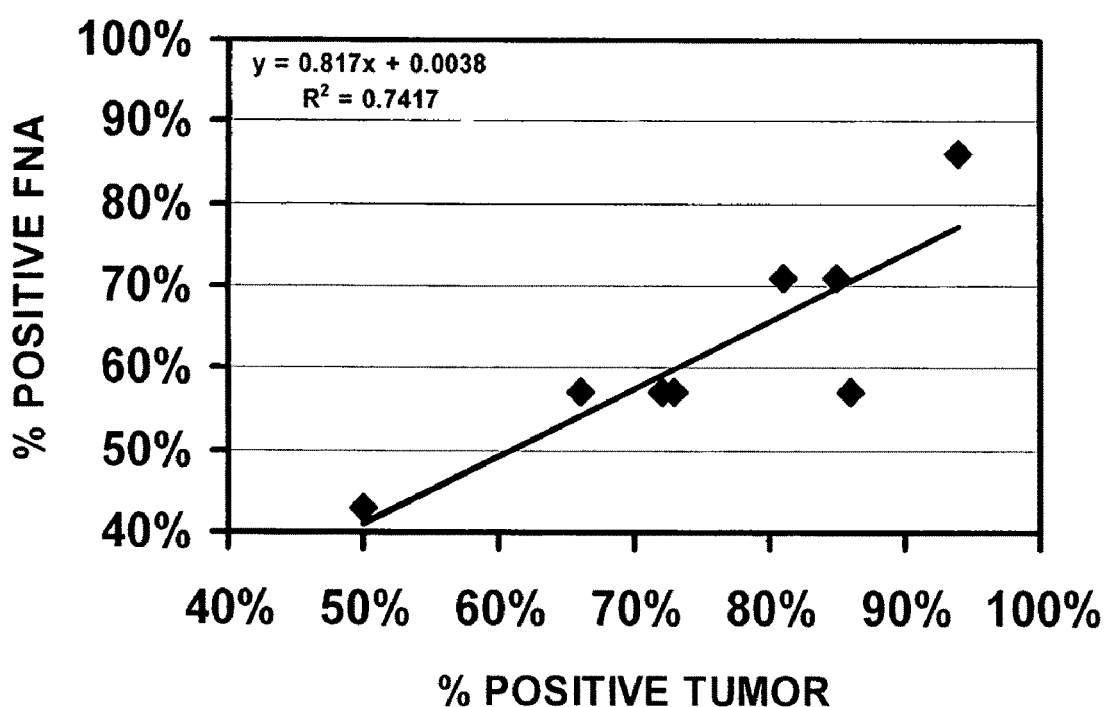

SEQUENCE LISTING

```
<160> NUMBER OF SEQ ID NOS: 265

<210> SEQ ID NO 1
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1g_00681

<400> SEQUENCE: 1
tcgtagtagg tcgcttttg catcgcgttg tttcacgatc ttgatcgcac actctgacag       60

<210> SEQ ID NO 2
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_39189

<400> SEQUENCE: 2
accctacagc agactctcta ccactaccga gtgatacaaa ggactgggat tctggacagg       60

<210> SEQ ID NO 3
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1g_00644

<400> SEQUENCE: 3
cagttcctcc accgcagcgg tcacaccgtt gatttgatcc agaaataaga cggatagtac       60

<210> SEQ ID NO 4
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_81674

<400> SEQUENCE: 4
ctttcggtct cctccccatt ttcctagtcg tcttcggttg tggatgttgt aaactcgacc       60

<210> SEQ ID NO 5
```

```
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_81149

<400> SEQUENCE: 5
cccaggaggc tatgggaatc agaatcacac ttgcacaaga gaagacccct atgggacaag    60

<210> SEQ ID NO 6
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_83841

<400> SEQUENCE: 6
aaataccacc ttcttaaata ccacccagct gtccaagatg gagacttcct ggcatccagg    60

<210> SEQ ID NO 7
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_38705

<400> SEQUENCE: 7
ggaggagtaa aggctgttta caaacttgac gtacacacgc agtcctatcc ctacggtcct    60

<210> SEQ ID NO 8
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_40164

<400> SEQUENCE: 8
aaacaagcac cctgactggc gcattcttac tcattctagc ctgggtttca acttcaagga    60

<210> SEQ ID NO 9
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_23178

<400> SEQUENCE: 9
cccttactgc tgctgctgta acagctaagt gccaattatc tcccaagcgt gaaagcaaat    60

<210> SEQ ID NO 10
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_46057

<400> SEQUENCE: 10
gaaacatgca ctgcctgaca tcggcaagct gcccacacca agttacaggc ttatggaaag    60

<210> SEQ ID NO 11
<211> LENGTH: 60
<212> TYPE: DNA
```

```
<213> ORGANISM: Artificial Sequence
<220> FEATURE:
<223> OTHER INFORMATION: OGHAv1.0 microarray feature identifier
      ha1p_40959

<400> SEQUENCE: 11
cgtgggcctt agccaaataa cttctggtag gcaaattctc cccttcttca gttgagagct    60

<210> SEQ ID NO 12
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_104423

<400> SEQUENCE: 12
gagagggaag cctgatctgt ttcctcactc gcttgctcgt ggatgtcatt ttctgtcttc    60

<210> SEQ ID NO 13
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1g_00847

<400> SEQUENCE: 13
atacgctgga acagagcacg agcatacact cgaacacacg cgcacacact caggacatct    60

<210> SEQ ID NO 14
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_08347

<400> SEQUENCE: 14
atggtttctg aaaagccctc agtcctggtt cttggcttcc tgattctgtg gttgggattt    60

<210> SEQ ID NO 15
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1g_02416

<400> SEQUENCE: 15
caacgacaag aagctgtcca aatatgagac cctgcagatg gcccaaatct acatcaacgc    60

<210> SEQ ID NO 16
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_87540

<400> SEQUENCE: 16
gaggcaattc agggagacag gaacacccct ctctcttcac acacctcatc agttccactg    60

<210> SEQ ID NO 17
<211> LENGTH: 60
<212> TYPE: DNA
<213> ORGANISM: Artificial Sequence
<220> FEATURE:
```

<223> OTHER INFORMATION: OGHAv1.0 microarray feature identifier
      ha1p_110107

<400> SEQUENCE: 17
tgtgtgtgtc catttggcga gatgtcgaga gcgggggag tgtccttgtc ggtgtatctg    60

<210> SEQ ID NO 18
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_89799

<400> SEQUENCE: 18
tctcccagca ccttgttaat ttctctcaat ctccagccac aaatccgaga cacaacgctc    60

<210> SEQ ID NO 19
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_45173

<400> SEQUENCE: 19
agcgtgccta gaggagtggt caggatagtg agggatctgt gatccttcgt tctgaatcta    60

<210> SEQ ID NO 20
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_80771

<400> SEQUENCE: 20
ccggagagcc tgtcaaggga agagctgaat cttttatctt ttgtaacgac tacccagtga    60

<210> SEQ ID NO 21
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_69407

<400> SEQUENCE: 21
ggcctgtctc cttggcatgt tcccttgctt ctgcttgtcc agttaatcct ttctgacata    60

<210> SEQ ID NO 22
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_05406

<400> SEQUENCE: 22
gaaggaatgg cccatctctt agggctctct gcttgtcacc taccaggttg gtcagaaacg    60

<210> SEQ ID NO 23
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_80287

```
<400> SEQUENCE: 23
gctccagaca cagagaaagg tttcttaaca ctcaggttcg cttctcctaa ggtgtgtgcc        60

<210> SEQ ID NO 24
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1g_02345

<400> SEQUENCE: 24
ttttgacctg tgatttgttg tccggcagct ttcagtgtcg gttttacgag gtagagtgat        60

<210> SEQ ID NO 25
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_36172

<400> SEQUENCE: 25
tttcctagtc gatcccagct tctctaggga gtgtcaggcg cacacagggt taagttagtt        60

<210> SEQ ID NO 26
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_70459

<400> SEQUENCE: 26
tttccatgac agaggtttca ggatctctta gaaggaagaa agtagagacg gtgaagagct        60

<210> SEQ ID NO 27
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_105937

<400> SEQUENCE: 27
atcctcagga gtaataaccc ctccgattgt tgctcaggtc cctccctctt gaaattcctg        60

<210> SEQ ID NO 28
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_89099

<400> SEQUENCE: 28
ggctcggaaa gccttcatag taagggcgca gttaagactt ggatttcctg ccattacaca        60

<210> SEQ ID NO 29
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1g_03099

<400> SEQUENCE: 29
```
catgcagaaa gctgggcagc atagaaagtt cacagccacg aaagatcaa agagatggtg    60

<210> SEQ ID NO 30
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_67625

<400> SEQUENCE: 30
tttgccatct ctacagattt caccatctct cttccctct cccctcgtt cgctttcctc    60

<210> SEQ ID NO 31
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1g_00218

<400> SEQUENCE: 31
ttccatcttt tgtggcgcga aataaccct ttgctccctc gttggttttg ttgaggttga    60

<210> SEQ ID NO 32
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_12535

<400> SEQUENCE: 32
tgctatcttg tacctaaact gagcccttt ggtggaggca gtgagggttc ttgtgtgttc    60

<210> SEQ ID NO 33
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_105474

<400> SEQUENCE: 33
ttctccttcg agcatattcg ggaagggaag tttgaagagt gagtccctgt gagggccgtg    60

<210> SEQ ID NO 34
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_74707

<400> SEQUENCE: 34
ggccttgagg gcaagacgag gaatttcgac ttaggtcctt gaatctggag agctacagaa    60

<210> SEQ ID NO 35
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_93325

<400> SEQUENCE: 35
tggagcacac aggcagcatt acgccattct tccttcttgg aaaaatccct cagccttata    60

<210> SEQ ID NO 36
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_101161

<400> SEQUENCE: 36
agagagataa agagagatga cctcagagac aaagagactc agacccagcc agaggcccaa    60

<210> SEQ ID NO 37
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_101251

<400> SEQUENCE: 37
tattctttgt tgcccatttg tctagggact gtctgcgtgg ctgtgactat gagtgtcagc    60

<210> SEQ ID NO 38
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_69214

<400> SEQUENCE: 38
acaacctggg aactgaataa ctttcaaagc cagtgctcag cttctctgct ccgtactagc    60

<210> SEQ ID NO 39
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_88517

<400> SEQUENCE: 39
ctgtgtcagg tatttaacag ttctggggac acgggtgtta cctcctttca tggtgctctc    60

<210> SEQ ID NO 40
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_103824

<400> SEQUENCE: 40
agactcgctg ttcccgactg tcgctcccta gctctgatga aacccgaca tttctttcag    60

<210> SEQ ID NO 41
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_108445

<400> SEQUENCE: 41
gtgttcttgg cacatggtag gcatctgtct ttgttgggca gttgcatcag aagggttaag    60

<210> SEQ ID NO 42
<211> LENGTH: 60
<212> TYPE: DNA
<213> ORGANISM: Artificial Sequence
<220> FEATURE:
<223> OTHER INFORMATION: OGHAv1.0 microarray feature identifier ha1g_02210

<400> SEQUENCE: 42
ctgcactctc ggcttctttc tgtggcttcc ctcttttct cttcacctct gttttcagga    60

<210> SEQ ID NO 43
<211> LENGTH: 60
<212> TYPE: DNA
<213> ORGANISM: Artificial Sequence
<220> FEATURE:
<223> OTHER INFORMATION: OGHAv1.0 microarray feature identifier ha1p_103872

<400> SEQUENCE: 43
gctaaaatcc tcctggcccc atcatttctt gggtcctttc cagacagtgc tgtgtcttta    60

<210> SEQ ID NO 44
<211> LENGTH: 60
<212> TYPE: DNA
<213> ORGANISM: Artificial Sequence
<220> FEATURE:
<223> OTHER INFORMATION: OGHAv1.0 microarray feature identifier ha1p_56412

<400> SEQUENCE: 44
gggatgtgtg cctccaactt cattaagtga gggaaacatt tgctggggct tgtcagggag    60

<210> SEQ ID NO 45
<211> LENGTH: 60
<212> TYPE: DNA
<213> ORGANISM: Artificial Sequence
<220> FEATURE:
<223> OTHER INFORMATION: OGHAv1.0 microarray feature identifier ha1p_18292

<400> SEQUENCE: 45
tttggtttgt cacctgtgag ttgcctactg gacacaaaga tgaagctgtc gggaaagtga    60

<210> SEQ ID NO 46
<211> LENGTH: 60
<212> TYPE: DNA
<213> ORGANISM: Artificial Sequence
<220> FEATURE:
<223> OTHER INFORMATION: OGHAv1.0 microarray feature identifier ha1p_12075

<400> SEQUENCE: 46
gttgatcttc aacatggcta accaaatgga cgatcagcag gcagacacga ggtattttca    60

<210> SEQ ID NO 47
<211> LENGTH: 60
<212> TYPE: DNA
<213> ORGANISM: Artificial Sequence
<220> FEATURE:
<223> OTHER INFORMATION: OGHAv1.0 microarray feature identifier ha1p_22519

<400> SEQUENCE: 47
tgtttggatg atgggacaca tcaccctggg aactgtctca aagcacaacc acatcttagg    60

<210> SEQ ID NO 48
<211> LENGTH: 60

-continued

```
<212> TYPE: DNA
<213> ORGANISM: Artificial Sequence
<220> FEATURE:
<223> OTHER INFORMATION: OGHAv1.0 microarray feature identifier
      ha1p_29531

<400> SEQUENCE: 48
cctccttctc cctcagagta cagttcaact cttttaagag gaaagccact gaatgaacct      60

<210> SEQ ID NO 49
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_58853

<400> SEQUENCE: 49
ggggagggtc tctgcacctt tcctgacatc ttttcttcgg gagatcctca tagaaccata      60

<210> SEQ ID NO 50
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_35052

<400> SEQUENCE: 50
gagacaacgc cctcagaaat gagagaacag taccctctta tccttgctgc actttccagc      60

<210> SEQ ID NO 51
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_67002

<400> SEQUENCE: 51
atgctctttg tgcccagact gccctctata aatcagcact atcaaccctg tccagagact      60

<210> SEQ ID NO 52
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_45580

<400> SEQUENCE: 52
gccatctgca tagcctaact ctgccaccct ggcttggaca attatggtga tttctctgat      60

<210> SEQ ID NO 53
<211> LENGTH: 60
<212> TYPE: DNA
<213> ORGANISM: Artificial Sequence
<220> FEATURE:
<223> OTHER INFORMATION: OGHAv1.0 microarray feature identifier
      ha1p_12646

<400> SEQUENCE: 53
agggcctcta gtttgagttt tgccatctat taggatagaa agcacacagt ttgcctgatt      60

<210> SEQ ID NO 54
<211> LENGTH: 23
<212> TYPE: DNA
<213> ORGANISM: Artificial Sequence
```

<220> FEATURE:
<223> OTHER INFORMATION: OGHAv1.0 microarray feature identifier
      ha1g_00681 left PCR primer

<400> SEQUENCE: 54
agatcgccga gctgtcgtag tag                                          23

<210> SEQ ID NO 55
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_39189 left PCR primer

<400> SEQUENCE: 55
cgttctcgat ccagttccat ctc                                          23

<210> SEQ ID NO 56
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1g_00644 left PCR primer

<400> SEQUENCE: 56
tatcatcatt agacccggga tgg                                          23

<210> SEQ ID NO 57
<211> LENGTH: 24
<212> TYPE: DNA
<213> ORGANISM: Artificial Sequence
<220> FEATURE:
<223> OTHER INFORMATION: OGHAv1.0 microarrayfeature identifier
      ha1p_81674 left PCR primer

<400> SEQUENCE: 57
ttcggtctcc tccccatttt ccta                                         24

<210> SEQ ID NO 58
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_81149 left PCR primer

<400> SEQUENCE: 58
gcaaataggt caatgctggg aac                                          23

<210> SEQ ID NO 59
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_83841 left PCR primer

<400> SEQUENCE: 59
aagttcccaa gcacgaagtg ttc                                          23

<210> SEQ ID NO 60
<211> LENGTH: 23
<212> TYPE: DNA
<213> ORGANISM: Artificial Sequence
<220> FEATURE:
<223> OTHER INFORMATION: OGHAv1.0 microarray feature identifier -continued ha1p_38705 left PCR primer

<400> SEQUENCE: 60
tccaggtagt cgtttctgaa gcc                                            23

<210> SEQ ID NO 61
<211> LENGTH: 19
<212> TYPE: DNA
<213> ORGANISM: Artificial Sequence
<220> FEATURE:
<223> OTHER INFORMATION: OGHAv1.0 microarray feature identifier
      ha1p_40164 left PCR primer

<400> SEQUENCE: 61
gcccgccctg caaccaacc                                                 19

<210> SEQ ID NO 62
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_23178 left PCR primer

<400> SEQUENCE: 62
ttctcagagt gttggtaccg cag                                            23

<210> SEQ ID NO 63
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_46057 left PCR primer

<400> SEQUENCE: 63
ggttgccagg acacaaagta agc                                            23

<210> SEQ ID NO 64
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_40959 left PCR primer

<400> SEQUENCE: 64
tcagttgaga gctcagagca agc                                            23

<210> SEQ ID NO 65
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_104423 left PCR primer

<400> SEQUENCE: 65
tgatctgttt cctcactcgc ttg                                            23

<210> SEQ ID NO 66
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1g_00847 left PCR primer

```
<400> SEQUENCE: 66
atgggtggat ggatggatag atg                                              23

<210> SEQ ID NO 67
<211> LENGTH: 24
<212> TYPE: DNA
<213> ORGANISM: Artificial Sequence
<220> FEATURE:
<223> OTHER INFORMATION: OGHAv1.0 microarray feature identifier
      ha1p_08347 left PCR primer

<400> SEQUENCE: 67
ggaggactgc cccatatttt cact                                             24

<210> SEQ ID NO 68
<211> LENGTH: 21
<212> TYPE: DNA
<213> ORGANISM: Artificial Sequence
<220> FEATURE:
<223> OTHER INFORMATION: OGHAv1.0 microarray feature identifier
      ha1g_02416 left PCR primer

<400> SEQUENCE: 68
gcgccccggg acgaggtgga c                                                21

<210> SEQ ID NO 69
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_87540 left PCR primer

<400> SEQUENCE: 69
gttaatggag ggtgagggtt tcc                                              23

<210> SEQ ID NO 70
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_110107 left PCR primer

<400> SEQUENCE: 70
gctgggtgaa tagtcacgga atc                                              23

<210> SEQ ID NO 71
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_89799 left PCR primer

<400> SEQUENCE: 71
aacgctcttc ctccaaagag gtc                                              23

<210> SEQ ID NO 72
<211> LENGTH: 27
<212> TYPE: DNA
<213> ORGANISM: Artificial Sequence
<220> FEATURE:
<223> OTHER INFORMATION: OGHAv1.0 microarray feature identifier
      ha1p_45173 left PCR primer

<400> SEQUENCE: 72
```

```
gttcttctaa gcttcattcc acaagag                                          27

<210> SEQ ID NO 73
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_80771 left PCR primer

<400> SEQUENCE: 73
ggtgaaatat gtgcggactg atg                                              23

<210> SEQ ID NO 74
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_69407 left PCR primer

<400> SEQUENCE: 74
ctcattcatg cataggtcac act                                              23

<210> SEQ ID NO 75
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_05406 left PCR primer

<400> SEQUENCE: 75
ctccttccca ctaggctgca gag                                              23

<210> SEQ ID NO 76
<211> LENGTH: 22
<212> TYPE: DNA
<213> ORGANISM: Artificial Sequence
<220> FEATURE:
<223> OTHER INFORMATION: OGHAv1.0 microarray feature identifier
      ha1p_80287 left PCR primer

<400> SEQUENCE: 76
aggcctggga ggtgactcat ag                                               22

<210> SEQ ID NO 77
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1g_02345 left PCR primer

<400> SEQUENCE: 77
gtagatgcgg aaattggcct cag                                              23

<210> SEQ ID NO 78
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_36172 left PCR primer

<400> SEQUENCE: 78
cctagacagc aacacaccca ctg                                              23
```

<210> SEQ ID NO 79
<211> LENGTH: 24
<212> TYPE: DNA
<213> ORGANISM: Artificial Sequence
<220> FEATURE:
<223> OTHER INFORMATION: OGHAv1.0 microarray feature identifier
    ha1p_70459 left PCR primer

<400> SEQUENCE: 79
ttcaccgtct ctactttctt cctt                                          24

<210> SEQ ID NO 80
<211> LENGTH: 23
<212> TYPE: DNA
<213> ORGANISM: Artificial Sequence
<220> FEATURE:
<223> OTHER INFORMATION: OGHAv1.0 microarray feature identifier
    ha1p_105937 left PCR primer

<400> SEQUENCE: 80
ctctaaacac tcgcctctac ccg                                           23

<210> SEQ ID NO 81
<211> LENGTH: 23
<212> TYPE: DNA
<213> ORGANISM: Artificial Sequence
<220> FEATURE:
<223> OTHER INFORMATION: OGHAv1.0 microarray feature identifier
    ha1p_89099 left PCR primer

<400> SEQUENCE: 81
tagcccttga cagcagttgt gac                                           23

<210> SEQ ID NO 82
<211> LENGTH: 23
<212> TYPE: DNA
<213> ORGANISM: Artificial Sequence
<220> FEATURE:
<223> OTHER INFORMATION: OGHAv1.0 microarray feature identifier
    ha1g_03099 left PCR primer

<400> SEQUENCE: 82
agagccacgt gagctgcatt aac                                           23

<210> SEQ ID NO 83
<211> LENGTH: 22
<212> TYPE: DNA
<213> ORGANISM: Artificial Sequence
<220> FEATURE:
<223> OTHER INFORMATION: OGHAv1.0 microarray feature identifier
    ha1p_67625 left PCR primer

<400> SEQUENCE: 83
cctggagtcc tagagagcct cg                                            22

<210> SEQ ID NO 84
<211> LENGTH: 21
<212> TYPE: DNA
<213> ORGANISM: Artificial Sequence
<220> FEATURE:
<223> OTHER INFORMATION: OGHAv1.0 microarray feature identifier
    ha1g_00218 left PCR primer

<400> SEQUENCE: 84
gccgcgccac cccacctgag t                                             21

<210> SEQ ID NO 85

-continued

```
<211> LENGTH: 21
<212> TYPE: DNA
<213> ORGANISM: Artificial Sequence
<220> FEATURE:
<223> OTHER INFORMATION: OGHAv1.0 microarray feature identifier
      ha1p_12535 left PCR primer

<400> SEQUENCE: 85
agtgttgggt gctgggagga g                                              21

<210> SEQ ID NO 86
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_105474 left PCR primer

<400> SEQUENCE: 86
ctctgggctt tctctagctt ccc                                            23

<210> SEQ ID NO 87
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_74707 left PCR primer

<400> SEQUENCE: 87
agtttgtgag ctcaggagaa gcg                                            23

<210> SEQ ID NO 88
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_93325 left PCR primer

<400> SEQUENCE: 88
ccagtcccat agtggaaatg ctc                                            23

<210> SEQ ID NO 89
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_101161 left PCR primer

<400> SEQUENCE: 89
actaccttgg gtgtcagtcc tgc                                            23

<210> SEQ ID NO 90
<211> LENGTH: 24
<212> TYPE: DNA
<213> ORGANISM: Artificial Sequence
<220> FEATURE:
<223> OTHER INFORMATION: OGHAv1.0 microarray feature identifier
      ha1p_101251 left PCR primer

<400> SEQUENCE: 90
tggacacatg tgctacacgc taag                                           24

<210> SEQ ID NO 91
<211> LENGTH: 23
<212> TYPE: DNA
```

```
<213> ORGANISM: Artificial Sequence
<220> FEATURE:
<223> OTHER INFORMATION: OGHAv1.0 microarray feature identifier
      ha1p_69214 left PCR primer

<400> SEQUENCE: 91
aggtcactgc agaaggatgg aac                                              23

<210> SEQ ID NO 92
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_88517 left PCR primer

<400> SEQUENCE: 92
gggactcatt caatgtcaag tgc                                              23

<210> SEQ ID NO 93
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_103824 left PCR primer

<400> SEQUENCE: 93
tctttagacg ctgcgctctt agc                                              23

<210> SEQ ID NO 94
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_108445 left PCR primer

<400> SEQUENCE: 94
catctgtctt tgttgggcag ttg                                              23

<210> SEQ ID NO 95
<211> LENGTH: 21
<212> TYPE: DNA
<213> ORGANISM: Artificial Sequence
<220> FEATURE:
<223> OTHER INFORMATION: OGHAv1.0 microarray feature identifier
      ha1g_02210 left PCR primer

<400> SEQUENCE: 95
cccaagtact cggcactgca c                                                21

<210> SEQ ID NO 96
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_103872 left PCR primer

<400> SEQUENCE: 96
tgagattcaa tttctcgccc ttc                                              23

<210> SEQ ID NO 97
<211> LENGTH: 18
<212> TYPE: DNA
<213> ORGANISM: Artificial Sequence
<220> FEATURE:
```

```
<223> OTHER INFORMATION: OGHAv1.0 microarray feature identifier
      ha1p_56412 left PCR primer

<400> SEQUENCE: 97
tgccggtctg ctctgctc                                                    18

<210> SEQ ID NO 98
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_18292 left PCR primer

<400> SEQUENCE: 98
ttctcctggg tctttccaaa cag                                              23

<210> SEQ ID NO 99
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_12075 left PCR primer

<400> SEQUENCE: 99
gtttgccaaa tgacagctgt ttg                                              23

<210> SEQ ID NO 100
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_22519 left PCR primer

<400> SEQUENCE: 100
ctcacgttaa tcaacccgag tcc                                              23

<210> SEQ ID NO 101
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_29531 left PCR primer

<400> SEQUENCE: 101
ctccagcact ttgggaatga aag                                              23

<210> SEQ ID NO 102
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_58853 left PCR primer

<400> SEQUENCE: 102
atgtcaggaa aggtgcagag acc                                              23

<210> SEQ ID NO 103
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_35052 left PCR primer
```

```
<400> SEQUENCE: 103
atcttcccag tagggctgaa tcc                                              23

<210> SEQ ID NO 104
<211> LENGTH: 24
<212> TYPE: DNA
<213> ORGANISM: Artificial Sequence
<220> FEATURE:
<223> OTHER INFORMATION: OGHAv1.0 microarray feature identifier
      ha1p_67002 left PCR primer

<400> SEQUENCE: 104
cagtgctccg tgtccccaag tagt                                             24

<210> SEQ ID NO 105
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_45580 left PCR primer

<400> SEQUENCE: 105
gggtgcagga tgaagactag ctg                                              23

<210> SEQ ID NO 106
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_12646 left PCR primer

<400> SEQUENCE: 106
gccttaggaa tttccatccc aac                                              23

<210> SEQ ID NO 107
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1g_00681 right PCR primer

<400> SEQUENCE: 107
aggccaagga gcagaaacta agc                                              23

<210> SEQ ID NO 108
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_39189 right PCR primer

<400> SEQUENCE: 108
accgagtgat acaaaggact ggg                                              23

<210> SEQ ID NO 109
<211> LENGTH: 23
<212> TYPE: DNA
<213> ORGANISM: Artificial Sequence
<220> FEATURE:
<223> OTHER INFORMATION: OGHAv1.0 microarrayfeature identifier
      ha1g_00644 right PCR primer

<400> SEQUENCE: 109
```
gggttaatgg agcactacat gcc    23

<210> SEQ ID NO 110
<211> LENGTH: 24
<212> TYPE: DNA
<213> ORGANISM: Artificial Sequence
<220> FEATURE:
<223> OTHER INFORMATION: OGHAv1.0 microarray feature identifier
      ha1p_81674 right PCR primer

<400> SEQUENCE: 110
acggccccag agcagcagca agac    24

<210> SEQ ID NO 111
<211> LENGTH: 19
<212> TYPE: DNA
<213> ORGANISM: Artificial Sequence
<220> FEATURE:
<223> OTHER INFORMATION: OGHAv1.0 microarray feature identifier
      ha1p_81149 right PCR primer

<400> SEQUENCE: 111
atgcctgccc tgaccacac    19

<210> SEQ ID NO 112
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_83841 right PCR primer

<400> SEQUENCE: 112
ttagaaccag gtctctgcct tgc    23

<210> SEQ ID NO 113
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_38705 right PCR primer

<400> SEQUENCE: 113
ccttccttct ctgcctttca atg    23

<210> SEQ ID NO 114
<211> LENGTH: 19
<212> TYPE: DNA
<213> ORGANISM: Artificial Sequence
<220> FEATURE:
<223> OTHER INFORMATION: OGHAv1.0 microarray feature identifier
      ha1p_40164 right PCR primer

<400> SEQUENCE: 114
tgccctcccc agcgtcttt    19

<210> SEQ ID NO 115
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_23178 right PCR primer

<400> SEQUENCE: 115
gaataaagac atgccaaggc cag    23

<210> SEQ ID NO 116
<211> LENGTH: 23
<212> TYPE: DNA
<213> ORGANISM: Artificial Sequence
<220> FEATURE:
<223> OTHER INFORMATION: OGHAv1.0 microarray feature identifier ha1p_46057 right PCR primer

<400> SEQUENCE: 116
catggaagca taagaccatg ctg        23

<210> SEQ ID NO 117
<211> LENGTH: 18
<212> TYPE: DNA
<213> ORGANISM: Artificial Sequence
<220> FEATURE:
<223> OTHER INFORMATION: OGHAv1.0 microarray feature identifier ha1p_40959 right PCR primer

<400> SEQUENCE: 117
acttccggag acagccgc        18

<210> SEQ ID NO 118
<211> LENGTH: 23
<212> TYPE: DNA
<213> ORGANISM: Artificial Sequence
<220> FEATURE:
<223> OTHER INFORMATION: OGHAv1.0 microarray feature identifier ha1p_104423 right PCR primer

<400> SEQUENCE: 118
gcgattgttc tacgaaagtg tgg        23

<210> SEQ ID NO 119
<211> LENGTH: 23
<212> TYPE: DNA
<213> ORGANISM: Artificial Sequence
<220> FEATURE:
<223> OTHER INFORMATION: OGHAv1.0 microarray feature identifier ha1g_00847 right PCR primer

<400> SEQUENCE: 119
gggcggtgat catttagttt ctg        23

<210> SEQ ID NO 120
<211> LENGTH: 24
<212> TYPE: DNA
<213> ORGANISM: Artificial Sequence
<220> FEATURE:
<223> OTHER INFORMATION: OGHAv1.0 microarray feature identifier ha1p_08347 right PCR primer

<400> SEQUENCE: 120
ctggctgtcc cctatcgtaa cctc        24

<210> SEQ ID NO 121
<211> LENGTH: 22
<212> TYPE: DNA
<213> ORGANISM: Artificial Sequence
<220> FEATURE:
<223> OTHER INFORMATION: OGHAv1.0 microarray feature identifier ha1g_02416 right PCR primer

<400> SEQUENCE: 121
gctggaggcg gcggtggctg tt        22

```
<210> SEQ ID NO 122
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_87540 right PCR primer

<400> SEQUENCE: 122
gttcattccc tccaacattc ctc                                           23

<210> SEQ ID NO 123
<211> LENGTH: 22
<212> TYPE: DNA
<213> ORGANISM: Artificial Sequence
<220> FEATURE:
<223> OTHER INFORMATION: OGHAv1.0 microarray feature identifier
      ha1p_110107 right PCR primer

<400> SEQUENCE: 123
caaggcatag tactcctccg gg                                            22

<210> SEQ ID NO 124
<211> LENGTH: 21
<212> TYPE: DNA
<213> ORGANISM: Artificial Sequence
<220> FEATURE:
<223> OTHER INFORMATION: OGHAv1.0 microarray feature identifier
      ha1p_89799 right PCR primer

<400> SEQUENCE: 124
gctgtgagag gagcggaaga g                                             21

<210> SEQ ID NO 125
<211> LENGTH: 21
<212> TYPE: DNA
<213> ORGANISM: Artificial Sequence
<220> FEATURE:
<223> OTHER INFORMATION: OGHAv1.0 microarray feature identifier
      ha1p_45173 right PCR primer

<400> SEQUENCE: 125
gggttaaggc tggactctgg c                                             21

<210> SEQ ID NO 126
<211> LENGTH: 19
<212> TYPE: DNA
<213> ORGANISM: Artificial Sequence
<220> FEATURE:
<223> OTHER INFORMATION: OGHAv1.0 microarray feature identifier
      ha1p_80771 right PCR primer

<400> SEQUENCE: 126
ccctttcatt cacctggcg                                                19

<210> SEQ ID NO 127
<211> LENGTH: 21
<212> TYPE: DNA
<213> ORGANISM: Artificial Sequence
<220> FEATURE:
<223> OTHER INFORMATION: OGHAv1.0 microarray feature identifier
      ha1p_69407 right PCR primer

<400> SEQUENCE: 127
tggggaggag caatagagat a                                             21

<210> SEQ ID NO 128
<211> LENGTH: 23
```

```
<212> TYPE: DNA
<213> ORGANISM: Artificial Sequence
<220> FEATURE:
<223> OTHER INFORMATION: OGHAv1.0 microarray feature identifier
      ha1p_05406 right PCR primer

<400> SEQUENCE: 128
aaacaaccac tgctcctgtc tcc                                           23

<210> SEQ ID NO 129
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_80287 right PCR primer

<400> SEQUENCE: 129
taaggtgtgt gcctaaccca tcc                                           23

<210> SEQ ID NO 130
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1g_02345 right PCR primer

<400> SEQUENCE: 130
atatttgagc ctcttgccct tcc                                           23

<210> SEQ ID NO 131
<211> LENGTH: 22
<212> TYPE: DNA
<213> ORGANISM: Artificial Sequence
<220> FEATURE:
<223> OTHER INFORMATION: OGHAv1.0 microarray feature identifier
      ha1p_36172 right PCR primer

<400> SEQUENCE: 131
gtcttctcct tgcaatgggc tc                                            22

<210> SEQ ID NO 132
<211> LENGTH: 24
<212> TYPE: DNA
<213> ORGANISM: Artificial Sequence
<220> FEATURE:
<223> OTHER INFORMATION: OGHAv1.0 microarray feature identifier
      ha1p_70459 right PCR primer

<400> SEQUENCE: 132
gttgctgttc ttatccccat tcta                                          24

<210> SEQ ID NO 133
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_105937 right PCR primer

<400> SEQUENCE: 133
cccatcctgt agacagatca ggg                                           23

<210> SEQ ID NO 134
<211> LENGTH: 23
<212> TYPE: DNA
<213> ORGANISM: Artificial Sequence
```

```
<220> FEATURE:
<223> OTHER INFORMATION: OGHAv1.0 microarray feature identifier
      ha1p_89099 right PCR primer

<400> SEQUENCE: 134
gactaatgcc catgacccag aag                                              23

<210> SEQ ID NO 135
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1g_03099 right PCR primer

<400> SEQUENCE: 135
catgcttaga ggtgaacgtg tgg                                              23

<210> SEQ ID NO 136
<211> LENGTH: 19
<212> TYPE: DNA
<213> ORGANISM: Artificial Sequence
<220> FEATURE:
<223> OTHER INFORMATION: OGHAv1.0 microarray feature identifier
      ha1p_67625 right PCR primer

<400> SEQUENCE: 136
gtgcagggtg ggtgagagg                                                   19

<210> SEQ ID NO 137
<211> LENGTH: 22
<212> TYPE: DNA
<213> ORGANISM: Artificial Sequence
<220> FEATURE:
<223> OTHER INFORMATION: OGHAv1.0 microarray feature identifier
      ha1g_00218 right PCR primer

<400> SEQUENCE: 137
gcggctccgg ggccaatgaa tg                                               22

<210> SEQ ID NO 138
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_12535 right PCR primer

<400> SEQUENCE: 138
tgagggttct tgtgtgttct tcg                                              23

<210> SEQ ID NO 139
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_105474 right PCR primer

<400> SEQUENCE: 139
gggtgctcct tccatctaca atg                                              23

<210> SEQ ID NO 140
<211> LENGTH: 20
<212> TYPE: DNA
<213> ORGANISM: Artificial Sequence
<220> FEATURE:
<223> OTHER INFORMATION: OGHAv1.0 microarray feature identifier
``` ha1p_74707 right PCR primer

<400> SEQUENCE: 140
ggcgttctgc tttgggagac                                                    20

<210> SEQ ID NO 141
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_93325 right PCR primer

<400> SEQUENCE: 141
ctccatgagg tggaggtgaa gac                                                23

<210> SEQ ID NO 142
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_101161 right PCR primer

<400> SEQUENCE: 142
gttgaagtga gcagaggaca tgc                                                23

<210> SEQ ID NO 143
<211> LENGTH: 24
<212> TYPE: DNA
<213> ORGANISM: Artificial Sequence
<220> FEATURE:
<223> OTHER INFORMATION: OGHAv1.0 microarray feature identifier
      ha1p_101251 right PCR primer

<400> SEQUENCE: 143
tgtctgtggg tattctttgt tgcc                                               24

<210> SEQ ID NO 144
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_69214 right PCR primer

<400> SEQUENCE: 144
atgcctagcc agtcaggaat cag                                                23

<210> SEQ ID NO 145
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_88517 right PCR primer

<400> SEQUENCE: 145
ggtgttacct cctttcatgg tgc                                                23

<210> SEQ ID NO 146
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_103824 right PCR primer -continued

```
<400> SEQUENCE: 146
aaacgtccgc tactcttgag cac                                          23

<210> SEQ ID NO 147
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_108445 right PCR primer

<400> SEQUENCE: 147
ataacacttg cacaccacca ccc                                          23

<210> SEQ ID NO 148
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1g_02210 right PCR primer

<400> SEQUENCE: 148
agagggaagc cacagaaaga agc                                          23

<210> SEQ ID NO 149
<211> LENGTH: 21
<212> TYPE: DNA
<213> ORGANISM: Artificial Sequence
<220> FEATURE:
<223> OTHER INFORMATION: OGHAv1.0 microarray feature identifier
      ha1p_103872 right PCR primer

<400> SEQUENCE: 149
agggatggac caagagggaa c                                            21

<210> SEQ ID NO 150
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_56412 right PCR primer

<400> SEQUENCE: 150
taactccacc ctgtacctgg ctc                                          23

<210> SEQ ID NO 151
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_18292 right PCR primer

<400> SEQUENCE: 151
ttagtgacca ggtgatggtg gtg                                          23

<210> SEQ ID NO 152
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_12075 right PCR primer

<400> SEQUENCE: 152
```

-continued ctcaggaatt gcagccttga gac                                          23

<210> SEQ ID NO 153
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_22519 right PCR primer

<400> SEQUENCE: 153
atcctgcaat gtttggatga tgg                                          23

<210> SEQ ID NO 154
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_29531 right PCR primer

<400> SEQUENCE: 154
tcaccctctt aatgtcagct ccc                                          23

<210> SEQ ID NO 155
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_58853 right PCR primer

<400> SEQUENCE: 155
caggctgttc tctcctagca atg                                          23

<210> SEQ ID NO 156
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_35052 right PCR primer

<400> SEQUENCE: 156
ggcatcaaac tgaaatcctc ctg                                          23

<210> SEQ ID NO 157
<211> LENGTH: 24
<212> TYPE: DNA
<213> ORGANISM: Artificial Sequence
<220> FEATURE:
<223> OTHER INFORMATION: OGHAv1.0 microarray feature identifier
      ha1p_67002 right PCR primer

<400> SEQUENCE: 157
cagtccgatt tcaaggtccc agtg                                         24

<210> SEQ ID NO 158
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_45580 right PCR primer

<400> SEQUENCE: 158
cagggcagtc actgagaatg agg                                          23

```
<210> SEQ ID NO 159
<211> LENGTH: 23
<212> TYPE: DNA
<213> ORGANISM: Artificial Sequence
<220> FEATURE:
<223> OTHER INFORMATION: OGHAv1.0 microarray feature identifier
      ha1p_12646 right PCR primer

<400> SEQUENCE: 159
tttctcctct ttcatgcctc acc                                            23

<210> SEQ ID NO 160
<211> LENGTH: 533
<212> TYPE: DNA
<213> ORGANISM: Homo sapiens
<220> FEATURE:
<223> OTHER INFORMATION: OGHAv1.0 microarray feature identifier
      ha1g_00681 amplicon

<400> SEQUENCE: 160
agatcgccga gctgtcgtag taggtcgctt tttgcatcgc gttgtttcac gatcttgatc    60
gcacactctg acaggggttt gacacccgtg agggcgcaca ttggcacgcc cccgcggtca   120
cgtgacactc cgccgccaat ggccgccccg cgcagacctg gtggggcgag aagcgcagcg   180
cggtgagggc tccgcgcaaa tccatcttac tctcaatagc taagtgacat gaaagccata   240
aaagaaaaag tggtcagcaa tatttagcag cacgacttgg ccccgggcgc agggagccgt   300
gctataaaaa accgctggaa tttactggca gctacaaata tttgcttaac ttgcgtctgg   360
agttggggga ttttccgggg agaaggagaa tgagtgaggg ctgcaagctg attctcagga   420
gccgggatcc aaaaggagaa aggcttgata ggctagaaag gaaaaggct gggatctttc    480 ttttccaggg aagaagaaac ttggggtgtc gcttagtttc tgctccttgg cct          533

<210> SEQ ID NO 161
<211> LENGTH: 535
<212> TYPE: DNA
<213> ORGANISM: Homo sapiens
<220> FEATURE:
<223> OTHER INFORMATION: OGHAv1.0 microarray feature identifier
      ha1p_39189 amplicon

<400> SEQUENCE: 161
cgttctcgat ccagttccat ctcgcacttc ccaaagcgtc gcagcgagtg gggaccgcag    60
ggaccaggcg ccgcgaagcg ggagcgtgag gcgctctctc cgaagccctg ggcgacgctg   120
gactagtgtg ccccggaagg acaggtcaca cccggggtg ggggtgaaga cgacggtggc    180
ggtggggagg acacctttag cagctgggac ctgatttctt cctccacaag gctgcagctg   240
gctatggccc tggtggaaag aaaaagcgag cttgaccaac tcgacttggg aagggggata   300
gagagagaaa agaaggacct tgtgtttgta ttcataccgg tgagcaccaa agaatagtct   360
cacgcagtta taggacccag gttcagcgat gtgactactt gtccaaggtc acacagcgag   420
ctggggactc ggggaccagt gtcggatctc ccacccggtt gggacttctg agcgcacagg   480
ggcaagatat gtgagtaaac cctgtccaga atcccagtcc tttgtatcac tcggt        535

<210> SEQ ID NO 162
<211> LENGTH: 451
<212> TYPE: DNA
<213> ORGANISM: Homo sapiens
<220> FEATURE:
<223> OTHER INFORMATION: OGHAv1.0 microarray feature identifier
      ha1g_00644 amplicon
```

```
<400> SEQUENCE: 162
tatcatcatt agacccggga tgagcggcg ggggggagtt tctctttact taccaaaccg      60
caacaacaaa caacaacga cgaacaaccg ccccctacaa acactcattc tcacacaacg     120
ttgccctacc tccctcgccg cttgccctgg ccgctgttgc acactcccct gggggctgtc    180
tgcacgccct agagcagaca ctgcggtcac ttaaagtgcg cccagttcct ccaccgcagc    240
ggtcacaccg ttgatttgat ccagaaataa gacggatagt accgagcgtt ggcgctaggg    300
gttgtctatg tcaaaggcga aggttggctg ggaagttctg tccgtttctc ttgccttagc    360
ataggagtca atccttttct tgtcacccga ttctgcaaat tctcgctgta ttaaaggagc    420
agagatctgg catgtagtgc tccattaacc c                                   451

<210> SEQ ID NO 163
<211> LENGTH: 464
<212> TYPE: DNA
<213> ORGANISM: Homo sapiens
<220> FEATURE:
<223> OTHER INFORMATION: OGHAv1.0 microarray feature identifier
      ha1p_81674 amplicon

<400> SEQUENCE: 163
ttcggtctcc tccccatttt cctagtcgtc ttcggttgtg gatgttgtaa actcgaccat     60
ccgtctctca aggtctttgg cttcaaggtt tcccaatgct ctggagctgt ccaagccccg    120
gtactccggg gtggaagacc tcagattcat ttgacgggct tgtggaggtt ggggggtctgc   180 ggagccccgt gtgggtgggg ctgggcgcgg ccggggcgga gccggcgagg agccctaggg    240
aaagggtgaa aggcacagtt gagaaaggcc cgccgggcat tggtttcaca gtttccacga    300
aggcttcgtg tgcaagcctg aggagtttag gtgcctccct cctgcctcgc ctttcttggt    360
tctagaacct tcagtaggct tttctgggtt gcagggaccc ggaaaagcag cggcttccac    420
tcggggggcg ggtcccaagg gtcttgctgc tgctctgggg ccgt                     464

<210> SEQ ID NO 164
<211> LENGTH: 505
<212> TYPE: DNA
<213> ORGANISM: Homo sapiens
<220> FEATURE:
<223> OTHER INFORMATION: OGHAv1.0 microarray feature identifier
      ha1p_81149 amplicon

<400> SEQUENCE: 164
gcaaataggt caatgctggg aacagatgcc tgcctggctg agtgctggga agaaaggca      60 gttggaggga tgtgtgggtg cctggagggg cgtgggtggt gcccaggagg ctatgggaat    120
cagaatcaca cttgcacaag agaagaccct tatgggacaa gtaaaatcag catagtttct    180 tgggcgggc aaaggtgtcc tgatgaggat gctaggggtc aaatatgtgt ctgggttctg     240
ccccaatcgg gaatgagaca cagtactgaa gtggaacggg ggtagcatct ccacccacct    300
tcacagcctc tggggaaaag aaagctttcc ttgcagccca actccagggg cctaaatatt    360
gagcaccaac acaagacagg tccttgagct tctcggagcg agtcggggaa gcagataatt    420
tcagatgcaa agtgccttga ataaacagaa cgaaagatag agagccagag ggggagaaac    480
ggcttggtgt ggtcagggca ggcat                                         505

<210> SEQ ID NO 165
<211> LENGTH: 425
<212> TYPE: DNA
<213> ORGANISM: Homo sapiens
<220> FEATURE:
```

<223> OTHER INFORMATION: OGHAv1.0 microarray feature identifier
      ha1p_83841 amplicon

<400> SEQUENCE: 165

```
aagttcccaa gcacgaagtg ttctgcgtcc cgaacattcc aggggccgcc agccaccatg      60
ggctctgtcc tgaggtgcca agcaggacat ccctgcccga catccttgtc ctcccgcacc     120
gcacacgcgt tagtggctgt ggcgtcgcca ccccagcaca cgctggcccg cccgcagtgc     180
caggctggaa gtgtcgggcg cttgccaggc caaggggcaa ttctgttgcc ttccaggcct     240
tttcggcgcg gtcccagtca ggaacgcgcc ctgtcgcctc ccactccgtc ttccggaccc     300
tcccgatcct ctctcgtcag cgatcgggcg tcgctcccct ggactaacct cccttgcccc     360
atcttcagct tttcgctgat ctgcatcttc ctgcgcctta gtgcaaggca gagacctggt     420
tctaa                                                                 425
```

<210> SEQ ID NO 166
<211> LENGTH: 585
<212> TYPE: DNA
<213> ORGANISM: Homo sapiens
<220> FEATURE:
<223> OTHER INFORMATION: OGHAv1.0 microarray feature identifier
      ha1p_38705 amplicon

<400> SEQUENCE: 166

```
tccaggtagt cgtttctgaa gccctagtcc tcagttccca agaaaccac gtgcgcacta       60
ccacctaaaa ctgccaatga aaatgaaggt cctgcgcagt aaaatattta tacaactgct     120
ggggccacta ggcttcagcg ggtgtggagg cggggagaga ggaggagtaa aggctgttta     180
caaacttgac gtacacacgc agtcctatcc ctacggtcct ggaattgggg gttactatct     240
tggaatctag gggcactcca ggctctgggc tcagacggct ggcttctgcc tacccgagcc     300
ttaacctttc aaggaccaga aggattccag agctcttgcc ctaggtcctg gggcagcgat     360
gactcactgc agcacccct cccacttcgc caagctgccg tctccgccca ccccaaaca     420
atctcgacag cgcatttcgg gagccacggc tccgggcgct ttgctggggg ctaaagggggt    480
ttatcccttt ccttgaatcc cagcaggcta gaactacccc ctcccagtct tcaggcttgc     540
cacgctctcc acccgatcct tccattgaaa ggcagagaag gaagg                     585
```

<210> SEQ ID NO 167
<211> LENGTH: 407
<212> TYPE: DNA
<213> ORGANISM: Homo sapiens
<220> FEATURE:
<223> OTHER INFORMATION: OGHAv1.0 microarray feature identifier
      ha1p_40164 amplicon

<400> SEQUENCE: 167

```
gcccgccctg caaccaaccc gctcaaacaa gcaccctgac tggcgcattc ttactcattc      60
tagcctgggt ttcaacttca aggagcttca gcgcccctca ctcccttgcc ctgaaagctg     120
gctaaactac gcacctttc tccccttttg aaatgacctt tccagatatt tctatggaat      180
tcagtgccat tttctgccgc tgttctcacc acattcattc atcatgttta gttttaaaag     240
taccagattc tgtcgatttc tccaactgaa ctctgaaatc tttgaggtca gggagcttgc     300
ctcattctat tttgtattcc cagtacgtga cacatggctg gacacaccag aaattgtccg     360
atcaagtttg tgggtattaa gagtggtcaa agacgctggg gagggca                   407
```

<210> SEQ ID NO 168
<211> LENGTH: 526

<212> TYPE: DNA
<213> ORGANISM: Homo sapiens
<220> FEATURE:
<223> OTHER INFORMATION: OGHAv1.0 microarray feature identifier
      ha1p_23178 amplicon

<400> SEQUENCE: 168

```
ttctcagagt gttggtaccg cagattcaac tggggccaga gaagcccatc acgggagccc        60
gaggaaaagc agccacagct ctccttccta gtacaagcat tcaacagtaa gctcccacgc       120
aaagaatcag actgcagcaa atttcagcgc tgcctcagga acactgtcct tggctcccac       180
attgcaaaga ttttccattc cctccacagt caccctcattc atggttaagg aagaaagcgc      240
agctaacaga cagggtgacg acagatgtcc aggcactgag ccatccatag ctgttatttt       300
tcattcacat aggcatgtgc cggatccagc agatgaaaac cagacctacc cccttcccca       360
tgtgtgtgtg ttttttcccc ttactgctgc tgctgtaaca gctaagtgcc aattatctcc       420
caagcgtgaa agcaaatatt gtgatagccc aacaaactct acaaatgtta gaggacacag       480
gtggggatga ctgttttttct gtcctggcct tggcatgtct ttattc                     526
```

<210> SEQ ID NO 169
<211> LENGTH: 404
<212> TYPE: DNA
<213> ORGANISM: Homo sapiens
<220> FEATURE:
<223> OTHER INFORMATION: OGHAv1.0 microarray feature identifier
      ha1p_46057 amplicon

<400> SEQUENCE: 169

```
ggttgccagg acacaaagta agcaacagct gcatgaccgg tttagtcctg acgtttacaa        60
agagggaccc tttccataag cctgtaactt ggtgtgggca gcttgccgat gtcaggcagt       120
gcatgtttca ctcgattagg gagagagcgc accctctcca gagggctttg gccacgctta       180
attttttctt tgtttccttc tatactgctt tatatctcac acatcccctc ttaactctcc       240
agacatggga agttgttgtg acaggtcagg aaagtcgtat gtttacccctt ctcctagaaa      300
ttagttatgt aagctattat tgtatgtatt tagtaatgag gggacatgtg cattaatctc       360
ttaaagcttt gaaataatta gcagcatggt cttatgcttc catg                        404
```

<210> SEQ ID NO 170
<211> LENGTH: 512
<212> TYPE: DNA
<213> ORGANISM: Homo sapiens
<220> FEATURE:
<223> OTHER INFORMATION: OGHAv1.0 microarray feature identifier
      ha1p_40959 amplicon

<400> SEQUENCE: 170

```
tcagttgaga gctcagagca agctgttgga ttaagcaaaa gcacctttta aaaaattaat        60
attcaaggca gctgtaccgc ggagggcctg ggtctcggag tctaaaaaat cagactggac       120
gttactattt tttttaggc aaacgacagc tcgtttctca tttgtaaaac cggggggaaca       180
tcttaccgaa taaaccttac acaaacagaa aggattccta agggctggga aaatactatt      240
ttgctgtccc caggatggaa tatcagcatc cttgtctttt agctcttaat aaagctctaa      300
ctagtcacag gaggagccag gctgcatgat cacgcacact ctggacgtct aggttttccg      360
acctaataag ggggcaggtc gcgtcgttcc ctgcttaaat tagagaccac ctccacctgc      420
caagggccct tcaaaccctc cgcccctagg tcgctaacga tcaccgcttt agttctagct      480
ccaggcgccg cctggcggct gtctccggaa gt                                    512
```

<210> SEQ ID NO 171
<211> LENGTH: 413
<212> TYPE: DNA
<213> ORGANISM: Homo sapiens
<220> FEATURE:
<223> OTHER INFORMATION: OGHAv1.0 microarray feature identifier
    ha1p_104423 amplicon

<400> SEQUENCE: 171
tgatctgttt cctcactcgc ttgctcgtgg atgtcatttt ctgtcttctt ggggcggcc      60
aaaaatcgac cggtgtcggg gaccagaggc ggccccgcac gccccgcgt gtgcgtccac     120
gggcgtctgt gcagacggac actgtgccgg ggcgagctga caggagttca cggctgcgat    180
agaacatgga gatgtcatgg gcgcgacaga gcctggcggg gataccagca gcgtgtgtgt    240
gtggacggca acgttgtctg tgcgcgtgtg tgtgagtgag tgaggagag agagagagaa     300
taggtgtgtg tagaggctcc cggtgcctct gtctggctgc tgaggctgag atgggagcaa    360
gtggctggcg aagctggtgg tggcttcaaa ccacactttc gtagaacaat cgc           413

<210> SEQ ID NO 172
<211> LENGTH: 560
<212> TYPE: DNA
<213> ORGANISM: Homo sapiens
<220> FEATURE:
<223> OTHER INFORMATION: OGHAv1.0 microarray feature identifier
    ha1g_00847 amplicon

<400> SEQUENCE: 172
atgggtggat ggatggatag atgaatgggt ggatggatgg agggatggat ggacggacgg     60
acggacagat atatggatgg atgcattatg gatggatgca tggacggacg gacggatgca    120
cggagagatg gatggatgca tggatggata gatagacgga tggacggacg gatagataga    180
tggatgccgg aaaggagaag aatgagagac ggatgtgaga ctagatgcac gcaggccaga    240
gcaccagcat acgctggaac agagcacgag catacactcg aacacgcgcg cacacactca    300
ggacatctgc gcacagacat acaatcctcc gcgtccgctt ccacgcaggc attcgcgcac    360
ctacatacac gcagttgcac gcgcgcgcac acacacaggc acacacacgc agacatgcac    420
acacacgcag acatgcacac acaccacaca tgcagacatg cacacacacg cagacatgca    480
cacacacacc acacatacac acacacacac acacagttcg cctctccctg ggtttctcag    540
aaactaaatg atcaccgccc                                                 560

<210> SEQ ID NO 173
<211> LENGTH: 430
<212> TYPE: DNA
<213> ORGANISM: Homo sapiens
<220> FEATURE:
<223> OTHER INFORMATION: OGHAv1.0 microarray feature identifier
    ha1p_08347 amplicon

<400> SEQUENCE: 173
ggaggactgc cccatatttt cactcccaaa aacccttag atgactccct gcctcacccc      60
cgcccccag gttctgaaag agccttcccg ccagactgca ttgattaacc attcattgcc     120
ccattttta ttaatcaaag acatatataa ttgctcatcg gagcttgtga tcagcgtgag    180
gccttactaa gcagctgcct tactatcctt ccagcccaga gcacgtgagc tgacgtcttc    240
tttggcctgt gtggccgttt ccttgccaaa agctcagttt ggggagagct tcttgcgtat    300
tagatgcagt ctgcagactc ccaaccccag ctacctggat cccctgaggg cccaggaact    360
ccagctattc caagcccact cctctttttt ttaagaggaa gaaatagagg ttacgatagg    420

| | |
|---|---|
| ggacagccag | 430 |

<210> SEQ ID NO 174
<211> LENGTH: 407
<212> TYPE: DNA
<213> ORGANISM: Homo sapiens
<220> FEATURE:
<223> OTHER INFORMATION: OGHAv1.0 microarray feature identifier
       ha1g_02416 amplicon

<400> SEQUENCE: 174

| | |
|---|---|
| gcgccccggg acgaggtgga cggccggggg gagctggtaa ggaggagcag cggcggtgcc | 60 |
| agcagcagca agagccccgg gccggtgaaa gtgcgggaac agctgtgcaa gctgaaaggc | 120 |
| ggggtggtgg tagacgagct gggctgcagc cgccaacggg ccccttccag caaacaggtg | 180 |
| aatggggtgc agaagcagag acggctagca gccaacgcca gggagcggcg caggatgcat | 240 |
| gggctgaacc acgccttcga ccagctgcgc aatgttatcc cgtcgttcaa caacgacaag | 300 |
| aagctgtcca aatatgagac cctgcagatg gcccaaatct acatcaacgc cttgtccgag | 360 |
| ctgctacaaa cgcccagcgg aggggaacag ccaccgccgc ctccagc | 407 |

<210> SEQ ID NO 175
<211> LENGTH: 542
<212> TYPE: DNA
<213> ORGANISM: Homo sapiens
<220> FEATURE:
<223> OTHER INFORMATION: OGHAv1.0 microarray feature identifier
       ha1p_87540 amplicon

<400> SEQUENCE: 175

| | |
|---|---|
| gttaatggag ggtgagggtt tccacccgtg ggtctctgaa agggctccca caggttcagc | 60 |
| aagagcgtct gggagaaacc atctgtggag tgggggacac aggcacagag tgtcccgtcc | 120 |
| tgggcaaggg gtcccctcct ctcgctgctc cctgccaaga gcccagaggg aagaaaggac | 180 |
| catggcatga gcatctatgt atgaagtctc ctctgatccc taggaggagg gatggggcgt | 240 |
| gtgttgtgtg tgtccacgcg tgtgcacagt ggaactgatg aggtgtgtga agagagaagg | 300 |
| gtgttcctgt ctccctgaat tgcctcccat gccctggctt ctcccctggc ttctccctcc | 360 |
| cacctggttg cccatcaccc ttactcacat ttctcaaggc ccgtgttgaa tcctgggctc | 420 |
| tcccgacagc gtcttcgtgc actgtgtgca gagggagccc gcgtcatgca cagcaggggag | 480 |
| gggagggttt tctgtggagt ggagggggga ccattcccgg aggaatgttg gagggaatga | 540 |
| ac | 542 |

<210> SEQ ID NO 176
<211> LENGTH: 432
<212> TYPE: DNA
<213> ORGANISM: Homo sapiens
<220> FEATURE:
<223> OTHER INFORMATION: OGHAv1.0 microarray feature identifier
       ha1p_110107 amplicon

<400> SEQUENCE: 176

| | |
|---|---|
| gctgggtgaa tagtcacgga atctcactca cgctcggctc ctccacccat cccgtctaca | 60 |
| gcgcgtgtcc cagtccaggg cgtgcgtgcg ctcggtgtcc gattccgggc tgtgtgtgtc | 120 |
| catttggcga gatgtcgaga gcggggggag tgtccttgtc ggtgtatctg ggcccaggtt | 180 |
| aggggacttc tcctcccac cccgcgtgg gtgtggggg tgtccgggc tagggcgcgt | 240 |
| gtgcttctgt gcctgtgcgt gcgtgtgcgg gtcagggtgg tgggaccgcg catcagggca | 300 |

```
gggtgcctgc gtctgcgtct gggtctgtct ggtctgcatg tcggcgcgat ctcgacctgg    360
attcgtgtcc ctggatgtcg agaggccagc gtggtggggg tgtccagcct cccggaggag    420
tactatgcct tg                                                         432

<210> SEQ ID NO 177
<211> LENGTH: 472
<212> TYPE: DNA
<213> ORGANISM: Homo sapiens
<220> FEATURE:
<223> OTHER INFORMATION: OGHAv1.0 microarray feature identifier
      ha1p_89799 amplicon

<400> SEQUENCE: 177
aacgctcttc ctccaaagag gtcgcgcctt ctctgtggtg gttctcaggg atccgcccca     60
gctccttctc cgttcccagc cccacacact gggatcacca ggcacccaag atcccacctc    120
tcaggtggta tcttcagcgc aggctgccac tcagcccccc tccagggatc tggggcagaa    180
ggcgaatatc ccagagtctc agagtccaca ggagttactc tgaagggcga ggcgcgggct    240
gcatcagtgg accccacac cccacccgca ccccaagcgc tccaccctgg ggcggggcc     300 gtcgccttcc ttccggactc gggatcgatc tggaactccg ggaatttccc tggcccgggg    360
gctccgggct ttccagcccc aaccatgcat aaaaggggtt cgcggatctc ggagagccac    420
agagcccggg ccgcaggcac ctcctcgcca gctcttccgc tcctctcaca gc            472

<210> SEQ ID NO 178
<211> LENGTH: 600
<212> TYPE: DNA
<213> ORGANISM: Homo sapiens
<220> FEATURE:
<223> OTHER INFORMATION: OGHAv1.0 microarray feature identifier
      ha1p_45173 amplicon

<400> SEQUENCE: 178
gttcttctaa gcttcattcc acaagagatt gaaatcgaag tattctgggc tggcacacga     60
tagctggaac atcatatttt attctagaaa cacatttgcc ttggcaaaga agagcgtgcc    120
tagaggagtg gtcaggatag tgagggatct gtgatccttc gttctgaatc tagaaaagtc    180
actggatatg cccctccccc gccccccaac acggtcttat gttctgaatg tagaagtcac    240
tggatgtgct gacacacaca cacacacaca cacacacaca cacacacaca cacacacaca    300
cacacagagt ctgtggcctc tttcccaggc attccaagtc cagcaagttc gcaggagct     360 gtcagtccgt ccaggaaggc ccgggcctgg gtttgcctct tcaagcagct actgcagggg    420
cgtggggagg gggcataaga gactttggac tttcctttga gacagtagaa agcgttacat    480
ccagaggcga gattctagcc tggggtcccc gccttccgg cctcctcttc ctctccctct     540
gactcccttt cctgtgcccc tccccctgcc tctttcccgg ccagagtcca gccttaaccc    600

<210> SEQ ID NO 179
<211> LENGTH: 410
<212> TYPE: DNA
<213> ORGANISM: Homo sapiens
<220> FEATURE:
<223> OTHER INFORMATION: OGHAv1.0 microarray feature identifier
      ha1p_80771 amplicon

<400> SEQUENCE: 179
ggtgaaatat gtgcggactg atgagtcaaa gctcttattc cctggactgc attaataccc     60
acgacgtgct tttcgctctc cagacaaaga gaccggtact tggcaggtcc ctcaagtggg    120
actcaaaaga ccgaaccgag ctgcagcctt tcgctagcac tggtcctcgc cccttttggc    180
```

```
atcttggtac ttgtagtttt gtccactcta tctttacccg aaaagccagc gctgagacca      240
caactcccat caccctgcga gcaccagcgc cttcagagcg catcctccga ggggcaccag      300
cgccattgac caccctgctg gccgaagggc ccgccttccc gaggccaggc gctcccgcga      360
ttggccagcc gccccgcctc tcatcggagg gcgccaggtg aatgaaggg               410

<210> SEQ ID NO 180
<211> LENGTH: 409
<212> TYPE: DNA
<213> ORGANISM: Homo sapiens
<220> FEATURE:
<223> OTHER INFORMATION: OGHAv1.0 microarray feature identifier
      ha1p_69407 amplicon

<400> SEQUENCE: 180
ctcattcatg cataggtcac acttctccaa agttggtatg gcctgtctcc ttggcatgtt       60
cccttgcttc tgcttgtcca gttaatcctt tctgacatac catgcatctc agggtgaagc      120
ggttgacatc agtaaactgt ctccttcttc tagcttcatc tgctaattcc agtgcttgta      180
caagaacaat atcatcatta gaggagaaaa tggtcagagg aggtgtatct ggatcaggga      240
agttacgctg aagtggatca tagtggatgc catcataaat aagcagaacc cttttggtat      300
atcctgcatc ttccccaaaa cgatcaattc ttactgtctg tgtatccact acacatattt      360
cacattggta aaacttggac aaaatcgata tctctattgc cctcccca                  409

<210> SEQ ID NO 181
<211> LENGTH: 411
<212> TYPE: DNA
<213> ORGANISM: Homo sapiens
<220> FEATURE:
<223> OTHER INFORMATION: OGHAv1.0 microarray feature identifier
      ha1p_05406 amplicon

<400> SEQUENCE: 181
ctccttccca ctaggctgca gaggcgggga agacccgcca caggctggcg tgcggagccc       60
caggccggcg gccttccgtg attaacgagt gtttacaaga ctctattagt aatgacacag      120
acaccaatgg ttggagacgt cgaggcgcag cgcgcactct acgcacaacc cctcgaaaca      180
taatttgcat tttaaaagat aaaggggagg gaggctcgtg agagggcagc gacctgacac      240
agctaaatat tcaaaccttt attgttaaga gcttcctcct tccaacctgg tgcactttaa      300
cctccaatca caggttcaaa gaatgaaatc aagagactta caaaagagag gggaagagaa      360
aaggctatct tggtaggaat ctgagcttgg agacaggagc agtggttgtt t              411

<210> SEQ ID NO 182
<211> LENGTH: 488
<212> TYPE: DNA
<213> ORGANISM: Homo sapiens
<220> FEATURE:
<223> OTHER INFORMATION: OGHAv1.0 microarray feature identifier
      ha1p_80287 amplicon

<400> SEQUENCE: 182
aggcctggga ggtgactcat agagtctgcc ccctctcgcc cttctgccct gggaggtcgg       60
gggtgaggat ggtggagggg aagcgtgcga aggggtgcc agggttagaa tgaggtgccc      120
accgaggaga gagacgtctg aagtctggcg tcttttcctt caaggctgct gtgtagattg      180
tgaggtggga gggctgaaga tcaagttccc tcgagggagg ttaaagaagg gctaagtgga      240 cccggaaaact ctgctcttcg gggtggtctc cgctctggga ggcggggact cccctctggt      300
```

```
atgggtgttc attgttctgg ccccattgga atctatcccc cagggacaac tcctttgtgc    360
aaagtcctgc aggatagaag aggggggcagt gcacaatcaa tttccaccgtc aaagggggaca   420 tgtctggttt tatgaaggga gagggaagaa gaaaggatca agtggggatg ggttaggcac    480
acacctta                                                             488
```

<210> SEQ ID NO 183
<211> LENGTH: 599
<212> TYPE: DNA
<213> ORGANISM: Homo sapiens
<220> FEATURE:
<223> OTHER INFORMATION: OGHAv1.0 microarray feature identifier
      ha1g_02345 amplicon

<400> SEQUENCE: 183

```
gtagatgcgg aaattggcct cagccgcgcc atgcagcgcg ccctcgtccg tcttgtcgca     60
ggcgcctttg gcgaggtcac tgcagagccc ggggatgttt tggtcgtagg aggcgcaggg    120
caggttgccg taggcgtcgg cgcccaggcc gtagccggac gcaaaggggc tctgataaag    180
ggggctgttg acattgtata agcccggaac ggtcgaggcg aaggcgccgg cgcccgcccc    240
gtagccgctt ctctgtgagt tgggagcaaa ggagcaagaa gtcggctcgg cattttggaa    300
cagagaagcc cccgccgtat atttgctaaa aagcgcgttc acataatacg aagaactcat    360
aattttgacc tgtgatttgt tgtccggcag cttttcagtgt cggttttacg aggtagagtg    420
atatatgata acattacacc cccagattta caccaaaccc cattttctttt tggacggagc    480 tcgccgcagc acgtgaccgc ccacatgacc gcctccgcca atctcagcag tcctcacagg    540
tggtctcgct ccgcagggcc cgcagccgcc tagaatggaa gggcaagagg ctcaaatat    599
```

<210> SEQ ID NO 184
<211> LENGTH: 584
<212> TYPE: DNA
<213> ORGANISM: Homo sapiens
<220> FEATURE:
<223> OTHER INFORMATION: OGHAv1.0 microarray feature identifier
      ha1p_36172 amplicon

<400> SEQUENCE: 184

```
cctagacagc aacacaccca ctggaaacgc acgtgaacaa agctctcgcc cccgggagcc     60
gctgcctgcg gtttcctagt cgatcccagc ttctctaggg agtgtcaggc gcacacaggg    120
ttaagttagt tccctcccctg gtaggaggga gaggaggagg aggggaaaag cagcatactg    180
tctcaggctg ggtaccttgt agttagttgt acgttcgaaa cctgtcgccg tcacttgcgc    240
gtttggcatt atccattgtc accgcggagg aacgagcgct cgagatatca tcagtgcccg    300
caaatctccg cgccaaggcg ctgagctact ccttttccgag gtgcgcctct ggtcctccgt    360
ccctggtgcc cagcagcggc gaggcggcat ctccgctccc gccgccgtgt ccaccgagcc    420
ctgggatcag ggtggcagtt ctcaacgatg ggcaggaggg acctcggcgg cgaccccctaa   480 aacaatacca tgccccggga tccccgctgc tgccgcgcca gcgtcttccc tttccaccctc    540 cctgaccctg tcggattcgg atgagcccat tgcaaggaga agac                     584
```

<210> SEQ ID NO 185
<211> LENGTH: 400
<212> TYPE: DNA
<213> ORGANISM: Homo sapiens
<220> FEATURE:
<223> OTHER INFORMATION: OGHAv1.0 microarray feature identifier
      ha1p_70459 amplicon

<400> SEQUENCE: 185

```
ttcaccgtct ctactttctt ccttctaaga gatcctgaaa cctctgtcat ggaaaagtac      60
cacgtgttgg agatgattgg agaaggctct tttgggaggg tgtacaaggg tcgaagaaaa     120
tacagtgctc aggtgttgca caaagaggga tacccttttgg gtgggatttg tacccccaa     180 ctccagtgga aaatggatct agaaggaatg tatttatacc agtttgtatt cctaaggtac     240
tgactccctc atacttctta tggagtataa gctttgaagt tggattattt gggtgcaaat     300
tccatctcca ccgctttcta gccctagaat tatggacaaa ttacttaact tccctatgtc     360
tcaatttcct tatctctaga atggggataa gaacagcaac                           400
```

<210> SEQ ID NO 186
<211> LENGTH: 408
<212> TYPE: DNA
<213> ORGANISM: Homo sapiens
<220> FEATURE:
<223> OTHER INFORMATION: OGHAv1.0 microarrayfeature identifier
ha1p_105937 amplicon

<400> SEQUENCE: 186

```
ctctaaacac tcgcctctac ccgccgcccc gcgaacccca cacactgcag acgcgacact      60
cgcaagtttc ggggatggcg gccggcgagg gccatactgc gtctttccgg agacacggaa     120
tacggcacca gccgtccctt tatgatgcaa tatgtctgcg cccaggggac gcttgctggg     180
agcagccatt ttcaacccta ctgccgtaga gcaggcggag tccctctttt cgcgccttaa     240
gacaggtagg ttctgacgat gaaaagcaat tgaaaacgac ccatttcacc ctttttccag     300
tccacgtgaa ctgctagatc ttggctttgc aacattagcc aggggcgcta cataaactgc     360
ttagtttctc aaaggctcaa gcctgccctg atctgtctac aggatggg                 408
```

<210> SEQ ID NO 187
<211> LENGTH: 591
<212> TYPE: DNA
<213> ORGANISM: Homo sapiens
<220> FEATURE:
<223> OTHER INFORMATION: OGHAv1.0 microarray feature identifier
ha1p_89099 amplicon

<400> SEQUENCE: 187

```
tagcccttga cagcagttgt gacggggagg attggaccgc ccggattagg gctaattaag      60
ggtggatggg tggcgggcgg ggaagtgcgg gtggctaaat aggtgcctga taactcagtt     120
aacttccctc ttggcttttc cctttgacct taacactttt ggggttatct ctgaggcgaa     180
tgctaaagga gacgctccag gactcgacct ctgaaggtcc ttggagccaa ttccgtaata     240
tgatcatgga aactgatcat tgcctgatcc ttctaccgcc ttggcgcgct tcttgaggga     300
atgtctttgg ttaatggctt cacggccatg gaggtgacat catgtggaca acaggctagg     360
atgccagagt tagctgctcg gtggagatca tttgaggtca gcagaggcca cgatattata     420
gatactaaca gaccccgata tggggagaaa agcaaaagca ggagcctgaa tatccagtgc     480
tttgtgagct gtcagttctg tgtgtaatgg caggaaatcc aagtcttaac tgcgcccta     540 ctatgaaggc tttccgagcc agccacagct tctgggtcat gggcattagt c             591
```

<210> SEQ ID NO 188
<211> LENGTH: 470
<212> TYPE: DNA
<213> ORGANISM: Homo sapiens
<220> FEATURE:
<223> OTHER INFORMATION: OGHAv1.0 microarray feature identifier
ha1g_03099 amplicon

<400> SEQUENCE: 188

```
agagccacgt gagctgcatt aacccccgtga actggccggc gcgcagctcc gagaggctgt     60
tgtagcgcag ggacaagccc agcaggccgg acaggttgtg gggcgcctcg gtgaggttga    120
gcgcctcgca gtacagcagc cgcccctcgc accggcacag ctgcgggcac ccgctgggg     180
cggcgggcag catctgaaag caggccccca gcagacacaa gaccaccccc gagggcctcc    240
tcagcagcca gtatagacag agaccgagca gcaggaaatc cattagcgag aatctttcca    300
gagagactgg agaatgtcca ttggaagcgc tcggtcagaa atctacatca tattttattc    360
cgagggaggg gaagcggggg aggggagaa aagggcaaaa aatcaaataa atacatagaa     420
ataaagaagg accccctcc ccaaaaacca cacgttcacc tctaagcatg              470
```

<210> SEQ ID NO 189
<211> LENGTH: 426
<212> TYPE: DNA
<213> ORGANISM: Homo sapiens
<220> FEATURE:
<223> OTHER INFORMATION: OGHAv1.0 microarray feature identifier
       ha1p_67625 amplicon

<400> SEQUENCE: 189

```
cctggagtcc tagagagcct cgccgcaccc cctcccctt tccgtcccct cctctcctca     60
gagccggctg agcctcccct cctgccctgc gcttcccacg gggagagaag gaaaaacagg   120
agggggagg aaggaccagg aaggggagag aggagtggag gggtactgtt tggagcggtc    180
cgcgcgcccc cgcccctcgc gctctcgcga cgaaggctcc tcgagcccag ccgggtacaa   240
caagtctgtc ctccgacgtc aggggtcat taataaccaa ttaggagggt cactgcggct    300
cctataaagg cgctgagatt ttgccaaggg gaagacggcc ccggccgagt gtgcgagagg   360
ctagcgcgcg cctgagcccc ttgctgccgc ttccctgcaa ccacccgcct ctcacccacc   420
ctgcac                                                              426
```

<210> SEQ ID NO 190
<211> LENGTH: 407
<212> TYPE: DNA
<213> ORGANISM: Homo sapiens
<220> FEATURE:
<223> OTHER INFORMATION: OGHAv1.0 microarray feature identifier
       ha1g_00218 amplicon

<400> SEQUENCE: 190

```
gccgcgccac cccacctgag tccgccggcc agcgcgggga cgcaccgggc agcgtgtgtt     60
tggcgaccct cccgcacctc tggtctcagt tgcgtgtgtg cacgagggggt tccatagggc   120
ccagggatgc ttggtaccca cggggagaa tccctcgccg aaccctgcgg gtctgcgggg    180
cgggccgcga gactggcgcg caaaagcggc tccaaggcgg ggctcccgcg ctccccgggg   240
ccggcttgcc gagtccaagt tgagcaaccg gcgtcgagag agacaccgcc cctgctgcgg   300
gcgggggcct ctcctcgctt ccgattggct gacgggggga acctatcgcc gtcggccgcc   360
tccgccagag cggtttgctg gttttcattc attggccccg gagccgc                 407
```

<210> SEQ ID NO 191
<211> LENGTH: 497
<212> TYPE: DNA
<213> ORGANISM: Homo sapiens
<220> FEATURE:
<223> OTHER INFORMATION: OGHAv1.0 microarray feature identifier
       ha1p_12535 amplicon

<400> SEQUENCE: 191

```
agtgttgggt gctgggagga ggggccatag gaccctgggc gggagcagag gtacccaggg    60
ctgcggggcg ctcaggtgag gccgggagat cttcctacgg gaggctgaga cgggagctgg   120 cttttgccctc tctgactgca cgcggggagc ctgattaaaa gcctggcctg aggagaagga   180
ggagttggtg atgggaggag aaagggagcc tccctccact ccgcacgcaa cactcctcgt   240
ttatctcctt tcctctccgt ttgctccagg tgatcacagg ttggaaagct tattatcttt   300
tgcaactaca ggctactgga aaagttttc ctcttcctat gatccccgtc atggtgaatt    360
cagcgacata agcagctcct gagctactgg aaaaagtttt cctcttcctg tgatccccac   420
gatggtgaat tcagcaacat aaatagctcc tgcgcacacg ccaggcaggg atggcgaaga   480
acacacaaga accctca                                                  497

<210> SEQ ID NO 192
<211> LENGTH: 590
<212> TYPE: DNA
<213> ORGANISM: Homo sapiens
<220> FEATURE:
<223> OTHER INFORMATION: OGHAv1.0 microarray feature identifier
      ha1p_105474 amplicon

<400> SEQUENCE: 192
ctctgggctt tctctagctt ccccagggaa gggaggctcg gggtgaggtg ggcacggggc    60
atctttcctg cccaactgtg aagtcctaaa aagcttcaca aagtttctat tgaatgacag   120 cttttcttctt ctctttctcc agggttgagt tccagaataa attctacagc gggaccggtt   180
tcaagttctt acccttctcc ttcgagcata ttcgggaagg gaagtttgaa gagtgagtcc   240
ctgtgagggc cgtgtgcccc atgctaccct ccccgcctcc ctccacagtg atcagctgtg   300
cctctctgcc tgttggttgt gatctgtggg caccagctca ttcgtgtcac cctgtctgtg   360
agtcatttag atagaatagt cctccttggg tctcccacca cccctagctt tgtgtgtagt   420
gtagtgattt tctggctgtc actcatactc actgggcacc agccttgccc tcttagcctc   480
catccatcca gacagccctt cccacctcct ggtggtgagc cagtctgcat tcccacgcca   540
tcccaaagcc ctttcatctt ccccgtgcat tgtagatgga aggagcaccc               590

<210> SEQ ID NO 193
<211> LENGTH: 489
<212> TYPE: DNA
<213> ORGANISM: Homo sapiens
<220> FEATURE:
<223> OTHER INFORMATION: OGHAv1.0 microarray feature identifier
      ha1p_74707 amplicon

<400> SEQUENCE: 193
agtttgtgag ctcaggagaa gcgctccgag ctcggcatct ggagcagttc aaggcagcag    60
cgagcaagtc caaagacgca ggagggaggg tggggtggag gagtagagag aaaacagaag   120
ccgtctacag acccttttc cctctggggc aactaaacct caagtgcagg aagcgcttgg    180
ggactgccca gccctcagct gtgttattat tcggtgatag gtatttgcta attacttcca   240
aaagcctccc atctgtcatc ccacccagac tgcgcgcttc taattcctcc taccccacat   300
gctgtgccca atgaaaagta tggtcagcga gcgaaggttt gcaaggagac agacgagggc   360
gaaattaagc caggcggctt ccctttaaat cctcgcaaag cagaagggcc ctcactctg    420 gcagcaggcc ttggccaagg ggcctttagc cctgacgacc cggggaagag tctcccaaag   480
cagaacgcc                                                           489
```

```
<210> SEQ ID NO 194
<211> LENGTH: 567
<212> TYPE: DNA
<213> ORGANISM: Homo sapiens
<220> FEATURE:
<223> OTHER INFORMATION: OGHAv1.0 microarray feature identifier
      ha1p_93325 amplicon

<400> SEQUENCE: 194
ccagtcccat agtggaaatg ctctcgtatc cagacgtgca ccgtctccag tcagcagctg      60
aaaataactc gttcttgaaa ggagaaagcc aaccgccccc tttctcctgc acaactgact     120
gagggcttga aggaggcttg tataaggctg agggattttt ccaagaagga agaatggcgt     180
aatgctgcct gtgtgctcca gtttttttt ccccctagtt ttgaatcctt tccagtgaaa     240
atacttcaca cacacacaca cacacacaca cacacacaca cacacacaca ctcacaggcc     300
tgcaggtgct cagaaaaatc ttttacaaac ctgaactcag gaattggaaa cggaattcca     360
acccaaacca atttaattac tctctgatgt catgctgtct aaactcattt aagtgcgata     420
tatttatgtg aaaaaaatca ccgctgccct ttcgaggcca tggctcacgg gggctcctgg     480
cacagagccc tgcagcggga ctctaggctt aggggggcctc cccctccacg gggcagactc     540
aggggtcttc acctccacct catggag                                         567

<210> SEQ ID NO 195
<211> LENGTH: 460
<212> TYPE: DNA
<213> ORGANISM: Homo sapiens
<220> FEATURE:
<223> OTHER INFORMATION: OGHAv1.0 microarray feature identifier
      ha1p_101161 amplicon

<400> SEQUENCE: 195
actaccttgg gtgtcagtcc tgcttcaaga ctccagagag ataagagag atgacctcag      60 agacaaagag actcagaccc agccagaggc ccaatggaca gtgggagggg tgggtggaag    120
aaggctggtc tctgtctgac caagcccccc cagaataacg caggctgccc ccctaggtgg    180
aaacaatgac acaatcagct cccaatacca agggcctgac atcacaaggg aggggaagg    240 cagctgaggt tgtgggggga ggtgccccgc cccttggcag gccccctacag ccaatggaac   300 ggccctggaa gagacccggg tcgcctccgg agcttcaaaa acatgtgagg agggaagagt    360
gtgcagacgg aacttcagcc gctgcctctg ttctcagcgt cagtgccgcc actgccccg    420 ccagagccca ccggccagca tgtcctctgc tcacttcaac                          460

<210> SEQ ID NO 196
<211> LENGTH: 400
<212> TYPE: DNA
<213> ORGANISM: Homo sapiens
<220> FEATURE:
<223> OTHER INFORMATION: OGHAv1.0 microarray feature identifier
      ha1p_101251 amplicon

<400> SEQUENCE: 196
tggacacatg tgctacacgc taagatgcag atgtcaggca cgcgcagccc acacacagct      60
gacacacgtc gcagggaccc tcatagacaa gcgcatcaca tacaaaggtg gacagccatc    120
agcagacggg gacacgtaca cgtcacacac aaagacgcag gaccgcacct ggaaacgcac    180
aggcaggcca gcttccagca cagatgcacc cggccacgca ggaacgtcaa agcatcacaa    240
agacccacac atgccccgga caaagtaaag ccccagatcc acagacgcac acgccacaga    300
caaagatccc cacggacacc actgtgacat gctgacactc atagtcacag ccacgcagac    360
```

| agtccctaga caaatgggca acaaagaata cccacagaca | 400 |

```
<210> SEQ ID NO 197
<211> LENGTH: 597
<212> TYPE: DNA
<213> ORGANISM: Homo sapiens
<220> FEATURE:
<223> OTHER INFORMATION: OGHAv1.0 microarray feature identifier
      ha1p_69214 amplicon
```

<400> SEQUENCE: 197

| aggtcactgc agaaggatgg aactgacctt tattccccag tgggcagtta ctgagctttc | 60 |
| ctcctcagag ccatgctggc agccctggga cagagaacgg tgtggctttg gctgcctctg | 120 |
| catggaatct tgccccggac tcctgaagac tgcacaagga atgaggaaga tcagggacaa | 180 |
| cctgggaact gaataacttt caaagccagt gctcagcttc tctgctccgt actagcgttt | 240 |
| acaggtctta attcaaacca gatgcctgta ctagttttta daccccaagt caacctttct | 300 |
| gagccacagc ttcccgctgg gaataatgat gcctgcccta tctacctcac agacttgtta | 360 |
| tgaggataaa gtgagattaa actgcctcaa agtgctttgt aaacctcagg tgaataggaa | 420 |
| aggggaaagt aaggctggag tgatgatggg gaggtcggag gataagggg ggctgggatt | 480 |
| gctaatgggg actaaaatgg ccagtctcct ggcaagattt tgagcaggtc atttcattga | 540 |
| ggcctcttag atttcatatt tgagaattag ggcactgatt cctgactggc taggcat | 597 |

```
<210> SEQ ID NO 198
<211> LENGTH: 527
<212> TYPE: DNA
<213> ORGANISM: Homo sapiens
<220> FEATURE:
<223> OTHER INFORMATION: OGHAv1.0 microarray feature identifier
      ha1p_88517 amplicon
```

<400> SEQUENCE: 198

| gggactcatt caatgtcaag tgcttacaac gggggctggc gcagaggaag cccacaggtc | 60 |
| cgtgcggccg aatcccaggc atcccgacgc ccgccctctc tggcactaag cgcagcccctt | 120 |
| tcccctcccc tccgtgactc tggccctccc ttcaacccgt tctccacaca gcagccgggg | 180 |
| ggagcttta agatgcgaaa gaggaggtgt cacttcggtc tccagtgact ccttggcccc | 240 |
| tgaataaagc ttaagactga acgccccact ccaggagcac cactctgacc ctcacctcag | 300 |
| gaccgcagcc acactgcttt ctctccggtc ctctatcccg ctccctcctg cccaaggcct | 360 |
| ttgcccatcg tgtcctctgc ttggtgtttt cttcctctgg ttaactccta cttattttac | 420 |
| agcgctcagc ttaagcacca cccattccag aacgcctttc ccgatttct catttatgca | 480 |
| gatctcctct ttcagaccct gagagcacca tgaaaggagg taacacc | 527 |

```
<210> SEQ ID NO 199
<211> LENGTH: 591
<212> TYPE: DNA
<213> ORGANISM: Homo sapiens
<220> FEATURE:
<223> OTHER INFORMATION: OGHAv1.0 microarray feature identifier
      ha1p_103824 amplicon
```

<400> SEQUENCE: 199

| tctttagacg ctgcgctctt agcctgtctc tcttccccac ccctcccct agctcattaa | 60 |
| gatgctcaac actcaaatcg gggtattgat ctccacggaa gccccaaacc ctcgccatcg | 120 |
| agagaccccc atggcccggg gtgatggctg tggggcttgg tgctcccaga gagctcagtg | 180 |
| gctacagaat gggtggggat tctgcgtgtc tcccggagcc tgaacccctt tcctggttat | 240 |

| | |
|---|---|
| ggccggtagc tgtctccagg gctaacgtgg gcagcgcagg ggggcggaaa ccgggtttta | 300 |
| gccaaatgcc tcgacatcgc cgcgcctccg cctcctcgtc gctgaaagaa atgtcggggt | 360 |
| ttcatcagag ctagggagcg acagtcggga acagcgagtc tgccgaagcc ggctgttgtg | 420 |
| tgagggtgtg agacggcggg gcggtgaggg gccaccgcgg cttggggat agtgcgtgtg | 480 |
| gggttgaccg tgtgtctgct tgagaggctg tgaagatatg gggggcagat atgggagaaa | 540 |
| tgctcgggcc tgaagtcccc agcccaccgt gctcaagagt agcggacgtt t | 591 |

<210> SEQ ID NO 200
<211> LENGTH: 405
<212> TYPE: DNA
<213> ORGANISM: Homo sapiens
<220> FEATURE:
<223> OTHER INFORMATION: OGHAv1.0 microarray feature identifier
 ha1p_108445 amplicon

<400> SEQUENCE: 200

| | |
|---|---|
| catctgtctt tgttgggcag ttgcatcaga agggttaagg acagctggga acacatcctg | 60 |
| cctctagtga acctcgtggt tctgtcatct gcctgcccct cacccagcct aaccctctg | 120 |
| aaccaggagc ctgagctgca cttactgctc cccctgccc ccggacggc ctggaccaag | 180 |
| cagcagctcc cagagcggtg gcccagcaaa cacgacttga ctcgaggcca aggtcttga | 240 |
| gggctgagca gtgtccccat gcacactcct gaaacacttt gtccttcgc cattcagaag | 300 |
| gcatcatttt ggggaaggca gcagccggtt tttcagagcc agcgagtggc cctgccagct | 360 |
| gctgagcagg gcaagctgag aagggtggtg gtgtgcaagt gttat | 405 |

<210> SEQ ID NO 201
<211> LENGTH: 494
<212> TYPE: DNA
<213> ORGANISM: Homo sapiens
<220> FEATURE:
<223> OTHER INFORMATION: OGHAv1.0 microarray feature identifier
 ha1g_02210 amplicon

<400> SEQUENCE: 201

| | |
|---|---|
| cccaagtact cggcactgca cagcacctcg ccgggctcct cggctcccat cgcgccctcg | 60 |
| gccagctccc ccagcagctc gagcaacgct ggtggtggcg gcggcggcgg cggcggcggc | 120 |
| ggcggcggcg gaggccgaag cagcagctcc agcagcagtg gcagcagcgg cggcgggggc | 180 |
| tcggaggcta tgcggagagc ctgtcttcca accccaccgg tgcgtatttc tgcataatca | 240 |
| ccgcttaaag gcacattttg acagccccct ttatctgctt gatgtttttt tcatgtctgc | 300 |
| acagcaaatc accccacacc tccaaccaat tttcccctct ctctctctta agtattcagc | 360 |
| aggtcttgcc tttcatatta atttttatga cctgggatgt tgcctgtgcg cgtgttgtgt | 420 |
| tgtgtttcgt tgtgtctaca ggctcactt cctcctcctc ctgcactctc ggcttctttc | 480 |
| tgtggcttcc ctct | 494 |

<210> SEQ ID NO 202
<211> LENGTH: 578
<212> TYPE: DNA
<213> ORGANISM: Homo sapiens
<220> FEATURE:
<223> OTHER INFORMATION: OGHAv1.0 microarray feature identifier
 ha1p_103872 amplicon

<400> SEQUENCE: 202

| | |
|---|---|
| tgagattcaa tttctcgccc ttcccccgct aaaatcctcc tggccccatc atttcttggg | 60 |

```
tcctttccag acagtgctgt gtctttaagg aagttgaagc tgctaaaagt gagtgagaga      120
gagagaaaaa acacaaccca aaaaaatttg gcatctcttc cccctcaag tttctggtgt       180 cacttatgaa acacaggtcc ttgttgctgc agagaagcag ttgttttgct ggaaggaggg      240
agtgcgcggg ctgccccggg ctcctccctg ccgcctcctc tcagtggatg gttccaggca     300
ccctgtctgg ggcagggagg gcacaggcct gcacatcgaa ggtggggtgg gaccaggctg    360
cccctcgccc cagcatccaa gtcctccctt gggcgcccgt ggccctgcag actctcaggg    420
ctaaggtcct ctgttgcttt ttggttccac cttagaagag gctccgcttg actaagagta    480
gcttgaaggt aagccagtgg ggaggagggc tccaggccca gcggcgggag cgggaggcct    540
gttggacata ggggctggtt ccctcttggt ccatccct                             578

<210> SEQ ID NO 203
<211> LENGTH: 495
<212> TYPE: DNA
<213> ORGANISM: Homo sapiens
<220> FEATURE:
<223> OTHER INFORMATION: OGHAv1.0 microarray feature identifier
      ha1p_56412 amplicon

<400> SEQUENCE: 203
tgccggtctg ctctgctcgg cgctgtgcca gcaggcggag agctcgcgcc ttccgcgctg    60
acgtcagcgc atcccgggcc gtatcccggg agaccctgtt gcgtggtgat gggttgccag   120
ggagacatac accttttctc tgggcctggg ccgcagctgc gcggagcgcc gggcacggat    180
ggcggcggct gaggggagcg aagcgaggga gggagagcaa gctaagaaac acccagcagg    240
tgctcccccg cctaggcctg gctggaggct actggcgcca cctgggggc cctgtcagcc     300 aggtacccaa ggggagggat cgaggtgggg cctcaggtca aggggcagtg ttggctgccc    360
ttgtgaggga cgggaacgtg atagaagaga gctgggcaat gccggggagg gatgtgtgcc    420
tccaacttca ttaagtgagg gaaacatttg ctggggcttg tcagggagcc ctgagccagg    480
tacagggtgg agtta                                                     495

<210> SEQ ID NO 204
<211> LENGTH: 545
<212> TYPE: DNA
<213> ORGANISM: Homo sapiens
<220> FEATURE:
<223> OTHER INFORMATION: OGHAv1.0 microarray feature identifier
      ha1p_18292 amplicon

<400> SEQUENCE: 204
ttctcctggg tctttccaaa cagccccatg acgaactgaa cccgtcttgc cccttccggc    60
tttcagttcc ccgcgcccag gcaggtcacg ggcagccgcc tgggcggggc ccgcggaaaa   120
ggaggtagtc ccaaccccca gagtagggag cggcggcact aggggatgtt gcgcatgcgc    180
catacgcctg cgcagaatcg agtgagtggg agactagtca aaaaggctga cgtcatcgca    240
catgttctgg tcatgtctgt gtggggagaa ccacggattc ggtgcttttc gtaaggtgta    300
gaaatgattg ctctgaaaga tacgaatttg ttggctacaa ctgcttctaa tacttcacct    360
aaacctagat gttgcaccag aagtctggat ctccacgcag acgtgtacac ttagcatcac    420
tttcccgaca gcttcatctt tgtgtccagt aggcaactca caggtgacaa accaaaaata    480
acctcttttt cctcccgcca acccactcct ccctctgct tgcaccacca tcacctggtc    540
actaa                                                                545

<210> SEQ ID NO 205
```

```
<211> LENGTH: 597
<212> TYPE: DNA
<213> ORGANISM: Homo sapiens
<220> FEATURE:
<223> OTHER INFORMATION: OGHAv1.0 microarray feature identifier
      ha1p_12075 amplicon

<400> SEQUENCE: 205
gtttgccaaa tgacagctgt ttgcctccca ggcaggcttt gctgtcatca gagacaggga      60
tggagggaaa ataatgccat catctagggg aagggtcttg tgttgatctt caacatggct     120
aaccaaatgg acgatcagca ggcagacacg aggtattttc attttcactc ttatttcaag     180
agatttgtga tggtgtttca tagtctaaaa ataaaggatc cgcccgcaga catttctccc     240
tccactaccc tcatcatatt agctgctgcg ttttcctctc cagattttga ttctattatt     300
ttttattata aatgaaaggt caaggaatac ttttcgtatt ccataatagg attggttctg     360
gaagaatctt tgaaaaaaaa aatacgttca agacattggg gctgggaata aacggaagc     420
atctcaaaag catgttttc tggttaagga aagcacacga gaacgtttca cagcggtgct     480
ctgctatctt ctctgtaccc ctccgcccta cgctcatggg agagctcatt tctctcccca     540
tcagacactg ggaaatactc ccaaggctct ggcagtctca aggctgcaat tcctgag       597

<210> SEQ ID NO 206
<211> LENGTH: 477
<212> TYPE: DNA
<213> ORGANISM: Homo sapiens
<220> FEATURE:
<223> OTHER INFORMATION: OGHAv1.0 microarray feature identifier
      ha1p_22519 amplicon

<400> SEQUENCE: 206
ctcacgttaa tcaacccgag tccatcttgg tgggattgtc ttgctccgag gccctcccac      60
tgagctttat tttcctgcct gatttcgggg tccgctaaca ggatgaacag cggaccatac     120
aggcacggtg aaaatgacac ttggtgacgt ggaagaccca gcttgccaca gttgaggcag     180
agctcctcag ggtcttttgt cttagttatc cccgagctat ttttcaggaa ccgacaggct     240
cccccacccc aacaccggat gaaggccagc aactggaggc caggaataat caagcacgct     300
ctcatttcaa agaggtgacg attgtgcccg tgtttaaaag ggatgcctga gaccatgagg     360
atttggagtt ttggaggcgg atctgccttt ggggagtgag cgtagggccc taagatgtgg     420
ttgtgctttg agacagttcc cagggtgatg tgtcccatca tccaaacatt gcaggat       477

<210> SEQ ID NO 207
<211> LENGTH: 525
<212> TYPE: DNA
<213> ORGANISM: Homo sapiens
<220> FEATURE:
<223> OTHER INFORMATION: OGHAv1.0 microarray feature identifier
      ha1p_29531 amplicon

<400> SEQUENCE: 207
ctccagcact ttgggaatga aaggaattgc aggagagccc cggagcacac ggagttttca      60
aggagcttct gtattcaata aaaacagcta cttgtctact tgcacccgtc tgttagcctc     120
tcgctggtcg gcgggagagg ggaggaggcc agcgcctgat cggccacacc gctggagtcc     180
tgggctggca gcggtaacct tatccttgtg caaaaatctg cttcgtatgg cagacgtgga     240
accagtggac tcattgcgct gcctactctg aaaagtgttt ttatttttat ttttttaacc     300
caataattag aagaaaggaa tgaagataga atggagggac cctagaagtc aaaacctaga     360
gcatgtaggg aagtcctctt tggagatctg aaactgacag gtttatctct taaacgttta     420
```

```
aattcagcac taggttcatt cagtggcttt cctcttaaaa gagttgaact gtactctgag    480
ggagaaggag gaaaaaattt atgggagctg acattaagag ggtga                    525

<210> SEQ ID NO 208
<211> LENGTH: 507
<212> TYPE: DNA
<213> ORGANISM: Homo sapiens
<220> FEATURE:
<223> OTHER INFORMATION: OGHAv1.0 microarray feature identifier
      ha1p_58853 amplicon

<400> SEQUENCE: 208
atgtcaggaa aggtgcagag accctccccc acacaccaca ttgttgttcc atccttctct     60
gtgcctttgg gcaaggactc tccgttctgt agggaccacc aggtggaatt aaagtctaca    120
ctcctccaag agctgatctt ggggcggccc cacctccatg cccctctaca gcgtgccatt    180
ctcatagaac acactaggac ctttgtcctc tggagctgtt cagtgcagca gctctgacct    240
catccttctc cagaagcctc caccttctct cccctctctc ctcctgcgct tgtgtgtcc     300 tgttcttcca cttcggtgac ctgtctcctc ccctaatctg gctcagagag gggtaccagc    360
tgctgctgct gctattgctt cttcttctgt taaaggtttt ttatttttt ccaatgacaa     420 agctatgctc attctgaaaa catgaaaaat aaaaatgctc aaaaaataaa actcactcta    480
cattcattgc taggagagaa cagcctg                                        507

<210> SEQ ID NO 209
<211> LENGTH: 526
<212> TYPE: DNA
<213> ORGANISM: Homo sapiens
<220> FEATURE:
<223> OTHER INFORMATION: OGHAv1.0 microarray feature identifier
      ha1p_35052 amplicon

<400> SEQUENCE: 209
atcttcccag tagggctgaa tcctagacca atctatcaat cccagactaa tcaggcattt     60
gcctggggat atgcatcttt ggcattttc caagggttca tcaggatgga gatatccggt     120
gcaccatgag ttctgtttcc ttaatcaaca ccgttgtaac ttgcccatcc agttttgtga    180
cattaattca aacctgtgcc ctagtcctct tttaggcagc gtatcagtgc tggaaagtgc    240
agcaaggata agagggtact gttctctcat ttctgagggc gttgtctcga taattaacta    300
acttgataga cttttagtg agtggcaggt gagatgcaag gtactgtgct aggtgctgtg    360
ggggatgtac agacaaacaa cacacctccc taaggaggta agtaatagct acttactatt    420
cactttgctc tttcactgta atgtatcctc aagcacaggt tttcactaca ccatcaggcc    480
cagaagtact agcttatttt ccacaggagg atttcagttt gatgcc                   526

<210> SEQ ID NO 210
<211> LENGTH: 451
<212> TYPE: DNA
<213> ORGANISM: Homo sapiens
<220> FEATURE:
<223> OTHER INFORMATION: OGHAv1.0 microarray feature identifier
      ha1p_67002 amplicon

<400> SEQUENCE: 210
cagtgctccg tgtccccaag tagttatccc tcccccggaa gactgaagtc cctggggcgg     60
gtaggagcgc acgctaggag tagtatgaat aaagtgtttt cttggaggtc atgggcaagt    120
ctctggacag ggttgatagt gctgattat agagggcagt ctgggcacaa agagcattta    180
```

-continued

| | |
|---|---|
| tacgatcgaa aagctgcttt ccctgccaac agccccatac cctccccagg agcgcgctta | 240 |
| cgccttaaaa gactcttttg ttatgtaaac tgacagttaa attaaacgaa ggtaatggat | 300 |
| actaaaggcg taacaggtat tgtaactatt ttactgttat cgatgctttt gaggttactt | 360 |
| acctcgcttg tattcgtatg gtgggaatac taggcgcata ccttctgagc ttcgaattca | 420 |
| gtaacctcac tgggaccttg aaatcggact g | 451 |

<210> SEQ ID NO 211
<211> LENGTH: 571
<212> TYPE: DNA
<213> ORGANISM: Homo sapiens
<220> FEATURE:
<223> OTHER INFORMATION: OGHAv1.0 microarray feature identifier
    ha1p_45580 amplicon

<400> SEQUENCE: 211

| | |
|---|---|
| gggtgcagga tgaagactag ctggctgtcc atagcaattc agtatgggag ggggacccag | 60 |
| gcacgaataa tcctaaacct gagcatgatt gcttacgttt gaaaaaggac atctaggccg | 120 |
| ggtgcagtga ctcacacctg tggtcccagc actttgggag gctgaggtgg gaggattgct | 180 |
| tgagcccacc cacaagttca agaccagcct gggcaacata gtgagacccc atctctaaaa | 240 |
| aaaaaaaaaa tctctttaaa ggcaatctaa ccatatgtga agggagctgc taaattcaga | 300 |
| ttgaggtggt agtatcaggg gcatcagaga aatcaccata attgtccaag ccagggtggc | 360 |
| agagttaggc tatgcagatg gcttccagag gacagcaccc agaggtaaca ttcatgaatg | 420 |
| cattcctgtt tgttggtgaa aagttcagcc tcaagactcc agggtcaggc ttcgtacatg | 480 |
| aaaagtgttt gccaagactc agctgtgtca ctgcagctgc ccgcccacag ctgagtcaga | 540 |
| aacgccgtcc tcattctcag tgactgccct g | 571 |

<210> SEQ ID NO 212
<211> LENGTH: 550
<212> TYPE: DNA
<213> ORGANISM: Homo sapiens
<220> FEATURE:
<223> OTHER INFORMATION: OGHAv1.0 microarray feature identifier
    ha1p_12646 amplicon

<400> SEQUENCE: 212

| | |
|---|---|
| gccttaggaa tttccatccc aacacgtctg tcctgtctgt cctctcggct aagcctctct | 60 |
| taattcttcc tgctctaaag accccgcaac ttgctatgcc ttcactgaga cttagctgct | 120 |
| ggcacttgct agcagaggac tagttagctc atgtgtgttg gctgttcctg gcccacccac | 180 |
| gcttttttgag cttttaattc caaatcatcc aggagtatct ttgcgccgtg gattattttg | 240 |
| tcagtttatg ctactcgcgc catctttcgc cttttaagaa tcaggcaaac tgtgtgcttt | 300 |
| ctatcctaat agatggcaaa actcaaacta gaggccctat ttcacatcca ggttataact | 360 |
| gtggcaagag ggtggggtgg cttggctaaa aactagtcta cttttcttag ctcttgtctt | 420 |
| aatgaaaatc tggaagtctt actggtgatg gaggtagggg agggctgcct tcaagatcca | 480 |
| atctctaact tggaacagct gtggagagga gagaatacct gcttgtaggt gaggcatgaa | 540 |
| agaggagaaa | 550 |

<210> SEQ ID NO 213
<211> LENGTH: 2400
<212> TYPE: DNA
<213> ORGANISM: Homo sapiens
<220> FEATURE:
<223> OTHER INFORMATION: OGHAv1.0 microarray feature identifier
    ha1g_00681 genomic DNA region

<400> SEQUENCE: 213

```
ggagctcagg ttgtttctgc acagaggtcc taactccaag agtggagcaa gaagagattc      60
caactgcact agaccctact tgcccttgga gaagtccaga gggactccca gcaggtctct     120
ggtgttttcc agcctacaga ggcctatcac ctccctaagt tgcaaagact atgaaaacct     180
ttttggtggg cagtggtgtg ggagcagtga attccagaca tgctccatcg ctcctaggct     240
gtgctggatg tcgtgggcag tagcttgggg accaggagcc aggccagagg accctcttcc     300
agaaggcact cctttacctg agctggagct gctggttttc tgctttgtgt tttgtcgaga     360
ctctttcatc caggggaaga tttgtttggc cactgtgggt gagttgagca gggggctctt     420
ggccgcgttg gcaggggtag ggttgttgct ggcattctga ggaggggagg cagaagaggg     480
aggcgggggc gcggcagggg taggtgcagg gggctgaggt gcgggctgag gcggctgtgg     540
ggcagggggc gcggcctggg gcggcggcgg gtgcaggggc ggctctccca ggcttggagg     600
ctggctaggt ggggcgctca gggtgcgcag gcacgcctca ctcagttcgt gtgccttggg     660
gtggcccccg gcgctggagg gagactggag ggagcaggcg ggtcggtggt actcgccgtc     720
ggcgcccaaa gcggcggacg ccgggtacgg ctgctgattg gcattataag cgaacccgtt     780
ggctgcctgg taggggtagc caccgtagat cgccgagctg tcgtagtagg tcgcttttg     840
catcgcgttg tttcacgatc ttgatcgcac actctgacag gggtttgaca cccgtgaggg     900
cgcacattgg cacgccccg cggtcacgtg acactccgcc gccaatggcc gccccgcgca     960
gacctggtgg ggcgagaagc gcagcgcggt gagggctccg cgcaaatcca tcttactctc    1020
aatagctaag tgacatgaaa gccataaaag aaaaagtggt cagcaatatt tagcagcacg    1080
acttggcccc gggcgcaggg agccgtgcta taaaaaaccg ctggaattta ctggcagcta    1140
caaatatttg cttaacttgc gtctggagtt gggggatttt ccggggagaa ggagaatgag    1200
tgagggctgc aagctgattc tcaggagccg ggatccaaaa ggagaaaggc ttgataggct    1260
agaaaggaaa aaggctggga tctttctttt ccagggaaga agaaacttgg ggtgtcgctt    1320
agtttctgct ccttggcctc ctccagaggg cccaagactc ctccactctg gaatgttgg    1380
gaagggaacg aggaggcaaa ggggagcttg ggtcgccaat gttttctccg ctttaggact    1440
gatgtttgcc aaaagagccc tgagatgggg taacttccca cccagctcct tcttggacct    1500
tcctgctccc aagagaggtt tgcacaaaaa atttcaggca atttgcccca tccaaccatg    1560
ctggatttca gaagctgagc ttgttaggaa gttaatccac cttgttgggg atatgactca    1620
cctcctccaa atgaacccct tgtggccaag ccaagggggg agggaaaact ttgtgtggaa    1680
cacattgcgt gtgtgtgtgt gtgtgtgtgt gtgtgtttag ggtgagggac caacagtaac    1740
accccaccca gcaagtcaca actaaaatcc tggagagttc tttactcctt tcctctccct    1800
gtttctcagg cacttcccag caagccaccc ccacttcttt acttctttcc cccagttaca    1860
gaaggttccc agaacctcct gtcttggact ttctaaggtg ctgttattcg gggcaactat    1920
caaattctac ctgttaaaac atgatggatt agagggggaa aaaaaacccc tccaggaacc    1980
tgaaaaacca gcgttcatct ccatgaccac agtttgaact ctccttccaa cttaacgata    2040
ataggttctg tcttagaaac tgctatgtaa tttgatgtat ggggtcatt tggctcccga    2100
cgagggatgg aagcacaagc cataaaatcc tgccagagtt cctgatcttt gtgtgctgt    2160
tgttgttgtt gatattttgt tacttggcct atttacctgc ttcagaaata ccaagtaaag    2220
gataaccctg aaaatctaaa aagcagttga aaacctcctc aaccctcttt catttagaaa    2280
gcagtttgca aaagttaaat ctgttttctt tttgtttca accactgcat ggtcaacctc    2340
```
tagttctcag cacagaaaag ttccatgtga gtttcaaata ttcacccaca cacacactca    2400

<210> SEQ ID NO 214
<211> LENGTH: 4100
<212> TYPE: DNA
<213> ORGANISM: Homo sapiens
<220> FEATURE:
<223> OTHER INFORMATION: OGHAv1.0 microarray feature identifier
      ha1p_39189 genomic DNA region

<400> SEQUENCE: 214
tacaaagctg tatgaacagc agcagggtaa acagaattga tgcaattatc tgaaaaaatg      60
cagggcagaa acaaatcac aatattgaaa gaaaaatgaa taatctctaa gaggattatc     120
caaattgatc atgtctttgg ttgaatttac cgctgaacgc tttctagatc caaaccctgc     180
ttttcttaat gtaacttaga tattcacaaa tcctacttga ggcaggaagt cagtcctcac     240
ttttaacgct taaagaccac aatggacttt tataagatat ctcgattttt aaagtggagt     300
ttctgggctg atataaaatt tattttaggg aaatacaaat atgggacatt tttgcatgaa     360
agagagaaag gagagacagg aagaaagaga cacaaagaga tagagacggt aagaaagaca     420
ctgacaaagt aaaggggggag gagagagaga gacagagaca gagagaaaga ttgagagatc    480
aaaaacatca ctcaagaaag caagaggaga gaataattga gagaaacgca gagagacaga    540
ggcccagaga aactgaagaa agaggtagcg actcagggggg aaatagagat ggagactcag    600
agagaaggga gaaggcacag ggagaggata ggacccgcga gagaaagcct gagcgcgcgc    660
tgagacccac ccagcatttt cacggtttgc ttgtggttct ggtccctgag cgaggcaccc    720
acgacagcat cgccgcgcct cctccgccac agcttcctgc cgatgagact gtagaggacc    780
gtgagacaga agacaggaag gaagaagaag atgctggaca cccacaccat gaccgtgagc    840
agtccagagc gcaccgcaaa ctcggtgggg cggcactcgt tggtgtccca agggtcggtg    900
ccgttctcgt gctccacccc gactagcacg aagatgggcc cggcgctgca gaaggccacg    960
gcccagatga cgaagatgac cagcttcacc cgccccttgg tgaccaccac cttggcccgg   1020
agtgggaagc agatggcgaa gtagcgctcg acgctcagcg ctgtgatggt gagcaccgtg   1080
gcgtaggtgc agctctcact gacgaattgg aagagtttgc agaggaggtc gccgaagttc   1140
cagggccggt actgccagag gcgaacgagg tccaggggca tgcagaggaa gatgagcaga   1200
tcggagaagg ccatgctgga caggtagagg ttggtggtgg tgcgcagctc gcggaagcgc   1260
gacaccacca gcatggtgag caggttgcca gcgatgccca ccacgaagag tgccacgcag   1320
gtggctgtga cgcccgccag cagcggcgcg gggaagagct gcagcagctc gtcgcccagc   1380
gagtcgttgc cgggggaagc atcccagtcc aggtcggcca gtgtgaggtt gaaccccggc   1440
tcttcgctgg gcgtcgcgtt ccacatgctg ccggctcagc tgaacaggct ctgggacgtg   1500
actgcgctgg gaggctggac cgagctggct cccgaggagg tccgcttagg cgcgggaggg   1560
tgcgagggag gagcgggtgc agacgcgtag ggaggatgct tggagaagaa agagagggag   1620
gtgagaggca gaagccgagg aagaaggtga gatggggaca aggaagaggg agagagactg   1680
gtggtcagtg ggtgagagag tgacccactg cttctctga cacctcccct ttcccccacc   1740
aactccccca agtttctcc caacacatcc tccggccggc gcccacacgc atacctgtca   1800
ccagccctgc ctcgcatttg cgttctcgat ccagttccat ctcgcacttc ccaaagcgtc   1860
gcagcgagtg gggaccgcag ggaccaggcg ccgcgaagcg ggagcgtgag gcgctctctc   1920
cgaagccctg ggcgacgctg gactagtgtg ccccggaagg acaggtcaca cccggggggtg   1980

```
ggggtgaaga cgacggtggc ggtggggagg acacctttag cagctgggac ctgatttctt    2040
cctccacaag gctgcagctg gctatggccc tggtggaaag aaaaagcgag cttgaccaac    2100
tcgacttggg aaggggata gagagagaaa agaaggacct tgtgtttgta ttcataccgg     2160
tgagcaccaa agaatagtct cacgcagtta taggacccag gttcagcgat gtgactactt    2220
gtccaaggtc acacagcgag ctggggactc ggggaccagt gtcggatctc ccacccggtt    2280
gggacttctg agcgcacagg ggcaagatat gtgagtaaac cctgtccaga atcccagtcc    2340
tttgtatcac tcggtagtgg tagagagtct gctgtagggt atattacttt tgcttgatgc    2400
aaacctggtg gcggggtgcc gaggttggtc agggagggaa caggagaaag gaaaaaggca    2460
gggttggagg tgtgtggagg cggcaagtga agaagaggct gtgaggctgg cgcgtcgaga    2520
gtgtgcagga acattttttt gaggcataac tgagagagat cagccattta gtagccgtat    2580
tcccttgggc aaggtcttca acctcctgag cattacgtct ttttctttga attgcaatga    2640
tttgtgcgga ccactggggg tgatatcaag tgtcagggac caccggaggc actcaataaa    2700
tagaagacgc gttgctgttg agaagtagaa gctgtgccgg tgggaacagg tcaaaggcca    2760
cccctacact agcaaggtga ccctctggac gcggtctgtg cgtctcctgc tcagagccag    2820
aaatcagcac ccgaaggcat gagactgcca gttgccagcg aattcacaaa tccgaccggc    2880
ccctcccggc ccaccgacct cgggaccgcc ccaggaacat attcagcact gtggccagcg    2940
ccacatccat cctaccgcaa agcgccgctg gaggaatggc ttccctgtca ctcccaccgt    3000
ttttaacttg cgcttctaac gcctcagtcc taccccacgg aggagcaggg cagactccca    3060
cgaagcacag gccggcgtta gtcactgcct tgaccataca catcggcgct cacccgatga    3120
gataccacgt actgtgtatg agagagtatc cccctcagtt gaatgcgttt gtacttgcct    3180
ttcacagaca gtttgtacca cctctactac ctaaattgtt aatacttaaa agtccacaaa    3240
gacctaagac tgaatgtgtg cacaaatgcg tgaaagactc catgcagtaa attactacat    3300
gagagaagtt tgatacagga aatttaacat agtggtttgg ttgccgctgg tgtgttagac    3360
attggaccaa actgagtttt gtttcgtttt gctttgtttt gttttgtttt gctggttttg    3420
ttttgttttg ttttgagacg gagtctccct ctgtcgccca ggctggagtg cagtggcgcg    3480
atctctgctc actgcaacct ccgcctccca gtattggatc tcccacccgt ttggacttct    3540
gagcgcataa gtccaggttc aagcaactct tctgcctcag tctctctagt agctgggact    3600
acaggcgtgt gccaccacgc ctggataatt ttttttttgta ttttttagaag agacagggtt    3660
tcaccatact ggccagtctt gtctcgaact cctgacctcg tgatctgccc gcctcggtct    3720
cccaaagtgc tgggattaca gccgtgagcc actgtgcccg gccccaaatt gagttttaa    3780
aacattaatt tcagactact attttttaag tattacaact aagtcaaact accaattaca    3840
aacaagtttt tatttaatca ataactttgt tactccctga cctatattat cagtaggttg    3900
atgtatgtgg aaagaaaggg agagaaagtg gactgggata aatcagaata ctatgggaag    3960
ttattgccta agactgagaa tcaggaaaat attgttggat atatttctag tctactcagt    4020
gctaaagcta tggctgatag ttgaaaaaac tgaaaacaaa aaccaccaaa actattgtga    4080
taaaaaaaat tttcatgtta                                                4100
```

<210> SEQ ID NO 215
<211> LENGTH: 5000
<212> TYPE: DNA
<213> ORGANISM: Homo sapiens
<220> FEATURE:
<223> OTHER INFORMATION: OGHAv1.0 microarray feature identifier
      ha1g_00644 genomic DNA region

<400> SEQUENCE: 215

```
tagatacata cgggattcag actagatttt tggaaggccc tctacccag aagcacagcc      60
ttagaactca tcagttttaa gatgtattcc tgagctctgg gggacacaga agttgctact    120
attctaggca tttccctgaa atgttcaact ttccattgac caagaaagca gctcgcccaa    180
gtgtgtggga agcacttggg tgggacactt ttctgcccca tttccagaag gattatcttg    240
gtctgaggcc ttctagtgac agctttagag aagctgactt tagtattcgg agagaaccag    300
gattgctcca actttctcag cggtattttt tcggaaagcc attaaattcg tggctcctct    360
gtgcgaagtt gatttctatt tggctttgaa ttgttgacgg ctatttcttc cttaatgaaa    420
gtgttgtctg ggtgaaaaat atatcaggtg gctgggaaat tggttgattt ttttttgaga    480
taggtgccca gtgtcctatt tttctatctg aggaaagatt ttctgcagac tacagaaatt    540
gacagcattg tccgggtaat aaccgtcgtc gacaatattt tcgaaagggc atttgagtgc    600
cgaaagcatt tggatattgc tttttccaat aagaaatttt ctgccctgag cttctttgat    660
tttatagggg gtggggagtt gactaggggg gcgatgggga agaaggagcc tcgcattggc    720
aaagagatgc cttccccatc ctcccagtcc tggaatacca aggtgcttgt cagcttcacc    780
tggaattcct ggatctgaag agccctcaaa taattcggct gcgagtcaaa agggaatttc    840
aggaatgagg aataacactc ttcttgcgct cctgtaaagc aagtgatgga agctctgaaa    900
gtttgcctgc tctcaagtgg gaagttagga agtgtgcgtt cttctgatt tttttaaaaa    960
taaaagtgt ctagctttga ttcgattcag gaaagctcct cttgggcaac cattgtccgt   1020
taggggcttc agatctcatt ttaagacctt aacagtcctc gccgttctaa ttaaggaaag   1080
gcaggcgagc ctgccagccg agagcggttg ggtcagcggc ttcatggtgc agccgagtct   1140
caaagcgggt ctgcactctc gcctccctct gcattctctt agccactatt tgcctggtcc   1200
cgtcgcgtgt gtgcaggaag tttcagtctt gatttatcca ctagtcaagt tcccgaccag   1260
ctctttttct ggatgtcagc actaaccccc tcccggagct tggtaaacac agcgcgcgca   1320
ttttctgcc tcagattggc atgttgacga ctctgcttga aggaatgtga caataaagtg   1380
ggaaaccaaa gcttggcaag cacttaatca aggataaaaa ggttccgttg taaggatgtc   1440
actcaattta ttgtgaaagt cgaatgaatt acgtttaatg aaagtgctcc ccagatgaat   1500
attaccagca atttcctgag ttggctctgt cagctcgaga tgaggaaatg ccaacccaga   1560
tcagaaaaga gcgcccgtct caattactat gcaagctttc caagagcggc ttttattga   1620
gataatatat tttggcggct tcttcaaacc cctccgcgcg cccaagagcg cgtttgcgca   1680
ttttccaagt ttgccctgcc ctcgcgggtt ggtggctgtt gtttaaactt ctgatgagcg   1740
cgctgcgttt ctgctacggg atgaaaacct aattacctcc tctgcaaaga gctttcccta   1800
gtatatttta ttgattgcgg aggtggggagc cggcaggggg tctgtggggg tgggcgggga   1860
ggggattctc ttgctccggt gccctctgtt gccgaaagtt ccttaggcgt ctagtcaggg   1920
gttcggggtg gtggaaagcg agatggcgtt gggagccagg gcgttgggac ggcacaagca   1980
gtggggtccc aggagcagca agacagtagc tcctctcggg ccacggctta cgaaaagctt   2040
tcctagctcc ttcttcctat aaattaatga gggtatttta ctcgttcaag ccggaaatac   2100
gatgggagg gggagacaca ggccgcatcc agagcgcatc gcctcatctg catgagaatg   2160
gagaaccggg aggcttttct tgtactgttt cttcctccca caataagaca aattgctgct   2220
tagaaaaact gagtgtttcc ttagaaactg gcttgcggga gctctgcgcg tccccgctga   2280
acctgcctct ggccgcgcct cgccatcacc cccgccgccc taatggattc tgaagcgaag   2340
```

```
gatcctagct gccgcggcta agggcgcagg gggaggccgc gcgtcctcgc cacaccggaa    2400
ggagagggca tccggctcac acatcccacc ctatgtctta gaccccgtcc tcacacattg    2460
actttaaaag gccattttcc ttcgtcttct acaagaagca agaaactttt ttcgacgtag    2520
gcttcatacc ctcccttcgg aaactcagtc cgctgaccaa agccgcagtg ttcaggcccc    2580
ggggtttccc agccgtagtg gccgccgcca cagctgcgcg ctttattgtc tgctttcagt    2640
cgcaggtgac ctcgagcgat ctcgacaggt ttatggaaac acagatgcag ccctctcgcg    2700
tccggagccc aagtcccat gcaaaagcgc tgtttctggg taattttcgt cgacgccacc     2760
aagcttcggt gcttttggga cagcgggctg atagcggca gttctcggga gataggccg      2820 cgggctataa gatttgatcg cgggcaggcg ggcgtggggc acgccagggc cgggagagcg    2880
actcttcagc accacggcca gcgccacagg ctccgccccg cctggtgcca gcagtagggc    2940
ctgcctcccc cgctgccgct ccggctgggt ccttaaagtc gagttagcac tctcggtttc    3000
cgcagatacc tcctcaaggc ccgctcgcga ctgtgacgac ccgcctaccc cttccagcta    3060
ttcggggggc agctagctcc cgtctctagg tccccagcat gacctgcggt cagaaactct    3120
tgcttgcacc cctctccatt accacactca gtggttgcgg cgtcacgtga tcaccacgga    3180
gattttgcga atccttcttt tccccaactt ctcccctac ccagtctccc attctttcac     3240
agttcattaa atctacccct cccccgaaac agaaacgtga aggctgtaac gaagagctag    3300
aagtgtctct agtaatgtaa aagtctcaac tgacagacaa ggaaactgag gcaaccaact    3360
tattcgcaag agtaaaaccc tatggggaga agcgattcct gcccctcttc ccccggcgag    3420
gaacacggct ggagccaccc aggcgccttc caggctaagg cgcctttagc ggcgcgcagg    3480
ggtgagggag agggtgggga gagtcctaat tattatgaat ttctaaaggc gcagtaatta    3540
ttcacgggga gcaggacaaa ccatggctag gcagggaaat cgatatattt gctatcgaaa    3600
gttcctggct cgccttaat gcagacgaat ggggatgca gcctcattat tttccgtggt      3660
taggctcgcc agcgtggggc ctgatgcagc gtgaaatcta tcatcattag acccgggatg    3720
gagcggcggg ggggagtttc tctttactta ccaaaccgca acaacaaaca aacaacgacg    3780
aacaaccgcc ccctacaaac actcattctc acacaacgtt gccctacctc cctcgccgct    3840
tgccctggcc gctgttgcac actccctgg gggctgtctg cacgccctag agcagacact     3900
gcggtcactt aaagtgcgcc cagttcctcc accgcagcgg tcacaccgtt gatttgatcc    3960
agaaataaga cggatagtac cgagcgttgg cgctaggggt tgtctatgtc aaaggcgaag    4020
gttggctggg aagttctgtc cgtttctctt gccttagcat aggagtcaat ccttttcttg    4080
tcacccgatt ctgcaaattc tcgctgtatt aaaggagcag agatctggca tgtagtgctc    4140
cattaacccg tagcataagt tagctcggac ataaggcaag ccctcgagaa gggaacgaat    4200
cagaaggtga aaagagcggt cggaaggtga ggaagagaag gtttaggcgc aacgcctcgg    4260
aggtattctc tgaggccctg gcgagatttc ggcctttagc ttaagggcca gcccgctagt    4320
tttctaggac tgggtatagg ccccgcctcc acccaccgag gtcactgaac tgcccagggt    4380
cttgcctgct ggattacaag cctattccca tttctcctct cttccgcagt ccaccctccc    4440
tggcacagtc ttttcacac tcagaagttg cctgatgccc ccgatggaca gctgctggga    4500
tgaaacttgt attcctgtac aggtgtcttc gcagttacct gcaataccat agtacttagg    4560
gttaactgag gtgtgtgtgt gtggtgtgca tttgtcagtg cctcgtcttc atcgtcttca    4620
tctagctcgc ccctccctta taacagtgaa tcaatcgctg caaagaagat aggatgtagc    4680
agttttaaaa taacctaact cctccttcat tgcagtaaaa tgatcgcatt tataataaca    4740
```

```
ttaatgagaa caaaattaaa aattatggcc ttccaggcat taaagtaata ctatctgtcc    4800
tcttctcttg gattttcttt tcctcagagc ccagcctttt tatggcatat tgtgattacc    4860
tgagtgtctt tgtttccttg tggtcagaga cagctagcca acacaatact aggactgtat    4920
gatgtagggc atgatttcct cccaccctct tcattttttag aggctttgta attaaactct    4980
gtgagatata cgtaacttac                                                5000
```

<210> SEQ ID NO 216
<211> LENGTH: 3400
<212> TYPE: DNA
<213> ORGANISM: Homo sapiens
<220> FEATURE:
<223> OTHER INFORMATION: OGHAv1.0 microarray feature identifier
      ha1p_81674 genomic DNA region

<400> SEQUENCE: 216

```
ctggtgtcag gagcacagaa gaaagaacag ctggtaagga gtagagaagg agaaagaaaa      60 ctacttttttg aaggttagga gaaatactgt ccattgattt acttcagcaa ctgcctgaca     120
cataatagat attcactaat actttctttg cacctcatag cttaaatgtc ttgaagaaac     180
aaaaattgaa tgcacaggat caaggcacta aagcttagat aacacactcc tgcatcgttt     240
ccctgtttta tcaagatatc tttcatcttt atatccggca atttagtggc aactcttcgc     300
tttccaactg cgcactgagt ctttcggtct cctccccatt ttcctagtcg tcttcggttg     360
tggatgttgt aaactcgacc atccgtctct caaggtcttt ggcttcaagg tttcccaatg     420
ctctggagct gtccaagccc cggtactccg gggtggaaga cctcagattc atttgacggg    480 cttgtgagg ttggggggtct gcggagcccc gtgtgggtgg ggctgggcgc ggccggggcg     540
gagccggcga ggagccctag ggaaagggtg aaaggcacag ttgagaaagg cccgccgggc    600
attggtttca cagtttccac gaaggcttcg tgtgcaagcc tgaggagttt aggtgcctcc     660
ctcctgcctc gcctttcttg gttctagaac cttcagtagg cttttctggg ttgcagggac    720
ccggaaaagc agcggcttcc actcgggggg cgggtcccaa gggtcttgct gctgctctgg    780 ggccgttttgg actcctggtg ttgggggagg ggtcaggag gtgctgctcg cgtctccttt    840
tgcgcctgcg cggcgggctc cgagcgggta ggagcgcgtg cgcggtgacg tggacgtccg    900
gtgcgcgcgc gcaggctctt cagctggagc ggacacacgg tgtgcgaacc gaacagaata    960
acccgccccc agcgggatgt gaaggactcc gggtgaggcc ggccacgccc cgcacggtaa   1020
ctctcgggcc tgggtggagg gcatcgctta gtactggccc gattggagtt tttcgagagt   1080
ttgaagctct tgtgtatttg aacggcgtga gaaacgttcc gctgagagag cttcgcacgc   1140
cctcgccagg ccgggccttg cgcagggccg ccttttggcgc gcccctgtgg tccctgagcg   1200
aggctgcgca tgtcacctcg cgcgcgtccc cggcctcact tccgcgtcgc tcagctacct   1260
aactgggaac atcgacgcca gagagagcgg ccacgaggcg ggagggggtga gaagcgccca   1320 tggctcggcc ctgccctcgc gtgtgtgggg tgccgctccg cgtggtacgg tccgcgtgac   1380
gacttctcgc ccggcgccgg gctctaggtc gagagccacg cttacgcgct tttcagttta   1440
gagcctaggt ctcgtggttc tagaactcca agggaaacgg tgtcggcgtc gcttttctga   1500
gaacttggcg cagcgttttg acacctgtgc aaacgtctttt tctaacaagt aatttccggc   1560
caaattgttt gaggcaggac gtcaagttta ataaggagg gcgaggaagt gagctgtagg   1620
agtggggact tggtaaacaa aggaccggtg gtgtgtaagt gcagaaatga gggaggggaa   1680
aacaggtggg aagagcaggt gttatttttct ttattcctct gtggggcagc cttttaccta   1740
```

| | |
|---|---|
| gttctgttta tggggtttcc cgtttctgtt aaatggtcaa gtaggtctct gccctcagtg | 1800 |
| caaggtatct gggacattaa catcacccc ccaccgcccc cccaaagctc cagtagccaa | 1860 |
| agttgaggga tctatgtgtc agaagaatat ggggaaacta gggatcgttt cagactgggt | 1920 |
| cgggagtgca aaagtggtag tgtcttgctg tacagatttt tgccttgcct ttcgaaccct | 1980 |
| gggaatgcct tctttctctg gccggggtgg aagcaggaac gggtaaatga ggtctgaaag | 2040 |
| gaggggttac tgatggcaga ccaacacgag aaaccaaagt gcactctttt attgggaaga | 2100 |
| taactttccc aaggttcgcc tcgccggagc aaacacgtgg atcatgagaa gtctcgagcc | 2160 |
| cacccgcgcg tgttgttgta gagcttgcca ggcttatgcg gctgagtccc tggttaacaa | 2220 |
| ctgcttgctc tgttcgttct ttttgggcac gatgccgcgg ctaggctgca gggaaagtgc | 2280 |
| ctggggcgg cgtgacggct gctgggaagg gggttggcag gggagggtct ggtggctggt | 2340 |
| tctgtagtct ccaaggtaac agaacgcggc tgggtcccgc agagcgatca tcgggttccg | 2400 |
| gccggcggca cgtgatctgt cgggactctt ccccggaaga gctttccttg cggcattttt | 2460 |
| tcacgtggtt cttggccagc tgtcctttgc agttgaaaag cggcggtttg tgggtcatta | 2520 |
| atagtcgacg gcgtctgctc ctctcgggga aggcagtgag accgagcctt ttactttcct | 2580 |
| gcgtatcgga acagcgctag tgtttcttgc cgccaacggt tgtttctagc gtttgtgtgg | 2640 |
| gttaagtggg ttgggtccac tttacagaaa acacaggcta aagacttgag gaaattcagt | 2700 |
| gccctgggta ccttggcata cttacttcaa gtttgactac tgccagtttc tgccttaaaa | 2760 |
| gttcttcaaa ttctgcttac ccaactgcta gagacctgtc agctttctgg ccctgagttg | 2820 |
| tagttagggt ccattcttag gaataaaaaa tactcctgcg gctagcagta acaaatgata | 2880 |
| tctgggaaga gaaggaggca gtactctctt acgcaggtgc aattctgtgc cttaaaacct | 2940 |
| aaaagtgttt cagataatat tttgacattt gccctataag gttgtgacga taaaatgccc | 3000 |
| aggatattgt ctgttccgaa gtgagtagtt cttaataaat ggcaagtacc atttattaaa | 3060 |
| ttagtaaaaa taagcaaatg atggttaaga gcgattaaga aagtattaat agttggctat | 3120 |
| tttactgtct ttgccaccat ttgctttcat tttattatat ttatatccac attctgtttt | 3180 |
| taagaaactt aaaatttctt gacccagtgt ttattggcta aatactgaaa tctgagtgaa | 3240 |
| cctgttctct tgaaatttga gtttcacaaa tgtaatttaa ccatattctt atagtgaagg | 3300 |
| atcatattaa ggaatatact aacatcttgg tgcctgccat actactgtat ttattgtatg | 3360 |
| aaaggttgta gaagtttgta gcaatttgga aaacgttcag | 3400 |

<210> SEQ ID NO 217
<211> LENGTH: 2100
<212> TYPE: DNA
<213> ORGANISM: Homo sapiens
<220> FEATURE:
<223> OTHER INFORMATION: OGHAv1.0 microarray feature identifier
    ha1p_81149 genomic DNA region

<400> SEQUENCE: 217

| | |
|---|---|
| ggcaaatagg tcaatgctgg gaacagatgc ctgcctggct gagtgctggg aaagaaaggc | 60 |
| agttggaggg atgtgtgggt gcctgggagg gcgtgggtgg tgcccaggag gctatgggaa | 120 |
| tcagaatcac acttgcacaa gagaagaccc ttatgggaca agtaaaatca gcatagtttc | 180 |
| ttgggcgggg caaggtgtc ctgatgagga tgctaggggg caaatatgtg tctgggttct | 240 |
| gccccaatcg ggaatgagac acagtactga agtggaacgg gggtagcatc tccacccacc | 300 |
| ttcacagcct ctggggaaaa gaaagctttc cttgcagccc aactccaggg gcctaaatat | 360 |
| tgagcaccaa cacaagacag gtccttgagc ttctcggagc gagtcgggga agcagataat | 420 |

-continued

| | |
|---|---|
| ttcagatgca aagtgccttg aataaacaga acgaaagata gagagccaga gggggagaaa | 480 |
| cggcttggtg tggtcagggc aggcatccat gagacctaaa cgaagagggg gcattccaga | 540 |
| caaaaggaac agtgatcaca gaggccccga gtcaggaacc agctaagggt cttagagaag | 600 |
| agctgcctcg taaagctaag caacaataac cagggaacgg tgggcatggg ccctgataga | 660 |
| caaggcaggt cttggctttt taagccatag aattggattt taggagggat gggcccgccg | 720 |
| acaaagccaa caaagtttta acccgaagat cgctatctta tttatgcttt aaaaagacct | 780 |
| ctctggcctt tctgcgaagc tctatcctta gctttctctt gttagcattt tgattaacga | 840 |
| atgtgggcac gaacagccag ctgaccgacc gcgcgcgcag tcgagcgtcg gttcctcgcc | 900 |
| ttgggaggga ccactggagg ccccgccccc tggccgcgag cgcacctcgg ccccgctccc | 960 |
| gaggccctac gggcgtggcc tctgtcccgg gtcccgcccc ccagcactcc ggaacagcgc | 1020 |
| gctcgcagcg ggaggtcgcg aagcctggga ctgtgtctgt cgcccatggc cgccgcgctg | 1080 |
| ctcgcccggg cctcgggccc tgcccgcaga ggtgagtgcg ctggggatcc gtacggcggg | 1140 |
| gcttcagccc gcgtctggcc cagcgggcgg aggtcctggc ggccggctct gtcagagccg | 1200 |
| ctggcaggcg gagccccact ccgggagcgc tcacggcctt tgccccagtt ctgctgctcc | 1260 |
| ttgcgccgac ccagcccggc ccttcaggcg tccctggttc ctgcacagac ccctaccccc | 1320 |
| cgattgaccc cagccaccag cccagttccc agttcccata tctccctccc ttcatttcac | 1380 |
| ccccactaga ggttcagggt gcgtccttct tccggagcca ggcctgggat tgaaccagac | 1440 |
| ccgcatctgt gaccttgggc aagacagccc ctcctcagcc tcggttggcc catgtgtaaa | 1500 |
| atgtccacag agaaaatcag agttgttggg aggattaaat catagggtat gtaaagcact | 1560 |
| tcgtgcctgg cgtgtaacag gtgttccaca aatgctcgtt cttgctggtt aatacagtac | 1620 |
| ctttcccatc ttacgtgtct ccagttgtag cagccgtgac acatatagcc acggcttcct | 1680 |
| ttgcctggcc tgaattacaa ggggaacgct actgagaact gtgttaagcg ctagttagtc | 1740 |
| tttctttcgc actccgagga gcggaatact attcgcctcc acttgttata gaaacggagg | 1800 |
| ctcactgacg tttaaaaccc ttgcctaagg tcacagagct gaggtcttat tactgttggt | 1860 |
| attatactga ggactgaagg atgtagtgta tggaaatgtc tagtgagtgt actaagcatt | 1920 |
| cagttagtat gggttttca gtggccgcca tggacttttt gggctgacag ttctttgttg | 1980 |
| tggggctgt cctctgcctt gttggatgtt cagcagggat cccggacccc tatccactgg | 2040 |
| gtaccaatag tattccctg ctctagttgt gacaactaga actggctcca gacattgcca | 2100 |

<210> SEQ ID NO 218
<211> LENGTH: 3200
<212> TYPE: DNA
<213> ORGANISM: Homo sapiens
<220> FEATURE:
<223> OTHER INFORMATION: OGHAv1.0 microarray feature identifier
   ha1p_83841 genomic DNA region

<400> SEQUENCE: 218

| | |
|---|---|
| ccatgtcact ctttcaaatc taatcatttc caggcacaga aataaatcca aatttccttc | 60 |
| cttcaaggcc tgtagttact cctgcaacag catctcgcag tcttccttgt tcagtaggcc | 120 |
| ctcgccagtc atactgacct tgccaagcct ggagttcacc aagcacactt ctctctggtc | 180 |
| agcatttctg ttccctccct ttagaaggca ctttacccat acagtcacat cgtttcttcc | 240 |
| ctcactgtat tcaaatctct gctcaggtgt tacctcctca aagagaactt ccaaaactgc | 300 |
| tgcttgaaat aattccccgc cccatcacac cctaacccct aacagtagtg ttatcactac | 360 |

-continued

| | |
|---|---|
| cagataaaata ctttctactt gtctgacccc tcctctagta caattaaaac tccatgagtg | 420 |
| cagggttttc acagctattt ctccagcccc tggactcggg gttcttactc tctggagccc | 480 |
| agtttgagtg acctggagtc acgagggagg cgagagagaa gggttaccag cgatactcac | 540 |
| acaacatcct cccctctgg tgctttgccg ggtccctggg aactgctaca ggggctgcac | 600 |
| agcggctgac cctggccttg tcaagcactt gacacataag tgctccaaag tgtctatgga | 660 |
| atgaaatctt caataaaact ccaaacagaa tgctgtagtc actgacactg cttcctaaaa | 720 |
| cgtggccaac aattccgtat gtgacaaaca ggtcacattc ttgattttt ttaacgacca | 780 |
| acaaagttaa aaccctctca tctttccttc ctgagctcca tgcaaattac ctattcaaaa | 840 |
| gcaactaagt atctccagtt ggatattctt aggcatcatc tcatccttgc cagtctctgc | 900 |
| aaaatatggt cgacaaaaat aaataccacc ttcttaaata ccacccagct gtccaagatg | 960 |
| gagacttcct ggcatccagg cgccttcctc tccctcgtcc ccacctctga aagttccca | 1020 |
| agcacgaagt gttctgcgtc ccgaacattc caggggccgc cagccaccat gggctctgtc | 1080 |
| ctgaggtgcc aagcaggaca tccctgcccg acatccttgt cctcccgcac cgcacacgcg | 1140 |
| ttagtggctg tggcgtcgcc accccagcac acgctggccc gccgcagtg ccaggctgga | 1200 |
| agtgtcgggc gcttgccagg ccaaggggca attctgttgc cttccaggcc ttttcggcgc | 1260 |
| ggtcccagtc aggaacgcgc cctgtcgcct cccactccgt cttccggacc ctcccgatcc | 1320 |
| tctctcgtca gcgatcgggc gtcgctcccc tggactaacc tcccttgccc catcttcagc | 1380 |
| ttttcgctga tctgcatctt cctgcgcctt agtgcaaggc agagacctgg ttctaaagcg | 1440 |
| aacggaacgg aaccgattct gtaagttgca atgagcgcgc tgaggtcggc gtggagggt | 1500 |
| ctctgggaaa ggtagtttcc gcgcctaaag cgccggggcc gggccctgtt cccgcaggcg | 1560 |
| caaggcagca ctgtctccgc cgattgtccc tctgggaagt ggagtctggc cggcggaact | 1620 |
| gcagcagccc tgagacttgt gggaattcgg cccaagggtt cccagggcaa cgcgcaagcg | 1680 |
| cagttcggct cccggctgca gactccagct cattgtgttc tgactgcgat gtggcgcttg | 1740 |
| cgatctctcg ccgccggcag aggctcctcg aagagcgaca cggggctgac caggcacggt | 1800 |
| ggtcaaagcc gcagagggag agcggagcg gtcgtgaggt cgtctgggga aagggcgga | 1860 |
| ggcaaagccg aggaggtgcg ggttgtggtc cattctggag gacgctgatc gaatgcccca | 1920 |
| aacttcccgg aatgtatgtc tgagatttga tcccagagag ggaggacggc caggggtggt | 1980 |
| catcctgggc tgagggtcga gtctgtgagt gcctgtggag gagatggagc cagggcctct | 2040 |
| ggcatgtgtc ttggagcgga ctccgagaag cccagggttt cctctcaggt gatagataca | 2100 |
| cgcctggcgt ggttccgagt cctgcgccag gaactcgcca aggccggagg cagccgctgc | 2160 |
| gcagcccctg ccacagcccc cgagggacct ggcgaagcgg caggggcggg acggggctgt | 2220 |
| gtgtgattag ggttcctaac ccttccctct cccctcccgc ccagctcaca caaacgccgc | 2280 |
| ttctgcccac ccgtgactcc aggccaccca gactgggccc cagagagtga gaacactgag | 2340 |
| gccagagaag ggtttgcctg agaggcttcg acagtgaaga gccttcttag cctccttct | 2400 |
| gaggaggaag aagaccaccc tccttttcct cttctcctgt cactgccaga taaggcagct | 2460 |
| gttccaaagc cgcagaggga gagcggagcg tcttccaat ccagtcgaac ccagacactg | 2520 |
| ccctccgttg cctctcccca gcgctcccac cttttcgggt acatcctggt gggttctgga | 2580 |
| gctgaataac ttgttaaaga gataattctc ggccgagtgc ggcggctcac gcctgtaatc | 2640 |
| ccagtacttt gggaggccga ggcgagccga tcacctgagg tccggagttc gagaccagtc | 2700 |
| cgaccaacat ggtgaaatcc cggtctctac taaaaatata aaaaattagc cgggcgtggt | 2760 |

| | |
|---|---|
| ggcgggtgcg tgtaatccca gctactccgg agactggggc gggagaatcg cttgaacccg | 2820 |
| gaaggcggag gttgcagtga gccaagatcg tgccactgca ctccagccta ggtgacagag | 2880 |
| cgagactctg tctcaaacaa acaaacaaaa aagaattct cttgagatcg ctcagtgagg | 2940 |
| ctgaagggaa agaccagagg gtgggtggaa ggcatgagaa ctggacctgg agcaggcttt | 3000 |
| ctgcagggaa aagtcaatgt atagtaccct cagaaggagg agagagaatg gggagcaaac | 3060 |
| aggaaccaaa acactcactg cttggggtac tggaggcctc ccaggatgtg aatgctcact | 3120 |
| gcctcgctct ggactgctgt atgagagctt ttgacccagt tctctcctaa tagcaggtgt | 3180 |
| gtggacccctt ctagcctgag | 3200 |

<210> SEQ ID NO 219
<211> LENGTH: 5900
<212> TYPE: DNA
<213> ORGANISM: Homo sapiens
<220> FEATURE:
<223> OTHER INFORMATION: OGHAv1.0 microarray feature identifier
 ha1p_38705 genomic DNA region

<400> SEQUENCE: 219

| | |
|---|---|
| agaagaccaa gtaaattcca aggcacaaag gcaatgaaga ctaggattga gggtggggtg | 60 |
| cagagaaagc agtgtaaaac ccatggcctg aaatgcagga tttgtggagg aaagattggg | 120 |
| agctgagact ggacatgtgg atgtgagtga gtgcactgta aatagtctta aatgccaaat | 180 |
| ggagttagcg atcgaggaga aagactggag aagaagccca gtgtaatatt tcttagacat | 240 |
| cagtcctaag gagagagggg gagaaaagtg aagcgggata gatttagggt agagatgttc | 300 |
| aggagaggcg ggcgacccat ctcagatgaa attcagaaaa actgacaact gactaggggt | 360 |
| ggcaggatgg cacagcccac tccaaaatct ggtagactct ggtagactct tcaagatttc | 420 |
| ctggaagact cctaggcgga gaactagcaa catcttgatg ccactgctgc agaagtggta | 480 |
| aggggaagtc ttgggaggag ataacttcca gaaggaagac aaaggggcag gggttttgga | 540 |
| gctagattaa tggctgaaga tacgaagaac cagaacgcat atctttaaga tgtatgaggg | 600 |
| cccttttccc caaagaggc agactgcgaa ttaaacgcaa tataaatgag gttatcacag | 660 |
| tccaggtagt cgtttctgaa gccctagtcc tcagttccca aagaaaccac gtgcgcacta | 720 |
| ccacctaaaa ctgccaatga aaatgaaggt cctgcgcagt aaaatattta tacaactgct | 780 |
| ggggccacta ggcttcagcg ggtgtggagg cggggagaga ggaggagtaa aggctgttta | 840 |
| caaacttgac gtacacacgc agtcctatcc ctacggtcct ggaattgggg gttactatct | 900 |
| tggaatctag gggcactcca ggctctgggc tcagacggct ggcttctgcc tacccgagcc | 960 |
| ttaacctttc aaggaccaga aggattccag agctcttgcc ctaggtcctg ggcagcgat | 1020 |
| gactcactgc agcacccct cccacttcgc caagctgccg tctccgccca cccccaaaca | 1080 |
| atctcgacag cgcatttcgg gagccacggc tccgggcgct ttgctggggg ctaaagggt | 1140 |
| ttatcccttt ccttgaatcc cagcaggcta gaactacccc ctcccagtct tcaggcttgc | 1200 |
| cacgctctcc acccgatcct tccattgaaa ggcagagaag gaaggatgtg cttgggaact | 1260 |
| ttaagaccca cgaacgacag cgcactgatg gagcagccca gtgtctgggg gtgagtatcc | 1320 |
| aaggccccgc ttagaaaagg gagggagggg ctgtgggtgc ttcgggaaga ataaaggcat | 1380 |
| caccgggcac agtgcctacg acccccattgc gcttacagcg ccgtgcgctg ggagagactg | 1440 |
| acccgggaaa gtttctgcgt cacacgcgcg tggcagaaac gcacgtcgct tgggaaagtc | 1500 |
| aaggaccacc cttgctcggg ccagaaccgt accgcagcga ctcctcaaat gtcgtggaga | 1560 |
| agtgggggc agatgccttg taagatccac tggagggcac atgcgggggt cgacagagag | 1620 |

```
tcggggaacc aacgtggatt ccctgctaaa tgctatttgg cagcgcaaga aggcggcctc    1680
cccgccctgc ctcagtccct agggaaacgt gcgccgcagg ctccctctct ccactccctg    1740
gaacccgtga gtagtagaaa ccccagagga accgaaatca cgtccggaca gcctctccag    1800
gctgtctccc actatcccgt ttctcccggc caccccgcca gtagggtgca gagttggact    1860
gcgctgcacc cccactctcg gttccacccc aattcaaagc gtccggggta ggctccgcct    1920
tctcccccgc ccccagagcc ctcggcccac ccttccgttc ctgggacggg acctgctccc    1980
tgtcaatcca gttcagcctc agggttcctg gcgcgtgaat aaaggccctg agagaaagcg    2040
gggactctag attacgcacc gccctccaca acacacactg aaggaactcc cagtgccttg    2100
ggcaggggat cctcagcccc catcccccga tgcaaggcgc accaataagg agtctggtcc    2160
gccctgcgct cagcggctcc gctcccgggt ggccaagttt gctgcaggga accgcaactc    2220
cagtaacttt ctccgagttt ggaaactgac ttccaggccg cctcgcagcg ttgggcaacg    2280
cgccgctgaa ccgagtccaa actccagaaa gctctgaaac atccagaagc ccctgggggc    2340
gggtgtgtgc gctccacgcc agtgtactcg cacgcacaga gctagctacc caaaccatac    2400
gagtttctag ctgatatttta acgccggaga ggagcggagc ctcgccacag tgagggtctc    2460
taggcttaga ggacaattaa gtcttctaga agcgggcgag gaggcggaag gggagaggag    2520
gtggcgcgcg cccacttacc attcctgagc agaggctgat gacggccgtg tgctcggagt    2580
tggtattgac atagcctttg tagaaacagt gcttgagttc cgcttcctct tcggaataaa    2640
acttggtctg attcaccccg ggcgtcccga ggagggtgac agtgaacagt ggagcgataa    2700
atccggcatt ggcggtgaga ttaaatagaa actgctggcc gaaggcagag aggcggtaat    2760
gcgcctggga ggaggtagag gaggaagagg aggaggcgaa ggcaggccag gggtcagtgg    2820
cagagttaat gctccgtcgc gttcttttga agtggacgtt cgtgggaaag ggttctccga    2880
gagcgttcac tcggatggga gacacgattt cgtattcgct cagggtctct aataatttca    2940
ctgcggagag aagcagaggt atatgaacca ataattcatt tttccttaag ctttaattta    3000
aaacgaaggt ggggactttg ttctgacctt attttccagc ccattcgagt caatcccttc    3060
acccttaatc agtggacaaa tatttgctga gcacctacta tgtgccagta acaggacctg    3120
tgctaggtgc tgaggataca ctattccgag ccagacaatt aacaagtcaa atatatatg     3180 atttcagata ttgataaata acctgaataa aataaaacat gacgctatct ggtgccccca    3240
attactaagt tactttagtt tgcggcgtgg gagtggggat ggggatatat ctggcaacag    3300
caaggtaggg gggggttgcc taaattcgtt tccatagtgt ccctccctag caattggttg    3360
gggatgaccc aaagaaggga gaggctgcaa agcgggagat aattctttct aggaaaagga    3420
gagaagcctc cgctgcgggg tgcccctgcc caggagcgag gaccgggagg cggcgtcggg    3480
gccggcgggg tcccggggc cggagcctgg ttaccttgcc tcgggtgcag cctgtccttg     3540
cgcacggccg ccgcggcgtc tgggctcccc atctcggcca ggtcccgcac caggagcgtt    3600
agcagtgtgg cccaggatac aaactgcatg gtgcttccca cccctccctc cgctgccccc    3660 accccctcc ctcctgccct ccttggctgc ggcggcgacg cgaggcagcg gccgtggaga     3720
gcgcgcggag cccggcgccc gccgccaact tttgacttta ggagtcgctg aggtctcgct    3780
gcgagggtcc cgtctgcgct cggctgagca acgccgccgc ctgccgagag ctgagccgct    3840
cgggccgcag gaggagccgg aggagcagga ggaggaggag gactgggct cggctgcttg     3900 gccgcataat gcccagcgag cgggcaggag aaggcgagga acttgcgctc cgaggcgcgc    3960
cgggcgccct gtgctggccg ggatagctga gcggcttctt gaatgggggg ctgggggggc    4020
```

```
ggaggcgggg gggccgcggg tccacagcct ctcaaatgcc cccggtgcac gcctctaaga    4080
ggaggagagg ggaggagaaa gcgagacgaa cggggaccgc ctccttccag accatgtccc    4140
ctcctcggcc ggcccgtgcg ggactcgcag ccggaggccc tgccggctgc aagaggcgga    4200
ggccagaggc gtcaccagcg ccggggcagc tgttcctggt ccccgccacc tcgctgaagt    4260
ggggttttct gagattccct gccccgggga gggaaagcag ggaaagttct ctcccttttcc    4320 tggcgcgcgt gcagccactt ccctctcgt cttttctc tcctctcctc tctctcctcc    4380
cttccgagtc tcttttcct cctccccctt gtctctctgc tgctgtgcct ctcggactct    4440
gtcccttctc cccattttcc cctgtgatgt ctgtcttctc cccgcccac cgtgtccctg    4500 tctgtttctc acatttctcc ttttcctttc ctttctcttc cgtccccatc tcttgccacc    4560
agtccccatc ttttggtttc ttacaagtga aagtggccca gcgccggagc gccttccctt    4620
cctacacttt ttcattcggg aagagatttg gcacctgagc tccgctctcg atttaatcac    4680
cccaagtcaa gagttttaga aatggggttc ttaatcctgc aggtcggagt gtgtttctaa    4740
tacgtggtct cttgaaaatt tcgcaaaata tttaagctgt gctttccacc aacctctgtc    4800
accattcatg gagggtccat agcattctgt aggtcccctg ccccaaaaaa ggttaagaac    4860 aaatttggc agcaagaagg ggcggggact ctggcgcccc tcactaccag ggggtttaga    4920
gatgggaggg gaagggggga tggagtgtaa agttgtagat ccctgtggga ggcaccagtc    4980
cctggaggga tttctcaatc acttccgctt gctttcagcc tgagagatgc ttggaaagac    5040
tgggaaagac tgaaagcagg cgcttcaagc tacaccttcg tgtgtgtgtg tgtgtgtgtg    5100
tgtgtgtgtg tgtgtgtgaa ttgttcaatc ttgggtggtt cagtggcgcc ttttctttaa    5160
ccagccctca ggaagataga atttcaagat aatttcaaga ggaaagacat gacaatatcg    5220
ttaaaaatat ataaatatat gactaataaa tatatatttg cccaagtatc ctagaacggg    5280
ggttgaggtt ctgttgcgtg gtaggttagc actcaggact agaaatacca aagattgcca    5340
acaccaggaa ccaaatcgca atatgctagc aatgtcaact attcttgaga tactaataca    5400
tatatttctt ctggtgaagg gtaaaaatga cttggcaaga cgaatttgct aaataattgt    5460
taacccaaat tgataatgtt accatcgtct tattactgga atttcataat ggatatgtaa    5520
aatgtaagga tggaaaaata acatctgtat tgtgcacaat tagagatttt tagagaatgg    5580
catttaaacc ttgaacctcc aaattaattc actaaaatac gtttcttcta atacacaatc    5640
tttcttttta ttataacaac attccccaca atcacagtgt ctgggagttg ctgaaaattt    5700
agtaaggaac agaaaaatat caagaaatca atctattggc tgattcctgt ggaaaatatt    5760
ccagtacttc cattgtaaaa ttactcaaaa atatagcact ttccagtatt tcccattaaa    5820
tctttttttc tctttcagtt caaatccttc ctgacaaaga gaagttaact aatggtatag    5880
aaattacgat atgtagggac                                                5900
```

<210> SEQ ID NO 220
<211> LENGTH: 3400
<212> TYPE: DNA
<213> ORGANISM: Homo sapiens
<220> FEATURE:
<223> OTHER INFORMATION: OGHAv1.0 microarray feature identifier
      ha1p_40164 genomic DNA region

<400> SEQUENCE: 220

```
tcaattgata gaagttgagt aagatgacag agaagtgact aatgtatttg gaaagatgga      60
gttattactc ctctcggcaa gacagtttta ttagatcggg agctcctcca ctggagctga     120
```

-continued

```
agagagaatg gactgtgaaa gtggagatat gtatagacat ctcaaaggca gcacctgatc    180
cttgacactc tctcctacct ccttctctct ctaaattttg atctctattg gcggcccaag    240
ctagaaatct gggagacact ctcaagtctt tcctctcttt cagatcgcat aggctattat    300
ttacagttat tcccatttta cctcctaaat aattactgat tttcttctgt gccattcctg    360
ctttttattg ctaacaggcc ctcgtcatct ctaatcgtta cgactgcagc atcttcctaa    420
taatcctcac agttttcagc ctctagcttt gacgccctca aaattctgtt agtaaagcct    480
gagggctccc agaaagcgac gatggtgctg tgctggcaga ccgaatgttt tttaaaacac    540
aaagcttgca gtcctgctgc tgtgctcaaa atccttgcat ggctcttctt gaaacaggtt    600
tagtgtttct actcgagttc cttctctgtc gttcaacaca aacacataca cacccagttc    660
tgtttcacgc ttttgtcttt attatccctc gtaactgccc gccctgcaac caacccgctc    720
aaacaagcac cctgactggc gcattcttac tcattctagc ctgggtttca acttcaagga    780
gcttcagcgc ccctcactcc cttgccctga aagctggcta aactacgcac cttttctccc    840
cttttgaaat gacctttcca gatatttcta tggaattcag tgccattttc tgccgctgtt    900
ctcaccacat tcattcatca tgtttagttt taaaagtacc agattctgtc gatttctcca    960
actgaactct gaaatctttg aggtcaggga gcttgcctca ttctattttg tattcccagt   1020
acgtgacaca tggctggaca caccagaaat tgtccgatca agtttgtggg tattaagagt   1080
ggtcaaagac gctggggagg gcagtgctgg gagaagggca gcgcgcgtct tggcgacccc   1140
agcgcagttc gaactactcc ggagtctggt gtggagccga gagggagccc cgcacttttc   1200
tccccgcgga gctgcgctga gtctgaaata ggtgtacgcg tcagcggggc aggaaacgga   1260
aagacagtgc agtaattggt ggaaagctgg aagtgggcac ctcgagggcc tcagccccac   1320
gaacacagtc acccaggaaa agcgaaccgc gccaggccct gtcatcgacc gctgggtccg   1380
tcctcccagc gctcgcggcc gctcacatgg gcgtggccct gcgtgacctg ccggggcgtc   1440
acgtgagctc ccggagtcat gtgaccgccg tcttgacagt gttccacggg cgctgcttcc   1500
tgcctgggtt tggagttgtc accactttcc cctctccgtc tcctgcgggc gcaatggagg   1560
aggaggatga ggaagcgcgg gcgctcctgg caggcggccc tgacgaggcc gacagaggtg   1620
ccccggccgc ccctggagcc ctgccggccc tctgcgaccc cagtcgcctg gcgcaccggc   1680
ttttggtgct gttactgatg tgcttccttg gctttggtga gccggccggg tgggttgggg   1740
ctgatcttta aggaattccc gactttctct tcgaggtaga tcgtcatcgt ggtcactggt   1800
gccacggggc ctcagcgcag cttctgtctt aagctcctgg gcctccttat tttccccttt   1860
gcgatcgatt ccagccacac ctgtggatgt tgctagttac tccgcgtccg gaacgtggag   1920
gtcgaggac tgagctgggc gagttttgtg gcactccttt gctcttcagt aagtcccagg   1980
ggctagcgac tcgccctaga ggcgatagat atgaaggtaa ctccagattt tcaaggttcc   2040
tcttttggca cacgtggtcg gaggaaattc agaaagcttt aactgttcct aaacaacttt   2100
tgtttgtttg gttttaggtg agacagggc ttgctctgtc acccagcccg gagtgcagtg   2160
ttgtgaaagt ggcttactgc agcctccacc tcctgggttc aagcaatcct cccgcctcag   2220
cctcccgagt agctgggacc acagatgggg cgccaccaca cccggcttta ttattattat   2280
tattttaga cacagggtct tacaatgttg tccagctttt aaaaaacgtg aatgatttcg   2340
tcggcagtct tctatatatt tttcaccctc tttgagaaaa tgtatgagtg tgtcttgctg   2400
atagcttcag tgaatagata ttgttctctt aatcttccac tctgccactg tgaagcaatc   2460
atattggacg ggacttgtgg tagtcttgac agtggttggt ttctcttatg aaatctgatg   2520
```

| | |
|---|---|
| tctccgaaaa cagtttcttg ataattagaa aaaaattttc cttcctatgt tacagttttt | 2580 |
| aatttattaa gcaaaattct aatattaatt tggtatgaat gtgttttca ggaggctagc | 2640 |
| tggagcccgt gtaatcagca ggtttaagaa cattatggtg gataactatt ctagcgctga | 2700 |
| acatataagt agacatgaag gatgctttgg gctttggttt ccttgcaact cctttttccc | 2760 |
| ccctcccctg ttttttaaaa gatgatgccc atccattagc tttaaagcag gacgttgaat | 2820 |
| ccttaaaaga gattaaagca gggtttagaa acaaccacca ccacaacaaa gaaagaacaa | 2880 |
| caataaaaca ttaaaaaaaa tggtccccac tcaagcagac agacagtttt tggtaaattc | 2940 |
| tggttatctg cctagaattc agaagccaga ttcattcctt tctaatgaca gttttattg | 3000 |
| tcattagaac caatagcctc gtgcacttgt agagttagta gagctatgga ggcaatattt | 3060 |
| tcttgtagcc tacgaaggaa tctcaattat tttatcttta aaataaatcc gagtgcatgg | 3120 |
| tcagatctct ccctacttct ctctttccag ttccccaaa gacatgtttt aatttaatcc | 3180 |
| tttagaattc tcagtttcat tttttttca ctcctggccc tgtattcact aaattatttg | 3240 |
| attttgggta gtttgtagaa ttagagaact tgtttcaaat attggttttg tcagaatggt | 3300 |
| tacactccat tcctttgtcc ttaagctaac attattagga aactgatgag gttgtaaagt | 3360 |
| ttttagtgta tgtgtgtttg taaataagga aataaataaa | 3400 |

<210> SEQ ID NO 221
<211> LENGTH: 1700
<212> TYPE: DNA
<213> ORGANISM: Homo sapiens
<220> FEATURE:
<223> OTHER INFORMATION: OGHAv1.0 microarray feature identifier
    ha1p_23178 genomic DNA region

<400> SEQUENCE: 221

| | |
|---|---|
| ttttgggaaa caatacagtg atctatatca agacataaaa atactcacat cccttgactc | 60 |
| attctctgga aatgctgaag gaagttattc aaaagaggaa agaagctata cccaaaaagt | 120 |
| tattcattgt tgggtttttt ataacaagta ttggaaatgt ttaacaatga gggagggtga | 180 |
| acttaaccac ggtacatccg ctctgaaata ataccacaac tataaaatag tgctgatgaa | 240 |
| gagaaacaat gtaagaacat gtttatcata aaattttaag tgaaaacaat atatattata | 300 |
| caaaaattct attcacacac tgattataat tacgctgaag gatgttggca ggtgggtgaa | 360 |
| aactgaaaaa aaaaaaaact aaaaacagtt atgcttggtt ggtgggcccg taagatgttt | 420 |
| atttccattc tgtttctgta agattctcag agtgttggta ccgcagattc aactggggcc | 480 |
| agagaagccc atcacgggag cccgaggaaa agcagccaca gctctccttc ctagtacaag | 540 |
| cattcaacag taagctccca cgcaaagaat cagactgcag caaatttcag cgctgcctca | 600 |
| ggaacactgt ccttggctcc cacattgcaa agattttcca ttccctccac agtcacctca | 660 |
| ttcatggtta aggaagaaag cgcagctaac agacagggtg acgacagatg tccaggcact | 720 |
| gagccatcca tagctgttat ttttcattca cataggcatg tgccggatcc agcagatgaa | 780 |
| aaccagacct accccttcc ccatgtgtgt gtgtttttc cccttactgc tgctgctgta | 840 |
| acagctaagt gccaattatc tcccaagcgt gaaagcaaat attgtgatag cccaacaaac | 900 |
| tctacaaatg ttagaggaca caggtgggga tgactgtttt tctgtcctgg ccttggcatg | 960 |
| tctttattca ttgtaacagc tctcattaaa ggaggatctg gtaggtgcaa agctttctgc | 1020 |
| taacaccttc agcactttgc attctttatt ttctcattta tctcttggca ttttgttgtt | 1080 |
| gcccgtatcc ccacgaccca cgaatccaga ggtaagtttt gcttttcttt gcctagaaaa | 1140 |
| agctccatta aaccacctat tctcaggacc caacttcaca tgggctgata tgaatacttt | 1200 |

```
cttcaaatat ttgaaggcct gatgtatcgt agtattgtat tgcagtaggt agtattgtag    1260
tattatagta ggtgctttaa tcagggtttt ccagagaaac acagccagta ggagatgata    1320
gtcatagaga gatagataga tacatacata catacagatt tatttttcag gaattgaatc    1380
acacaattat agaggccaaa agtctaaagt tttcagggta ggccagtgag ccggagaccc    1440
agggaagagt taactttaca gctagagtct gaggactgtc ttaaggcaga gttccctgtt    1500
ccttgaggga tctgtctgta ttttcctaag gccttcaact gtttggatga ggcccaccca    1560
cattatgagg gggtaacctg cattactcaa aatctactga tgtaagtgtt gatctcttct    1620
aaaaatacct tcacagcaac atctagagtg gtgtttgacc aaatatctgg gtacctggcc    1680
tagtcaagtt catatataaa                                                1700
```

<210> SEQ ID NO 222
<211> LENGTH: 2000
<212> TYPE: DNA
<213> ORGANISM: Homo sapiens
<220> FEATURE:
<223> OTHER INFORMATION: OGHAv1.0 microarray feature identifier
      ha1p_46057 genomic DNA region

<400> SEQUENCE: 222

```
cttcccttat gtttgcaatg attatgaaca gtttagttag aacctttatt tgttgttttg      60
ccttgaagtt actggactgt tgcttagctt gcaagtcttt tgtgggtttt gtatgttggg     120 gaagggatg ttaaaaatgc aggctgctgt gaattaatga gttgcctctg tttatagaaa      180
tgcgatgatg ttcaataatg atttgatggc agatgtacat tttgtggttg ggccaccagg    240
tgggactcaa cggttgccag gacacaaagt aagcaacagc tgcatgaccg gtttagtcct    300
gacgtttaca aagagggacc cttccataa gcctgtaact tggtgtgggc agcttgccga    360
tgtcaggcag tgcatgtttc actcgattag ggagagagcg caccctctcc agagggcttt    420
ggccacgctt aattttttct ttgtttcctt ctatactgct ttatatctca cacatcccct    480
cttaactctc cagacatggg aagttgttgt gacaggtcag gaaagtcgta tgtttaccct    540
tctcctagaa attagttatg taagctatta ttgtatgtat ttagtaatga ggggacatgt    600
gcattaatct cttaaagctt tgaaataatt agcagcatgg tcttatgctt ccatggcaag    660
ctaccctgtg taccttggct ttttcaaagc agtagatttt aggtacgcta tgtttactaa    720
acctgattgc ctagtgttgt ttttctgcat tgatttgctg gaaatgcctt caatttagtg    780
tatgaaataa gatttccctt tctacacagt atgttttagc tgttgggagc tctgtgttcc    840
atgcgatgtt ttacggagaa cttgcagagg acaaagatga aatccgtata ccagatgtcg    900
aacctgctgc ttttctcgct atgctgaagt aagcatcatt cgtgtgtttg gaaagagttt    960
gtttatgctg tatttgtacc ctgctggttt cacagttaaa tttaagttct gcataacaga    1020
aaagaagact gatgaagaaa gagggtgctg cttaccttgt aaatgttttc ggaaaagaac    1080
actttagctt tccgtggaaa gcatatggaa ttatgcagca tttataatcg caccttgacg    1140
tagaatttgg gagcaagtgg catgtatagt gatgattttt aacaacttaa aattaaagac    1200
aaataacttt ctggtattag cattatttaa tagaagatgt tctctctgaa agcattgtgt    1260
gtgaaaaagt ctttaaacaa atgttttttgc ttcacaattt cagaagttaa gtaccttatt    1320
taagtaacac cagttgggag atttctgagt attctaagag ttattgtctc ctaagagcaa    1380
atgaaaaact taccatctgt tgaaataatc tgatctttgt gtacacatac atatacatac    1440
tcatataaaa tcagacactc tcaagggtaa aaagtacttg catttgacat tacaggggaa    1500
```

-continued

| | |
|---|---|
| atcttagaaa gatatggata gtctcgtaca gtttcatgtg gatttataca gaagaacttt | 1560 |
| cattggtaat acagaagtat gaaacttaaa gatacgttat atatttataa aaaagatagt | 1620 |
| tttctgtctg gtgggtcttc tgcaggcacc agtatgtgtt aaacaggtta tagaatcagc | 1680 |
| ttctttatca tgtacggtac tagacagtgt ggtagttcac caagtgatca taatctaatt | 1740 |
| attattctaa gtagtattta tatgattttt cctaatcttt attctagcac agcaaagtgt | 1800 |
| attactttaa ggttatctgt tgctctaggg atttcagttc attggaataa gtaaatgtt | 1860 |
| tgttgaaaaa agtattcagt gggtcaacaa gttggacagt actcctacat atagttaaaa | 1920 |
| tgttgccata cattgtttac tgtcttctga aaaataagta ctgtagttag ttctagaact | 1980 |
| taaaagtatt taattcatta | 2000 |

<210> SEQ ID NO 223
<211> LENGTH: 2300
<212> TYPE: DNA
<213> ORGANISM: Homo sapiens
<220> FEATURE:
<223> OTHER INFORMATION: OGHAv1.0 microarray feature identifier
    ha1p_40959 genomic DNA region

<400> SEQUENCE: 223

| | |
|---|---|
| ccaagatttt aattaaaaca aggtagtaaa taaatgtcaa ataagtgggg atgagaataa | 60 |
| cgtttcattt tcagaagagt ccatagggaa caattcagag ataaatttaa tcacaaaagg | 120 |
| tctgagaatg ggaatattcg gttccaccct ggttttcaca tctgttcatt ttcactactg | 180 |
| gttgcgtttc ctacggagac tcgggtggaa cataaaagtg gggctacttt ggacaaacca | 240 |
| ttaaaaacct tacccttttt tctcgctaca cacaactaga ccacattgct cttagctaaa | 300 |
| gggacacctt aaatctattc gttcagcaaa acttataaca ccgtgttcct tttctactca | 360 |
| gagggaatcg cacaaattaa ttcttgcaga tactcagctc tcctgttttt taagcttcca | 420 |
| cgtgggcctt agccaaataa cttctggtag gcaaattctc cccttcttca gttgagagct | 480 |
| cagagcaagc tgttggatta agcaaaagca cctttttaaaa aattaatatt caaggcagct | 540 |
| gtaccgcgga gggcctgggt ctcggagtct aaaaaatcag actggacgtt actatttttt | 600 |
| tttaggcaaa cgacagctcg tttctcattt gtaaaaccgg gggaacatct taccgaataa | 660 |
| accttacaca aacagaaagg attcctaagg gctgggaaaa tactattttg ctgtccccag | 720 |
| gatggaatat cagcatcctt gtcttttagc tcttaataaa gctctaacta gtcacaggag | 780 |
| gagccaggct gcatgatcac gcacactctg gacgtctagg ttttccgacc taataagggg | 840 |
| gcaggtcgcg tcgttccctg cttaaattag agaccacctc cacctgccaa gggcccttca | 900 |
| aaccctccgc ccctaggtcg ctaacgatca ccgctttagt tctagctcca ggcgccgcct | 960 |
| ggcggctgtc tccggaagtc gcctgcgagc ctcggggtcc tgaccgctgc tgggcctgcc | 1020 |
| cgtagatttg cctgactcta gcgaacctgg ctccgcccct cccccactat acgttgagga | 1080 |
| ttttaagacg gcgatgaaag ggctgaggtt gtggcgacgg gggcgtccag cggcatctcc | 1140 |
| actcccccaa ggatggcgga atcaggccgt tgtcgggcag ctctcgaccc ggaagtcgct | 1200 |
| cgcggcgcga ggccccgtt gccgagcgcg ggcgcggggg gcggagctcg gcggagacgg | 1260 |
| ggaaggggtc gccgtggctg ccggtcctcg agttgggggc tgccgcggac actgctaggc | 1320 |
| agacggcgag taccgagcgc gggtggccgc ggtgtccgtg ggccacgctc agctgcggtc | 1380 |
| agaggcgaca tgagtgccgc ggggctgctg gccccggccc cggcccaggc tggagcgccg | 1440 |
| ccggcccccg agtactaccc cgaggaggat gaagagctgg agagcgccga ggacgacgag | 1500 |
| cgcagctgtc ggggccgcga gtcggacgaa ggtgagtcct gccgctcgcc cggccgcccg | 1560 |

```
gagcggaggt gggaccgctg ggggaggggg tggggctgtt cgggagaggg cggggcggc   1620 ctccggggcc tggggctgcg tggaggggcc gccgggagtt gcgggctcg gggaagttac   1680 ccccatccgt gctggagtag cggggaagcc ctgggtgcgt tacactcgac cgtgatgggg   1740 agagggact tagatgttgt cacgctgggg gtcccttaa accccgtcc tccctcccag      1800 ccgtttctga ttgaacctca ctcactagta ggaattagaa actcatttac tgaatacatc   1860
gagtgtagtt cgcccctttt ttgtgtgtga gagcatcaga gtccaaagtt gcccctcccc   1920 accccccgaaa tgcataagtc atctatactt taggtagtac actattgaga actcaggttg   1980
gttaaaggaa agggacctag aaccagccag atacaggttt aaatttggct ttgtcactta   2040
actcagcttt gtaaacttaa gttttccagc ctcgatttac ccaactgtaa tggagctgtt   2100
taattcccac acctgcccta gaaggcactt cctagggtcg gtatagggat taaatgacat   2160
gcgcataaag tacttggcct ggtactgtaa atactccgta aatgttctcc ccacccgccc   2220
ccctcccgga aacaggtaag agaggagag atttgcttaa tggtcccag gtgttgtgtt    2280 ttcagtccca cgctctttgc                                              2300
```

<210> SEQ ID NO 224
<211> LENGTH: 4100
<212> TYPE: DNA
<213> ORGANISM: Homo sapiens
<220> FEATURE:
<223> OTHER INFORMATION: OGHAv1.0 microarray feature identifier ha1p_104423 genomic DNA region

<400> SEQUENCE: 224

```
caggtaagaa aactaatctc aggtcaactg gagagggcag atctggagaa ttaaatgcct   60
gtgcagtggt gaggggcgtt ggtcagattc cttgcctctg ctcagaggta gtgtccatct   120
ttttgccttt gtcacttctc cccgggtctg gctgttgttt gtggctgcgt gtagagcttg   180
tcaggcggag tgctgtgaca ggaggctatt ttaataaact gttgcagttt ctcgagccga   240
gctgtgttgc gttggcatcc ctcgtcaccg ctaatggagt gtgcgtggct gggtgtgggc   300
cgaaggagga ggctgagctt gctgggggct ggggagaaag ggaggacgt gtggggtgct    360 ggcctccccc ttgtctgaga gtgctccttc agcagccaga cctggggca tcacaaggtg    420 gcagtacccct gggcaccaga tccctgcccct ggaagtactg ctggcatgga cactttctga  480
gctctctttc ttcttatttc tattcatagc accgcaggcc cgtgtgtatg tggccgggga   540
ggaaaacttc cactcgcccc tgtgtgctcc ataggaagaa aaaaaaaag aaagaaagaa    600 atagaaacag aaaagagag tgtgcaggcc cgagagaaag actgaaacca aaacacagag   660
agaaggcgca gctgcttccc caaggccttc tggggctccc gcccgccagc ccgccggag   720 tcaggccttt atttatttat ttttcaggct taaaaaaaaa tttcgagtct tccacaatcc   780
cagtcccccc caatgcccca cccaccccc agatttgctg ggtggctgct gccaaatgga   840
cccgagtggg agcctggaat gaaaaattca taactgctgg actttgcttg ttcattagac   900
gtgaacttgt cgattgggca aattgttttt ggtctccaac tgccggggc tctccccacc    960 ctccctgctc gcccggttcc ctcctcccct tggacgcagc cattggctgc tcgtggatgt   1020
ctctttgcca aataggtgga tccttctctc tctttctctc tctctctctc tctctctctc   1080
tgtctctttc tccccccacc ccttttttact ggcttggcac aagcaaatgg atggggattg   1140
agcctgaaag gagagagaga gagggagttt gagagagaga aaggagcaa aaaaaaaaa    1200 cacccccaaaa acccaaccag tgcgcacaca cacgcgcaca ctcacacaca cgccccatcc  1260
```

```
catccacgtc ctccctcgat cctcgatctc tccctccccc ccttcttcct ttcctccctc    1320 cctgctccc tctctctctt ttgcacgcgt ctgccagcaa cggtctgcag ccggtcagaa    1380
ctcgtcctct tccccgggaa tctgcgagct ccccctttc ctccgatcag gcagctcgaa    1440
gtttacaccc ctgtgccgct gccaaagccg aaagccttt tcttcagctg ccgcttttc    1500 cctcctgggt tttgttttg tttttgtttt gcacggggt ggggtggggt gcgttgttgg    1560
ttgtggggag atggtgggag gctggttttg atttttaaat tttgcatttt tttctttttt    1620
ttttttttta aactggaaga ggatgcacag gggaagaaat tgaaaaaaa attttgttgg    1680 cttttgttta cctggcgtgt gtggcagccg gctcgctccc tctctctgct tgctatccct    1740
gacctttctt tcttttgct ccttttcaaa aaaatatta atttccccct tctgtgcaat    1800
ggagcatggg gggggggagg aggggaagg gtttgagaat ccacccaagc ccggcccta    1860 ttccccagaa caccaataat aaccccctt aaaacattta ccttcctccc ctgctcctcc    1920 tcctccccc tccccccacc cgccccaac tcacaactct tttgagtcca gaatctcaga    1980
atcgggcgtt gggctttgcc gggtgcttca gatcaatggt aattatttaa tttttccag    2040 ttttattttt gtaaacagaa atcaattatt atttaaactt caaacaagca acaaccaaa    2100 aaaaaaaaa aaaccaaac aaaccgaga gagcccatcc ttctgtcacc tgactgagtg    2160 ggaaaaggg tgaaggggtt gtgggaggct ggggaagggg tcgcaagaag acccatgtag    2220
cttttaaccc taatgtggcc gagacaagca ccttatttgt gctaacaaga agtgttttgt    2280
tcattattac tgtgattaac attagtattg gtgtcgataa caaagctgaa atcacatatt    2340
taggatttag gtctgattaa aaaatgttgg ggtggatgtt ccaactggat caggagaaaa    2400
gaaaatgaaa acagcctggg gagagggaag cctgatctgt ttcctcactc gcttgctcgt    2460
ggatgtcatt ttctgtcttc ttgggggcgg ccaaaaatcg accggtgtcg gggaccagag    2520
gcggccccgc acgccccgc gtgtgcgtcc acggcgtct gtgcagacgg acactgtgcc    2580
ggggcgagct gacaggagtt cacggctgcg atagaacatg gagatgtcat gggcgcgaca    2640
gagcctggcg gggataccag cagcgtgtgt gtgtggacgg caacgttgtc tgtgcgcgtg    2700
tgtgtgagtg agtgagggag agagagagag aataggtgtg tgtagaggct cccggtgcct    2760
ctgtctggct gctgaggctg agatgggagc aagtggctgg cgaagctggt ggtggcttca    2820
aaccacactt tcgtagaaca atcgcaagag aaaattgttg gggggaggga ggaggaggag    2880
aaggcggttt tccttgtgcc ccccttcta acgctgcttt tctccttctc tctttccccc    2940
tcatcccgtc ttccctcct cccgtcctcc ctcgccccgc atgctccgg cttgccgcct    3000 gcaggatgag ttccacccgt tcatcgaggc actgctgcct cacgtccgcg ctttctccta    3060
cacctggttc aacctgcagg cgcggaagcg caagtacttc aagaagcatg aaaagcggat    3120
gtcgaaggac gaggagcggg cggtgaagga cgagctgctg ggcgagaagc ccgagatcaa    3180
gcagaagtgg gcatcccggc tgctggccaa gctgcgcaag gacatccggc cgagttccg    3240 cgaggacttc gtgctgacca tcacgggcaa gaagcccccc tgctgcgtgc tctccaaccc    3300
cgaccagaag ggcaagatcc ggcggattga ctgcctgcgc caggctgaca aggtgtggcg    3360
gctggacctg gtcatggtga ttttgtttaa ggggatcccc ctggaaagta ctgatgggga    3420
gcggctctac aagtcgcctc agtgctcgaa ccccggcctg tgcgtccagc acatcacat    3480 tggagtcaca atcaaagaac tggatcttta tctggcttac tttgtccaca ctccgggtag    3540
gtcgttctca accattttc cctctcattt tattttcctt gctggcattt gttctgttta    3600
ttgttcctct aatttccaag cgataactcg ccatgggcct aactggtgta tgcccgtcct    3660
```

```
gcggggcctg caacacggtt ctatgggccc ttttccttttt tcctgtcttc tgtctccccc    3720
gacctgttct attcttcctc ctctgccccc tggccatggt atcgactttg tgcatctcca    3780
tctttggagg acttatctga tcagaaagat gctgcaggtc ttaggattgg ggacatgatg    3840
cccccagaat tatccatgat ggtgagagtt tgagatgaac aacaacagca aaccagtaat    3900
tgctcttatt aaaatgagtc agaagaagta ttgaggggca ggtgctagtt ttactgcagc    3960
ttcacctcca gtcccaggaa aaactgggtt tggtacaagc gggatgggca ggagtccggt    4020
ggagagaagg ggcatgtgaa accctgggat atgagactga atgaacagaa aagaggagag    4080
aagacagtag tgggcagatt                                                4100
```

```
<210> SEQ ID NO 225
<211> LENGTH: 5800
<212> TYPE: DNA
<213> ORGANISM: Homo sapiens
<220> FEATURE:
<223> OTHER INFORMATION: OGHAv1.0 microarray feature identifier
      ha1g_00847 genomic DNA region

<400> SEQUENCE: 225
ataactcatc agggtgacag agccacaagt gaattctctc ttctatcaga gagtatccta      60
tccaaagggt caggaaaagg ctctccctaa cattttccct tccacaacca agtaaatagt     120
ccctgaatat ggtatccgct gcttttttaa atatcaaagt ttcagaaaga gggaatgcca     180
gacgtgcaga atcagaatgc aaacgtaccg aaagtattct ctctttctca agatgtgttg     240
ggggacaatc agagactcgt cttccacccg taggaaatca ctggcttgaa ttttaggtat     300
ggagtgctgc ctaacggctt tagtgtgctt gtgctacacc tgagtgcgtc aaagcttggg     360
gggaagggag acagcccac cgagctgcgg taccccgctc aggctagaag agcgctaggt      420
aaggggaaca tccaaaggga cgcaatgaat tcaaaacctc tctttcccac cgagatctgc     480
agtcctgggg gtcgaaaggc ccactcaaa ggaaccactg ggttattaat ttgatcagcc      540
aggctggctc ttcaggctgg gggaggggtg ggaatgggaa gccgccatcc gtgctcatgc     600 gcacccaac actcaagctt accccagac ccctggattc tgcccacttt ccctctcatt       660
tcacctcaaa gtcaatggag ttaaaaatca gtctctttcc cctacttttc ccggggagtc     720
tgaattcctg gggtctgtta atgattttaa aatgtagagc cttccctggg tcgctcccgc     780
ctggagttcc cgccccttc cctcctctcc tctccccacc gccaaccccc accgcaacca      840
ttctcttctc tctgtcccta gagaaaagcc cgctacatcc atttggattt atgtaaggtg     900 gatttagggac acaaaggaaa caataagacc caatttacaa aaaaaggagg gagtagaaag    960
ggagggtaaa agagagaaaa ggaaacgtga tgggaataga aagcaacaaa gtgaattaat    1020
ttttaagggg gaggtggggg aggggagggg aacagacctc cctccctccc cttcaacatt    1080
agcctagggc tctcagagcc ttttttgtctt gggctcccaa gttttcctcc ccccccccca   1140 aaaaagagg gggtttaaaa aaagaaaga aaacagtctc tacatctggg gcgagagagg      1200
tctcagggga cgtcctaaca agtgtgtgaa gtggccagga gaacgcggga tccacgattc    1260
ctctcagggg aatgaataac cctagggacc gaggggcggc gacggccgag atggcaccag    1320
aaccaccaga agccacgtcg gaaggagatg ggagatccag agggcgagag agggccccctt   1380 tcctcccaag cgatgtctgt gggcaggtgt ataaatctct cagagcctcc gtctggaggg    1440
ctccgggtac cggctgccca gccaaggcta agttggtttt tggctcccctc cttcggaaca   1500 gagaaaacga tagattacac agggatggat ggacggatgt ctggagagat ggaaagatga    1560
atggatggat ggatgggtgg atggatggat agatgaatgg gtggatggat ggagggatgg    1620
```

```
atggacggac ggacggacag atatatggat ggatgcatta tggatggatg catggacgga   1680
cggacggatg cacggagaga tggatggatg catggatgga tagatagacg gatggacgga   1740
cggatagata gatggatgcc ggaaaggaga agaatgagag acggatgtga gactagatgc   1800
acgcaggcca gagcaccagc atacgctgga acagagcacg agcatacact cgaacacacg   1860
cgcacacact caggacatct gcgcacagac atacaatcct ccgcgtccgc ttccacgcag   1920
gcattcgcgc acctacatac acgcagttgc acgcgcgcgc acacacacag gcacacacac   1980
gcagacatgc acacacacgc agacatgcac acacaccaca catgcagaca tgcacacaca   2040
cgcagacatg cacacacaca ccacacatac acacacacac acacacagtt cgcctctccc   2100
tgggtttctc agaaactaaa tgatcaccgc cccccgccc cgccccacct ccgacacag    2160 acacacaggc acatacaatc ctcccagcac gtccgaacgg atgcacagaa aactgagcac   2220
ccagacgggt cccgtcgacc ccgcacgtta gctctaaact gtgtgcaatt ctggggcgaa   2280
aagctaaaac tcgactgcgt tcaacttgcc ggcgggttcc ccaagtctgc ggggcgaaga   2340
gctcgggccc ctcaggcccg caatcgcacc ctcggggcgc tgggcttggc gaggagaaag   2400
gtgtctgact ccgggtgcta gaaatcaggt cactggcgcc tgacgagcgg cgccacgacc   2460
gctgcgctgc ggagcaggcc ccgcagcccg gtcccgagaa gcgcagggct cgggaaactt   2520
tgcagaaacc agagctcgaa aggctttcgc tagaatccgg gagcaccaag ccttcactgt   2580
gctccaggct gcgttttccc ctcgccccgg gctggctcag gagaggacgt ggttcttgta   2640 atttttttt taaatcccgg cgttgtctcc cgtgcatccc ctcagggcgc ctcgagcggg    2700
cctctctggc ggatgctgat aaactttggc ctttggttac aaacttggac agacccgccg   2760
cgtgcacggg tcaccgcctc ggggcaggct gtccggcggt tccccgctgc ccttcgccg    2820 atcccctcgc ctcagccccc ttctcccgaa tcgggacgca ccattcacac tgggctcccc   2880
ccgcaccacc tggccctgcg ctcctgagga cccctcaccc gcgatggccc ctcgctgtcc   2940
ccgaccacag aaaggccgtc ccgctcttac cttcattcgc ggggtatacc ctggaacctg   3000
tgacagcgtc gcaaatcccg aagagacacg aaaatagggc gaaatagaaa atcccagcca   3060
tggttcgccg gtgccaacgc tgctcctgcc gcttctatcc cagtggaata aatgcttaag   3120
ttaggagagc agcgggctga agacattgcc aaggggcgg gccggccgg tgacgtgagc    3180 ccgccagtcc ggggcccgcg gccaatggcg gcgcagacag ggcggccgag ccccgccttc   3240
accgagcagg gcccgcccca gggttccgcc ccctccgggc tccacggggc gcgcggtctc   3300
ccggggctct agggggcgag cacggccggt ccccgccccc gcctgccgga gggagccagc   3360
gggatccccc acgttacctc gaaggtcgag cccctggacg gcggagggac tttggaaaag   3420
ctcggaattg accgagggga gccagagaag aggttggaaa ccttttctcc caccacgggc   3480
ggtttaagat ggaggaaaac gctctttat tgaaataaaa gaagtctaag ctgacctgcg    3540
gttgcttctt taggagagtc gacgtgtctg cgtccagcgc gcccgggctg agctgcagac   3600
tcgcgcctgc caccgccacc ctctgccacc ttgccctgtt ttgtctttat ggcgcttccc   3660
cctctgaaat actctttgcg gggagttttg tggctctatc actcgcttct tccctggctc   3720
cccagatgcc tggagagcgg ggacctactt ggtccccaac gtccagtccg cagcagggct   3780
ccgtcactgt ctccagagac tgaacgaatg actttctagc agtaaggaag tccccgctgg   3840
ccccgtcccc ctgcacacgc cgtggacctc gcccagggcc caggacgccc cgagatggcc   3900
ttgggcaggg aaccagttgt ggattcccg ggggcagggt tggggcagt ccctggaacc     3960 gggcctagcc cgtctgggag cggtggggta gaagtgaaag gcttaagtgt gggtgcgggg   4020
```

```
acttgcagcc gcacagacaa ggcagaccgg gactgggaag ctgcccggag cggctgctgc   4080
gactctccgc tccgacctag ccggggcagc cctccctgcc ccgggagaag acggcgagca   4140
ggaggacccg cagagccccg cccggctgct ccggccccgg gggcactggc accatcgggc   4200
tgtggtcttt tcccgatgcc cgagccgtgg acgcggccac ctaagagcgg tccggcgaag   4260
gcagcgcagc cggtgtccca gggaccggtc cccaacgcca ctcggtgcat tccccaggc    4320 gctggcaggg gcactgattc ctagcaatga ggcctccctt ccccttccca ggccgcccct   4380
cctctgactc cctccagagc agggccgagt tttcctgggg agcctgggtc ccggcggccg   4440
ggcggccgct gggaggtgga ggagcctctc cagccccggc cgcagctcat cgtgagccaa   4500
ccgcgccacc tgccggccag atgcgggagt gtgcggcccc ggaggaaggg cgagcggaca   4560
aagaccgcaa cccgcaatcc gcaaccccgc agagaggtgg tgcgtgcgtt tgggcgagct   4620
tttcagccac cgccaagtct cgtgcactag ggctactcct accgtggggc tgcggacagc   4680
gctcaagagg tcctggagtc tgtcgtgact ctcgcctgct ggatttcaaa agatggaatc   4740
ggaaagcgtt tcaaggagaa actcctaaca aaccttccgg gggttgcctg agtggctgct   4800
ctcggaaaag cggatcctaa ataaagcggg agggttatag ggcgacgtcg aggagaggac   4860
aggtctcgag tcactgctac agtttcaggt cactgggctc cgcagcagat cgtgttttct   4920
cccgtggctc gagagctgcg ctggtttctc atgcaaactc agagccgagc taatgacatg   4980
agcaactttt acttttacac aagatgagca cgcgtgccga ggcgctgggc ggcggctgtg   5040
tgagttggtg gccagacgaa acagcttgtg cgagactctg ggcatttcgg tttctagata   5100
caagatttgc ttaaatgtca cagtccaaag aagtggattt cagtcattgt agctactgat   5160
tgcacacaag taaaagggga aaaaatatgt actcggggga tatatgtatg tgtgtgtgcg   5220
tgcataaatt atttaaaata actgcactaa atcccttttaa gaaatgcatt tctgggttct   5280
ttcatgtgtc tttctgagtt ttacagaaaa agaagacgaa tattggtccc tgtcatttgg   5340
cacacagatt caaaagagaa aagagcaatc cgaattcttt ttgaaacctt tttaaacaat   5400
agatgctggc tgcctctctg caggatcttg agtgttgcat gtatctatct gtgtttgaaa   5460
cgggaaactg actgcctgca ttgttataaa cagtaaaatt tctaaaacat gtaccatttt   5520
tttccccagg atatgcacat tgaatattaa acaaagtctt tccagacaca gctgcctgaa   5580
agcaaggcat catttgctag agtacattca ctgactttcc ctttttttctt cctatgtttt   5640 agttcaggac ccaaggcagc ccgataatca ggagaaccaa gaagcaggaa atgctaactt   5700
ggaaaaactg aactataact tcctctttaa atcatttctg ggttgcagaa cagaaatgag   5760
ctgctgaaaa ttcctctgtc cattgtgact acctagaaca                          5800
```

<210> SEQ ID NO 226
<211> LENGTH: 4000
<212> TYPE: DNA
<213> ORGANISM: Homo sapiens
<220> FEATURE:
<223> OTHER INFORMATION: OGHAv1.0 microarray feature identifier
      ha1p_08347 genomic DNA region

<400> SEQUENCE: 226

```
ctgctgaccc ttcctctcat catagaaaga ggggtgggca gggggcagag tccttcctgc     60
tccttgccac cacgtgggag ccagacttaa cttccttaga aaagtcatcc ctgcccttac    120
cagcctgccc tgtggcattg ccaatcggcc cagcatctgg tccacacaga tccttaaagt    180
aatcttcatt cttgaagaca aacactagtg aaggccagcc aaagaggacg ccagcaaagc    240
```

```
ccaggcattc cagcagccca gtcagcagtg tggccacgtg caggggcagg ccctggcccg      300
ccatgagcag aagtggagtg gatcttcaaa tcccactttg tcctcctgga cggatcacag      360
gcgccgtaag cctggcgttt gagcacttgg aaaattcctc tggcaagcca agcccttcct      420
ttcccgtagc tctctggttg tttcaggcct gggcaaaaac catcagcggg tgattctctg      480
gatcctgtag aataaagata gaggctgctg aagaggagg cctgcgggaa agggaaggt       540 agactagagt tatttgtgag gtgcattaag aggcaggatg atcatggccg ctggcagcaa      600
atgtggggaa taaatactcc aatacatcat cttaggcact gcatttgagt aaccacgtgg      660
caagtagaga ggcaggtctt gatggccacc tggagtcaca ggtgagataa acgacttacc      720
caatagctcc ccgggagcag gtggagaagc ggagctcctg cgctcgaatt ctgaataccg      780
tcccctaaaa taatgacagc aactcaacca ggtgcagagg cagggagatt tcatacagaa      840
gacacaaact cccgctgcca agttggtgtt atcttcagtt tactgacaat gaaacaaaag      900
ctcccatgga tttcaggaac ttgcccaagg tcacagggct agtttagtca cgacgcaggc      960
cattctactg ccagaaatac ccccaactcc catgaccctc gcctaggact cgcaaacctg     1020
gtccccgccg cccttcctcg catcaacttc taccaggaaa gcctccgggg gccgctcccc     1080
gccagcctcc gcaccccgct ccagcctgcg gcctgccctc ccgcagagg agcccgaggg      1140 gccaggccgc gctcggcgcc ccatggcgcc cgaaagggga cccttcgccc tacccgcctg     1200
ctccgcgccg gggctctccg cgcccttttcc gcacgggcca ggttcgcatt cgcgcctctc     1260
gcagcccctc ccagtcccct gctcgcctcc gcccccctcct gcccgccccgg aaggggctgg     1320 ggcagacctc ccactctcca tcacttcctt ctttcttttcc cttgctcaca gcctcccgcg     1380 cccttttttac ctctccctct tgaaacttct ccctctagaa cccccctagaa ccccagcggt     1440 gtctttccct ccctcctcgc tgcctttcag cctcccagcc ccttgcctc tgcctcccct      1500 aaccaagtta gttgaatgct gttactcgct caggcccacc tagggaaaat gtcacaccca     1560
gcacccagag gacacacaga cagcacatga gggcataggg acacacacac tctatttgtg     1620
cattttgcct tgaccgctgg gttggcaggg aacatattt tcctatttgc tcaccagctt     1680
aaccgtctct cccagtttca cactcccaga gctgccaaaa aaatcccaac cacagaatca     1740
ggaagccaag aaccaggact gagggctttt cagaaaccat cccctggagg actgccccat     1800
attttcactc ccaaaaaccc cttagatgac tccctgcctc accccgccc ccaggttct      1860 gaaagagcct tcccgccaga ctgcattgat taaccattca ttgccccatt ttttattaat     1920
caaagacata tataattgct catcggagct tgtgatcagc gtgaggcctt actaagcagc     1980
tgccttacta tccttccagc ccagagcacg tgagctgacg tcttcttggg cctgtgtggc     2040
cgtttccttg ccaaaagctc agtttgggga gagcttcttg cgtattagat gcagtctgca     2100
gactcccaac cccagctacc tggatcccct gagggcccag gaactccagc tattccaagc     2160
ccactcctct ttttttttaag aggaagaaat agaggttacg ataggggaca gccagaactg     2220
aggattttcc agctcaccac caaagcacaa aagataaaag tctgcaacca ccctagtgac     2280
ttgactgaat ggaggaaggg tggctggggt cctgtacccc aagctactca ctagttatac     2340
aacctgaggc aagctctttg gctgccccac ctgtaagacg aggacaatag taccttaatt     2400
ataggaattg tcataaaaga agtataagat gggtgtatga ggtccctgca tggcgcaggt     2460
gctataggca gattgtaggg tagtagattt tctagtctgc agttatgtag acagagccag     2520
agaagcagct ctggggagga atttcaaagg aacttgccca cggtcattct acaaagctgc     2580
agtaccttcc caactctgaa acgtatgctc tcatcacccc gtcttaacaa acatttggac     2640
```

```
attagagaaa acaagtcttt tcttaaaata acattattta tgggagaaaa tccacaaaaa    2700
tatagcatcc caggacaaac agggcttaag atgcaagatt ttctatttta ctgcaagaca    2760
caaagactct gaaattaatg catgccctat cttctgctct ggcatacatt ttagtctcct    2820 gggggggatca gtaagtgtgg aagtagcaag ggagaaacag aaaaaagtca aagtaaagag    2880
acagatttta gaatgttaat ctgcaggagc ctgccagaaa gatctagctc atgggctatc    2940
tgtacatcca ggactgaagc acgggacacg ggcaggtcg tccagggttc tgtccacctt     3000
atcttgttac ctctcttgac tcttagagcc tccactccac atctcccatc aatgtctgca    3060
gaagacgtgg cctccactaa cacaagtctt actgaactga tgggacagga aattagaata    3120
tcctctgaac cattcccatg ttctttggtt cgaattccag cagctagaaa aggcagatgc    3180
tattctgatc actctcctgc gtggctccaa tgaggattaa tgagtaacat cagagagaga    3240
agtgattata ataaggtctg acggtgcacc cgatgtcttc atccttttct cttcgcctcc    3300
ttcctcatca tctcacacct tttttttttt aattgactga ttggttcaac aaatacatgt    3360
ggtacctcag gctctgtgcc aagtgccggg attcgtagag aagagattca gtgcctgctc    3420
tcaaggggct cattctcttg tgggagagac agacaaagaa acccaagatt tctggagtgt    3480
gggaatggtc ttccaggcag atgctagcac agcacattga aaggcacgga acctcaacaa    3540
aacaataaca tttaggaacc agctagagca caggtggtg aagaaagtgg aaagatttga     3600
ggccagcgtc gccatctaag tgagggcatt aagaattcag cccacatcaa tcaatcatgt    3660
cctattgatt tcacccctta atatctctcc tatctatccg tggccactgc tctatgcaga    3720
cactcatcat ctctcacaga ggcatcatct gcttccaagc catcgccatt ctcctgcaag    3780
agtttatttc catggttccc actggatggc ttcacttaac tgctcaaaac ccttctgagg    3840
tccagtcaac tggctggtaa ggaccagtcc agggtctggg gatgccagcc atgagacatt    3900
gctttgaggg gaagagggag catagaactg gatctcctgc atcctactgc ccaagtacca    3960
atgctggagg tggttttcct tcccatcatc agcaagtctg                          4000
```

<210> SEQ ID NO 227
<211> LENGTH: 4200
<212> TYPE: DNA
<213> ORGANISM: Homo sapiens
<220> FEATURE:
<223> OTHER INFORMATION: OGHAv1.0 microarray feature identifier
      ha1g_02416 genomic DNA region

<400> SEQUENCE: 227

```
gaagaagaaa caggtgaaga ataatgtctt aaacatcatt ttagcaccct attctgccat     60
tctgtatctt tataggatat gtccagtcca gtcccagaaa atctactgcc caaggagttc    120
tagatgacag gttagatcaa gccccggcaa atgtttgcga aaacaacatt caactgcctc    180
tggacattgc aaagacatat tccagggagc tatctcttgg gctctttttt aacatctctc    240
ctagaggatg agactccttt cgggattaca gccactggga aagtaaaagc aacagtagca    300
tcaacaggtt gcatcgcact cccgcgcccc aggggcggtg caggagagcg cccggagcca    360
gagccagggc gcgctgggcg caagctgggg gcgcccagg gccaatgagc ttctgattgg     420
ctctttgctg tgaatagact aggccgaggc taataggacc ggaggggcg ttcacctggg     480 aattggcctc ccccccttgc caaggacctc cctgattgta tggggcggag tggggtgggg    540 gtggggggctg gaaaggggaa gcccacccta actaaacgga ggggcgggag gaggttaaac    600
tgaggaagcc acgagcccgc agtaaagaga gggcgatcga ggcaaagggg taggtaactt    660
gggacttctg tgccttgaaa gtgttaagga ttgcagggaa tgcaggcgcc tttcattta     720
```

```
ctttgggcac cctcccctgg ctgggcattt aatgaggagt cctactgtgt gtgttgaaac    780
tctgcataat accgtaaaat attctggccc taaattacac tcaacggaga gatttaggca    840
gattacaatc ctaattggcc gcagggtgct ggggaaaggg gacagagaga attgggggat    900
ctggaatttg gtgtgctatc actacaccgc agctctattt tccattaaga aaagatcat     960 atgacgaagt cgaactaaga gatctgaagt aaaaaatgaa aagatggagc aaaagtaaga   1020
aacatactct gagacgagtg ggttttcccc ctttattcca acagcaatct taaatgatgg   1080
acgtcatgta gcagttatat atctatgaac atgcatgaga gatttataaa tacctgcata   1140
cataaataca aacatcctat tatacatgag aaatcgtaaa tgcttgggca tcagaagtgg   1200
gagctgtgat cctagcttgg gggcagcaca gggtaggcgg ccttctctct gctttgagtg   1260
gcttctgggc gcctggcggg tccagaatcg cccagagccg cccgcggtcg tgcacatctg   1320
acccgagtca gcttgggcac cagccgagag ccggctccgc accgctcccg cacccccagcc  1380 gccggggtgg tgacacacac cggagtcgaa ttacagccct gcaattaaca tatgaatctg   1440
acgaatttaa aagaaggaaa aaaaaaaaaa aacctgagca ggcttgggag tcctctgcac   1500
acaagaactt ttctcggggt gtaaaaactc tttgattggc tgctcgcacg cgcctgcccg   1560
cgccctccat tggctgagaa gacacgcgac cggcgcgagg agggggttgg gagaggagcg   1620
gggggagact gagtggcgcg tgccgctttt taaaggggcg cagcgccttc agcaaccgga   1680
gaagcatagt tgcacgcgac ctggtgtgtg atctccgagt gggtggggga gggtcgagga   1740
gggaaaaaaa aataagacgt tgcagaagag acccggaaag ggcctttttt ttggttgagc   1800
tggtgtccca gtgctgcctc cgatcctgag cctccgagcc tttgcagtgc aatgtcccgc   1860
ctgctgcatg cagaagagtg ggctgaagtg aaggagttgg gagaccacca tcgccagccc   1920
cagccgcatc atctcccgca accgccgccg ccgccgcagc cacctgcaac tttgcaggcg   1980
agagagcatc ccgtctaccc gcctgagctg tccctcctgg acagcaccga cccacgcgcc   2040
tggctggctc ccactttgca gggcatctgc acggcacgcg ccgcccagta tttgctacat   2100
tccccggagc tgggtgcctc agaggccgct gcgcccggg acgaggtgga cggccggggg    2160
gagctggtaa ggaggagcag cggcggtgcc agcagcagca agagccccgg gccggtgaaa   2220
gtgcgggaac agctgtgcaa gctgaaaggc ggggtggtgg tagacgagct gggctgcagc   2280
cgccaacggg cccctttccag caaacaggtg aatgggtgc agaagcagag acggctagca    2340
gccaacgcca gggagcggcg caggatgcat gggctgaacc acgccttcga ccagctgcgc   2400
aatgttatcc cgtcgttcaa caacgacaag aagctgtcca aatatgagac cctgcagatg   2460
gcccaaatct acatcaacgc cttgtccgag ctgctacaaa cgcccagcgg aggggaacag   2520
ccaccgccgc ctccagcctc ctgcaaaagc gaccaccacc accttcgcac cgcggcctcc   2580
tatgaagggg gcgcgggcaa cgcgaccgca gctggggctc agcaggcttc cggagggagc   2640
cagcggccga ccccgcccgg gagttgccgg actcgcttct cagccccagc ttctgcggga   2700
gggtactcgg tgcagctgga cgctctgcac ttctcgactt tcgaggacag cgccctgaca   2760
gcgatgatgg cgcaaaagaa tttgtctcct tctctccccg ggagcatctt gcagccagtg   2820
caggaggaaa acagcaaaac ttcgcctcgg tcccacagaa gcgacgggga atttccccc    2880 cattcccatt acagtgactc ggatgaggca agttaggaag gtgacagaag cctgaaaact   2940
gagacagaaa caaaactgcc ctttcccagt gcgcgggaag ccccgcggtt aaagatcccc   3000
gcacccttta atttttgctc tgcgatggtc gttgtttagc aacgacttgg cttcagatgg   3060
cagctacatt tgatggtttg caaatgccgc cgctgttcca aacttcctac ggtccatatt   3120
```

```
gtttgatgaa aactttctgt taaaattgtg tcctttccgc ccaccttctg ctcccccttt    3180
agatagatac ggtataattg taggtacccg tatatggcat cattattcta gttccctgct    3240
gccaatacgc tgctaaaacg tcgcatcttc tctgtcactg gtttgggttt aatttatttt    3300
acgccctggg catccatcct tgtgtgttgc gcactcaagt gtgggagatt tagtcttccg    3360
aagttgtttt ccaaaatgca caatgaaacg caaaattagt gcttccaaag tggataactt    3420
ttgactatgg aattgttaga aaacaagaaa ctttaaggtt tatatattgt ataaacatac    3480
ccagtatgtg catccgatcg cgagaacgtt ggcgtctttt aggaaactcc gcgcacgcac    3540
tttatcagcc gctgctgcgg tggtggctcc aggagaaact caactgccaa ttgcagacca    3600 gtttttttt ttttaaacac agccacttat aattcttaag ctctttgcaa atgtttgttt    3660
aaaaaatgaa aaattaaaaa aaatctagta gtgtcaaacg catttggtca atttatttt    3720 gctttgttaa tattagaaaa cttatttatt attgtttgct accatttcta cttatcttga    3780 ttcattttt acgttttcta ctcgagatca ttttattta atttagcaaa gccaactgcc    3840
cttgtttaat gtattttgtt ttgcaaatga ttaaaataaa tgtgaaaaga agcctttttgt    3900 cacttattcc ttgagtataa ctactgaaaa caatttcaa atgaatgact ttgaagaatt    3960
gagttaagtc ttctattcaa tgtcattat gcgatcttac agttttgaag aaaaatgttg    4020
taaacttggt gccttcaggt agtatcaaaa ccccttcaaa gaaaagcact caagtcaata    4080
attaaattgt gagataaaac ttcttccaaa tttgcagcac agttttgcct ctttgatggc    4140
caggatcttc ccagtcttct ttactccttg ccccaacaac atctgcaagg ggggaggcc    4200
```

<210> SEQ ID NO 228
<211> LENGTH: 6288
<212> TYPE: DNA
<213> ORGANISM: Homo sapiens
<220> FEATURE:
<223> OTHER INFORMATION: OGHAv1.0 microarray feature identifier
       ha1p_87540 genomic DNA region

<400> SEQUENCE: 228

```
aattcctcct ggggtgctgg gccggctctc tcccctcagc cctgggctct tacctctatg      60
agctggtagc cttgcttgca ggtagcaatg aagtagtcac ggaactggta ctgaggctgc     120
aggttctgga tgatggtgaa ctcgtctagg gtcttgggct gggggcactt gatgactgtt     180
ggggagacca gggggcatat ttatttcaga gccacttgtc cttccttctt ccccccttt     240 ccccattgct ggccatcgag ggaggcctgc agggagcctt actctcggtg gtgtagcgca     300
gcttccagcc ccggctgtcc cccgactcat ctgtgaagaa cagcagatcc acagcattgc     360
tgctggtgtc gaggtcgggg ggcctttgct tcccacagaa ctcgccaatg ttcttcccgt     420
tggcatagat ctagtagggg aggagggttt ttttttttca gcttggacgt ttttacacag     480
ggccaactgg gtagtagcct ggtggccagg tggtggtgg tggtgatgaa atcctgcctt     540
atgtgtgttt tcaggggaag gtgaaaaggg atccccatga cccaattcta gttgtgtggg     600
aacttaccca gccatgggt gatgttggcc gttcctgccc cagctggcca ggggatccag     660
gaggaagttg ggacaagagg agccaagtgc agacagaagg ggaggaaggg gtctttcagg     720
ggtaggacgg ctgtacctgt agctggtcat aggggcagtg tacttgctgg tggtcatcaa     780
tatcaaaagg ctccaggaac ttgaggtgca gggtgaggcc ccgctccacc cggatgctgt     840
agttgcagcg caggtcaggg gggtaggacc gagggtactc caggctggag atgtagcctg     900
atgcctccgt gtacagctcg ctgctgcact cagctgtgag agcagagcca cagggcatta     960
```

-continued

```
cgggggactc cagctggccc agcaagccct ggctcaaccc cttcccctct gctacaccac    1020
tctggctcac cctggcagga atgcgtgtct tcctgaagct catagcctgg acggcaggaa    1080
cagaagtagc ctccaacgta gttgtgacac aggtgctggc actgggctg gggatcctcc     1140 tccctgatt tgctccggga agcacattca tcaaggtctg gaaggcattc aggaaggagg     1200
gttaagcttc tgctgggaga cctgagtagt ggctctgatc ttagggaggt cactcaccag    1260
agacctaaag acaaaggcat ctttaggcca cctggacctc caggcctctc caatgctctc    1320
tggggactgc tccatgggga cagagcccag gttgacaggc ctcgttagga aaagctctct    1380
cgaggggagg aacaaggaaa gccaggcttt cggcttcttt gcattcaaga ttcccttct     1440 tggccccca ttcaatatgg ctgaggtcag agaaaaggga tccctggggg gctactcacc     1500
cacagcttgg tagtaggcca ggaagccctt gtagaacatg atggtcccat tctcctcgtt    1560
ggagaagtct gtgtggaagg tcagcagcat cttgttccct tgggacataa attccttctt    1620
tcccgggggg ttgcccagtg gagaacccag ttgcccacag aacctcccca ggcttttctt    1680
atcagcagag atctggtgga agaaggacag tgggtaggaa gaagatctgt tgcggagtgg    1740
cgcacgtggt ggctcagtga tggtcctcct tgtctcgccc agagtgcatc atgcaccgca    1800
atggctctgg ctggtcacta cctgctgggc tcagctgctg caaacttccc catgtgactt    1860
tcagctgttc cctgagtctc ccactgattc actctttgcg tgttgtcctg gactgggtac    1920
ctcacccttt ccctgttttc tgctcctctg gcaggtttca ggtccttctc catccccacc    1980
acctcctatg gcctgttccc ctgggtcct ggttgtctgt acccagcctt tacctgcccc     2040
tcattcccag agctcagaca gctccgcttt attttctgtc ttcagattcc acctcagcct    2100
aatcaaacca ttcacacctc gagtgcctcc tgatgccctc ggcggaacat gagccctgaa    2160
gcccacccat ctcagtgtca gcaggcactg cctcgtccct cttccttcct cctcacagcc    2220
tcctcaacct ctccttgact ctgccagcaa acgccctccc ccaacactgc acactcgcca    2280
agtcttctga gccggtaaga cgtgccattg tcatgtaatt cacgcataat ctccaggggt    2340
ctcctgggaa tggtagttgt tggaccttcg caggctctgc ttgagccctg aatctcattt    2400
ttactggata gagaaagaca ggcctgggaa ggtacccttg gttgccacag aggtgagggt    2460
tctgagcaca ctgtccttgc tgaaggctat tcctgtgctg ccagagccca catttctcct    2520
cctcatgtcc ctgtgttcct gttgaagcag gcagccatgt caatcatttc cttgagaca    2580 gggaagctga ggcacagtgg tttcccaaag actctcagct agacagcaga tggggaaggt    2640
tttcctgact cagtggatgt tgaatttcct gagtgggtcc tgtccccttc cttctctgtg    2700
cttctcccct cagtgctcac cgagggcctc tacaccagtg agcgcccatc cagggcatcc    2760
ccgggctctc agagaggccg ttggccatca gctcttgtgg ggctgggctg tgtctggggg    2820
tgtgcatgcc atacagatcc cagatcccag agggcccagt tttgtctccc ctctgcccgc    2880
ccatcctgcc cctaccttga cataatcata gaagcagcct tcagaaggct ccaggtcaaa    2940
ctgctggaag acgagcttca ccctgtatcc cgtgggact gtgatcacag tggttgtttc     3000
aaagttgttg gggtaaggct tggggaacag aggggaagtc acctccccaa ataacttctg    3060
agggatggga atggagcctc ctgccctgca gaacagggcc ggcaccagga ggtacaagag    3120
ccacctgcca aaacaaaaga gagtatctgg agctggaggg gttcagcact cttgccatgt    3180
gggcagtggc tgtggcaggg gatgagacgg ccataccact gggcattctc ctctctgccc    3240
accctgaacc tcacagacat gttctcagca ggggtgcgtg ggtggggagg atggcctgtg    3300
cagctgctgc atcgggtcac tctccagggc agtgtccagt ccagaggcca ccacactccc    3360
```

```
ctcacactcc ctttccagcc tcctcccctg cccggacgcg tccctcccct cccctccag   3420
gaataggact ggcttgggac cagttaatgg agggtgaggg tttccacccg tgggtctctg   3480
aaagggctcc cacaggttca gcaagagcgt ctgggagaaa ccatctgtgg agtgggggac   3540
acaggcacag agtgtcccgt cctgggcaag gggtcccctc ctctcgctgc tccctgccaa   3600
gagcccagag gaagaaagg accatggcat gagcatctat gtatgaagtc tcctctgatc    3660
cctaggagga gggatggggc gtgtgttgtg tgtgtccacg cgtgtgcaca gtggaactga   3720
tgaggtgtgt gaagagagaa gggtgttcct gtctccctga attgcctccc atgccctggc   3780
ttctcccctg gcttctccct cccacctggt tgcccatcac ccttactcac atttctcaag   3840
gcccgtgttg aatcctgggc tctcccgaca gcgtcttcgt gcactgtgtg cagagggagc   3900
ccgcgtcatg cacagcaggg aggggagggt tttctgtgga gtggaggggg gaccattccc   3960
ggaggaatgt tggagggaat gaactatttg cataaacaaa agatctgagt ttccacttta   4020
atttagtttt ggttttgaaa tccctgtttg tggtgccacc tgctggtcgg tgagggaaag   4080
ggctaaggag acgggagtct ggcttttag ggcccgggga gccttgggtt ggaggcccag    4140
atgtctcagt ctctaaatct gatcagcttc tcccttcttc caagactttc ctggggctg    4200
ctgctgtgtt tacaaggttc ctaccaaagc agtgggagac cacaggtggt ggtgaattct   4260
cttttctggg ctgtcctttc ccattgaccc tgttcttcct gccctcattc agcccacagc   4320
cctggtccaa gaatggcccg ggtttcaatg cccaggacgt aatgatagga acactggggc   4380
agaggagggt gtgtgggagc gggcagagga gagaggagct tggttgcctt ggggccctgg   4440
cctgctttag ccatgaatga cacttggaca tagaatagg ttggccatgt cagggcaacc    4500
ctaaatcagc cctgggtttg agaccctctg gggcggctgc ggagggggta aaatgtcccc   4560
atctccttag catctgctca acacaactgc cagggctgaa gctaaggatg cgggtgtgga   4620
gcaagaggga ctcggttttt ctgagatgaa gccaggcccc tgggagggag gagggaccct   4680
agtctctcct gtccatcagg ccatagtgtc ctgctttaaa acttttgctc ttggccacgt   4740
gtggtggctc atgcctgtga tgccagcact tttcgaggcc agggtgggaa gatctcttga   4800
gcccaggagt tcgaaaccag cctgggcaac atagtgagat ctcgtctcta aaagttaaaa   4860
taaattaaaa aacaatttca ttgtttttgg aaggctttct tcatcaactc tccatggcac   4920
caaatatctg atggcacttc atcccacgga ggggcttggg ctgcagagca ggactctgcg   4980
ttcttaagcc tttgtaggct gttctgcttg tttcccttat tagatgaatc cctccaacct   5040
ccacccttct gcccccaccc ccgttcatcc atttatgggc tacctgttta atgtgcaaga   5100
cactttccca ggcaatagat tgcaagaatt cacagagctg atgcagttcc ccatcaggca   5160
gtgaccacat catcagtagt tagacagcag gcacacagaa ggtgcaagat ccaccaacgc   5220
ttggagggtt tctccagcag gcctgtgtgt cagagctgag gactgaacct aacggagggc   5280
tggtctgtga tgggatcagc atatgatcca cagccttgtt agatcaggaa agacaaaaga   5340
tgggggagaa ggaaaagcac cagatcagag gacgagaagg aagggaaatc tcgtctaaca   5400
aactgcacat taatatccta gcagcagttt gtgtgtgtgt gtgtgtgtgc acgcgcgcat   5460
gtgccgtatg ttcataatgg aggcagaggg aacaggtaag gaggtaagtc ttagctgaag   5520
ctcttccgtc catcctaggg attctcagtt ctgcattggc attgtgcaac acgcttggag   5580
agcggcaaac ctggatgtca ttagctcagt cccagccctg tctccactct gcccaaccat   5640
tcaaaataac cttactcac acattttgt tatgtccttg actttgtttt gtccttgact    5700
cataccaaga aggaaaaaaa tgccatatga aatgctgctg catttgtttt aaaacaatta   5760
```

-continued

```
ttgaggatat agtcggttac agtgtttgtt cctttaagga tttgattctt gggaaaaaga   5820
tttctctctt aaagtagtgg taggtttcc tctgtggata tgtctctatc gctagctcat    5880
ctatctccat caagtctatc tcttacctcc ctctctctct cattgtcgat atctctatct   5940
ctagacagag acagcgatgg agatgtagag atatagatct agacatacac atataaatat   6000
aggtatatat atatatttt tgccttggca gggagaaact catatcattt tttgcaatca    6060
taaaaataag caaataaaa taaaacatt tcatgctcat taaacaaatt ttagccaata     6120
gagaatagtg gaaaaccaaa cagccaaaat cttatcaata aaaccacctc tgtttagtat   6180
tttgagagaa ttattattat attttggag atggggtttc actatgttgc ttaggctgga   6240
cttcaactcc tgggctcaag cgatcctctt gcatcagcct cctgagtg                6288
```

<210> SEQ ID NO 229
<211> LENGTH: 2800
<212> TYPE: DNA
<213> ORGANISM: Homo sapiens
<220> FEATURE:
<223> OTHER INFORMATION: OGHAv1.0 microarray feature identifier
      ha1p_110107 genomic DNA region

<400> SEQUENCE: 229

```
tataccctga tcagggtggg ggtcatggtg gtcatctaga cattctatgg ctgggtggtg    60
gtggagggca ctcaccttgt gaacactcgg acatggtgaa ttggcattgg cattgctgtt   120
gaaggacaac tcagccgtgt tcttagccat ggccatttag gcctgttctg atgcagggtt   180
ctgatccaag gtaccagtgt ggtccctcag ggaagtactg gggatcgtca cttatgcctg   240
ttctggacat ggtcaccgag aactgtcctg taggcattca cttaggaatc attcgaagtg   300
gaattgctcc tggatacgtt ctccttgtac tctgtttcct cctccagtg tctctgtgtg    360 aagaagccct cctcactcag ccctcggcga ccctctggta ccctggacag ctccccgggg   420
agcagtctac cgctaggcgg cggctgctaa gagaggaacc ctcctgacgc ggagtctgcc   480
gctccggggc tcgctctccg gcaggcccgg ggagaggtgg ggtgacaatg ggttggggtg   540
cgcgcgtgcc tcataggtgc gagacagagc gagccgccgg ggtgtgagtc agcgcgctgg   600
gggctaagaa gctgggtgaa tagtcacgga atctcactca cgctcggctc ctccacccat   660
cccgtctaca gcgcgtgtcc cagtccaggg cgtgcgtgcg ctcggtgtcc gattccgggc   720
tgtgtgtgtc catttggcga gatgtcgaga gcgggggag tgtccttgtc ggtgtatctg    780
ggcccaggtt aggggacttc tcctcccac cccgcgtgg gtgtgggggt gtgtccgggc     840
tagggcgcgt gtgcttctgt gcctgtgcgt gcgtgtgcgg gtcagggtgg tgggaccgcg   900
catcagggca gggtgcctgc gtctgcgtct ggtctgtct ggtctgcatg tcggcgcgat    960
ctcgacctgg attcgtgtcc ctggatgtcg agaggccagc gtggtggggg tgtccagcct  1020
cccggaggag tactatgcct tgacaccttc gtttcaccgc cccaaagctg gcctggggct   1080 ccgtaggag tggcctgcat ggggagggcc cgcgtgctgt gtttctggga ggggtaagag   1140
agtgggggcg caggggggcgg gccaggtccc tgggcgcggc gcgggctcgg ggaccccgcg  1200
cggctgacgt caggccactc cttaaataga gccggcagcg cgctccgctc ggcatttccc   1260
gaagagccag atcgcggccg gcgccagcgc caccgtccgg tccacccgcc agccccgcaca 1320 gccgcgccgc cgccgagcgt ttcgtgagcg gcgctccgag gatcaggaat ggggcttcgg   1380
gcgctgggcg cgctccgaac ccggcgcacg taagagcctg ggagcgcccg agccccgcgg  1440
ctgcccggag cccatcgcc taggaccggg agatgctgga aatgcaaccg cctgttcccc   1500
gaggagccgc tgcccccggg acccctggc actgtgcgca ccctggtcag cagccccgcg   1560
```

```
agaagacggc gcccccaacg cccgacccgc gtggccgtgg cagcgccacg cgagccctct    1620
aggcgaccgc agggccacag cagctcagcc gccggtgccc cctcggaaac catgacccc     1680 ggcgcgggcc catggagcca tggcctatag ggtcctgggc cgcgcggggc cacctcagcc    1740
gcggagggcg cgcaggctgc tcttcgcctt cacgctctcg ctctcctgca cttacctgtg    1800
ttacagcttc ctgtgctgct gcgacgacct gggtcggagc cgcctcctcg gcgcgcctcg    1860
ctgcctccgc ggcccagcg cgggcggcca gaaacttctc cagaagtccc gcccctgtga    1920
tccctccggg ccgacgccca gcgagcccag cgctcccagc gcgcccgccg ccgccgtgcc    1980
cgcccctcgc ctctccggtt ccaaccactc cggctcaccc aagctgggta ccaagcggtt    2040
gccccaagcc ctcattgtgg gcgtgaagaa gggggcacc cgggccgtgc tggagtttat     2100
ccgagtacac ccgacgtgc gggccttggg cacggaaccc cacttctttg acaggaacta     2160
cggccgcggg ctggattggt acaggtaagg accaggagct ccgctccgtg cgccgggtct    2220
ctgatcgctt ccattgggag agccatccgt ctcttgtgtt ttctctttct tttaacccaa    2280
ctcattgtat gggttcaggc tgacacacag ggccatgggg ggctatagca gaatttaccc    2340
agaacttccc agtgataatc tagacgggca gtttctggaa ctgcaaaggg cgttccctcg    2400
tcactggagt cgttggaaaa ggattatctc cagtcaaacc taagtgccag ctaaagggct    2460
aactccctct gtgaccagcc cttagggtgc ccaaggaagg acaggcgag gacctgtgct     2520 gcctgaacac ggcaccatcc taaccctctg taggtctttg ctggtaccca gcccctgaag    2580
gaccctgaga aagataaggc agttcagaga ccccttgcag caaggctctg tttgggaaag    2640
gtccccagag ttcaggccaa atgacagtgc atcgccagag gtctccagta agaaagatgc    2700
cttagggagt ctcaatctca aacccaggta tttgctgctg tactggggct gagaccccca    2760
gtagctctgg ccctggtagg tggtcttga gtagtggaaa                           2800

<210> SEQ ID NO 230
<211> LENGTH: 2500
<212> TYPE: DNA
<213> ORGANISM: Homo sapiens
<220> FEATURE:
<223> OTHER INFORMATION: OGHAv1.0 microarray feature identifier
      ha1p_89799 genomic DNA region

<400> SEQUENCE: 230
tctctagaac ttctggagaa aaaagtaata aagctaccag gttaaatgac tgaaattcct      60
gagagaaaac aacatgtgtg tgtttctcta gaaggggc ccaatactga ataccaggaa       120
gtcctatagt aaatggaatg tgactctatg tgggatccgg cgttcctatt tcatccgaat     180
gcatgtctgc tgcttcagtg ggaagggtgc ttgcacacca ggtacccact ccctggtgtc    240
atgtgctatg cagtccaaag acagaaccag gaatggtgag cccatgagcc tgctggaccc    300
agcccctccg aggtccggag tgacaaccag tgccgtattt ctagatcaaa cctgaacccc    360
tcctacaggg aaaagatttc caggggattt tgaaagttcc aacattttac agggaagaag    420
gaagataagc aggatatgaa agaagagttc atgttataca gccctggctt ccactgacgc    480
taacactgga ttcagctttt gacactgata atctgttgcc accaaatgga aaacgtaaac    540
aagatattct aagtgtggtt agagaatatg caacacaagg aacaagcaga acattcttct    600
ctggaatctg acataatgga ctgtactttc acagacagca ctgatgttag atgtacgtga    660
aataggctaa actgaaaata agaaaggctg aggcagagag gataatatag ctccagccta    720
tctcccagca ccttgttaat ttctctcaat ctccagccac aaatccgaga cacaacgctc    780
```

-continued

| | |
|---|---|
| ttcctccaaa gaggtcgcgc cttctctgtg gtggttctca gggatccgcc ccagctcctt | 840 |
| ctccgttccc agcccacac actgggatca ccaggcaccc aagatcccac ctctcaggtg | 900 |
| gtatcttcag cgcaggctgc cactcagccc ccctccaggg atctggggca gaaggcgaat | 960 |
| atcccagagt ctcagagtcc acaggagtta ctctgaaggg cgaggcgcgg gctgcatcag | 1020 |
| tggacccca cacccaccc gcacccaag cgctccaccc tggggcggg gccgtcgcct | 1080 |
| tccttccgga ctcgggatcg atctggaact ccgggaattt ccctggcccg ggggctccgg | 1140 |
| gctttccagc cccaaccatg cataaaaggg gttcgcggat ctcggagagc cacagagccc | 1200 |
| gggccgcagg cacctcctcg ccagctcttc cgctcctctc acagccgcca gacccgcctg | 1260 |
| ctgagcccca tggcccgcgc tgctctctcc gccgccccca gcaatccccg gctcctgcga | 1320 |
| gtggcactgc tgctcctgct cctggtagcc gctggccggc gcgcagcagg tgggtaccgg | 1380 |
| cgccctgggg tccccgggcc ggacgcggct ggggtaggca cccagcgccg acagcctcgc | 1440 |
| tcagtcagtg agtctcttct tccctaggag cgtccgtggc cactgaactg cgctgccagt | 1500 |
| gcttgcagac cctgcaggga attcaccca agaacatcca aagtgtgaac gtgaagtccc | 1560 |
| ccggaccca ctgcgcccaa accgaagtca tgtaagtccc gccccgcgct gcctctgcca | 1620 |
| ccgccgggt cccagaccct cctgctgccc caaccctgtc cccagcccga cctcctgcct | 1680 |
| cacgagattc ccttccctct gcagagccac actcaagaat gggcggaaag cttgcctcaa | 1740 |
| tcctgcatcc cccatagtta agaaaatcat cgaaaagatg ctgaacaggt gagttatggt | 1800 |
| ttccatgtac acaggcgact ggagccgttg gtcagaaata ctggcatgtg cccctaaaa | 1860 |
| ataaaatcag gaaaacccag gggttagttg aaggactaga aattgggatt attgttttca | 1920 |
| caattaaggt ttcctttacg ataattactg ctctggtgcc agaggatatt cccaatgcct | 1980 |
| ggcgtcccca ccctggttct tccttcgttc caatgaatgt aggtaaaact gccttcattt | 2040 |
| gaggcccagt aggacaaaca gcaacaggtt ctggctgttt ttaatccaat agtacagtgg | 2100 |
| agaccaccgc cccaccccac ccccattcct aaaagagcat cccaagctta gaggtccctg | 2160 |
| ccacacagca cagctgtcat aggcagtagc cacttggttg ccaggctggg gaaactgcat | 2220 |
| tcggaaaact ctagaggctg gaggagcagg gcaggagaag agtgttgtgc aatcagcttt | 2280 |
| cccgagcacc tactcagggc acccattttc tcattgcagt gacaaatcca actgaccaga | 2340 |
| agggaggagg aagctcactg gtggctgttc ctgaaggagg ccctgccctt ataggaacag | 2400 |
| aagaggaaag agagacacag ctgcagaggc cacctggatt gtgcctaatg tgtttgagca | 2460 |
| tcgcttagga gaagtcttct atttatttat ttattcatta | 2500 |

<210> SEQ ID NO 231
<211> LENGTH: 2200
<212> TYPE: DNA
<213> ORGANISM: Homo sapiens
<220> FEATURE:
<223> OTHER INFORMATION: OGHAv1.0 microarray feature identifier
      ha1p_45173 genomic DNA region

<400> SEQUENCE: 231

| | |
|---|---|
| tgttctgaaa catccggtgt catccaagtc caaaattgga cagcttttt ttcagttctt | 60 |
| cctgtaacat ttggcagtgt tggccactct ctgcttcttt ggcaagaatc tcagaaaaca | 120 |
| ctaataactg ctccaggcag gagcctggaa gaggttacca agctagagaa ggaagcaaca | 180 |
| gcatagcttg ctaagggcaa acagcccaga ggaaacccac ggctctggtc aatcctgttg | 240 |
| ttgattgcta gatccagaga ctgttgtaga cctcccagtt acagtgaggt atctgacaac | 300 |
| ccctcacaag gttcttgaag ctccgtggtg gagggtatct tggataaatc cacagagaca | 360 |

```
cattcaagag taaattctcc actgttggag acctcactca ctctgtttgg tctccaccaa    420
agacacggtt tttaattcat ggagctgcac tacaacagct caagaactcc cagccaaagt    480
tttagttttt ctaggaacat aaacgagcca atagtgtgga atcggtgat taaaaacaaa     540 cctcgcacat tttaagacag aattattaca agtagcatgt acaaaaggaa aataatagcc    600
tacatttagt tcttctaagc ttcattccac aagagattga aatcgaagta ttctgggctg    660
gcacacgata gctggaacat catatttat tctagaaaca catttgcctt ggcaaagaag     720
agcgtgccta gaggagtggt caggatagtg agggatctgt gatccttcgt tctgaatcta    780
gaaaagtcac tggatatgcc cctccccgc ccccaacac ggtcttatgt tctgaatgta      840
gaagtcactg gatgtgctga cacacacaca cacacacaca cacacacaca cacacacaca   900
cacacacaca cacagagtct gtggcctctt tcccaggcat tccaagtcca gcaagttcgc    960
agggagctgt cagtccgtcc aggaaggccc gggcctgggt ttgcctcttc aagcagctac   1020 tgcagggggcg tggggagggg gcataagaga ctttggactt ccttttgaga cagtagaaag  1080
cgttacatcc agaggcgaga ttctagcctg gggtccccgc cttcccggcc tcctcttcct   1140
ctccctctga ctccctttcc tgtgcccctc cccctgcctc tttcccggcc agagtccagc   1200
cttaacccgg gcagagggcg gagtcccgtt aagggggtgt ggggaggagg cggggccagg   1260
gcaggggcgg ggcagagccg ggccaagctg ggcgggtcat gcgccctggc cttcgcgcat   1320
ctcccaggtt agctgcgtgt ccgggtgcta ggctgcagac ccgccgccat gacgctgcgc   1380
gcggccgtct tcgaccttga cggggtgctg gcgctgccag cggtgttcgg cgtcctcggc   1440
cgcacggagg aggccctggc gctgcccagg taagggggcc cagcgccgcc gccgcagtgg   1500 gtcgggcct caggaggcag accgcgctgg gcttgcagcc cagcttttcag attgctcctg    1560 tgccggagcc ctgcgaatca tgcgaatcat gaaactgaag acctggccct gaagtcccag   1620
tgcatatgag gagatccgtt gtcttttctaa atgttcataa ttaaacgttg ccaaggtctc   1680
caaaattgct ttctgtgaac ttttccaaaa gggagaggag ttactcatgg agctttgtgc   1740
ttctgctgcc tcctgtctaa tggggtggcg cttaaagatg cgagccgaga ttcaggagag   1800
aagaaagttc tctccccagg tgtgggttgc atgcttactt gtgtaatagc aaactgcagc   1860
aaccgcccaa agccacatca ctgggaaatg gtagatgggg tgtgcagagt gagagctcag   1920
ggacttggga aaacacctgt tctactacat gaaaaaacca ccccaccaga atctgaagct   1980
atttatacaa tatggtttca gctatggaaa aaggtacat gcagaaaagt gcctgaaaga    2040
aataggccaa agtacatcaa atgagattag gaataatgta atgattttct ttctctctct   2100
cttttttttg tgttttttttt ttttgtagtt ccaacttct aaatttataa acaatgtatt    2160
attcccacat tcagaaagga gagaagtata cttatttata                         2200
```

<210> SEQ ID NO 232
<211> LENGTH: 8800
<212> TYPE: DNA
<213> ORGANISM: Homo sapiens
<220> FEATURE:
<223> OTHER INFORMATION: OGHAv1.0 microarray feature identifier
      ha1p_80771 genomic DNA region

<400> SEQUENCE: 232

```
tcaaaaacta ctaagaattt taagagggca atggcagagc attaaaccag gcatcagccc     60 tttcctttt tttaattttt aaaatattta tttagatttt cttttttgtta gtaattaaat    120 ctttcttctt cttcttcttc tcctcctcct ccttctcctt cctctcctc ctcttcctct      180
```

-continued

```
tcttcttctt ccctcttccc tctctcctcc tcctcgtcct cctcctcctt gaaacagtgc      240
agtggcacaa tctcagctca ctgcaacctc cactttccat gttcaagtga ttctcatgcc      300
tcagcctccc gagtagctgg gattacaggt atgtgtcacc atgcccagct aattttgta       360 ttttagtag  acactgggtt ttgccatgtt ggccaggctg gtctcaagtg atccgcccgc      420
ctcagcctcc caaagtgctg ggattacagg tgtaagccac cgcacctggc tcttttttg      480 ttttgttttg ttaagtataa aacctcacct ggaagcacca gcccttttctg agtgtgcggg     540 cctgtgccac tgcgtgggtt gcacgtccat taagctggtc tacctgccat ccacttcctc     600
aacccaatgg cattctcctg tttcttagat atgtaccaac cggttttctg ttttatctta     660
gcatggctca ctactcctca ttagggtctc tcagcgaagg gggtagcctt tttttttttt    720
tttttttttt ttgagacaga gtcttgctct gctgcccagg ctggagtgca gtggccagat     780
ctccactcac tgcaatctct ttggttcaag cattctcctg cctcagcctc caagtagct      840 gggattactg gccacgcccg gctaatttt tgtatttta gtagagatgg gtttcacca        900 tgttggccag gctggtctcg gactcctgac ctcaggtgat ccacccgcca ccactccagc     960
ctgggcaaca gagtctgaga ctccgtctca aaaaaaaaaa aaaaaaaaa aaaaagtca      1020 tactggcata gagtgaaccc ctaatccaat atgactggta tccttataaa aatactttt    1080 ttttggagac ggagtctctc tctgtcgccc caggctggag tgcagtggcg cgatctcgac   1140
tcactgcaac caaaaggaga cattttgaca tggagacata tacagggaat atgccctgtg   1200
aacatgaaga tggccatatg caagcccagg agagaagcct ggaagagacc gtttcctcac   1260
agcgctcaga aggaaagaac cctgccaaca tcttgctttc agatgccccc aggattgtca   1320
gacaataaga tctgttattg acgccaccgg gttggtgata cttaggtaca gcagccctag   1380
caaacgaata caccccatg agaactaagc tccctgagag cggtaagctg ccttgtcttg    1440
ctcacagctg acaagaacac gcctgtacgg tcacttagca cctagtactg ccatttaacc   1500
gtttcactag tatgtatgaa ccggagagcc tgtcaaggga agagctgaat cttttatctt   1560
ttgtaacgac tacccagtga agaaaccgc gggtatgcaa taaaaacctg ttgaatcgat    1620
taaaccattt cccttatttc cagattttg cggaaagcgc cagtaggtga aatatgtgcg    1680
gactgatgag tcaaagctct tattccctgg actgcattaa tacccacgac gtgcttttcg   1740
ctctccagac aaagagaccg gtacttggca ggtccctcaa gtgggactca aaagaccgaa   1800
ccgagctgca gccttttcgct agcactggtc ctcgcccctt ttggcatctt ggtacttgta  1860
gttttgtcca ctctatctttt acccgaaaag ccagcgctga ccacaact cccatcaccc    1920 tgcgagcacc agcgccttca gagcgcatcc tccgaggggc accagcgcca ttgaccaccc   1980
tgctggccga agggcccgcc ttcccgaggc caggcgctcc cgcgattggc cagccgcccc   2040
gcctctcatc ggagggcgcc aggtgaatga aaggggggcg tgtcggtgcg cggtgctccg   2100
tggctgcgct gctggaaccc gctggaaggt gagcgcgaag aagcgggttg gcgctgccgc   2160
tttcgttggt ttggggagga ttcctagcac ccgggaggct ggctggagat tggggttagc   2220
gggcagggtt gccccactc agtcatcctc cttcggaccg cttggccctg caactcctg    2280 ggacctccgc cccgcgagcc cttctagcgt ggggagggc aggcgcggcc gtgggccccc    2340
agcttccctg tcattgggtg tcctccgcgt cgtccagccg ggggtcgcgg cgccgactac   2400
ttccacggtg aatggtgccc aggcgtgggg ggctcggcca cactggagaa gtgccagcgg   2460
cagcgatggc cactttgtcc gcgggaggcc atgggagggg ctaggccttg ggtcccacc    2520 ctcgggggcc gtgccctgta gctggttctg gtggcctctc tgcaggtcgt ctgatgctgg   2580
```

```
acgggggagg gtctgtcttg cgagcagttt agatgcagtt gaccctgaaa ttcttcgtat   2640
ggaaatggaa acttctccag tgtccttctc ctccgatcca tgcctaaaag aaaggagtga   2700
cttccccaac ctgtcgcatc gtgtcctgga gggtttgagg aggccggtta gcatagtggt   2760
taaggatgtc aacccgggag tcagtcggat ctctgttcta ttactaactt ggtgatgtta   2820
tctgcatctt tgaatctcag ttcctcctct gaaaagagg atgtagttag agtatctgtc    2880
gtactggatt attgtgaggt gaaaactaat gtgcttgtaa aagccaggca tggtggcgcg   2940
cacctgtagt ccctgctact cgggaagcta aggttgggag gatctcttga gcccaggagt   3000
tccaggctgc attgaggtag gatcgtgcac tccaacctgg gcaaccgagc aagaccgtgc   3060
cttttaaaaa ttttaattta aaaagtaaaa tgaatatgct tgtactttgt acagtgtttt   3120
ataaggaata gtgcttaata tttactaaaa ttgaggagca ggttttttgtt attctcaggt  3180
tggtgggact ggaggagtct tgtcagaaag ggtcggaggt ggaattcaag gctgcttttg   3240
gcctctgaac agagacagtt gtgtgatctg gctaggactc cctcaagggt atatgagagt   3300
ttgtattgca ggtagttgtg ttggcatctg ctgtctcctg gaggacaggc actatacttg   3360
gttcatttttt ctattcctgg catcttcctt gtgtcaggca ttgtatgtag ccggtaaccg  3420
ttgaattgag ttggaaccgt gggatggttg ggaggttccc tgccagagtg cggataaatg   3480
tgcttctgag agcagtctgc cctaagagct gctcttctgg gataagtggt gatcctcagc   3540
acttcccggg gcagcagagc acttcaggca aatgggggtg atataaataa atatttacac   3600
aatatatacc aagtacagga ttggggaaaa ttttgaagaa atactatac ggatagactt    3660
ttgcaacgtc aggaagtaga ataaaaataa ttgcaataga ataaaaaata atttcagtaa   3720
gaaagccaaa agaaattggt tttaggtgct atttctggaa aggaggcttt tccagtgaaa   3780
gacggaagtg ccctgggaag agcccctata gatcagacca tactacaagt taagaagtgt   3840
tgtgcgtact tacatattta tctacctggc ttaccaactc cttacccctc tgccctgcct   3900
cctttttttc ttagttaaca agaaaaaag ccaaggcaga aggatcactt gagtccagga    3960
gttcaagacc attgagacca gccagggcaa catagtgaga ccccatctct acaaaaaaat   4020
gttttcagaa ttagctgagt gtggtgctgc atgcctgtag tcacagctac ttgggaggct   4080
gaggtaggag gattgcttga gcctgggagg tcgaggcggc agtgaactgt gatcatggac   4140
tgcactccag cctgggtaac aaagtaagac cccgtctcaa aagaaaagaa agcaataca    4200
tgcacatagt aaaacattct atcagaaagg tttaaaatga aaggcgaaag tccctccaca   4260
cacttgtttt ttttttttt tttgagatgg agtctcgcac tatcgcccag gctggagtgc    4320
agtggcacaa tctctgctca ctgcagcctc cgcctccacc gcctctggg ttcaagtgat    4380
tctcctgcct cagcctcccg agtagctggg attacaggtg cccgccacca tgcccagcta   4440
attttttttgt atttttagta gagacggggt ttcactacgt tggccaggct ggtctcgaac   4500
tcctgacccc aggtgatcta cccaccttgg cctcccaaag tgctgggatt acaagtgtga   4560
gccaccacac ccggccccaa gtggatttta aacttggttt atagtttatc tactaagcag   4620
ttaagaaatg aatattcctt ttttgcttaa caaatctatt ttgtccaaag cactctgcca   4680
gatactgtaa gggatataaa attgaataag acatggctca tgctttcaaa gggcttgtag   4740
ttcattgaca gagaagggcc aggacataaa taataaacag gagttaacca agggtagtgg   4800
aatcagtcag ttaggagtct cccagttgca tgaaatagaa acccaactc agaggccagg    4860
tgtggtgtct cacacctgta accccagcac tttaggaggc tgaggggggc agatcacttg   4920
aggccaggag ttcgagacca gcctgggcaa catggcaaaa ccctgtctct accaaaagta   4980
```

-continued

```
caaaaaaaat tagcctggcg tgggggtggg tacctgtagt cccagctact cgggaggctg    5040
aggtaggatg attactttag ccagggaggc ggaggtcaga gtgggccgag atcacaccac    5100
tgcactgcag cctgggtgac agagtgagac cccatccccc atctcaaaaa ataataataa    5160
taatatttaa aaaagaaaac ccaactcaga ccagctaaac caaaaaggaa cttaattggc    5220
ttctggcact gcttgagttg gggctccaat gttgtcccca ggctccatca gcctgagctg    5280
ggctgtcatc tttgttaggc tgacttccct ggtggtatgg cagcaacatc cctcacatcc    5340
tgcatcccac agagcaaaga gtgctctttt ttgaaattcc agcaaatgtt tcattgcttt    5400 tcattgctc tgaaaactac atggccatct ccgagccaat cactgtggtc acagggtggg    5460
atgccttaat tttattagcc tacattatag cttacacacc tggtgcttga ggatggcacc    5520
agctttatgc aaagcatgtt ggccaagaat ggggaagga tgcttccatc aaagccgaaa    5580
aaaggcacta gaaccaaaag aatggggaat gcatgctggc tagcccaaga atccaccaaa    5640
tacttcagta taatgatgat aaaggggagac cagtcttgtt cgtgaccagc ctgggtaaca    5700
cagtgaaacc ccatctctac taaaatacaa aaaattagct gggtgtggtg gcatacacct    5760
gtaatcccag ctacttggga ggctgaggca ggagaatcgc ttgaatatgg aaggcggagg    5820
ttgcagtgag ccgagatcgc gccattgcac tccagcctgg gcgagagagg gagaatctgt    5880
ctcaaaaaaa aaaaaagacc agtctcaaag ttttgaattg ggacactgga ggctgggtgt    5940
ggtggcttat gcttgtaatc tcaggacttt gagggtgga ggcaggagga tcgcttgagg    6000
caaagagctt gagaccagcc taggaaacat accaagactg ccatctctac aaaaaaaaat    6060 tttttttta ttggccaggc gcagtggtat gcacctgtag tcctaggtct tgggaggctg    6120
aagcaggagg gttgcttgag cccaggagtt tgaaggtgta gtgagctatg atcacaccat    6180
ttgcactctg gcttgggcga cagacccaag acccttcctc taaaaagaa aaccagtttc    6240 agattgatac actaaacact caagtataat ttttttttt tttttgaga cagaatctca    6300 ctctgtcgcc caggctggag tgtagtgcg cagtctcagc tcactgcaac ctccgcctcc    6360
tgggttcaag caattctcct tcctcagcct cctgagtagc tgggactcag gtacccgcca    6420
ccacgcctgg ctaattttta gtagagatgg tagttttagt agagatgggg ttttgccatg    6480
ttggccaggc cggtctcaaa ctccagacct cagctgatct gcccgcctca gcctcccaaa    6540
gtgctaggat tacaggtgtg agccaccgtg cctggcctca agtataattc ttagatgtgg    6600
atattttcta tagtttgagc cttgaagaaa gtagaatgta gtacattaga gcattggctc    6660
tggaggccaa tagacctgat tttgagtccc agatctgtta caactgggtc atctcctacc    6720
ctcaatttcc ttatcagaac aagggagaca atattaatat ttacttacaa ggtttttata    6780
aaaattcatt gaaagaattc atgtaaaaca gtaagcactg tgctcacatg caattagcta    6840
tagttatttt tttccataaa ttaacccagt tggataacct cttatttta ttagatccaa    6900 agcagaccat attattatta ttattttgag acagaatctt gctctgtcac ccaggttgga    6960
gtgcagtggc acaatcttgt ttcacgcagc ttacatctcc tgggttcaag cgattctccc    7020
acctcagctt ccctagtagc tgggattaca ggcccggcta gttttgtat ttttagcaga    7080 gaagggttt caccatgttg ggcaggctgg tctcaaactc ctgatttcaa gtaatctgcc    7140
tgccttgtcc tcccaaagtg ctgggaagcc catatcctaa agcactatt gcaccactgg    7200 ttttggaaaa gttgtttaaa attttaaaa gaaatcttat tggccgggcg tggtggctca    7260
cgcctgtaat cccagcgctt tgggaggccg aggcgggcgg atcacgaggt cagaagatcc    7320
agaccatcct ggctaacacg gtgaaacccc gcctctacta aatatacaaa aaatttgccg    7380
```

| | |
|---|---|
| ggcgtggtgg caggcacctg tagtcccagc tactcgggag gctgaggcag gaggatggcg | 7440 |
| tgaacccagg aggcggaggt tgcagtgagc cgagattgcg ccacttcact ccagcctggg | 7500 |
| caacagagca agacgctgac tcaaaaaaaa aaaaaaaaa aaaaaaaag aaatcttgtt | 7560 |
| tgtaaaggtt gggatttgtg aattaactta agaaaaatct tggcagagat acaggtttgc | 7620 |
| tctggagcag cagcagctgg cggagcaatg gagatgcaat cctattatgc caagcttttg | 7680 |
| ggggagctga atgaacagag aaagagggac ttttctgtg actgcagcat cattgtggaa | 7740 |
| ggcggatct tcaaggccca caggaacatt ttgtttgcta acagcggcta cttccgagcc | 7800 |
| ctgctcattc actatatcca ggacagcggg cggcatagca ccgcctcctt ggacattgtc | 7860 |
| acctctgatg ccttctccat catcttagat ttcctctatt ctgggaagtt ggatttgtgt | 7920 |
| ggggagaatg tgattgaagt gatgtcggct gccagctacc tgcagatgaa tgacgtggtg | 7980 |
| aacttctgca agacatacat taggtcatcc ctcgacattt gccgaaagat ggagaaggag | 8040 |
| gctgctgtgg ctgcagcagt ggcggcggca gcggcggcgg ctgcagcggc ggcagcagcg | 8100 |
| gcggctcatc aggttgacag tgaaagcccc agttcaggcc gggaggggac ctcctgtggt | 8160 |
| accaagagct tggtctcctc tccagccgag ggagaaaaga gcgtggagtg cctgagagag | 8220 |
| tccccttgcg gtgactgcgg agactgccac cccttggaac tggtggtgag agacagcctt | 8280 |
| ggcggtggct cggctgacag caacctctct actccaccca aacgatagaa gcccaaggtg | 8340 |
| gaatttgatg ctgatgaagt ggaggtggac gttggtgaac agctgcagca gtatgctgcc | 8400 |
| ccgctgaacc tggcccacgt ggaggaggcc ttgccaagcg gccaggcggt tgacttggct | 8460 |
| tacagcaact accacgtgaa gcagttcctg gaggcgctct tgcgcaacag cgctgccccg | 8520 |
| agcaaggatg atgcagacca tcactttct aggagtttgg aaggaagacc agaaggtgca | 8580 |
| ggagtagcca tgagttccat gatggatgtc caggctgact ggtatggaga ggactcaggt | 8640 |
| gagctccctt agcattcatc agccctgcca gtgattgagt acacactgtc tgtgccttgt | 8700 |
| gttctcccat catcatgatc attatcacca tcatcattgt cactaccaac attatcagta | 8760 |
| ccatcatcac cagtaccatc atcattacca tcatcaccag | 8800 |

<210> SEQ ID NO 233
<211> LENGTH: 2800
<212> TYPE: DNA
<213> ORGANISM: Homo sapiens
<220> FEATURE:
<223> OTHER INFORMATION: OGHAv1.0 microarray feature identifier
      ha1p_69407 genomic DNA region

<400> SEQUENCE: 233

| | |
|---|---|
| cctcattcat gcataggtca cacttctcca aagttggtat ggcctgtctc cttggcatgt | 60 |
| tcccttgctt ctgcttgtcc agttaatcct ttctgacata ccatgcatct cagggtgaag | 120 |
| cggttgacat cagtaaactg tctccttctt ctagcttcat ctgctaattc cagtgcttgt | 180 |
| acaagaacaa tatcatcatt agaggagaaa atggtcagag gaggtgtatc tggatcaggg | 240 |
| aagttacgct gaagtggatc atagtggatg ccatcataaa taagcagaac ccttttggta | 300 |
| tatcctgcat cttccccaaa acgatcaatt cttactgtct gtgtatccac tacacatatt | 360 |
| tcacattggt aaaacttgga caaaatcgat atctctattg ctcctcccca agtgtcatcc | 420 |
| cttttgatcc agtcacagta ctcttgattt gttttttccca gtattgcctc actatagaag | 480 |
| tctggatcgc ttgctacaat ttgtgctatg aggcgtctca tctcagggc acaagctgga | 540 |
| ttcaagactc ctccttcgac gacatagtac acactagtaa agaggcaaga gttgtctgct | 600 |
| gggaccacgg ttctggtaag cacaggcaaa gtttccctga cgtaactaga agcaccacgt | 660 |

```
ttagtaaatg caggtgaact tctgggcctg gtttggtctt cttcaatgat cagcatgtca    720
cctgttaaaa ataaaacaaa tcccgatctg caaagaaatt acagaagaaa ccgagtgttc    780
tctagccaag tctgtaaatt acaaactgaa ggagttaaag cataaactgg ggttactaag    840
gagaatacag ttttgcaagt aagttaccag taagaatctt tgttcactga attttcataa    900
agatgaaaaa agaacaaaaa acacttgagg ttgcatccca atttagtgaa ggggtctgga    960
gtaaacaact tcaagcttac ctaaaaagat acatttcaaa aacaaaattt cctttcctta   1020
tacagtattt tacagaaggt gctcactaca gagtaggccg ctaggggttt ctccttctcc   1080
ggaaacttat ctactctaga gtgtttacaa catccttgat acagcaactg aaagctttta   1140
attataaaca ctgatgttca agttttgata tggcacagaa ataactgctg ctggttagaa   1200
attgaaagag ctttcagtgg gtgttttaaa agctaactcg aaaatgagta tgcctgtcaa   1260
acgaagtatc tacgaagggg actgcaaaaa tgaatcaaga aaaaaaaaat cctgcaccct   1320
tgagatctca tcggtgatat agggaaaaag agacataagg acagagaaaa taggccctac   1380
tttatatttt tgtggacgcc gagggaaaac aaaatgggat agtttcaaag ccgaccagaa   1440
agcggaatgg ggaagggggt cttcaaggct ttgggttccc tttcaaccct gtgtcaagac   1500
aaggagttgc tagacacttg ccctggcccc cgtcagcatt ctctgttctt tgatctatcc   1560
tcgcccctgg cctcaaagcc ccccgccga ctcacagcca ccttgccttg actggtgttt   1620
tgttctctct cacgcccctc tccatcctcc cgggactttc cctggcccca gccctgattc   1680
cttaccagat tggatgggca agtcttccag aatggtatcc ccattgctga atccaggca   1740
ctcgggaggg tatccgacga ggattcgctg accgccgggg gcgatcccgg tgatggcggc   1800
aatttggccc tggagttccc gcacccgggt ccggctggac agcccctgca aaacatgggt   1860
gccgtccttg gccttgcagc ggagccgcca catcgtgtcg gtccggctgc ccacaggcca   1920
ggcacccgcg gggccagctt tggtcccggc agcctgttgg gagacgccgc cggggaaacc   1980
aggcgccggg tggactccaa aatggcgacc tttagcgggg ccaaacatcg cgagaagttg   2040
cgggtggttg cagttatcgc gacgcttcgg tgcggcttct gccttagtac cttagcaagc   2100
gcgaactctt ttaaagtgac aactgatttt tcccccaccc tcagaacgaa gatgtaaacc   2160
tccgtattcc taaaggacaa cgggtcttgc tacctataga gcgagtgagg tgccctccgc   2220
gtgggtagca tatatgctca agaaaagagg gcggggaag gagttcctga atgaaggtct   2280
ggagattgga atgtgacctt gcacttagtg aggtcggaaa ttattaaatt ggggcttcca   2340
cactacaccc agactacacc aggagaaaca gaatcatagt tcacaacgca aacgaatgcc   2400
aggaatggtc agtgagtcaa aggaccagtc aaaaacaatc acacttgtga ctagactcgt   2460
ggctgcatta aacattgact cattgggtt ccaggggcca aaagactggc ctttctgcct   2520
ccctgggact gtgcttgaaa acgtctattt gccacttcag aaagcacagt atgaggtcag   2580
catctgggcc cagggcagct gcctcattca ggtggtggca gtgtaaggag gagtcgtgta   2640
acgcgtgtca tcagattcca gttcagttcc tgggcataca aatatgaaga cttcattcct   2700
gccttcattg taacaagtat tcattgcagt tgggagacag ggtggggtgt gagacacaca   2760
gccactgaat ttcaaagcaa cgtgataatg ctagattatc                          2800
```

<210> SEQ ID NO 234  
<211> LENGTH: 6900  
<212> TYPE: DNA  
<213> ORGANISM: Homo sapiens  
<220> FEATURE:  
<223> OTHER INFORMATION: OGHAv1.0 microarray feature identifier ha1p_05406 genomic DNA region

<400> SEQUENCE: 234

| | | | | |
|---|---|---|---|---|
| agatggaagc | ccaccccgaa | aacagctgtc | attgtgggca | catgttgtag | agggggtgtg | 60 |
| ggggttacta | ctttgcttta | ctacaagtgg | aaagcgggc | tcaggagctg | acaagtcgcc | 120 |
| agaatcatcc | cccagacaca | ccaggcccat | caggtggaat | tctgagctgg | gctctggccg | 180 |
| agggaacagg | cagaaaaccc | ctcctgctgg | ggacactta | tacctgccca | gaccaggttt | 240 |
| ggcgtttggt | acttttctt | ttttgatcct | ccatttattc | ctgctgcaaa | tccggccaga | 300 |
| gttatcctga | ccagtgatct | atgctcattg | gattgagtca | acatattaaa | tcccagattg | 360 |
| attgttttac | tgaagggcct | tgacaaatag | tgtccacaat | gttggagcag | gcccgagcct | 420 |
| ggcgtctcca | ccaggtctgt | cttggctcag | cccttggcag | agccctggcc | agaagctgtt | 480 |
| ctctctggct | ccgtcccact | tttgggtctt | cttgcagctg | aacaggttca | atcgcccagt | 540 |
| gcccaatccc | acagaaagat | ctgaagggcc | tgggagttgc | ctggaggtgt | ttaatgcccc | 600 |
| gcaggctgac | tttgttcagg | taaaacccct | tgcaaaccac | aacaaaagcg | tcctgggaag | 660 |
| atacaggcct | gatcagaggg | agctcccccg | agccgctgaa | aggccaacac | agccgcaaac | 720 |
| aatgcaggac | aaggcgatct | tatcaaagaa | aagccctttc | aatgccttaa | taacaaccac | 780 |
| attctgtttg | aattaccact | actgagcaaa | tggcggcccc | ggctttcatc | ccctccccg | 840 |
| ccaggcgcat | taacataaac | acgaccctgc | aggcgcattt | gaatgggct | gcggccccga | 900 |
| ccccgcgcct | gctatgaaag | taagggaac | taacgcgact | ttctccgcgg | tggacgctcg | 960 |
| gacacgcgtg | accgcctcaa | acccactcca | ggctgccatt | ggtactcgcc | ccttttaca | 1020 |
| gatgaggaaa | tggagaatca | gaccgggtca | cgcagatagt | atcaggcggg | gttggcaccg | 1080 |
| gagcctggct | ggagccacag | aggacacctc | cggagctgag | gcgcagggca | gttccctcag | 1140 |
| ccgaacaccc | cggagggag | actcgcctgg | aagtgtctcg | gagcgaccct | tgctcgggtg | 1200 |
| ctgccccttc | agtgtcccgg | acgtgccggg | caacgcgatg | accagaccct | gagcgctctt | 1260 |
| cgacccatgc | cccaagggcc | ttggaggcgc | cccacacccc | ctgggaacct | aggagcgggg | 1320 |
| ctatggaggg | gagggatgag | agggacttgt | cagaattcat | tattgactgc | gaaagtcacc | 1380 |
| accctctttc | cgggccctaa | aagagacaat | ggcagggctg | ggaaggtgta | tatcaaagca | 1440 |
| agccaggccg | cgtcccccc | tccacccca | caccttgaca | gatgacgctc | cgcagaggag | 1500 |
| cccggctccg | gcccgcgggc | tgcggccacc | ccacattaac | atcacaaggg | cacccggcgc | 1560 |
| cgactgcggc | cttgccacct | cggcgcagga | cttcacagcg | gcctctcatc | tgctgacccc | 1620 |
| gcggcctggg | ctctggcggc | ttccctcccg | cccccttccc | ggccctcacc | ccgcggccgc | 1680 |
| tctccccggga | cacgcaaagg | tcttccttag | ggcgtgcgcc | accccgcca | accgcgcccc | 1740 |
| agacagggc | tgtagaaagt | gggtctttgg | gagccaggat | ctgggagccc | ctgctaggag | 1800 |
| aaaggcgcct | cctctaggag | aagggaccaa | gccaaagctc | tgaggctcac | ccgaggctga | 1860 |
| tctgtggcct | tctccccggt | cggcggcatt | cccaccagga | ctctccctag | catgtgcaca | 1920 |
| gtgacgcaga | aaccgatgcc | cagagacagc | ccccaaaggg | cgctttgatt | tatacagttg | 1980 |
| taattggcta | taaacttctg | caaagtgccc | ataaccagcg | tgcctgccca | attggggcat | 2040 |
| caaggagcga | agcaagaaaa | gcggaagcgc | tgagggctgg | ggaaagactt | taaaggggc | 2100 |
| actcaactag | gactctcccc | accgcacttc | cttgccacct | ctaggcacac | tcgaacacca | 2160 |
| gaaggggcag | acccagagtc | aatgagcccc | acagtccggc | aaacctagga | tcttttcag | 2220 |
| ttgcacacac | acactcacag | acatccctga | cacccttgaa | aggaagcttt | gggagaaatg | 2280 |

```
accccctacct ggagcggcgg cttaattccc accagggttt cctccccgtc tccctgctct    2340
ctccgcagac gcctgcccct aggcttcttg cccctagcct tccagctttt gcttgaaatg    2400
accccttcac aggtcagagg ttcagagacg gggcgcgccc ccgtcgcctt agcagctggg    2460
gctagcacct tcttcccagc gacagcagct ctccctggtc tgcctgctcg ctgtaccttg    2520
aattggcccg agtggccaaa cccggtccca cacacagcct agccatcctc cgacccccc    2580
aggtcacttc tcttcttaga tggctcagat ggggaaagag agagcggaga taaatggcct    2640
agacctagcc caagaaggtt cgagcctccc tctctcctcg gcggccagga gccacgcaag    2700
gaatgcatgc cgcagcaagt gccggaggac gcgattctgc cggcgtccag cagtgctcac    2760
gccgacattc cccggagctt cccgaaggtg tcccgggtt gcgaatgagg agctcttgga    2820
aagaggacgc ctgaacacgg tgttgagact cagaatattc actcccaggc tcagtaggtc    2880
agagaagccc cgacgggcca gaggcccccg aatttgtctc cgggccgtgc ccctcctggc    2940
gccgagctcc cagacagccc gggacgcccc tgtgcgcact ggacgcgcga cgcgcagcag    3000
ccactggctc gacccgcgcc ttcccaagca ccctccgaag gggcgcagcc tctgcttacc    3060
ttggctgccg agggactgct cgccggcctt ccgcatccac tcgcacaggt tccgccgctg    3120
gccgccggga gacagctgct cggcggcagc ggtggcggcg ggcccaggag ggccggggtt    3180
gagcgtttgc agcagcccag aagcgcagga aggcgcggcg gccgggtggt gcgggtggtg    3240
atgcgggtgg tggtgcggat ggtagtctgc ggggctgctg tagcccatgg ctgcggccgg    3300
ggagccaccg ttgaggccgt gagccacggc gttggcggcg gccgcggcgc ctccgggcgc    3360
gtagccattc cagtcctccc ggagtggggc gccatacgct gccggccagg atggccccgg    3420
ggactgcgcg ctgtccaagt tcgctgccgc tgcagctgcg gccgccacgt ggtaaccgcc    3480
gtagtccggg tactgcgggg ggctgacgaa gttctgcggc gccaggttga ggccgccaga    3540
gtggcgcacg gagctagggt acatgctcac gtccttgtcc aggaggtagc tcacgtacat    3600
ggtggcgagg gtccgggagc agacctcacc atgctgcctg ggaccgacg ctggaggctg    3660
ccggggggca cgaagggaaa ggggcgaggg gactcgagga gcggcgggtg gctgcgcccc    3720
agcccgcggt gctccgctgg ctcctcgcgg ctcttctgcc tccgaggcgg tcctcccctc    3780
tggcctgcct cctccctccc tcccttcctt cttcttttcc tcccacctcc ttcccactag    3840
gctgcagagg cggggaagac ccgccacagg ctggcgtgcg gagccccagg ccggcggcct    3900
tccgtgatta acgagtgttt acaagactct attagtaatg acacagacac caatggttgg    3960
agacgtcgag gcgcagcgcg cactctacgc acaacccctc gaaacataat ttgcatttta    4020
aaagataaag gggagggagg ctcgtgagag ggcagcgacc tgacacagct aaatattcaa    4080
acctttattg ttaagagctt cctccttcca acctggtgca cttttaacctc caatcacagg    4140
ttcaaagaat gaaatcaaga gacttacaaa agagagggga agagaaaagg ctatcttggt    4200
aggaatctga gcttggagac aggagcagtg gttgtttatg catttgcagg gaagagggcg    4260
gtcaagaaac tccttctgtc ccaaagagaa agaaaagag aaccattgct tgatgagaa    4320
cgtttctgac caacctggta ggtgacaagc agagagccct aagagatggg ccattccttc    4380
ccgccctgtg ctcctggccc ggacgactgc agccccaaac aactgtcacc tccagttatt    4440
ttcttgccca aggaaattac tcgccctccg cacaagacaa attatgatcc tagattcagg    4500
ctgcatctct gacttcatct tacatttgaa atttgagtta aattcaagcg atttattgtt    4560
aaacgtttac attcaagaat cagaagttt aaactacaga agtaatgggc atgtggtaga    4620
agttaggcta gtggttattg gcgtgcataa ctggaggcga gctaggggat cgttggtaaa    4680
```

```
gcagtttctt aggctgctgg ttacacagaa tgtcagtttg tgaaaattca ttgagctaca    4740
cttgtatgtt tattatactt aaatataagg aaaagagaat ttctgctaat gcttacctag    4800
gtatttatgt gtcttacatc atacctgtat ctttaaaact ctctgtcctt tacaaaggga    4860
aacgttctcc gaagaaattt atttctcatt tccaggagat gataaggcaa ctcagggcca    4920
ttattaacga ctgctaatga aaagctctga gttgagaaag gatctctctt ggtttgggaa    4980
gcgctgcggc caaggggcct agggctgaa gtggccgtct tggggaccga agccgcgcag    5040
cccgggatcg ggagctgccc cgacaggagc gcggaggcgg cgagattcgg cccccgcgcg    5100
cgcccagctc ggtttcagca accgcgtgga gtgggcctgc ggccgccgtt cacctcctaa    5160
tacaagcctt tgacagcgct gccagattcg ggaatgagga tcactgcggc gaggcccggc    5220
gggctgggca gcctgactcg gcggctttga gcgctctcag aacccgcggg cgctcgcggc    5280
actcctggag acctgcactt gtctgttctc attgtcaagc gtttcgctcg gatatttgtc    5340
accatcgcct tcatcctgtc atttctaggg tgctctccag tgtcctttat ctcccttgag    5400
cctcacatcc ccctaggatc tagaacaaaa tctgggaggt gttttatcc tccccatttt    5460
acaggtgaca accagcaact tgcctctgca gacacctgaa agcgatcaga actagcctag    5520
ggctgcggga tcccctgttt tctggttcct cccaccctcc gtgtttgtaa ggaagaaggc    5580
tggaaatggg ggtggtgggg tactcagggg ccaaggagct gtgcactcaa gaggtgggag    5640
accgagctgg tcctcctggg ggacttccag cgcctggcct ggacagccga gtgtcatcgg    5700
acttcctgag aaatacaacc ggaagcaaat tgcaaacccc gttacaaaat ccgaatcatt    5760
gagagaaggg cagtagggga ggtccgcaga cctgatgggg tgggaatgtg ggaggttaag    5820
tggtgggcac ttcgaacttt tgatctagca aacatcttcc tcctcttcct ggagacacaa    5880
ttccccttc catccccat accatccccg ctcccaggcc tgagctctgg aagccgaggc    5940
tgaggctcca gcctatgtct tcggaatgcg ggcattcttt ggaacaatcg ctttattagg    6000
gacagccatt ccctccgccc tgcggtggcc gcttcctgct ttttatggc ccaggctgcc    6060
ggccgctggc taattgtccc tgttttccag ctgtgtctct gtgctgtgcc ctgaagacgt    6120
ggctctggcc tgctcatcca actgctttgg gagtggccag gctgctctg gccccctcagg    6180
tcaagccagg cctcagagca ggccaagcca cagggaagcc cgaggctcac ttggagtgct    6240
ccagccatgg aaaggaaatc attgtgaaca cgaatgtttc cctcattgca aaaatgggt    6300
ctccttagca atggcatggc acagctgtgg tcccagggtc tagacctgtt cggtgagggg    6360
aaaggagctg taaatgatg tcctcggaca agcttcttag aatgtaagcg tccccataca    6420
tcctggttgc tctcagccag gagagggccc agctgggtcc ctgaaaaggc agggttgtgg    6480
gagcagtcag agaggggtag aaggtggctg acagaactct aggagcctgg ttgtcttggc    6540
atttagacag ccctggcccc tagcaggttg gtgccccatg actggcctct ggagattcgc    6600
tctgctcagg ggcagcctct ccagcttcta agtgcaggcc tgtgtccctg ggaggaggca    6660
gaagccaccc acatcaaggc cccatgcagg gctttcttag tcctaggccc caggtgcttg    6720
gcgtctttct taggagcctt ttggcctgca ctgagaagcc cccaggaagg gacagggatg    6780
gtcatcccta accctcgatg ccagaagggc ccttctaccc tgtaagtcct gctgctgggc    6840
cagagaagcc tgtagcaact cactctggga gaggcaaact tgtttgggaa gcttgggcct    6900
```

<210> SEQ ID NO 235
<211> LENGTH: 5100
<212> TYPE: DNA
<213> ORGANISM: Homo sapiens
<220> FEATURE:

<223> OTHER INFORMATION: OGHAv1.0 microarray feature identifier
ha1p_80287 genomic DNA region

<400> SEQUENCE: 235

| | | | | | |
|---|---|---|---|---|---|
| ttctacccaa | ccccatctca | tagaactcac | aacaaccttg | ttgggagaaa | aggaggggat | 60 |
| acagggcgtt | aaagagggg | aaataaccat | atagctggta | ggggctgaaa | tgaagcccca | 120 |
| aggggtggt | tgtttaccct | cgctatgact | acagagtttc | ctgggacctc | ctctctttgt | 180 |
| tgtgggtgtc | cctaactcac | cccacggtgc | ctgtccggtg | ctcctggcag | gcgcaggtga | 240 |
| cgcggggtg | gaagtctttg | tgcccgtgca | aagcggcctc | cttcctcagg | cacttagtgg | 300 |
| gaaggatgga | agagaatgga | gcttcctact | cctggcccct | gtcccgcagc | caagcggccc | 360 |
| gggtaggggt | ggagtgcagg | gaccacccag | aagcaccagg | cctagctggg | tggcagggct | 420 |
| gggcccagtc | ctctaactgg | tctggtgccg | cctcctcctc | gcccacaccc | cgggctgtag | 480 |
| actgaagccc | gacgtggccc | cggcgcctac | ctggggcagc | tccgccagga | cgcgatccct | 540 |
| ccgcacgggt | gccagaatgt | tcatcctgcc | tgcggccttg | cagggcgccc | tgagaaggcg | 600 |
| ccgaggccgg | atccgcgtca | gcgacccggg | cgcgtggaga | cccgacgatc | acccgcggcc | 660 |
| ggggtgtccc | gactacaact | cggggccacg | ggaccctac | gggagtccgc | ggtctcggag | 720 |
| acgctacgac | caccgcgggc | cacggagatg | aaacaatcac | ccggggccgc | ggcgagccca | 780 |
| aaatcacccg | ggcctgggc | gtcccgaaga | tgactctggg | gcgaggagac | tcttcggccg | 840 |
| ccaattgggg | gcggggagtc | ccgtctggtg | ggggccgggc | ccgcgcagac | cctacgatta | 900 |
| cgcggggccg | gatagttcct | acgattacgc | ggggccggat | ggttcctaca | ataacccggg | 960 |
| gccgcggaga | cccgacgtca | tctcggggct | gaggctgccc | taccattaca | gagcggcccg | 1020 |
| ggggcgcgga | gcgcccccgc | cacacggggt | cagtgtgggc | aggggcggcg | ctgccaaggc | 1080 |
| ccgcaggccg | ctggaggagg | gggcgagggg | cccagtccgg | ctacagggcc | tcgagtccca | 1140 |
| ctccgctcgg | gctccgccaa | cgctgtaaca | cgatccccgg | aaattcctgg | agaagggccg | 1200 |
| cccccgccc | ctctcctggc | ggctccaggc | ctcgctgccc | gccctcgcca | ccccctcctc | 1260 |
| tccacccttc | tgcgttgccc | cgctcaggct | ccctcttttg | acgcttcacc | gggcaccagg | 1320 |
| accgccccga | cccaggctgg | agcctatcca | gatagggact | cccccaggctg | ctctcccctg | 1380 |
| cacctctata | cccggctgcg | ccttcatggg | gaccccttacc | cagccgaatt | ggtgatgggg | 1440 |
| aatcggagac | tgctgcgcag | catctggcga | tgccaggaac | cagcagggag | gggaaagggg | 1500 |
| gagagaaggg | gccaaggag | aggcggcgct | tccctcctca | actccaggcc | tgggaggtga | 1560 |
| ctcatagagt | ctgccccctc | tcgcccttct | gcccctgggag | gtcgggggtg | aggatggtgg | 1620 |
| aggggaagcg | tgccaagggg | gtgccagggt | tagaatgagg | tgcccaccga | ggagagagac | 1680 |
| gtctgaagtc | tggcgtcttt | tccttcaagg | ctgctgtgta | gattgtgagg | tgggagggct | 1740 |
| gaagatcaag | ttccctcgag | ggaggttaaa | aagggctaa | gtggaccggg | aaactctgct | 1800 |
| cttcggggtg | gtctccgctc | tgggaggcgg | ggactcccct | ctggtatggg | tgttcattgt | 1860 |
| tctggcccca | ttggaatcta | tcccccaggg | acaactcctt | tgtgcaaagt | cctgcaggat | 1920 |
| agaagagggg | gcagtgcaca | atcaatttca | ccgtcaaagg | ggacatgtct | ggttttatga | 1980 |
| agggagaggg | aagaagaaag | gatcaagtgg | ggatgggtta | ggcacacacc | ttaggagaag | 2040 |
| cgaacctgag | tgttaagaaa | cctttctctg | tgtctggagc | tgaatttgag | gatgtaaaga | 2100 |
| tgaccaggac | acggaaggga | agactagttt | agggcagggg | attgtgagtg | aagttactaa | 2160 |
| ccggaaaaac | tagcgaatct | tggagaaatg | tgtggaattt | tcatgaaact | tcaaatgcat | 2220 |
| tatcaggaaa | cgcagtaaaa | cttgacagta | tcagtgtcgc | aggtaaagag | gggcaggtgt | 2280 |

```
ggccgccttg tacttcctct gacacttccc cctcgtgact cgattattta tttatttatt    2340
tatttattta ttttgagaca gggtctcact ctgccaccca ggctggaatg gctcattgca    2400
gcctcgacct ccagggctga agcgatcctc ccacctcagc ctcccaagga actgggacta    2460
caggcacgca ccaccacgcc cggctaattt ttgtattctt ttgtagagac agggtttcgc    2520
cgtgttgccc agggtggtct cgaactcctg ggctcgaagc aattcgtcca cctcggcctc    2580
acaaagtgct gggattacag gcgtgagtca ccgcgcccgg ccctgacttg attttttttct   2640
gccaccaaat cactgtgtta ttgataaacc acattcctct ctggacctca gttcgaccga    2700
gcaaatcctg ctccagcact ctagaactta gctgtatcta actcccgagt caatccaaat    2760
gtgttctttc ctcttggcag cgttcctgcc tcctggcatg gcaatcctct tccctgagac    2820
tggcagttgc tcaagatagg aagctcccgg gaccagaccc gagcgccagc cggctacgcc    2880
gtccgctggc ctgagcaaat aaacgcgtgt cttcaaaaaa ctacaatccc catggtggca    2940
cgcgcctgta gtcccagcta ctctggtggc tgaggcagga gaatggcgta aacccgggag    3000
gcggagctta cagtgagccg agatcgcgcc actgcactcc agcctgggcg acagagcgct    3060
caaaaaaaaa acaaaaaaca aaaacaaaa aactacaacc cccatgaagc tttagtgcct    3120
ttgaggggag gagtggcgca tgtttgttca cgcacgaaaa agaaattaaa cctaactacc    3180
gttcccagag ggcgccgctc tgcaaattac ccaatcagct ctaagtacaa agcatcgcga    3240
gtctttagtg ctctttggcg ctataagccc gtgggaacga gcattggaga cccttttcac    3300
aagatggcgc cgaaagcgaa gaaggaaggt gtgtgttggt gatggggccg cagctggttt    3360
accggggatt gccgcgccgc agagcgaacg aattgggaac acggctgctg ggctaagccc    3420
tgagggctct gctccggggc tgctccctgc gtttcggaca cgctgcagta tacgtgggcc    3480
gcgtgggccc agcctcgtgg gctgagttcc ggtagaggga gttgggggg ggcaacgcgg     3540
caggcatcat ccgccaggga gggccagaca ttcggttctg ggaagctaca tgcatccact    3600
ggttggagct ccatgtcccc gggcctgtaa ggaattagtg ccctcagctt taaccatttt    3660
ccttctggtt catgttcaac cgggctacat tacccgcccc tctctccgca gcgtggtttt    3720
gcgatggggt atgtgtaaaa ttcgtaggac attttctgga aagtatcaag cgttcattca    3780
gtgctactttt gtttcatagt cgtatccctg gagttactta gagttggtcg ctttcgcctc   3840
tggtatcgtg catatgatgg aaaagtttta atctcctgac acttgtgatg tcttcaaagg    3900
aaccactgat gcacctgtgg ccagggtggc ccactgcagt tcttggggcc ggaagtgacc    3960
gatttctaaa tcccgcaccc acgttttctt tccttttctc ccagctcctg cccctcctaa    4020
agctgaagcc aaagcgaagg ctttaaaggc caagaaggca gtgttgaaag gtgtccacag    4080
ccacaaaaag aagaagatcc gcacgtcacc caccttccgg cggccgaaga cactgcgact    4140
ccggagacag cccaaatatc ctcggaagag cgctcccagg agaaacaagt cagtactgcc    4200
ccctgtaccc atgaaaagat ttgggtattc tccattggta atttggaaat tcactcactc    4260
tgcgtgatgg tttctcaaac gcaaattgtg tccagtgtgc ttctctaatt ggaagtatga    4320
ggagattgtt tctgctgcat ttacaaaact ggcaggatca gcccagaggc cgggcgcggt    4380
ggctcacgtc tgtaatccca gcactttggg aggccgaggg ggggcggatc acttgaggtc    4440
aggggttcga gaccagcctg agtgacatgg agaaaccccg cgtctattaa aaatagaaaa    4500
ttcgccggga atggtggcgc atgtctgtaa tcccagctac tcgcgggagg ctgaggcagg    4560
agaatcgctt gaacccggga ggtggaggtt gcggtgagcg gagatcgtac cattgcattc    4620
cagcctgggc aataagagtg aaactctgtc tcaaaaaaaa aaaaccctg agtctctcaa     4680
```

| | |
|---|---:|
| aatttgttag gttaattatt gcttcacatg tggtcacggt ttgaaaactt attttggggg | 4740 |
| gagtataaag tagaatacag agattccttg ctcatagctc ctactgctat cgggaacaat | 4800 |
| ccttgagggt gagaacgtgg attgattctt gattgatagt ggggattcca ttatctgtat | 4860 |
| ttggcagtta tggcctgctg cggtgtatag aagcttcttt ccattcattt tcccgaattt | 4920 |
| tcatactgct caaggaacag ttgggggga atgggcagaa ggttgggcac ttgagtattt | 4980 |
| gagctatcgg taataactga cttttaggg agcacagatt tgagtagagc catggtagta | 5040 |
| gttagtacca atgggttttt gctgcttcta ctctttctta acagaaaaag tggattgtgt | 5100 |

<210> SEQ ID NO 236
<211> LENGTH: 1900
<212> TYPE: DNA
<213> ORGANISM: Homo sapiens
<220> FEATURE:
<223> OTHER INFORMATION: OGHAv1.0 microarray feature identifier
ha1g_02345 genomic DNA region

<400> SEQUENCE: 236

| | |
|---|---:|
| gtgagaggcc ctggagggct tggctctcct agcttttgag aaagaaatgt caggcagcaa | 60 |
| ggaaaatgag gagagagaga agaagaaagg gagggagggt gacagaggag ggagaaagag | 120 |
| agacagaata gcgaacaaac ttaatgttaa aattccaaga caaatggagt taaataaatt | 180 |
| tacgaggatc gaacccatta attgggccat aaaaagtttt atgagcctca tttacataca | 240 |
| atgctatggg ctccacgcaa tggcgcctcc gctccaatta aaaccagaaa ggctgcgccg | 300 |
| ggagtcacgg ggctaccggc tcgcaacagc ctggctccgc tcttccggcc ccgcgccccg | 360 |
| cgctccgcgc tccccagcgc tgcgctcccc gctcccggtc ccgctccgcc agcctggccc | 420 |
| gcctagcgac tgcgcctacc tgaagaccgc atccaggggt agatgcggaa attggcctca | 480 |
| gccgcgccat gcagcgcgcc ctcgtccgtc ttgtcgcagg cgcctttggc gaggtcactg | 540 |
| cagagcccgg ggatgttttg gtcgtaggag gcgcagggca ggttgccgta ggcgtcggcg | 600 |
| cccaggccgt agccggacgc aaaggggctc tgataaaggg ggctgttgac attgtataag | 660 |
| cccggaacgg tcgaggcgaa ggcgccggcg cccgccccgt agccgcttct ctgtgagttg | 720 |
| ggagcaaagg agcaagaagt cggctcggca ttttggaaca gagaagcccc gccgtatat | 780 |
| ttgctaaaaa gcgcgttcac ataatacgaa gaactcataa tttttgacctg tgatttgttg | 840 |
| tccggcagct ttcagtgtcg gttttacgag gtagagtgat atatgataac attcacccc | 900 |
| cagatttaca ccaaaccca tttttctttg gacggagctc gccgcagcac gtgaccgccc | 960 |
| acatgaccgc ctccgccaat ctcagcagtc ctcacaggtg gtctcgctcc gcagggcccg | 1020 |
| cagccgccta gaatgaagg gcaagaggct caaatatgcg gccaaagaat ccgcccgcgc | 1080 |
| ccggcgggcc tggcgcgtcc cgcggaaaaa gacctggagg ctccgcggga gcgcccagct | 1140 |
| ggcggccaac ctccgcactg gggtctgcgg acgccaggcg gccggccccc acgcagcacc | 1200 |
| ccccacccg cccccccgcc gactcctgct agtgagccct ggaccaagct tgggatcctc | 1260 |
| cccatccctc tcctgtccgc ctgcccagac cctggaaggg tctctgtccc ccgcaacagc | 1320 |
| ctgccccgcg gtggccttgt gggcaggact cagctatgag cagatcgact ctgcccaagt | 1380 |
| cttctctcac ccaggtccag tgggcgacag gccggactta gactcggatc cagacgggga | 1440 |
| aggcgcagca tctcttgcag ctgcagagag attgccaccg caaactggag ccatgtggtt | 1500 |
| cgaataaagt caacgtctcc cagcttcctt tccttaatcg gaggcacact gtttatccgc | 1560 |
| cctaaaggaa gcagtgaaat atttatctat taatgagact catttgccaa cagatttatt | 1620 |

| | |
|---|---|
| aacgtggggt tcccctccct cctcccggac gctgtagtgc tgcaggctct gtgccttcgc | 1680 |
| tcctgggcac ctggctggct ccagcagtcc gataaattgc taaagattcc tttgtccttt | 1740 |
| ccacaacttc tggttcccct ctggcgcatg gggagccagg gctgtttccc ccagcttgga | 1800 |
| aaaatctcgg gcctgcaccc ttccaggcac tcccaatact ggaaggtttc tggggtaggc | 1860 |
| cggggtgcct gggaacaata catgctttag agcggatttg | 1900 |

<210> SEQ ID NO 237
<211> LENGTH: 4000
<212> TYPE: DNA
<213> ORGANISM: Homo sapiens
<220> FEATURE:
<223> OTHER INFORMATION: OGHAv1.0 microarray feature identifier
ha1p_36172 genomic DNA region

<400> SEQUENCE: 237

| | |
|---|---|
| cctcttctgg ggctggcaag gctcagagag gcatttgaaa tggctattat tgacacccat | 60 |
| agacttgggt atgtttcaga gagaaactat aacatctatc tcatgggaaa acacactttc | 120 |
| tctgttttta ataactccg tttcagcaag atccatgtgt gtagcctctg aatactctat | 180 |
| aaaggctccg tatttctttc tttctttcct tagtccggaa tggagacaga agaaagattc | 240 |
| ggttgaagat gtccctgtgt ggatctcagt ttgcgctctg agcgacgtcc tggctcattt | 300 |
| gggtgtgacg gtgagagcag aggcgctctg ctgacagttt tttcttgtct aagcttccat | 360 |
| tccgcatcca caatatgact cgccttccac tccagttaac ttcttggaag tccagagcac | 420 |
| ttagtcaaag ctgtttacaa aatgcaaagc atctgggcgg ccaaggcaga ggctcctgtg | 480 |
| ttctctatgt aaccgcctcc aaaaaagctg ggaaatttcg cggatcaaaa tgtaggcgct | 540 |
| taaagctgac cctctgctgt caatgttggg acttagatac atttttttgca tcgtcattct | 600 |
| tgtgtgtgtt tcccgtttat tccattctaa ggctcaggct cgcgctgttt ctctcgcgcg | 660 |
| cgctgtcccc tctctccatt tcccattcac acatcaaact ccgtcctccg caccccctatc | 720 |
| ttcccgtgtc ttcttagtta tgtgaatgtg tgtcattagg cttactcgga cactggatgg | 780 |
| gtgagtggga ggcagctttt cttgcggttt catttacact tggcatgggt gggtgggtgc | 840 |
| cctccacaat tcgtctcgca cacggaacac agttaaaatc tgtagctaga acgagtgaaa | 900 |
| agttccgaat ctttaaagcg cagctaggac aggaaataat acagggttgg gggatgtgga | 960 |
| cgggggcgga gagcagagaa gtaaaggaat aaaaccaact tcgctggcaa cttcaataaa | 1020 |
| tccggtaact ggaggcaaaa aatagactcc gagggctggg tctggtccgg atgaaacgct | 1080 |
| agggctcctt cccttccttg aatcttgggc gctggaagcc agccacgggc gtcttgccac | 1140 |
| gcgagtgccc ctagacagca acacacccac tggaaacgca cgtgaacaaa gctctcgccc | 1200 |
| ccgggagccg ctgcctgcgg tttcctagtc gatcccagct tctctaggga gtgtcaggcg | 1260 |
| cacacagggt taagttagtt ccctcccctgg taggagggag aggaggagga ggggaaaagc | 1320 |
| agcatactgt ctcaggctgg gtaccttgta gttagttgta cgttcgaaac ctgtcgccgt | 1380 |
| cacttgcgcg tttggcatta tccattgtca ccgcggagga acgagcgctc gagatatcat | 1440 |
| cagtgcccgc aaatctccgc gccaaggcgc tgagctactc ctttccgagg tgcgcctctg | 1500 |
| gtcctccgtc cctggtgccc agcagcggcg aggcggcatc tccgctcccg ccgccgtgtc | 1560 |
| caccgagccc tgggatcagg gtggcagttc tcaacgatgg gcaggaggga cctcggcggc | 1620 |
| gacccctaaa acaataccat gcccgggat cccgctgct gccgcgccag cgtcttccct | 1680 |
| ttccacctcc ctgaccctgt cggattcgga tgagcccatt gcaaggagaa gacgcagccg | 1740 |
| tcaggtaaaa ggggctgcgt tgccaggtga agtttccagt aaccggccga gctgctgcta | 1800 |

-continued

```
cgctggcacc acgctgtctc ttcgggggat tttttttttt tgaaagagct ggggggtggtc    1860 atcttaagtg gggtgctcta ggctttgtct ttcacctgga gagaaaatag gcagcttagc    1920
tctctctcga ctttggggac atctgtctgc tggtcgaatc cacctcctct acggagcatc    1980
atgactgagt tctgggtcaa acgcaaatt ttcttgcctg gtagatgcat cgatgctaaa     2040
ttggggttct cagtgcccct aaccttgtca gagttcagtc tcctacttcc ctagattgaa    2100
tctcttaact ttcaccagta acaaccctct cccctccaca agctgttgtt aatgtcacca    2160
gcgttattat caggctgttg tatctaaaga caccaaccta ctacctgccc gtaatctggg    2220
atctattagc agttaaacag atgcggtgga tactaattcc ttttccttcc agttggtggg    2280
ggcgggtggg gcttttttcca aaaccaagtc ccttccagcc ctgcttgtcc tcttcgggct    2340
ggcgggcact gagctggggc catcacgcct ttctagagcg cctgcggagg tggcgaaggc    2400
ttggagagca tacgaggcgg aatccggatc gagtgagttc cttgagccgc ttgcgtggga    2460
cgcagggaga gggcgaataa cgccctcagg cgctgaatgc aggggcaagg agccagcgag    2520
ggtggctgga gcaggccttg ccagctgtta ccaagtctct ccacaggctt gggggcttgg    2580
ggcctcctgg aaagatccct ccgccgcgct gaccagtacg gggctcgctc ccgcactttg    2640
aaggctgccg cggtctttcg tcatttataa tcaagcccaa gatcaaggtt gcaagctgag    2700 gtcgggtac tgacaacggg aatgaagcca taggggaaga ggataactgg gacgggctgg     2760
acccatactt gatacccggg aaactcctag agcgtgtggt gctcctgcca gcggcagtta    2820
ctggtggagc tgaggccacc gctactgtcg tcgttggcgc tttgcttctg gaacctccca    2880
gcaagatggc actcactgtc tgttcccttc cgattagcac ccccagccgc gctccctcct    2940
ccccgggata cgtattagtc acatactgtg gggagaagat gggctatgta aatgtaagtc    3000
aacgcgcttt cccagccacc tttgcataat gcaacaggaa cagcgacccg cgcgcacgaa    3060
ccgggtagtg tgcgcgtgtg tgtgctcgcg tgtgtgagcg cgtgtgccag cgtgcgtctc    3120
cgcgcgggcg tgcgtctggg tggatccttg cgtggcttgg gaggcaaatc gggcgtttct    3180
ccaagtcgtc ttaacatgat ttaggctctc aaatacgtga aagcggtaga cacaacaggg    3240
atgcgaagga aataaaaaac aattggggaa gtggtgccaa gtcactcagg ctttgaactg    3300
aggacgagta gtgcggtcgc gcctggggcg cgtccggaaa tcatcctcag cctgtggcgg    3360
ccactgcccc acttaaactc ttctgcgggg agagttgagc ggatccctgg ggggttggtc    3420
ctgggctagt tttaaactct ccggttgcat ctcgcgtggc cccaccgacg gcgcgtctcg    3480
gcgtagctct tggcgcgggc tcgttctccc tcttctgttc agattcagcc tcaccggact    3540
tgttacaaca tgacagcaac ttactggagg caggaagagc agcacgaaat aagatgagaa    3600
aaccaaaaac atctcctcct tcctaaatag agacgtgcac ctagcttttt ttacttgttt    3660
gtttgttttt tacattaccc tttaaccttt ggaaagagac tgcgaagtgg aaacgttgcc    3720
tgtacagaaa tcaggcttct tagctgtcaa gactgtttcc taatctttag gctgaatctt    3780
tctttgtccg ctgcaatcta tgggaaaatt taacaacgct cttgccagaa gcagccaggt    3840
tgaaggaaga aagtgggggt gtttaaatta atcctattaa attttggatt actcccccag    3900
ttaaagtcat ttaaggtggt ccaggatgag ggaactagtg atggggtgag gagtgggggg    3960
cacatcacca aggttgcctg catttgaaat aacgccattt                          4000
```

<210> SEQ ID NO 238
<211> LENGTH: 3500
<212> TYPE: DNA
<213> ORGANISM: Homo sapiens
<220> FEATURE:
<223> OTHER INFORMATION: OGHAv1.0 microarray feature identifier
ha1p_70459 genomic DNA region

<400> SEQUENCE: 238

| | | | | | |
|---|---|---|---|---|---|
| agtgttgtta | agtcttaggc | agaaacttca | aaatataaaa | tataaagctt | cacacctcac | 60 |
| agataacagt | gtagttctgg | ctgacatggg | agtgggagtc | tcacagtact | acaggctgct | 120 |
| gcactcattg | ttgctgtctc | catggctcaa | ggtgtctccc | ctgaatctta | aaagttcccc | 180 |
| tgaacaggta | aactgtaagt | tatcccagcg | ctttgggagg | ctgaggtggg | aggatcactt | 240 |
| gaggccagga | gttcgagacc | agcctgggca | acaaagcgag | acactatctc | tacaaaaaat | 300 |
| aaaaaattaa | ctggacacgg | tggtcccagc | tacttgggag | actgaggcag | aagaatcacg | 360 |
| ggagcccagg | aggtcgaggc | tgtagtgagc | catgatcttg | ccactgtact | ccagcctggg | 420 |
| tgacaaagta | agactctgtc | tcttaaaaaa | aaaaaaaaaa | aagaagtttc | cctgaacact | 480 |
| ttgaaaacca | gtagtctaga | tactcttaat | aacggccagt | actagctggg | ctccctgaac | 540 |
| caatgtaaca | ttgaggtgta | gcctcagtca | agtggcgctt | caatacttcg | cccaccctag | 600 |
| ttatatgggt | cctggatggg | atggtggtaa | ggtggtgaca | acaaaatggg | ggaggggggc | 660 |
| cgggcgcggt | ggctcaggcc | tgtaatccca | gcactttggg | aggctgaggc | gggtggatca | 720 |
| tgaagtcagg | agatagagac | catcctggct | aacagggtga | aacccgtct | ctactaaaaa | 780 |
| tcacaaaaaa | ttagctgggt | gtggtggcgg | gcgcctgtag | tcccagctac | tcgggaggct | 840 |
| gaggcaggag | aatggcatga | acccgggagg | cggagcttgc | agtgaaccga | gattgcgcca | 900 |
| ctgcactcca | gcctgggcga | cagagcaaga | ctccgtctca | aaaaaaaaaa | aaaaaaaaaa | 960 |
| aaaaattggg | ggagtgggga | ctgaagaatg | tcctagtaca | aagaatctaa | ggtgtggagt | 1020 |
| cagacagata | tggatttcta | ttcataattt | tctatctttt | ggcaaatcac | tttacttctt | 1080 |
| tgggactcat | ctagtcttcc | caggtgcctg | cacctcagtt | attaatgaaa | aggaggccgg | 1140 |
| gtgtggtggc | tcacgcctgt | aattccagca | ccttgggagg | ctgaggtggg | aggatcactt | 1200 |
| gaacccaggg | gttcaagacc | agtctggcca | acatggcaaa | actccgtctc | tacaaaaaat | 1260 |
| acaaaaatta | gccaggcatg | gtggcacaca | cctgtagtct | cagctactcg | gaaggctgag | 1320 |
| gcagaaggat | cacctgagcc | tggggaggtc | gaggctgcag | tgagccgtaa | tcgcaccacc | 1380 |
| gcactccagc | gtgggcgaga | gtgagactct | gtctcaaaaa | acaaaacaaa | acaaaacaaa | 1440 |
| aaacagactt | aagtatatta | caaatccgtc | gtgatcctct | caactattct | gaggtaaatg | 1500 |
| ccacacccac | ttttttttt | tacagctgag | gacactgact | cacagaagct | agatggcctg | 1560 |
| ttcagcatca | cacagctaat | aaaatgtgga | gttaacccac | attgatccta | cttccaaatc | 1620 |
| ccagagtcct | tccatgttct | agtctttggt | taagaatgct | tgagagaagg | actagaggga | 1680 |
| ctttatatga | agtgtaaagc | tttattcata | caatagtcct | cactagtgct | gtgtgagaga | 1740 |
| gagaaggctg | aggaaagcgt | cggcggaaaa | aggctgatcc | aagggggaaag | ggggccggaa | 1800 |
| ctggagggca | ctggttctga | gaggagaaag | ggagatgggg | aggtctgatg | ggcaggcatc | 1860 |
| ccccaaagcc | cctgagaaaa | ttcatttgag | gaggagagaa | agggatggcg | tgaagctgga | 1920 |
| ggaaaaggga | tcgaaccgga | tgcggcgagg | cctgaactgg | cctggcgggc | gccgacccgt | 1980 |
| tctcctctca | ctcagatcag | cgcccctcca | ccctcccgtt | cccagtcca | gctttcccag | 2040 |
| agatgtcagc | atctctgcca | tccctcatcc | ctcgctccac | cccacacgcc | cgccgtacgg | 2100 |
| accgtctgcg | acagctgcta | ggcctctgga | ctagatccag | gctgtcagcc | aaagcccatg | 2160 |
| cccccaaagt | taccagtcct | cctcccctgc | agctgcagac | gcagacgccg | ccatatcttc | 2220 |

```
accggcccgc agccggaacc ggaaatgccc ttagggaagt cggaggcgga aaactaagag    2280
gggtgggcag ctagcgtcgt ttctaggcaa ccgcagactc cgggtcctta gccgggcctg    2340
atggccctga ggcagttcgg atgtgtccca ggaagtgccc atgtgtggtc cgccgtccat    2400
tccacacctc tgagcgcctt tgtcctctga acttctcacc agttctagcg agtaaaattg    2460
taagaaaggg agccgaaaga gaccggaggg agaggcgggt ggagaagaat tataagtcag    2520
gcaacgtatg caggcagcca gaagagatgg ggctaaacgc cagggaatcc gtcccttggc    2580
ctgaggagct tggagctcct aggctggggg tgagagaggg gctctggcct gcgaagcgca    2640
cgggccaggg ggtctgagag cgggtgctga ggagtctggg agtggcagga acttggggga    2700
gactcaaagg agcagggttg gttgggcgag gctaggttga aagagtaggg tcgagtgagc    2760
caggctgggt gagggagaag gggaaccagg tgttagttgg gcatggggcc gggttgggga    2820
caggaggatg aaagtgggga ggaactacaa agagaagctc tgtttgttcc aagagcgcat    2880
catctttgca tgcattccac cctcccatgt tttttgaggc tttattgtga aaagaggaa     2940 aaggcaaggt ggctaacatt tttcctttcc cgtgccccaa ctaggcgtcc cagatgttgt    3000
ggaactgtcc ctggatctat agctcttcac cgtctctact ttcttccttc taagagatcc    3060
tgaaacctct gtcatggaaa agtaccacgt gttggagatg attggagaag gctcttttgg    3120
gagggtgtac aagggtcgaa gaaaatacag tgctcaggtg ttgcacaaag agggatacct    3180
tttgggtggg atttggtacc cccaactcca gtggaaaatg gatctagaag gaatgtattt    3240
ataccagttt gtattcctaa ggtactgact ccctcatact tcttatggag tataagctttt   3300 gaagttggat tatttgggtg caaattccat ctccaccgct ttctagccct agaattatgg    3360
acaaattact taacttccct atgtctcaat ttccttatct ctagaatggg gataagaaca    3420
gcaactgatt gatggagttt gaggattaaa tatgttttca cattaaatca cttagtacag    3480
tgcctggctg ttagtaaaca                                                3500
```

<210> SEQ ID NO 239
<211> LENGTH: 2700
<212> TYPE: DNA
<213> ORGANISM: Homo sapiens
<220> FEATURE:
<223> OTHER INFORMATION: OGHAv1.0 microarray feature identifier
      ha1p_105937 genomic DNA region

<400> SEQUENCE: 239

```
atgcaaaaat attaaataaa attttagcaa ataaaatcca gtctcatatt aaaagaacaa      60
accattattg acaagtatgg tttattccct caggaataca tgaaattggg aaatagagca     120
acacaaatca aagaaaattt taagagaaa aaaataaatg aaaataattg taatggtcaa      180
aagcccttag gaaagagaaa taaaaacttg ataaatcaca gtaattattt attcagacca     240
tactacgtac ctagtactac actttgaaca tacttaaaga acatttgctc acttaatctt     300
cataatgatt ccatgaaaaa gaaactatga cagctttttt ccacaaataa ggaaactgac     360
tcagagatta acgtacccaa gtcagaggca gaggcaggta cttcttactc cacagtccat     420
acacttgcca cctggctaaa attatttgca gatgacaaaa atgctcaact agaaaaaaga    480
cgtcaattta taagttatat gtaatgacat gagtacaatg aagtgacaga ataaacatat    540 atattttaa cttctgttct tgtcaactaa gtaaaattag gaacaaaaaa ggaaagggg     600 aggggtctta tgcaaaaaaa aagtcacgat ttacaacaaa aagtattaac tatgtagaaa    660
taagcataac cagaaatgtc caagatacgt atggaaaaac actacagata gtcaaacaaa    720
taaaaatatt gggttaatag aaatccatca catgttcctg aaagtgttgt atctagatct    780
```

```
acatcaattc tacccaaatt aaagcaacca cttgatgaaa ctgcagcaat ttaaaaaact      840
ctcaaagagc atgtaatatg ggaatacgaa gttgacaaga tgttattaaa gacgaataaa      900
attataccaa tacctagaca cctgatccca acattaaaca tgaaatacac taaaccagag      960
ttattttctg gaggagtatt taaaatgatg gggatgttat tacttgggtc gcaatgaacc     1020
tgaaaaccca ttttctacag aatatacagc agcaggaag caaggggacc agcagacccc       1080
tttttaagta cgcatgtgat aagcaatgaa cacgaactgc ccagagcagt ctccaacact     1140
gacacgattc gcttccccac cacgacgccc tagcgctact gtgcaacgaa gacctcccaa     1200
gcactggttc caatgcggag accatgggct cccagactct gggaactcca acacgactgc     1260
gaaacgaact ccgagcgagg actccccgag agctccccgc aacacggacc tcacgcgcta     1320
gcgaacaaca gaaaaaaaaa agcgcgctct ccctgccct gaaacattcc cagaagccca      1380
cgcagaccag accgatgacc tgtctccact gctggaggcg agtcagggac ccgaagtctc     1440
taaacactcg cctctacccg ccgccccgcg aaccccacac actgcagacg cgacactcgc     1500
aagtttcggg gatggcggcc ggcgagggcc atactgcgtc tttccggaga cacggaatac     1560
ggcaccagcc gtccctttat gatgcaatat gtctgcgccc aggggacgct tgctgggagc     1620
agccattttc aaccctactg ccgtagagca ggcggagtcc ctcttttcgc gccttaagac     1680
aggtaggttc tgacgatgaa aagcaattga aaacgaccca tttcaccctt tttccagtcc     1740
acgtgaactg ctagatcttg gctttgcaac attagccagg ggcgctacat aaactgctta     1800
gtttctcaaa ggctcaagcc tgccctgatc tgtctacagg atgggtagag atggtcacag     1860
acatttaggc actttgatcc taagaagaat ggaaagaaac catgtggcgc ggcagtctta     1920
caggaatttc aagagggagg gacctgagca acaatcggag gggttattac tcctgaggat     1980
gcatctggct ggagaaagca gcctttgaga actgcctaag aagtatcttt acatctacat     2040
cagatgtagc ctcagaggaa ggagtcagtc atagaatgga taaaacaacc gcgtgttaaa     2100
gctttggtta taattggtgt ggagaatgga gaacacagtt gatcagcagt tgacaaagtg     2160
gggaaccaac acgaaaacag ggctctctca ccctggaaaa gccaaaggca gaacaagcct     2220
ttacatccag gaaggtggga gcaacttgaa atcaaaactc tgaaggggag atgattctgt     2280
tcaatactga aactcagctg atcaattaac tgatgaattc tagcaccaaa cctgctccct     2340
ataattttat aaccagcctc agagaacctt taagggatt gatcattcac tcatttatcc      2400
agcgaatgtt tataaaatgc ctaatgtgtc aaacactgtt gtgcgtgctg ggaatacaac     2460
agttggaaat tcaggcacaa agactctcat tcatggagat tacattctac tggcaatttc     2520
agtgtgtgag ctaaattgag tggtgctaac tgttgacttg gctggttgac tgaaacttgg     2580
actcaaaatt tgcctacact aaatgaagtt taaatgccag aaatttcctc atatattata     2640
aagtacccaa agataaatgg agtttggaat gctagaatga atttatcatg taaaatcaag     2700
```

<210> SEQ ID NO 240
<211> LENGTH: 2700
<212> TYPE: DNA
<213> ORGANISM: Homo sapiens
<220> FEATURE:
<223> OTHER INFORMATION: OGHAv1.0 microarray feature identifier
      ha1p_89099 genomic DNA region

<400> SEQUENCE: 240

```
agaaagttcc tggataaagt agacttaaga tcaacggcat aacctgggta agcaagtagt       60
atgacggtca tgtgaccttg gcattagtat ctcttgccga ggatcttcat ttattggctt      120
```

-continued

```
gcagtttggt ggaaacacct ttctggttct ttctgcaatc atgtatgata gtcatgcagg    180
aggttgtaca gaagtgctcc accccaccca agctcctcct atataaaaag tgcaagagtc    240
ccaaggacaa agaggagggc ctgaaggacc cactcttgtg ctcggcgtgg tcaccgaagg    300
cttaaataat aggcttggag aaatggaaac aggcagttcg ggaactgaca aggcccttcc    360
tacaaagcag aggacgaaat tagccactgc tccagagtga gcacatatct tcactcccgc    420
tccctccacc aaactgactg taactccagt ggaacaccac atctctagtc tctaccagag    480
gttcctgtct cggctccttg ctatttcagg gccacgcatc ccttcccctt tcatttcaga    540
catgcggggt gacagcaggg tcggcctcct cacgcgttct ggactgcggg ccgagggcgg    600
gcggcgtgca cttcaccccc aggagccaga agggaagcgc ggcacatggt cctgtagctt    660
cacgcagggc tggcggccag ccaagcgcag ggccctttaa ggcgcgcagg gtgcgcacgg    720
gtgtgggagg gagaccccgg cgccggaggg cctgcggtcg cctcagcccc accctgggac    780
ggcgtgctcc ctcccctcgc tgctcacctt ggttcccaag agccgggcgg ccgcagtaag    840
taaagccatg gcgggcgatc tccgggatct ggtgggagg taagaaaggg agagagctgc    900
ggcaggaaca ggagccgccg ccgctgcacc agaggccgcg ccgacgggtt gacaaggttg    960
aaaggaggcg gctgaaggaa agagtagacg aaccggcggc ggcgcccagc ccggggtcct   1020
caaggaggcc ccgcccactg gccggaaccc gagcccgccc ctctcaaggg actctccccg   1080
ggcccggcca ttggtccggt atggaagcgg ggcgggacct tagcccttga cagcagttgt   1140
gacggggagg attggaccgc ccggattagg gctaattaag ggtggatggg tggcgggcgg   1200
ggaagtgcgg gtggctaaat aggtgcctga taactcagtt aacttccctc ttggcttttc   1260
cctttgacct taacactttt ggggttatct ctgaggcgaa tgctaaagga gacgctccag   1320
gactcgacct ctgaaggtcc ttggagccaa ttccgtaata tgatcatgga aactgatcat   1380
tgcctgatcc ttctaccgcc ttggcgcgct tcttgagga atgtctttgg ttaatggctt   1440
cacggccatg gaggtgacat catgtggaca acaggctagg atgccagagt tagctgctcg   1500
gtggagatca tttgaggtca gcagaggcca cgatattata gatactaaca gaccccgata   1560
tggggagaaa agcaaaagca ggagcctgaa tatccagtgc tttgtgagct gtcagttctg   1620
tgtgtaatgg caggaaatcc aagtcttaac tgcgccctta ctatgaaggc tttccgagcc   1680
agccacagct tctgggtcat gggcattagt ctcactgcca ctctggtcac gtaaccccac   1740
acagcagctc accccacttt agccacagat taggagccgc agactagccc ctcatcgaag   1800
atcccctttg gtcacattct ctagggcctc tgggccactt ctcctacttg gcagtcttct   1860
atgctctctt atcttgtgct ccccagagac catgacacga ccctgaagtg atattccgca   1920
ccactttcta aatcctctgg gtagacgagg cttcaggact tttgtgcctc cctaagcctg   1980
tcgtagtcat tgaccccaag gacaagagca tcttatctac aaacctccag ccccaagtga   2040
aaagcctttt tttttttggg agacagatct tgctctgtag ctgaggctgg attgcagtgg   2100
tgcgatctca gcctcctgag tagctgggat tataggcgcc cgccaccacg cccagctaat   2160
ttttgtattc ttagtagaga tggggttttg ccatgttggt cagactggtc tcgaaatcct   2220
gacctcaggt gatccacccg cctcgggctc ccaaagtact gggattacag gcgtgagcca   2280
ccgtgcccag ctgtgaatag cccttttatc tcaccacata gcagtaacaa ggatcacagg   2340
tctcagtatc cacctaagcc aggtttagat agatctcctt tacaaagaac cgagtttcta   2400
gcttggactt ggaaaagag atagaaaacc cctatttct cttcttaatt ttctttatac   2460
tcagcttcac acctaacaac caatgctctt ctggcctggg gatcagatag ttaggtctca   2520
```

-continued

| | |
|---|---|
| ggaaaaaact ttaggcaatg ctccagagga gcactgacct cagctacctt tgaagacccc | 2580 |
| ggtgacttca aagcttcact gatcaatatt tgctccccat ttagcatctc ataaaggatt | 2640 |
| tccacataac cctagaatag tctgacctgg ttccttttct ctggttaatt atccacagag | 2700 |

<210> SEQ ID NO 241
<211> LENGTH: 4000
<212> TYPE: DNA
<213> ORGANISM: Homo sapiens
<220> FEATURE:
<223> OTHER INFORMATION: OGHAv1.0 microarray feature identifier
    ha1g_03099 genomic DNA region

<400> SEQUENCE: 241

| | |
|---|---|
| taaatgctat tttattttaa acattttagt ttacaaaaaa aaaaaaaatc aatgattggt | 60 |
| acctttttta cactctcaga ttcctgaata tggacagatc ttcaaaggga ggaaggagtt | 120 |
| ctcatatgaa atttaagata gactgtcctg aaggttgtgg ggtggggttt tttgttgtgt | 180 |
| tttaattcgc ttttgttttt aagacacaat aaagctaaaa tgtcaagtct ctgggagaga | 240 |
| tcccccttaaa gtttcagtca aggagcatat cagagcacag acaaggagac cccagcctgg | 300 |
| tgcccgccgg cccgtcccgg ctgcccaggc gtatttggta gcgcatgggt tgagagccac | 360 |
| tgggacaatc acacctcgca ttccctcgcg ggctgctggt ggcaggtaca cgagccatac | 420 |
| tcgttgatga tcaccagggc tccctcaatg tggttcggtt tgtaatcaac gtagtattcc | 480 |
| tgggcagaca tggcagccat ctgatgcatg gtctgtttct gcttttgctt cctgcgctgc | 540 |
| gtgacaaagc actgtctgag ctgcctgagg ctggctggga aacacttcca ggacacgtag | 600 |
| agcaccagga ccacgatgag gaaggagaag atgagggcca tggtgcccgt gaccaccttg | 660 |
| tggatctgca cggcgttctc ggcgtgctcg ccgcctggaa gagccacggt ggcaggctcg | 720 |
| aatgtgccgt cgtgctgccc ctccccgccg tccgcgagcg tggtggccga gctggcaggg | 780 |
| ggccccagat cactgcggtt ggtgacggcc gagagcaggt ggccgctggt gggctcggcc | 840 |
| ccatcctcgc acaggtggaa ggcgtacacg gcgtccagga cgtcctcgcc ctgtgcgtac | 900 |
| tccgggctgg cgcactgcaa gttgccatcg tagcgcccct ggaagttgtt gagccacgag | 960 |
| gctagggcac acacgttgcg cccgcaatcc cacaggttcc cggccagggt gatgcttgtc | 1020 |
| agggacttcc aagagttgag gatccggggc tcgatgtagg tgaggcggtt ggagtccagc | 1080 |
| tgcagggact gcaggtgcgg cacggtctcg aacacatggg gctccatgta ctcgatctcg | 1140 |
| ttgcccgaca agtccatttt ctccaggttc caaacccagt ccagcgagct gaccacaatg | 1200 |
| gccaccttgt tcctccgcag gcagagcgag tgcagggaga tgaggcgcgg gaagtgggcg | 1260 |
| aagttcacct tgaccaagtc gttgtgctcg aggtgcagct cggtgagctt aaacaagccg | 1320 |
| gcgaaagagt tgcgcgccag actcttgagc tgattgtatc cgatgtcgag aaacttgagg | 1380 |
| ctgcggcagt cctggaagat gcgcacgggc acaaactgga tggcgttggc ccgcatatgc | 1440 |
| agcgtggtga gcttccgcag cccgtggaag aggtcgggcg cgagcgcctg cagcttgttg | 1500 |
| tacgagaggt ccacgctgcg caggttgggc atgggccgga aggtggtgtt gggcagttgg | 1560 |
| gtgatctggt tggaactcag cgtgagttcc ttaactcggc gcagtttctg aaaggcgtcc | 1620 |
| ccctgcacgg agcagatgtg attgtgatcc agatagagcc acgtgagctg cattaacccc | 1680 |
| gtgaactggc cggcgcgcag ctccgagagg ctgttgtagc gcaggacaa gcccagcagg | 1740 |
| ccggacaggt tgtggggcgc ctccggtgagg ttgagcgcct cgcagtacag cagccgcccc | 1800 |
| tcgcaccggc acagctgcgg gcacccgctg ggggcggcgg gcagcatctg aaagcaggcc | 1860 |
| cccagcagac acaagaccac ccccgagggc ctcctcagca gccagtatag acagagaccg | 1920 |

```
agcagcagga aatccattag cgagaatctt tccagagaga ctggagaatg tccattggaa    1980
gcgctcggtc agaaatctac atcatatttt attccgaggg aggggaagcg ggggagggggg   2040 agaaaagggc aaaaaatcaa ataaatacat agaaataaag aaggacccccc ctcccccaaaa  2100 accacacgtt cacctctaag catgcagaaa gctgggcagc atagaaagtt cacagccacg    2160
gaaagatcaa agagatggtg atttggtcca tgttagatgc tgcagcaaag aaaagggagg    2220
aaaaaaaaaa tcttcgggaa agaatttaat taaaaagtgt cttacccacc cttttccaga    2280
gagtgacaac ctccattcag ctgctccctt tgtgtgcagg ctaattatat gcagggcgag    2340
agaagacccc tctgtgtttc cgaggcagcc ccggtccgcg gccggcggat ctggcaggcg    2400
cacaatgtct cactttgctg ctcggctcgg ggctgcaagg gcggccggca aggcggggag    2460
gcgacttcta ggacccgcaa gtttcccaac tacgtgccgg agcccgagct tcgccttcct    2520
gccgccttcc tttccctctg cagttcggac tgtgacgttg tggggggaaa aaactccaaa    2580
ctcggggctc gcgactcccc aggatctgac agtctggtta atgtccgtca ttggaaacga    2640
ccactgaccg gcgccacctt ttactccgcg gaaacagcct gccattcgcg ccccgggcag    2700
ctgcagagag cgggctcact catgctttgc gggcggcggg cggcgggcgg cgggcggtgg    2760
ggaggtgcgg acggcggcgc ggggagcggc gagcggcgcc cgggctcctt ccctccacca    2820
ggcagtgtgc ggcgcgagct tgcacaggca cctactgctc actgagtgtc gtaagctgct    2880
cacgattgtg cgtcttcccc gagcacctca gacatgggca gattgaaaag gggtgggcat    2940
aaaaccaaca ttttaccgaa ccactaaagt aatatatgtt ttttgatgaa acggaaaaca    3000 cttttcagctt ttttgtccat atttcaaaaa aaaaaaaaaa aaaaaaaagg aggggggagg   3060
gaggtggagg taggggtagc atcatccacg acaagatatt tccaagtggg aaactgaaat    3120
gttctgtgct ctccccccttg ccttttgggg atatattctt ttcccctttta aaactgtcta  3180 cgtgtaagag atacgtagga atctgtagag aaatcaacgt ttggaccttt gctttagaaa    3240
agcaacttga gagaagacac aggaaggcaa tgatttgggg cttggctaag attttttgggg  3300 ttttttcccc ctcttgcggg tactggaatt ctgcagtcag ccagcccttt tttgaggtgg    3360 agagggaaa tgctttccaa acccacctag tttgggaagc catccaagtc ccggtggtgt     3420
gagatccagt gtggcaaaaa ggtatgtctg tgtgcaggga gacttgactg agatccctcc    3480
ggggcttcat caggctccac agatacatat ggggtacaga gtggattaaa gaacgattgt    3540
actgtctgac atgggggaggg cttaccctga cttgtgctgt tcatggtgat tactgggccc   3600
tgcagtgcac cccactccaa gagagtgtga atgtgtaggg acgtgatagt ttaagccata    3660
atgaagccta cccgtctcca tacacacatc ctaattaatc tttgagactg cactaagttg    3720
tgccactttt tcctctgagt atgacgagaa gcctttgcct cattatttct attcataatc    3780
atttatagat aggagtcctt acaatgagct ctccccccac ctccccacac acacaccttg    3840
tgcctactgg tctgtagagg gtctgccctg gggagggtca gttggtcatc tgtttaaaca    3900
aagtcctcca agatggctga gaaagcctgc gggaagtgag tgtgggcaag ccttccttct    3960
tgacaaagat gcccagggag atggtaggga gagtcaaatg                          4000
```

<210> SEQ ID NO 242
<211> LENGTH: 8900
<212> TYPE: DNA
<213> ORGANISM: Homo sapiens
<220> FEATURE:
<223> OTHER INFORMATION: OGHAv1.0 microarray feature identifier
      halp_67625 genomic DNA region

<400> SEQUENCE: 242

```
ggctccttct ggctgccct agacccacca gaggggcagg caacagagga gggtgagctg      60
gaggctggag gggccaggga agacggacag ggagggcgcc tgcctccac  agaccccaac    120
cagcctgccc tcttcaacct ttccctgctg ttttccccag gactcctttt gccctcacac    180
tccagtctct ctgtagcacc ctgttgctcc ctcttggtga tccagctctt gaaagcctct    240
ccaggcctcc cgctctttcg gaagccgtgc ctctccccct ctgcttcctt catctccgag    300
tctttgtacc cctgcgtctc cgactcggcc tttcatctgc tccctccacc tcggcatcgc    360
cttgcctcag tctcccccga cccctgtctc gccccctctg cttccagaag cctgcgcctc    420
tgtctctccc accgcccggt ctcctggtgt cccggcgtc  tctcccgtcg ttcccgccgc    480
cttgatcagc ctgggctgtg gcgctggcat cgctggcctg gggaccgggg tgtgggcgat    540
ggaaggggt  tcgagaggcg caggggaggg gcttcccctc ctccgcccct gggcgcctgg    600
ggagactcgc gtgccagtca cctgccggtc ggggcgccga cttcgcgcct acgcactcca    660
cgtgggcgcc ccggggcgcg cctttgtctc tcccgagcct tgaaagctaa ttacattggg    720
aggggacagg ggtggggtgg gagaggggc  cgctgtcccc attcactgag ccgaggccgc    780
cactccgccg gcagcccgc  gcaggcctgg ccccgagtca cgtctgttga aaccgttttt    840
ttcggcctcg cccccacccg ccttggcagc cagccgcgcc tttgtacgcg ccggcggggg    900
cgccctggaa ccctgaaccg tcttacgggg aacggggtg  ggggagggg  agcggcgcgg    960
gccccacgcg aggaaggaat ttcctgggcc actgcgaaag attgaggctc agaaagccag   1020
agagagacgt gcgaggagga agcggagagg gtgtgcgaag ctggagaggg agtcggagcg   1080
ccagcgaaag aggggagcgc tggggaagga ggaagagaag gagaggggga gaagagagac   1140
gcggatgctg ggcgcgcgac ggcagcgggc ggaggagggg agcggccggg aacctgcgcg   1200
caggggaagc caggacggag cgcagcaccg gcaggggagg gttgccgagg ggctgtgccg   1260
aggagcccgg gtggggcgg  ctggaccgcg ggccgcggga ctcacagaca gtgcgaggcg   1320
gcgcgggggc ccctctccct atgcggggct ggggcgcagg ggctgggcgg ggcgggtggg   1380
cgtctgagcg cggcgcgggc gcattcttcg cctttcttc  ctcgggctca ttccggccga   1440
tcgatacctg cgcgggacct gccccgccg  ctaatatctt tttaatgagt tcgccaggct   1500
taaagcgagc gcgatctgcc ctccagggtg gatttccc   cggcagatgt ttcgggagga   1560
ggaggcgcgc ggagctcccg ggaggggga  caaatctctc cctccgaggg gcgagaacag   1620
gagactttct tctaaagttc aaagaaaga  cgggctttca ctcggccccc aaaaatgtat   1680
ttctcggcgg acaatgggct tctttctgcg cctctgaggg ccggcggggc gggcagggcg   1740
gggaccgtg  cgctttggcc ccgcctgacc gactcgcacc ccctccccc  gcacccaggc   1800
ccgggcccca gagcgagggc gcaggagccg cgaagccggc cgcccttccg agcgtccccc   1860
tgaagcgcac tgtcgggacc tggctctccc ggagctaagc cccggcgcac cggcgagaac   1920
gaaagcgtcg tgcggggccc tgggctgtcc cacacgcccc cgttctcata ggtgcctcag   1980
ccgggccgaa gggacgcgcg ctggtgcctc aaggggagga cgaacggacc tccgggcttg   2040
ggccgcggcc tccttcccct cggcgctccg ccctgagcgg ggcaacaact agaaattagc   2100
caaccccggg cggctgccgg gcctgagac  tgtcttgccc gccccggccc agccaccct    2160
ccgggtcgcc cctgctcttc tcctccactt ccccttcaat gtccctccgt ggggccgtcg   2220
gcctgccgcg gcgccctct  ctccactccc gtgggctcag gggaagaggg cacccgggcg   2280
gcgaggatga cctccgaaga gccgcggcaa attgattcgt tccgcccgga gccggggccg   2340
```

| | |
|---|---|
| cgtgaatggg ggcccgggcg gcggcggcag cggagaagag gataaagatg ttctccctga | 2400 |
| aagggggagg gggcgcggag cgggaagcgg ggccattcac tcctggcccg gcccctcggg | 2460 |
| aagccgcgcc gaagaaaggg ggccgaggcc tattcaagtc ctacgagccg cccacaatgg | 2520 |
| accgatatac tgagggcctc tctattaacg cccatgaata ttaaagagat cgccaagtgg | 2580 |
| cggccagcgg gcgaggggg cgacggagcc tgagagctcc ggcccggccg aggggagggg | 2640 |
| gcttttgcgc gagcacattc cgcgcctggg ccccgcggaa aatgacaaaa taacacgggt | 2700 |
| catccgctgg gaaagcccgg aatgtttccc ctcgaaatct cctcccgggg agatgtgagc | 2760 |
| acagggtctt gctccctatt tcaatgcacc ttgagactgg gcgctaccta cgggctcctt | 2820 |
| tttccccggg cggggggtcca ggtgggtttt gccgctagac tagaagcaca aaatgtgagc | 2880 |
| gcggtgagag tttgggcgca ccagctggga ggacgttctg cgctccggtt ctgcccggct | 2940 |
| cccagtactg ctctccgggc ttgcgggtcc ggaggagagg aatgggactc cctggccgca | 3000 |
| gtccgagccc gtggtcactg cgccagcgga atccaagcct ctaactctaa gccgggttc | 3060 |
| aggacccaaa cgctgcaccc cagcacggag gatgcacaga cctgagggct tcccgcagtg | 3120 |
| ggacgtggcc ctggagaggg caaaatcctc ggggttgtcg tggggtaaag tgatcttacc | 3180 |
| caaagagaga ccaagcaaag aaacctcagt tcacaaagtc caactcaaac cattgcacag | 3240 |
| acagggacac cgaggcccag agaggaaagg ggcagtccac aggacacaca gcagtccta | 3300 |
| tcccccttg gtgtcctgga ggaactgagg tcgctttcgg ggcttgggag ctgccgcagc | 3360 |
| gcttggctcc tggcagcgct ccccgacgtc gtctccctcg ctcctagcac tttgtcctct | 3420 |
| ccacctaggt cttcccagaa gccaagaagt aggcccggt gaggctcccc tgcaggagcc | 3480 |
| atcggactcc atacgccccc tcagactcga gctctggcca gggagccgat gcgacccaca | 3540 |
| agctgcgtcg aaaaatgagt ggagggttcg gcgaccctaa cccacctccc tcctcagcag | 3600 |
| cgctgccctc tgctggcgcc ctgcccaacg gtcctgcctt ctgccaggtg tgcccttcct | 3660 |
| tgggctccag cctcgggcgg acccggacgc agggtctgaa ggccagctac cgccgccttc | 3720 |
| ctcccttgc gtcccaacgg ggacggggga tgccggagac tactggcagg aactggggac | 3780 |
| caggggtctg gagtctggac gccaggtgtg agaccctctt agccaaggcg cgtccgggtg | 3840 |
| gtggaggggc gtctatgcca acaggcgttt ggacagggtc tcgctcatgg gaggtcagct | 3900 |
| cgctgttctt ccaccccaagt cctccgcgct gaggagaagg tctagggagt ccacacagtc | 3960 |
| cagcggagac taatccgtga gcctgaccca cgccgagagg gtccaggcac ctctgttagc | 4020 |
| ggcatctgaa attgtaggct ggtgatggga gccagaagtg cggcaggtgg ggtgagctcc | 4080 |
| ctcacccagc atgtcagggc ctggggtccg aggcttgagg ctgacactgg ggagccgcga | 4140 |
| agcctgcagg aagcggggcc ttccgctggg ctcagcagct acctgcttcg ggagagggga | 4200 |
| tcgctgggct ccgaggtgcc tcgaaaccgc cgcaaagcaa gtctgctcct gggatgatgg | 4260 |
| gcaggaggaa tagaggagag gaagggaaag aagagagagg cagagagaa agaaagaact | 4320 |
| aggaggcaag aaggaagggg cgccgcaacg ccaccggctt cccgaggttg cagctcagca | 4380 |
| aggagccgga aagccgggcc gcaagccgaa cccgcactga ggcctctcgc ggagctgcct | 4440 |
| gcagtttctg agggacttcg ctctcaggca cgcctgctcc cacctaggaa gggtctcggg | 4500 |
| accccttca atccccctat atccgtagg aaattctttt cccagagaca ggctgccagg | 4560 |
| gcgattcctg tccgcccatc tcgaccccg acctggcccc gcaagggccg ggagcctggc | 4620 |
| cttccatgaa gctgtctcag gccgggacca gccccagccc cgacggccgc tgcggccccg | 4680 |
| cctcggcagc cccgtgagcc cgcggaggag tttcgcaccc gaccgtgcac agcgaccgag | 4740 |

```
ttggcgcggc ccgtatgaag cgaagcgccg gcttcagcag cgcagtctga gcaggggatc    4800
cgcgtggcaa ctagggctgc gcgcgagctc ggggcgactg tggcggcccg gggagtgcag    4860
ggccggagag ggaagaggac gcgggctctg gccggggagg gagagcggtg cagggctggg    4920
ccggccagcc ggggcagcaa agtaaaggtg aacgccgggc tgggccaggc cggtgaacat    4980
agatcaggcc tgaggggagc gcggggcccg aagccaggcg tcccctcttg tctagcctgg    5040
tccctggagt cctagagagc ctcgccgcac ccccteccct tctccgtccc ctcctctcct    5100
cagagccggc tgagcctccc tccctgccct gcgcttccca cggggagaga aggaaaaaca    5160
ggagggggga ggaaggacca ggaagggag agaggagtgg aggggtactg tttggagcgg    5220
tccgcgcgcc cccgcccctc gcgctctcgc gacgaaggct cctcgagccc agccgggtac    5280
aacaagtctg tcctccgacg tcaggggtc attaataacc aattaggagg gtcactgcgg    5340
ctcctataaa ggcgctgaga ttttgccaag gggaagacgg ccccggccga gtgtgcgaga    5400
ggctagcgcg cgcctgagcc ccttgctgcc gcttccctgc aaccacccgc ctctcaccca    5460
ccctgcaccc cccgcacccg cctccgcctc cacccgcgtc tctccaccct ccgcgccgcc    5520
tttgccatct ctacagattt caccatctct cttcccctct ccccctcgtt cgcttttcctc    5580 ccagtcgccc cctcacctcc cgctccctcc tgcgtcctcc tcctctccgt cctccccctg    5640
ctctggttcc ttctccatcg cagcgctctc ctctcgcccc ttgggctccc ctctcgcccg    5700
cccacctccc ccgtcggccc ggcgtcccc cggcgccggg gagctccggg ccgcccatga    5760
tgggctccgt gctcccggct gaggcctggt gctcaagac cgggctgaag cgcgcggac    5820 tggcgctggc cgaggttatc acctccgaca tcctgcacag cttcctgtac ggccgctggc    5880
gcaacgtgct cggggagcag ctcttcgagg acaagagcca ccacgccagc cccaagacag    5940
ccttcaccgc cgaggtgctg gcgcagtcct tctccggcgg tgagtccagc cgtcggagcc    6000
cggcgcaatc cctcctcccg gcgacccca ttcccgtcct ggcgatgcgc gagacgcggc    6060
tgggataccc ggcctcgctg ctactcgcgc caacctgggc tctccggcg ctcggtgcac    6120 ctcagtttcc ccatgggcca aaccaggacg cgagccacca agcagctccg cagcccaccc    6180
ggctcaagga ccgaccccgg cgaccccgtc gctcggcccc gacgccccg ccggcccctc    6240 ccttcccctc ctgcgcttga gctggcgggt tcccggcatt tacagcctta ctaggcgtgt    6300
aatagcagtt gactcaaaaa gaaggggttt taaattcatt tagttaactt gggcttgacc    6360
cacgaaagtt cccacttaaa ccaagaactt taaaaggcag ccggggctgg ggaggggtg    6420 gagggagggc gggcggggag aaaaagccgc ggggagagcg agggagagaa agagagagcg    6480
agaaaagttt ctttctctta agatgtctca agttcttatt cctcattcat caacccgcaa    6540
acaatatctt tccctggctc tggcatctct gcgcgtcgcc ctcttttccc cctttacgat    6600
ttctgttcct ctcttaattt accgtgaaga ctaattccac ttccattcac gctatgtcaa    6660
ccatctaatc cccctttttt gtaagggaa ttcctcggcc ccttttaaac aagtcccctc    6720
cgcattgagc tacaatttac tgctacagca ttcttccagg gctaatgaat ttagaattag    6780
caatttcttt cgaatggagc cgaatgaatg cgatcacttt aacagcgtga caaattgccc    6840
gccgcgccgc aatggacacc gtttaacccc ccccttcag ccggcccgct cgccgggtat    6900
tttcccaggt agcttagagg ggaaccttgt aagacatgga ggccgccctt gtgcgcctcg    6960
ccgcttccag ccctgccgca gatgcccgac aggggaaccc tcggggagct gggggccgcc    7020
gcggctcctc cccgcccaga gagatgacat cggggtttgt ctgagcccgg gcgccgccct    7080
ccctggcacc ccagggcctg ggagcagaga gggactcggg cgcgcccggg gtcacacagc    7140
```

| | | |
|---|---|---|
| gagcgcagag cctggccagc tgctgccggt gcttctttgg cacctccaac acctgccagc | 7200 | |
| ccgaggtctg tccccagcgc tgatcacggc ccggctcctc tgccagtgcc cagagcctgg | 7260 | |
| acacacagtg ggctcccgga agccgactag gcgaaagagt ctccggttgg ccttcacctc | 7320 | |
| cttgcaggac ctggcctcag tttcctgtg cataaaaccg ctcgctgccg ttggctcatt | 7380 | |
| aattcttaaa cttatccggg gcagaggatg gaagaagttg cgaatgcttt gagaattcgc | 7440 | |
| ggagagacta aaaacccact tctaaaaatg atccccaacg caccactcgc tttccagggc | 7500 | |
| acggagggtc tccaggttgc aaacagagga gaggtcgttg agcctccgca catccgactt | 7560 | |
| cctccacacc cgggtggctt ctctggattt ggggccgact tgggtttggc tggtctgggc | 7620 | |
| aggaccgaag ccggggtccc ggcggggaag gaagggccgg gcctcggctg cctcgggctc | 7680 | |
| tgaccggttt cctggccccc gccgccgcag aagtgcagaa gctgtccagc ctggtgctgc | 7740 | |
| ctgcggaggt gatcatcgct cagagctcca tccctggcga gggcctcggc atcttctcca | 7800 | |
| agacgtggat caaggcggga accgagatgg gccccttcac cggccgcgtg atcgccccgg | 7860 | |
| agcacgtgga catctgcaag aacaacaacc tcatgtggga ggtacgcgcg ggctggggca | 7920 | |
| gaggggcgca agggccggcg aggggcgctg gtcgcgggta ggactcgggc gtccggccgt | 7980 | |
| cgccgcttcc acccgggctg agagcggcgg acactcctgg cctggacgcc ccctgagccg | 8040 | |
| ggactctaag ccgcccgagc ctggagctca ccccgcctct aggctcctcc caacccgtgc | 8100 | |
| cgaaaatccg accctccttc cccggacac cctggcagag caagactgtg gttggctcca | 8160 | |
| cttggcagat gagggcactg agacccagag cagtcaggtc gcttgcccag ggtccccacg | 8220 | |
| cgccatccct ccaggcctct tcccagccac ttacattctt ccctggcccc cggaagcagc | 8280 | |
| ctgggaagcc cctcaaggcc agtcctgggc tgggggtgag gtggggctgg aaaggagaat | 8340 | |
| gcctggtgaa agcagaatga cattcacgat gactgtggct gaggtggcat tgagtcagct | 8400 | |
| tctgtgtccc cagcctgcag tcacggatga cctcagtagc ccatgcctta ctgttccctt | 8460 | |
| ttcacggagg ctcaagagg cttccatcct aggcctttcc acccatcaca gtgccagtgc | 8520 | |
| cagggagggc caccctgtg cttcttccta actttgcaga acgggaaacc cactgaggcc | 8580 | |
| agactggtgc acacccttcc taaactcatt ccctcgcccg ctcccccact ccagctcccc | 8640 | |
| ccggcggacc ctggagaagc ccaacttgat agaactgcgg gatggcccag aggcctctct | 8700 | |
| tgacctcatc tccctcctct ggagggctgg accactaacc accttctcca gttgctgggt | 8760 | |
| caggaagttg gggtccagtt tgacctctga gtggccttgg cagctcccgt gaagggtttt | 8820 | |
| aggccaagct ggagtgccac agtgacccag ccctccctcc ctggactcca ggatcctccc | 8880 | |
| tctctgaggc ctggctgatg | 8900 | |

<210> SEQ ID NO 243
<211> LENGTH: 2600
<212> TYPE: DNA
<213> ORGANISM: Homo sapiens
<220> FEATURE:
<223> OTHER INFORMATION: OGHAv1.0 microarray feature identifier
      ha1g_00218 genomic DNA region

<400> SEQUENCE: 243

| | | |
|---|---|---|
| gatcttaggt agttgtcttg cactagcact tcaagtacaa agatacccttt ggtgaatttt | 60 | |
| caagaatgaa tataaaatca atttaagttc cagtttttt tttttaatga ctctcacaca | 120 | |
| aatcaactgg ttataggcta cttcagcttc ttcctgaagc agttgtagct cctaattaat | 180 | |
| gtgaactcca cgaagaaaga actcccacca ttttatgtgc tctgggatgc ggctgagtct | 240 | |
| ttccaattgc agtctgttta ctctttggac agctgcatct cctccttatc tgctgaactg | 300 | |

```
aggactgtac aaatgtttct tgtgggtcag tgtaatatta aagaatagct atgtttagaa    360
ggccagttac cgttgctgta cccacacgtc aggggcaaag gctgagtggg cagatggggg    420
gctgccaccc ctcctcacgc ccggcttggg accagcctgg agtctcaagc cgaaacccct    480
cacgcgggtg ggcacacaat gcccggcgtg tcgcctgggc ctcctcggag gtgctttaac    540
aggctcttgc gcttttgaac ggccctcctg gactctgatc tgtttaaact agaggcgtta    600
ataagtgata acctggatct gccctccttg gaagctgcct gcctatattt tattgtttaa    660
aataaataaa aatggtgccc cgggagagaa gatgggggttg tttccttttt cctctggctc   720
tgccccgaga aagagggcgg gatcctcacg gctcacagtg ggagggtct ttcgtcggcc     780
gccggctcgc ctcggagggc ctggaccact ggaccgccct tccccggggc cctgccgcgg    840
gaccgcgggc ttctggctcc tcctggggct gcgtccgtat gcgcggagcg tgtggccggg    900
ccgtcgccgc gccaccccac ctgagtccgc cggccagcgc ggggacgcac cgggcagcgt    960
gtgtttggcg accctcccgc acctctggtc tcagttgcgt gtgtgcacga ggggttccat    1020
agggcccagg gatgcttggt acccacgggg gagaatccct cgccgaaccc tgcgggtctg    1080
cggggcgggc cgcgagactg gcgcgcaaaa gcggctccaa ggcggggctc ccgcgctccc    1140
cggggccggc ttgccgagtc caagttgagc aaccggcgtc gagagagaca ccgcccctgc    1200
tgcgggcggg ggcctctcct cgcttccgat tggctgacgg ggggaaccta tcgccgtcgg    1260
ccgcctccgc cagagcggtt tgctggtttt cattcattgg ccccggagcc gccctggat    1320
ttccatcttt tgtggcgcga aaataaccct ttgctccctc gttggttttg ttgaggttga    1380
ggggtgggac tgtgttcccc tctgctcgct ctcgttttc ctgcccttta acagctcgcc     1440
cccagcccca accccaagg aagaaagagg gaggtaacgc tgaggaaggg tggaaagcag     1500
ttctgcgtcc gtgggtggag cccgccccctt ggctgaccgc atggtgcccg cacggtccct   1560
tcccttcccc cagcgtccag cgcccggagg ttctggattt gcgccatgct cagcagctgg    1620
agtcacatct tcgtttccct gcccatttcc aacatcttag agttgatgcg tcctttttta    1680
cttaaaacaa ctacaaccaa ccatgttctc aggtaccaga acttttctgg gcttctagag    1740
aaatcgactc gccctgcccg ctcccttcct aaacccctttt gtggtccaca gggttgtttt    1800
aagcaaaatc aaacaacccc tccaaaaaaa gcaaacgaaa aattccgggt aaaatcaact    1860
atgctgagac cacgttttcg ttgaagctgc cctaagacca atgaagctga accgaccttt    1920
caaggattaa cgatttctgt agctgaaatg ttctaatttc actgacgttt ggtgagacg     1980
gtgagaaaaa ataaatatga atttgacttg gaaaagcaca aaacaaacga aataataata    2040
tttaatttga ttaactgaga aggcaaacag ccacagtggt gtattctagg tactggtgtc    2100
tttggtgagt ttgtaattat ataaataaat tgctgttggt ttcatcaaaa atacagatca    2160
gaactctggc cgtgacaaaa aaggaaggaa gtataaattt gtttggtata tctaattta     2220
taacagactt taccaacctt tcattatctg gagaaaagga aatgtaccag ttaacaatat    2280
aagttaatt gtttgcagat aattgttcat tttttgtctt gacaaaatac tctgtttggt     2340
taaaaacggt aaaatgataa ttcagtaaat atttaaaact ttgagagaat tggtttaaat    2400
cagggagttc aaagattttc tctgtgttgt ttactcttag tgatgttaca tcttgtgatg    2460
ttacatcttc ttctgagtgc ttttgaaaaa attattagtt ctgtgttagt ctctaaaaac    2520
taaagtaaca taaattgcca tgtaccaaaa ttttaaaaca aattttaaca actgaattgg    2580
ttagtaaaga aaaactactt                                                2600
```

-continued

```
<210> SEQ ID NO 244
<211> LENGTH: 6700
<212> TYPE: DNA
<213> ORGANISM: Homo sapiens
<220> FEATURE:
<223> OTHER INFORMATION: OGHAv1.0 microarray feature identifier
      ha1p_12535 genomic DNA region

<400> SEQUENCE: 244
tagcaagggc tctctttccc ctgcttcatg tgcatcctga aaccctaaca aagttagatg      60
tccatcagca taatcagtcc atgtgctgga tgtgtgaata tatgtcctcc aggtaacgga     120
ggaacttggg ttcagaaact agacagcctg agctcaccct gggctccact actctgccag    180
tgtagttgtt tatttatta ttgtggaaaa tatatacata acaaaaaatt cctttcaaa      240 tcgttttttg tttggttttt ttttgttttg ttttgttttg gagacagagt ctcactctgt    300
cgcccaagct ggagtgcagt ggcgcgatct tggctccctg caagctccac ctcccaggtt    360
cacaccattc tcctgcctca gcctcccgag tagctgggac tacaggcgcc tgccaccacg    420
cccagctaat tttttgtatt tttagtagag acagggtttc actgtgttag ccaggatggc    480
ctcgatctcc tgacctcgtg atctgcccgc cctggcctcc caaagtgctg ggattatagg    540
catgagccac tgcgcctgcc tcaaatcgtt tttaagtgca tggttcagtg cataagtac      600 attcatacta ttgtgcaacc atcaccacca tctatctcca gaactttttg ctattccaca    660
ttgaaactct gtacccatca aataataact cccattccat cttctcctgg gccctggcaa    720
ttaccaccct actttctgtc tacatgaatt tgactattct aagtacctca tataagtggc    780
atcacagaac atttgtcttt ttgtgtctgg cttctttcac ttagcataag gtcttaaggt    840
tcatctgtgt tatagcacgt atcagaatat cctttatttt taaggctgaa taatattccg    900
tcgtaggtgt atactgtatc ttgtttatca atggacattc gggttgtttc cacctttggg    960
ctattgggaa taatgctgct atgaacattg atgtaaacat atctaatcaa gtccctgctt    1020
tcaattcttt tgtgtataca cccagaaatt gaattgctaa atcaaatggt aattctatgt    1080 tcaattttg ggggaaccat acttgtatat ccttaaacct ctgtgtatca tagaacctct    1140
ctgaacctca tctgtaaaac acggataata acagcaatgc catttcaggg tggtctgaga    1200
attaatgcat atgaagcctt tggctcaaag actggacaca ttaataaatg ttcactaaat    1260
gtttgcttga tgtttaatct cttcatcctc tgaattgagg gactcatact aaaataattt    1320
ctaaagtcac tctcagctcc taaactccat gatcccatca ttaaattatt ttcctgttgg    1380
ggatgccagg agctctcaga ttgtatatta ggggaacacc ctcttcatga tccccgcaaa    1440
aatccacccg tgccaagaag gcccaatttt cctagctttc tcctaggaat ttgccaacat    1500
atcccagtgt aatctcacat ctcattttc ttgccactcc ttctcccttg ctttcttcc      1560 atgtttcctt tctcggctgg cttttcctgc ccactgaata tctgcacttc aaattatctt    1620
ccctggttgc atttatgttc attccccaca agttaatgtc tgttggaagc aacacttgtg    1680
aagttctcca gattaagttt tcattcccaa gagtcccata ttttaaatga ggttttcctc    1740
ttcggcagaa tcacactggc agagctaccg caatttggtg aagtcagtgg agttgggttt    1800
ctcccctcat tctgtttatg ttgggttatc gcttggcctc atgtttggat tctcatcctc    1860
ccaacatgtg tcacatgcca gtgagaaaca acactctctg gtaccatccc agtggatgtt    1920
tacaattcag caaatactct ttttagaaaa gttaattaga ggaaatacgc ttccaagctt    1980
ttcttgcctg gggccagatt cagcatccca gcagggagtg gacttccttc actccttgag    2040
gaaatatttt ccttctccac gctattcctc cgtcttccct cgaaatgtga gtaaaacatt    2100
```

```
caacaactaa aatatccttg ctaaacacat gaagctgcgc tctggttcag gcagcagttt    2160
agctaccaac aaactgcgta tcctctctga agcttttca cagccaaagg taaaagaggt     2220
tctcgggtca gaaataaatg attttcag attctgggct aggaaaaaga gccagctcag     2280
gtttttttat tttcttttaa acttttatgg ctttgaagcg cctcacctgc catgtaataa    2340
aacaggaagc aggggaacgc tgatgtaacc ctgaggaatc aaatccactg agccctggca    2400
ctctgagaag aaccaggtcc tctggagctg gtccaccgac accatgcaaa ggcgaagatg    2460
aagtagggag gtgccttaat gcaaagtcac ccacttaccc ctaggcaagt gtttaggttt    2520
atggattgtc agcccttatg aagggctcct tcttccttta ttattgtctt tgggctgctc    2580
cagacaccat ggaggcaaaa ttcaaatgaa acactcacca tctttattgt aaatcattaa    2640
ggaagatcct acctgggcag gcaggctcta ggtagatgga aagtattgac caaaatgaag    2700
ggcagggggg tttgtgtatc tcagcttttc gttgatcatg aagggatgtg cctatggcta    2760
agtttccctt ctacacaggt tattgcattt agtatcctcc ccacccgacc tggcctgttt    2820
cattctcagg cacttgccag ctacttgcag cggcagagca cccagctctc agatagagtt    2880
caggtgacag gtaaccagca cagaagggaa gcagcgaagg ctcgtacata acctgccct     2940 attcagagct gccccgtttg gtcatttctg tacatctcgg cctgccctca tctcatgagg    3000 tctcactta ccccctgggc catagaagga cagatgttcc tatgacgttc ccacttcccc     3060
gcctgccagc aagcaggatc tgccatgtcc tcgcttctgc ccttagctgg atctccgtat    3120
catgtcccag cctcatttgt ccccagaagc ccatttgacc tggggattgt ggcttagaaa    3180
atgatatatg aaaaccaaag aagccagagc tctttcaaaa caaaccctat gcatcccaga    3240
aacaatctgc acttttaacc ttggcttttt cttctttctc actctcatca gaaaggaagt    3300
gtgtctatat atgctgagtg agtcaatctc ctgtgcttgg atctactccg aagggggtatg   3360 gctgtaggag ttcgtgaagc aagattcacc agaagaacac caagcaagcc ctgctctta    3420 ttcctttctt tctttccctc tcttcttct ttcttgctca cctctgaggg agcccttcc     3480 aagagaaact tcgcttttgc aagtcagagc gggtaactca gaattgattc cctaaggcaa    3540
tttggtactt ttaaaatgat aaaaagagca aataaaatag gagctggtcc gctttcctga    3600
gacagtacag ccccacgatt tgggatgaca aaaccacgtc acagtctcag ggagggccac    3660
aggagctcca gcaccaccag ccaagtccct aaaattatca ctggaaaagc accacccccc    3720
ctcaacccct caccccaaac acacacagcc cacctcctga gactcccagt cctgctccca    3780
ggcagacccc aggaggaaaa tgctccctcc tagggtgtcc tcctagggtg tcccggacgc    3840
tactcacagt acctcttggc aaggacgaga tgagaaggag ctgaagaaaa gtgagcccca    3900
actgcgtcca gcaacccagc tccatccttg ccgcggctgg tgcccgagcg tctactgggg   3960
agggagagga gggacccagg gaggccgggg gcaggcgggt tttacaggga cctccccgag    4020
ccccagctga gcgggagctc gggtttcagc tcgccaggct ctcccatcct catctgaggg    4080
gaaccacctt cagccagagc gacgtcagcc caaacctctc ctctctgctg ccttaaccct    4140
tgcggggccc cggaggtgt ggccacgcct ggagacccgc ggacggcggc tgcaaaggaa     4200
gctgcggggg agggaggcca gcctgggtac aggtgggtc ccagtgttgg gtgctgggag     4260
gaggggccat aggaccctgg gcgggagcag aggtacccag gctgcgggg cgtcaggtg     4320 aggccgggag atcttcctac gggaggctga gacgggagct ggctttgccc tctctgactg    4380
cacgcgggga gctgattaa aagcctggcc tgaggagaag gaggagttgg tgatgggagg     4440
agaaagggag cctccctcca ctccgcacgc aacactcctc gtttatctcc tttcctctcc    4500
```

```
gtttgctcca ggtgatcaca ggttggaaag cttattatct tttgcaacta caggctactg      4560
gaaaagttt tcctcttcct atgatcccg tcatggtgaa ttcagcgaca taagcagctc         4620
ctgagctact ggaaaagtt ttcctcttcc tgtgatcccc acgatggtga attcagcaac        4680
ataaatagct cctgcgcaca cgccaggcag ggatggcgaa gaacacacaa gaaccctcac      4740
tgcctccacc aaaagggctc agtttaggta caagatagca agtgacatct cgaaatgagg      4800
aagaaggat tttcataata ggtgactttt taaaataaac tcctccgtgc caggtgtcat       4860
gtaccttaca tgtattaact caattattcc tcacaataaa cctagcctct gtattttaca      4920
attagagaaa cggaaccatt gaggattaca ataactcatc caaggccaca cagttagtga     4980
ggggcagagc cagggtttga acccgggcag cttaggccca caggctatag tcttagccac     5040
taggctatag agcttcttag gatgctacat atgcagaatt gtatttcacc atttgatatg     5100
gcttcgctgt gtccccaccc aaacctcatc ttgaattgtg gttcccataa accccacgtg     5160
tcatgggagg gaccaggtgg agataattga atcatgggga cagttacccc cataaaagtt    5220
ttaattttgt tctctagatg ttggcgggcc ctggtggttt acaagtaggg tgtgctgagc    5280
tcaaagcaaa gtctcgggaa gagaagtcac cctggactat tgatgaaggc ctggagtaag    5340
gattaagaaa tggaagtgga agggaaaaga taagggagaa aacctgagga aggtagaatc    5400
tgtaaagctc aggacagatc agaaggtcag gagccctgac acaggtgctc tactagaaag    5460
aatttctgaa ctccagccct gcttctgggg gcctattgca gtgaagtgac tggaagcaag    5520
aactcagcag gcctgtgttc taattttgtt gattcaccac tttctggctg tgtgacctta    5580
agcaagttaa ctctctgaat ctcagtcttc tcatctataa aatggaaata ataatcaaac    5640
ctactttgta gatcactgga agaattaat aagattacgc atgtaaggcc catagcacag    5700
agcctaccac atattaagtg cacactaaat attaatcatt atctctatta tctgacctga    5760
gactgccccc aagaacatct catggtatga gtcttgttcc tacactcaac ttccatatcg    5820
agatgaaatc agttaaaata agcaccaaga gtagccttaa acaggagcag aataccagag    5880
ggcagcatat acctaagagg tagagggcag aggttcgaag aagggaggtt caccttgttg    5940
ctggccaacc agtcctggtc ctttggtgat gggagtggga agaagatgac ttagttccca    6000
ataactgta ggcataagag cctctcagga gtctgtttca actccagctg acggcacctg    6060
agctttacag attctacctt cctcaggttt ctccccttat cttttccctt ccacttccat    6120
ttcttaatct ttactccagg ccttcatcaa tagtccaggg tgacttctct tcccaagact    6180
ttgcttcgag ctcagcacac cttactccta aaccaccagg gcccaccaac atctagagaa    6240
caaaatgaaa acttttatgg gggtaactgt ccccatgatt caactatctc cacctggtcc    6300
ttcccatgac acgtggggtt tcttttcatc ttccctctcc ccacctccca gccccacca    6360
cacacacctc tctgagtcaa taccaagcag cctcatccct acatgaattg catcccctg     6420
acagaatggg gctctaagtg atgaacctga aggatagcag tctataccac ccccaaatat    6480
gccccttggg cataaggatt attttgagct gaaagcagtt aagaagaagt agatacaaga    6540
ataggtctct gttctccccc cattttccta aaagcagact tgaatttata aaagtatagt    6600
gtctccacct cccctctcta ccaggacgga cagaagttaa tcattggaga caaccctaga    6660
cccttatcag cccagaggaa tctacatacc aaaacttact                          6700
```

<210> SEQ ID NO 245
<211> LENGTH: 1060
<212> TYPE: DNA
<213> ORGANISM: Homo sapiens
<220> FEATURE:

<223> OTHER INFORMATION: OGHAv1.0 microarray feature identifier
      ha1p_105474 genomic DNA region

<400> SEQUENCE: 245

| | | | | | |
|---|---|---|---|---|---|
| gctcgccctt | ttgctccccc | aaggaaaaat | aacaagcaaa | cagaggtgct | tgcccagtgt | 60 |
| ctctggaggg | gcttccctta | gaggtgggct | gtgtgatccc | ctgccaggag | ggggcgatgg | 120 |
| gggccacttg | ttcattaacg | atgttaggct | caaggtaact | gaactttttt | tgcacatgcc | 180 |
| tctctgcaga | gagttgtgca | taaacacact | gctcggcagg | acagagcaag | attgggaact | 240 |
| gagggcaaat | cccttcctcc | gtgcgtcgaa | ctcttgatcc | caggccttaa | aagtgggatc | 300 |
| tctgcactct | gggctttctc | tagcttcccc | agggaaggga | ggctcgggt | gaggtgggca | 360 |
| cggggcatct | ttcctgccca | actgtgaagt | cctaaaaagc | ttcacaaagt | ttctattgaa | 420 |
| tgacagcttt | cttcttctct | ttctccaggg | ttgagttcca | gaataaattc | tacagcggga | 480 |
| ccggtttcaa | gttcttaccc | ttctccttcg | agcatattcg | ggaagggaag | tttgaagagt | 540 |
| gagtccctgt | gagggccgtg | tgccccatgc | taccctcccc | gcctccctcc | acagtgatca | 600 |
| gctgtgcctc | tctgcctgtt | ggttgtgatc | tgtgggcacc | agctcattcg | tgtcaccctg | 660 |
| tctgtgagtc | atttagatag | aatagtcctc | cttgggtctc | ccaccacccc | tagctttgtg | 720 |
| tgtagtgtag | tgattttctg | gctgtcactc | atactcactg | ggcaccagcc | ttgccctctt | 780 |
| agcctccatc | catccagaca | gcccttccca | cctcctggtg | gtgagccagt | ctgcattccc | 840 |
| acgccatccc | aaagcccttt | catcttcccc | gtgcattgta | gatggaagga | gcacccatgc | 900 |
| cattcacatc | tagactttga | gttccctgca | tctgccaccg | tagtttctag | caggagtagt | 960 |
| gggggagta | atacagattc | ttccctagaa | ggggacactg | gtaacatgtc | ccactcttgg | 1020 |
| attagcaggg | gtgggtccag | gaagatgata | tttgcgtctt | | | 1060 |

<210> SEQ ID NO 246
<211> LENGTH: 2800
<212> TYPE: DNA
<213> ORGANISM: Homo sapiens
<220> FEATURE:
<223> OTHER INFORMATION: OGHAv1.0 microarray feature identifier
      ha1p_74707 genomic DNA region

<400> SEQUENCE: 246

| | | | | | |
|---|---|---|---|---|---|
| tttctggtga | gcagaatttt | gaggtctgtt | cctttcactt | cttggtattt | cggttgtttc | 60 |
| tgtaatgact | gtatcttgct | tttgtaatca | taaggacag | taaggaaac | ttcattttga | 120 |
| aaataataca | aagggattcg | gggacttcaa | aagaaggtga | ctctcctcgt | ccactccaga | 180 |
| gaatcaggaa | aggagtgttt | aaagacccac | agaattccta | caagtgacgt | tggggggggg | 240 |
| ccagccagcc | agggcgcatg | ccggccagcg | agtggggtgg | gctctgggtc | cgggagaagt | 300 |
| cagatcagtg | ctctgtacag | ggccttgagg | gcaagacgag | gaatttcgac | ttaggtcctt | 360 |
| gaatctggag | agctacagaa | agtttgtgag | ctcaggagaa | gcgctccgag | ctcggcatct | 420 |
| ggagcagttc | aaggcagcag | cgagcaagtc | caaagacgca | ggagggaggg | tggggtggag | 480 |
| gagtagagag | aaaacagaag | ccgtctacag | acccttttc | cctctgggc | aactaaacct | 540 |
| caagtgcagg | aagcgcttgg | ggactgccca | gccctcagct | gtgttattat | tcggtgatag | 600 |
| gtatttgcta | attacttcca | aaagcctccc | atctgtcatc | ccacccagac | tgcgcgcttc | 660 |
| taattcctcc | taccccacat | gctgtgccca | atgaaaagta | tggtcagcga | gcgaaggttt | 720 |
| gcaaggagac | agacgagggc | gaaattaagc | caggcggctt | ccctttaaat | cctcgcaaag | 780 |
| cagaagggcc | cctcactctg | gcagcaggcc | ttggccaagg | ggcctttagc | cctgacgacc | 840 |

```
cggggaagag tctcccaaag cagaacgccc ggtccggcgc ccagaccaaa cgcggggaa      900 ccggaagggc gaggcctcca cgtaagtccg cggtaaaagt ggcagggagt ggctgcctgc     960
aaagacccca agacggcttg aagaaggagt gggtggcggg tgggggttag ggcgactagg    1020
cggggaaaca gggagagggt cgggctccgc ggggcagctg gggccggggc tcgccgacct    1080 gggcggggc gggggcggg ggggtgcgg cccgggcggg gccggtgggg cgggaggcgt      1140
ggccggcggg gggagtgggg gcggcttttc ccggcacatg cgcaccgcag cgggtcgcgc    1200
gccctaagga gtggcacttt ttaaaagtgc agccggagac cagcctacag ccgcctgcat    1260
ctgtatccag cgccaggtcc cgccagtccc agctgcgcgc gccccccagt cccgcacccg    1320
ttcggcccag gctaagttag ccctcaccat gccggtcaaa ggaggcacca agtgcatcaa    1380
atacctgctg ttcggattta acttcatctt ctgggtgagt gagcgcgact gccgcgcgct    1440
cctctcaggg cccacctgtt cgcgggcccc ggacactggc cgcggccgcg agtgccggca    1500
gctggcactg cccgcaccgg gcaggcaccg ggcgggaaga gagagcgccc tgcggctgcc    1560
agctggctcc aaggccgggt ccagagccgg gcgggacggc cgcgacgggc gcattcgggt    1620
gggggctcat caccgcccag ccggcgtggg gagccgggcc ctcttgagat gaggcgtgcg    1680
ggagggtcct gagcacttta gctcgcctag gatttgagct ggggtgtgtg tctgctccca    1740
gctcaagtcc ctccgagtgc cagagaggaa ggcagggaga agcggagcac ccctctttgg    1800
gccaaggcca aggaggactg tggtgagcag tatggcttgt gaccgggtgg ggtctcccag    1860
gtagtagggg gcgccaggaa gggagggtgc gggcacggcg agagctcagc caagagcggc    1920
tctcactttt acgcaggagc ggcaggggtg cctcggccgc gggtccggcc ccgggaccca    1980
gtccctgaga gtcgggggcc cctccacct tgaggaggaa cctcgcaggc ccccgttccc    2040
tcagactttg attctgagcc accgtgagag cgccgaactc cctggtagct ccctgaaaga    2100
ctagcttgtc ttgatttctt tcaaggacga taagtatctt cactggagag aactcagagt    2160
tcgggagagg aggggcaga tacctatctg cgcctctagt gggatgagtc ctgtgtgtgc    2220
atttccggga gagatcaggt gccagccagc tgcccgccca ggagagcctt ggccttgccc    2280 tctccctcc ccgccagccc aggcggccca cccaaggcca ggcagggcgc agagcggacg    2340
ttcatctgga gaggccagcg gggccaggag ctccagagac acctgctgca ggccactcag    2400
cctctacaaa tgggaaggct gagaggcgac agaagcaagg aataggaaac ccttgtgtcc    2460
ttgtttctat agccacattc cctgcacaca catgacaata cttgccgctc tgcaggcagg    2520
aagagagtct ctatgccact ctcaagatag atggatgtag aaacaggtgc atgccaccag    2580
agtcttgtaa caaaaaagtg cacttggcca ggcacagtgg ctcatgcctg taatcccagc    2640
actttgggag gctgaggcag gaggatcgct ttcatccagg ttcaagacca gcctgggtaa    2700
catagtgaga cccccatctc cacaaaaaaa taaaaaatta gctgggcgtg ttggcatgca    2760
cctgtgatcg cagctactca ggaggctgag atgagaggat                          2800
```

<210> SEQ ID NO 247
<211> LENGTH: 1060
<212> TYPE: DNA
<213> ORGANISM: Homo sapiens
<220> FEATURE:
<223> OTHER INFORMATION: OGHAv1.0 microarray feature identifier
      ha1p_93325 genomic DNA region

<400> SEQUENCE: 247

```
ctgaagacgt tccggccag ggggggcctc tccttggcct ctgctttggc caatcctggc       60
ctggtcccct ggggtctctg gcccaagtca ggggcaccca acacagtgca gatgaattcc     120
```

```
aggtccagcc aagccaggta ccaaagcaag aaagtgagga gtttggggag tctcatcctc    180
tggccagccg ctgaatgaca ccaaagagaa cagcggcagc agcaaaggtg cctctggttt    240
ggcaggaaaa accatgaaag gagtggactt tcaaaagcag cggcagcagc agtagcagca    300
gaaggaaagg cttctcctc agtctgagac tcttgaagtc tgccgggtgt gtgtttgtat     360
ccagtcccat agtggaaatg ctctcgtatc cagacgtgca ccgtctccag tcagcagctg    420
aaaataactc gttcttgaaa ggagaaagcc aaccgccccc tttctcctgc acaactgact    480
gagggcttga aggaggcttg tataaggctg agggattttt ccaagaagga agaatggcgt    540
aatgctgcct gtgtgctcca gttttttttt ccccctagtt ttgaatcctt tccagtgaaa    600
atacttcaca cacacacaca cacacacaca cacacacaca ctcacaggcc               660
tgcaggtgct cagaaaaatc ttttacaaac ctgaactcag gaattggaaa cggaattcca    720
acccaaacca atttaattac tctctgatgt catgctgtct aaactcattt aagtgcgata    780
tatttatgtg aaaaaaatca ccgctgccct ttcgaggcca tggctcacgg gggctcctgg    840
cacagagccc tgcagcggga ctctaggctt aggggcctc cccctccacg gggcagactc     900
aggggtcttc acctccacct catggagcag cccaccccac tttcccgagg agagatgctg    960
aagaatgagc tcaaagatct taagccccag aagcatgggg agtgtgggtt tgtagttaag   1020
ttcttagagt gtttttaaag cagtttcaac tcctgcatct                         1060
```

<210> SEQ ID NO 248
<211> LENGTH: 1060
<212> TYPE: DNA
<213> ORGANISM: Homo sapiens
<220> FEATURE:
<223> OTHER INFORMATION: OGHAv1.0 microarray feature identifier
      ha1p_101161 genomic DNA region

<400> SEQUENCE: 248

```
gcagattgct tgagcccaga aatttgagac cagcctgggc aacatagcga gaccccgggc     60
aacatagcga gaccccatct ctaaaaaaat aaaataaaat tagccaggtt ggtggcacaa    120
gtctgcaatt ctaactactt ggatgggctg agatgggagg atcacttgag cctgggaggt    180
caaggctgca gtgagctgtg attgtgccac tgcactccag ccgaggggac agagtgaaac    240
cttgccttaa aaagactgct atggcccgag tccctctgct gtgccgggca ctgtgctggg    300
catgtaacag gcatattctt ctgatctta caactctccc atgaggcagg cactatcgtt     360
agcccatttt acagatgtgg ccatagaggc ccagagagga gaaggggctt acctaaggct    420
atagactgtt ggtatctgga gataaacccg ggatggtgct cactaaacta ccttgggtgt    480
cagtcctgct tcaagactcc agagagataa agagagatga cctcagagac aaagagactc    540
agacccagcc agaggcccaa tggacagtgg gaggggtggg tggaagaagg ctggtctctg    600
tctgaccaag ccccccaga ataacgcagg ctgccccct aggtgaaaac aatgacacaa      660
tcagctccca ataccaaggg cctgacatca aaggggagg ggaaggcagc tgaggttgtg     720
gggggaggtg ccccgcccct tggcaggccc tacagccaa tggaacggcc ctggaagaga     780
cccgggtcgc ctccggagct tcaaaaacat gtgaggaggg aagagtgtgc agacggaact    840
tcagccgctg cctctgttct cagcgtcagt gccgccactg ccccgccag agcccaccgg     900 ccagcatgtc ctctgctcac ttcaaccgag gccctgccta cgggctgtca gccgaggtta    960
agaacaaggt agggctggag ggcctccctg gctggcccca cacgtcctgc caggccagag   1020
ccctgagctt ggggtcccctt gaaccccctc ctgcctatcc                       1060
```

```
<210> SEQ ID NO 249
<211> LENGTH: 1060
<212> TYPE: DNA
<213> ORGANISM: Homo sapiens
<220> FEATURE:
<223> OTHER INFORMATION: OGHAv1.0 microarray feature identifier
      ha1p_101251 genomic DNA region

<400> SEQUENCE: 249
atggagcgtc gtcatggcaa ctggctcccc cgtagcattg gctgccagga gggaggggag      60
gaaatgggag ggggagggac agacagggac cggcacacac ttgcagcggg ggtggggggg     120
cagggcccac gggtgcctgg cccggacacc gctgtgacat gccaccagca tggacacatg     180
tgctacacgc taagatgcag atgtcaggca cgcgcagccc acacacagct gacacacgtc     240
gcagggaccc tcatagacaa gcgcatcaca tacaaaggtg acagccatc agcagacggg      300 gacacgtaca cgtcacacac aaagacgcag ggaccgcact ggaaacgcac aggcaggcca     360
gcttccagca cagatgcacc cggccacgca ggaacgtcaa agcatcacaa agacccacac     420
atgccccgga caaagtaaag ccccagatcc acagacgcac acgccacaga caaagatccc     480
cacggacacc actgtgacat gctgacactc atagtcacag ccacgcagac agtccctaga     540
caaatgggca acaaagaata cccacagaca caagtatcac atacatgcac gtcacacaga     600
catgcacaga cagcaattgc acagacacac gcagacacac acatcacatg aactaacata     660
gacacggaca cagcagctac acagagacag gcacatcaca tacatgagta cacagaaaca     720
taatacatgc atgtatacgg acacgtaaca tgcatcactc acacggacac aagcttcact     780
cacatggata cacacagaca cactacatac acatgcatgc gggcacacac aactcataca     840
tacagggcta cataaatcac atgcaaaaat acacataaat acaccacaca ctgatacata     900
cagacacata taacatgcac atatacacag tcacacatac ataagcacag acataggcac     960
acagatcaaa tacacagaca cacagagttg cacacatcac atacctaaac agacatggac    1020
acacacatca caaatacaca caccctttcac acaaggttac                          1060

<210> SEQ ID NO 250
<211> LENGTH: 1060
<212> TYPE: DNA
<213> ORGANISM: Homo sapiens
<220> FEATURE:
<223> OTHER INFORMATION: OGHAv1.0 microarray feature identifier
      ha1p_69214 genomic DNA region

<400> SEQUENCE: 250
cctctcttga gtcgagggct gaatctttct cctctaagca gtctggtcag gaaccttggt      60
ttcttgagag gccccaaga tgccgcagct ccagggctct tcctcctcac cagaaatccc      120
tgggcttcca caatgtgaac tcactcattg tcaggtgtcc gtggagtgtt tttggcatgg     180
tgacctgtct gggcccagca tgttgcagat gtgtatttat gcgcaatggt atgcatatct     240
ctgtgtgact gtcagtgttg caagctggct ggatccaacc atctcttctg aaataatgca     300
tccaaagggt tgatattctg ggggaggtca ctgcagaagg atggaactga cctttattcc     360
ccagtgggca gttactgagc tttcctcctc agagccatgc tggcagccct gggacagaga     420
acggtgtggc tttggctgcc tctgcatgga atcttgcccc ggactcctga agactgcaca     480
aggaatgagg aagatcaggg acaacctggg aactgaataa ctttcaaagc cagtgctcag     540
cttctctgct ccgtactagc gtttacaggt cttaattcaa accagatgcc tgtactagtt     600
tttagacccc aagtcaacct ttctgagcca cagcttcccg ctgggaataa tgatgcctgc     660
```

| | |
|---|---|
| cctatctacc tcacagactt gttatgagga taaagtgaga ttaaactgcc tcaaagtgct | 720 |
| ttgtaaacct caggtgaata ggaaagggga agtaaggct ggagtgatga tggggaggtc | 780 |
| ggaggataag gggggctgg gattgctaat ggggactaaa atggccagtc tcctggcaag | 840 |
| attttgagca ggtcatttca ttgaggcctc ttagatttca tatttgagaa ttagggcact | 900 |
| gattcctgac tggctaggca tggtggtcac tggcttgagt cagaccagga atgtctctta | 960 |
| gaaatggtca ctgataggca tccttctcct ccagtcagga ggggctggtt tccttatctg | 1020 |
| ttgcagtctc gactgccaga gggaggcgag cgtggtaggc | 1060 |

<210> SEQ ID NO 251
<211> LENGTH: 2500
<212> TYPE: DNA
<213> ORGANISM: Homo sapiens
<220> FEATURE:
<223> OTHER INFORMATION: OGHAv1.0 microarray feature identifier
    ha1p_88517 genomic DNA region

<400> SEQUENCE: 251

| | |
|---|---|
| ctacttggga agaaggaggg tcaggtccct tccagccagg gctgtggtca aggtgctgag | 60 |
| tcactagggg cagtggggag ggggtgggag acagctttgc ctccctctgg agttggggca | 120 |
| tgagggggcc aggacagagc cgagcacagc ggtgaacggt ggagaaaggg ctcagggccg | 180 |
| tggctggtgc ccatggtggc cgcagggcca cccatggccc catggagggg tgactctgag | 240 |
| cagcccttac caactgtagg actctgctgc cctggagtgg ggcctgaaga actctggggg | 300 |
| cggcactaga gtcaggagtg aggggccctt gcgtttccag gctccccttc cccagtcagc | 360 |
| ccagcctgga gctgccacag agtggggtga ccgctgctgt gattgtcgcc agccccccgc | 420 |
| caacaccaga cacacaaatg gggtgggctg aggggtggga ggcagcaggg gcagtgacac | 480 |
| tggagcaggg acaagaggag acatggagag acagaacagg tcacacaagg gcagaaaggt | 540 |
| caagagaaaa cagcagggcc agagagaggg gaagagaccc agaaacagcg gcggggcccg | 600 |
| aacaaccccg gagggtgaga ctaacagaga ctcgggtagg gagacaccgc gagcagagcc | 660 |
| cgcgcccact cacgtcctgg aagagcgtgt gtccggcggg ccccgggtcg ggcgcgagct | 720 |
| gggggtgccg cggggtctgg ggctggggct ggggcgcggg cggccggagc aggcacacgg | 780 |
| tgagcagccc cgcgcacgcc atggcgccgc caccgctcg ggctcggctg cggttgctgc | 840 |
| cgaccctgga cgccgcggcg gactcggtgt ggctagaggc cgcccttgg cgccggcgcc | 900 |
| gacgcgcggg ctcaggcccc gccccgccc cgccccgcg gacgccgggt tccctcgcct | 960 |
| caaggtccaa ctccagcgcc gcgggcctcc gcgcttccgc ggccacggcg gagggggagg | 1020 |
| cgcccgaggg ctccggtccc gcgacggcct gtcgggagca gaacctaggg gctgcgggcc | 1080 |
| tacccagagg gacaggatga ccaagccagt gccgaggtca gggtgacaca agtgggtaaa | 1140 |
| acccaccagg acttcacctt ttggggcgtc tgtatcctca tctacaaaaa tggtactggc | 1200 |
| agacacccta tgcaattgtt gggactcatt caatgtcaag tgcttacaac gggggctggc | 1260 |
| gcagaggaag cccacaggtc cgtgcggccg aatcccaggc atcccgacgc ccgccctctc | 1320 |
| tggcactaag cgcagccctt tcccctcccc tccgtgactc tggcccctcc ttcaacccgt | 1380 |
| tctccacaca gcagccgggg ggagcttta agatgcgaaa gaggaggtgt cacttcggtc | 1440 |
| tccagtgact ccttggcccc tgaataaagc ttaagactga acgccccact ccaggagcac | 1500 |
| cactctgacc ctcacctcag gaccgcagcc acactgcttt ctctccggtc ctctatcccg | 1560 |
| ctccctcctg cccaaggcct ttgccatcg tgtcctctgc ttggtgtttt cttcctctgg | 1620 |
| ttaactccta cttattttac agcgctcagc ttaagcacca cccattccag aacgcctttc | 1680 |

```
ccgattttct catttatgca gatctcctct ttcagaccct gagagcacca tgaaaggagg    1740
taacacccgt gtccccagaa ctgttaaata cctgacacag aaccagccca ctgtatttgt    1800
tacatgttta ctaatgtcca gaaacgtctg gaaggaagac agcaaactga gcagagtggc    1860
ctctggggct ggggaaagga gaggccactc attactctgc acttcgggca gcactgaata    1920
gcattcttgg ctttctacaa caaaaacctt tactggatct gcttttgagt taggaccaaa    1980
acagcgagga agctgacctt tcttcgagtt atgaggctca aatcaaatcg ggcacggaca    2040
gggagaaggg aagtggagaa tgggcatttc cccagcaacc ttggcctctc cgccccgaa     2100 atgttcccaa cagagtccca aaacccggcc caaacgtcat caaaatattt attaaaacca    2160
aagcaggagg gaacagagct gttaggaagc aaatcaaagt gcagattgga gggtggggca    2220
gagcagtggg gaggcaggcg cttcagacac tgcaggaggg accacaggt ctgggctggg     2280 ggaggccttc accaccccte ctgcccacat cagtgaaggt cccccactca cctctcccat    2340
ctcatatcca tcctgggggg cagctggggc cctgaactgg cccctggag agggcccacc     2400 ccaccatctg accacccatg ctgtcagtc agtctgtctc cctccctcac tttcccaata     2460
aataaatcac ccaggcctca gttccttcag tatggggcag                          2500
```

<210> SEQ ID NO 252
<211> LENGTH: 5600
<212> TYPE: DNA
<213> ORGANISM: Homo sapiens
<220> FEATURE:
<223> OTHER INFORMATION: OGHAv1.0 microarray feature identifier
      ha1p_103824 genomic DNA region

<400> SEQUENCE: 252

```
agccaaggtg ctcccctgtg gaggaggcag gacacaagcc tgtaggggtg tgtgcagcag      60
aaccttttat caaacttgtg tcccactctg caaggcaata ataatggcta attcagctat     120
tatataaaaa acgtatctca agtactgagc actaagtgtc aggtactaag tgctttgcgt     180
acattgattc atttaatcct caaggtgacc gaaaagcata ggtatttttt ttttttttt     240 tttttttttg agacagagtc tcgctctgtc gcccaggccg gaatgcagtg gcactatctc     300
ggctcactgc aacctctgcc tcccgagatt ctcctgcctc agcctcctga gtagctggga     360
ttacaggcat gcaccaccac gcccggctaa ttttttgtatt tttagcagag acgaggtttc    420
accatgttgg tcaggctggt ctcgaactcc tgaccttgtg atccgcccgc ctgggcctcc     480
caaagtgctg ggattattac aggtgtgagc caccgcgcct ggtcagtact cttatttatg     540 ccttttttc ttgaggcaca gagaggttaa atagcttggc taaggacaca cagtcagtac      600
ataatggagt ctgacgctag gacctgcccg cctgacgact acatagaacc tgtacaagga    660
aaggccggag gagggagtat aaacagggcc tggcttccct gaggagtgat ctttcgactg    720
gaaattagaa aaggaaagca gcttcttgag ggtgtgggc tggagagaac atttgtgtgt     780
gtgtgtgtgt gtgtgtgtgt gtgtgtgtgt gtgtgtgtgt gtgtgtgtgt ctgtgcgcgc    840
agaagctgaa agatgggaag tagtgagtgt tcagggctt ctgactggag ggcagccttg     900
gggaaggtct ccgcagcctt aaccggctgc tatgctgggg atgtttgatg cccatctggg    960
ccccggcttt cttattctca gaggcccttc ccacatcttt aggcaagtcc attaaatcct   1020
ccgcgtgcca cattaaaata caagggcaag tacaactctg agtgcagttg caacagaatc    1080
gtttgcacaa tgtcgcatgt cttaaacatt caatcaaaca tcgattactt ccaatttgc    1140 agttttcttt gcccctgtta gcgccaacag attttttttt ccagatctca gacatttatt    1200
```

-continued

```
ttaataggcc cctgacaaag tcataagact cagagagaag ggagagtggg agaggtgtat    1260
aggaaggttt tgtgccaggg actagtcgct caagaattag gagacgccct gggcactgga    1320
aactacgcag cgcgaagtag ggacagcgcc tgtgttgtgt agtggaccag aggttgctga    1380
tacctgggac atagactggg tgggcacggg aagtaaagcc tcgggacttt ggttaagcgc    1440
gccccactgg cgtatcgcgc cgcgggactg cagagccgtg agcagcggtc gccttggtgc    1500
agggttccag ccacatcttc ctcgcccagc cagcaccctc tgccgttgac ccgcctctgc    1560
gcccggcaag cggcttccag caggggggcgc gcgcggacca ggcttgggcc ctagaacagc    1620
gcggatggag tcgctggagc aagtcccag atccaaccgg tttcaaccct ccccacccctc    1680
ccgacgctcc gggttcgcga cgttgaagtt aagggtcgat ccgcagaaag cggccagggg    1740
ctccagctct ccattcctgg gtctgtctgg ggtcggctcc agcctggtta gaagccttag    1800
tctggattcg gcagattctg aatctgggac cctctgcgct agcggcttgg aaccttgtca    1860
ccctcccctc ccccacccct acttccacac acctgattag ttgtctgttt ctttaatgat    1920
caaagacgtg ggcggcggcg ggatgaggtc ttggttcccg gctccacagc cctccctaac    1980
tgtcattatt aacgttataa acattagacc cgcttctgcg cgccggacgg cgccggacga    2040
ggtgcgcgca gtcttctagc tgagctcgga ggcagatcca gaagtcgcgg ctcccacccc    2100
aggcctcggc ggactctgcc tggggcgact cgggctccag ccctgcccgg gcgggcactg    2160
ggctctccag ggtcgaaggc aggggtaagg ggcgtctttc cccagggca gcctccggga    2220
acaaaagcat ttgctgtaga gtgagctaga gcctccgggc ccgcgggagt cagctcccgc    2280
ccaggggtgg tcaccgcgtc cttaaccacc ccaggagccc cgtctccctg ccgaactcct    2340
tggcttctgc aaccctgtca agacagcaag gaaaggggt cttccctggt cctcgggccc    2400
cgaagtttcg gggttgctta taggacgggt tcctgcagtc cagggaagct ctgggcagat    2460
agcgagccca ttctcccttc cattacccag attctgcctc cctgcggaag gcaaaaaaga    2520
aagaaagaaa ataggtaaaa accggcgag ggccttgagc ctccccgcct ggcgcccctc    2580
actcagtccc gaaaagtccc ctggacacgc catgccggac cggactcagc tcccgctgct    2640
gggcccctgc ctccaaatat ccttcccagg cacaggctcc caagaccgcc ccctcagggt    2700
tcccaacacc cggacaactg cccaagacgc cgctccccgc ccccaccccc accttgttcg    2760
gcagacaaag aagggtgtgc tggccccgcc gtctgcctcc ttctcccgac cccacaaggc    2820
ctagaaacct cagggactca ccccgggcta gggacccaat cctggctgtc ccaccacagg    2880
atccccggca gggacgggtc acagtgctct caccctcga ccattttcga agacaccttc    2940
cctgaaaggc gccttgcgcc ctccccatgg gtcggcgggg ggggactcca ggcccgagca    3000
ggcggtgtga agttctgtgt tctgaactgg ggctgagcaa gatgcgatgg tctcagcccg    3060
ctgggccgcc cgtagcgacg gcaggagtag gggagaggga gggacgcttg gagtgtgagc    3120
gcaccagtct gttcatattt aatttacaaa gcagcctcgg aacccccgggc cgggtggtct    3180
ctttagacgc tgcgctctta gcctgtctct cttccccacc ccctcccta gctcattaag    3240
atgctcaaca ctcaaatcgg ggtattgatc tccacggaag ccccaaaccc tcgccatcga    3300
gagaccccca tggcccgggg tgatggctgt ggggcttggt gctcccagag agctcagtgg    3360
ctacagaatg ggtgggggatt ctgcgtgtct cccggagcct gaaccccttt cctggttatg    3420
gccggtagct gtctccaggg ctaacgtggg cagcgcaggg gggcggaaac cgggttttag    3480
ccaaatgcct cgacatcgcc gcgcctccgc ctcctcgtcg ctgaaagaaa tgtcggggtt    3540
tcatcagagc tagggagcga cagtcgggaa cagcgagtct gccgaagccg gctgttgtgt    3600
```

| | |
|---|---|
| gagggtgtga gacggcgggg cggtgagggg ccaccgcggc ttgggggata gtgcgtgtgg | 3660 |
| ggttgaccgt gtgtctgctt gagaggctgt gaagatatgg ggggcagata tgggagaaat | 3720 |
| gctcgggcct gaagtcccca gcccaccgtg ctcaagagta gcggacgttt tgccaccatc | 3780 |
| cttgtctgtg ctactgtctg ctgcagcttc cgtgccccgt tctcctggag caggcaagac | 3840 |
| ctggagtgag gtgcttgggt gcgctcgaga gagcttcccc ctgctccacc tgtcccgcgg | 3900 |
| tgcgcgcagg ccaacgcgtc gggcagtggg cttcaagcgc tggtttagcc acaaaagacc | 3960 |
| agaagtaaag agttccggct taagaggctg ggcagggctg cggtgggctg ggagggggg | 4020 |
| tgtccccttcc cagcacgccc tgcagggctg tgcgttctgg tgtcgggtta gactagcagg | 4080 |
| cggggcgggg gggttggggc ggcggggcgg gggagactag ggcttatatc agcccagatc | 4140 |
| caggcaaaaa tggtagggag ggtgcggcgc tctgctaaca ctatcaatta tgcatcatgt | 4200 |
| tgaacgtggc ttcggggagg aggcggctag cagcgggggg tgcgggaggg aagggtccgc | 4260 |
| gcgagctcgg ctgcgcgcag ctcagcgggt cccgctcgaa gtctgtcggt gccaccgcct | 4320 |
| gcatttgcaa aaagagttta aaggcaaaga cacgccttcc cccccactt cagccgcgcg | 4380 |
| cctttccttc ccccaaattc ctcaaagatg gtttgtctca cgtgttgcag ggcgtaaaag | 4440 |
| cggcttgcat tcaattagca gcgaagctcg cgggcgctgg cgggacaggc gcgtgagggt | 4500 |
| gagttcgcgt gaatgtgtgt atgcgtgtgc gagaggagaa cggtaagtgt cccgggtgca | 4560 |
| ggtgtgcccg tgaaaatgcg tgtgaatgta gcaggggctg aacacattga tgcgattatt | 4620 |
| acctgaccat ggatgattgt aaactgtgaa ggtcggctat ggggagggtg tgagggactg | 4680 |
| tgtgcgcgaa tgtgtttgaa cgtggggtgg gggaggtggt gtgatcaggg acagtaacaa | 4740 |
| tgccagcggc tgtgtaaatg tggggtacg tgggttatgg gggtgcagta ggctgcgaag | 4800 |
| agcccagcca ggacagtggg cgtgggatgc cccttatgac cgacgtgtct tggccttggg | 4860 |
| gagggtctcc gtggctttaa caaaagtaga ccaagcagga ggcgggagag gctatgcgcg | 4920 |
| tccccgccag gcccgggagt gcgcaaggac tttctccaac ctgcagccag agaggtgggg | 4980 |
| gaaacggacg caaaaggaaa aattgaagtg gtactttggg gccaccaagt ccccaaactt | 5040 |
| acctgtccct ttctttgccc cccgcccccc gttttcccca cagccacaac acatgcgtgt | 5100 |
| atcttgcttg ggctatcttc cctgctctgc cacgccgggt ctggagaagg ggtttcagcc | 5160 |
| ccaggacatt tactgagagt cggcgaatat tgggtaagca atgggggcca ccccacaacc | 5220 |
| ttgacccagg tggggttagg tccagcctag ggcacctgat ggggtgcggg gctggtgggg | 5280 |
| gtgctgtctg gcaggaaccg ggaagggagg gaagggaccc tcccagaaga gcaaaggcag | 5340 |
| agtgaaggag caggttccca aagacaagtt gtgggagggg ctctgccaaa cctgacaggc | 5400 |
| gctcaaatg ggggcaggga gtctgtgcaa gttcgtttgt gtgaccgggc ttaaggtgtt | 5460 |
| atggggaggg ggtccttagg caccgcagag ctgtggagaa aggcgcagaa tctttcatct | 5520 |
| tctccagctt cattagctag tggcagcccc atgacctgtt ggctgaggac gcctctgccc | 5580 |
| aatgggagcc gcctgaggga | 5600 |

<210> SEQ ID NO 253
<211> LENGTH: 1060
<212> TYPE: DNA
<213> ORGANISM: Homo sapiens
<220> FEATURE:
<223> OTHER INFORMATION: OGHAv1.0 microarray feature identifier
    ha1p_108445 genomic DNA region

<400> SEQUENCE: 253

| | |
|---|---|
| ccccatctct actaaaaaat ataaaaaatt agccaggcgt ggtggcaggc gcctgtaggc | 60 |

```
ccagctactg gggaggctga ggcaggagaa tggcgtgaac ccgggaggcg gagcttgcag      120
tgagctgaga ttgcgccact gcactccagc ctgggtgaca gagcgagact ccatctcaaa      180
aaaaataaat aaaataaaaa ataaataaat aaataatatt ccactcagaa cagcccctgc      240
taacatttgg tgaacaactt gttcaccagt tggtaggcac ttactcagcg ccaggcctgg      300
tgccaagctc tttatcagct gcgaagcatt catcttattt actgctcaca ggggatccta      360
ctgctagccc caaattacag actgggaaag taaggcctga acatctggga cgcaaacaca      420
gtctgcttca ctgagtctct actacaagcc ttctgtgggg gctcccaggg gaatggctgg      480
cccagtccga ggggacctca gtgttcttgg cacatggtag gcatctgtct ttgttgggca      540
gttgcatcag aagggttaag gacagctggg aacacatcct gcctctagtg aacctcgtgg      600
ttctgtcatc tgcctgcccc tcacccagcc taacccctct gaaccaggag cctgagctgc      660
acttactgct cccccctgcc ccccggacgg cctggaccaa gcagcagctc ccagagcggt      720
ggcccagcaa acacgacttg actcgaggcc aaggctcttg agggctgagc agtgtcccca      780
tgcacactcc tgaaacactt tgtcccttcg ccattcagaa ggcatcattt tggggaaggc      840
agcagccggt ttttcagagc cagcgagtgg ccctgccagc tgctgagcag ggcaagctga      900
gaagggtggt ggtgtgcaag tgttattctc tcttttttgtt tttgttttttg ttttttgaga      960 tggagtctta ctctgtcgtc caggctggag tgagtgccgt ggcatgatct cggctcactg     1020
caacctccgc ctcctgggtt caagcgattc tcctgcctca                           1060

<210> SEQ ID NO 254
<211> LENGTH: 3600
<212> TYPE: DNA
<213> ORGANISM: Homo sapiens
<220> FEATURE:
<223> OTHER INFORMATION: OGHAv1.0 microarray feature identifier
      ha1g_02210 genomic DNA region

<400> SEQUENCE: 254
cccccgaggg tgtgtgtgtg tgtgtctgtg ttgtggggtg tattcagcag catatgcgct       60
gtgtaatttc tgaccttccc tctccctgtc agttgcccct tcttcctttg attgtggcta      120
atgaagaata ataaatccag gggcagggtt tgccagtgga tccttccaag actcaactcg      180
aactgtactg gatacaggga ggaggaggaa gagaaagggg gggcaagagg agcgtgtgtg      240
tgtgcctgtg tgtatgtgtg tgtgtgttgt gggaggggtg gggacagcgg ggaggggag      300 gagtcgcatg cgcacagacg acccgagcct gctccgcggc tgtccaatcc gctgagagct      360
gcgagaaatc gagtgagaga aagccctgca gcccctccga ccccatgtct ctttggcacc      420
aggcacccgc cgggccgtgg ggggctcgta gccgaacgcc gacctccgct cgtattgggc      480
tgggagttca gagccgcgcg cagaacccgg gttggccgca acgtctgtgt tctcagcggt      540
ggccgggaac ctgggatcag ggtcacctga gctgacgggg tggggcgggg ccgagtgggg      600
ttggaagcct ggaacttagt ggtaagcagg aggcgtagga ggtggcagcc aggtaagagg      660
cactcttacc tacccaacgc tggcttgggc cgcaacttta tttgggagtt tcttttttccg      720 gtgagacaga gaccggcag aagaagcggg aggggctgga ggctggtcct taggtaggca      780
ctgcccggcg actggagcgc ggacctggcc atttgggtgg ggttgagtgg gggcgcgatt      840
gtgagtagca gccgcgggac gctgcgaagg ggcggcggca acagagcacg ggcgggggca      900
gaaaagaggc ggcggagggc gcggtggggg agcgcgaggc gagtgctgag agagcagaaa      960
ggactcaagc ctgaggggag tagagaggaa gaaggggcaa cgcgagaaac cgaacaggag     1020
```

-continued

```
ccggcgtttc ctggcaaggg agggcggagg cgcgcgggag agagggagag agggagggcg    1080
gggggcgcgg gggtaggcgc ggggagaggg gagtataact cgccggccgc gaggagcggg    1140
ggcagtttcg ggtgccgagg tctgcagcta gcggcaagcg gagtcaggca tccgttcaga    1200
ctgacagcag aggcggcgaa ggagcgcgta gccgagatca ggcgtacaga gtccggaggc    1260
ggcggcgggt gagctcaact tcgcacagcc cttcccagct ccagcccgg  ctggcccggc    1320 acttctcgga gggtcccggc agccgggacc agtgagtgcc tctacggacc agcgccccgg    1380
cgggcgggaa gatgatgatg atgtccctga acagcaagca ggcgtttagc atgccgcacg    1440
gcggcagcct gcacgtggag cccaagtact cggcactgca cagcacctcg ccgggctcct    1500
cggctcccat cgcgccctcg gccagctccc ccagcagctc gagcaacgct ggtggtggcg    1560
gcggcggcgg cggcggcggc ggcggcgcg  gaggccgaag cagcagctcc agcagcagtg    1620
gcagcagcgg cggcgggggc tcggaggcta tgcggagagc ctgtcttcca accccaccgg    1680
tgcgtatttc tgcataatca ccgcttaaag gcacattttg acagccccct ttatctgctt    1740 gatgttttt  tcatgtctgc acagcaaatc accccacacc tccaaccaat tttccctct    1800 ctctctctta agtattcagc aggtcttgcc tttcatatta attttatga  cctgggatgt    1860 tgcctgtgcg cgtgttgtgt tgtgtttcgt tgtgtctaca ggctcacttt cctcctcctc    1920
ctgcactctc ggcttctttc tgtggcttcc ctctttttct cttcacctct gttttcagga    1980
ttattattat tattatttta acgatctggg aatgttgtag gcgcggcgac ggtgtcgagc    2040
cctgggccgg ggcttccgga gagagggcgt acaattccct gctgagcgta atgtgtgcct    2100
tctacttaca attgcagagc aatatattcg gcgggctgga tgagagtctg ctggcccgcg    2160
ccgaggctct ggcagccgtg gacatcgtct cccagagcaa gagccaccac caccatccac    2220
cccaccacag ccccttcaaa ccggacgcca cctaccacac tatgaatacc atcccgtgca    2280
cgtcggccgc ctcttcttca tcggtgccca tctcgcaccc ttccgcgttg gcgggcacgc    2340
accaccacca ccaccatcac caccaccacc accaccaacc gcaccaggcg ctggagggcg    2400
agctgctgga gcacctgagt cccggggctgg ccctgggcgc tatggcgggc cccgacggcg    2460
ctgtggtgtc cacgccggct cacgcgccgc acatggccac catgaacccc atgcaccaag    2520
cagcgctcag catggcccac gcgcacgggc tgccgtcgca catgggctgc atgagcgacg    2580
tggacgccga cccgcgggac ctggaggcat tcgccgagcg cttcaagcag cgacgcatca    2640
agctgggggt gacccaggca gatgtgggct ccgcgctggc caacctcaag atccccggcg    2700
tgggctcgct tagccagagc accatctgca ggttcgagtc cctcacactg tcccacaata    2760
atatgatcgc gctcaaaccc atcctgcagg catggctcga ggaggccgag aagtcccacc    2820
gcgagaagct caccaagcct gaactcttca atggcgcgga agaagcgc   aagcgcacgt    2880 ccatcgctgc gccagagaag cgctcgctcg aagcctactt tgccattcag cctcggccct    2940
cctctgaaaa gatcgccgcc atcgcggaga agctggacct gaagaaaaac gtggtgcgcg    3000
tctggttctg caaccagagg cagaaacaga aaagaatgaa atattccgcc ggcatttaga    3060
agactcttgg cctctccaga gacgcccctt tcctcgtccg ctctttctc  tcctctcttc    3120 tgcctctttt cacttttggc gactagaaac aattccagta aatgtgaatc tcgacaaatc    3180
gaggactgaa gagggagcga acgagcgaac aactgagccc aagccggtga gaatgtgaaa    3240
cagtttctca aaggaaagaa taacaaaaga tggtatttgt ctgttgtagc aaagttgtcc    3300 ctttgaacccc cacctcggct tcttcagagg aagtgtggag atggctgttt gcaggaaggc    3360
agacgagaca gtgtttaaaa agtccacaag aatgatcaag taagatttgt ttttattctt    3420
```

| | |
|---|---|
| acagacatca cccgtgttca agtttaaaag tacactttgc aactattttt cagaaataga | 3480 |
| aattgattca ggactaaaac tttaaactag agttgatgct taatgtgata gagacatctc | 3540 |
| taaagtattt tgaatttaa aaaagatgg cagattttct gcatttacac tgtatattat | 3600 |

<210> SEQ ID NO 255
<211> LENGTH: 4000
<212> TYPE: DNA
<213> ORGANISM: Homo sapiens
<220> FEATURE:
<223> OTHER INFORMATION: OGHAv1.0 microarray feature identifier
ha1p_103872 genomic DNA region

<400> SEQUENCE: 255

| | |
|---|---|
| ttctgtggcc ttgcttggtg acagggaatg gggtgtgatg agctggggca ggcttcctgg | 60 |
| ggatgctttc agccaaagat gagccctgtc tgcccttggc cctgctgaga gggtaagttg | 120 |
| agtcatgagc agaattcaac cagttatcag atggaaggcc aaggaagctt ggggagggct | 180 |
| actgagggga tacggtaggc ttgtctgtgg agagcaaaat tcttcagtct acaaagttct | 240 |
| tttctgggct ccttcatctt tcggtttctc ttccagctcc ctcgttttgg gcctcttttg | 300 |
| tttccccatt cccctcccct gggccttccc gtttggaaaa ggggtcacat atcctcaccc | 360 |
| tggaggcgtc tgccccttcc acacagttgg tgttggaaca gtggagctca gagaggccga | 420 |
| tgctgaccgc gtagatgtcc agcaccaaca gtgggatttt gggccctgtg ggggacacag | 480 |
| agagaactct ccgggagtgc ggcccctttgg cctcccctct gggtgcccag tgggcagtgg | 540 |
| gcctgggtgg ctcagaatcc cagccaggag cactgaaggt caacaggctc cgcccctgag | 600 |
| ttttctgagc caggcctccc tgtttcctcc ccagccagtg gggagcgcag tgaggggcgg | 660 |
| ggcctggagt cttgggagct ccctggacaa caacatgcat ttagcgcagc tcagtctcag | 720 |
| agccagcagg atatgttttc ttaaaaaaaa aaaaaatgcc taacatcttg gctttcaccg | 780 |
| aagggttggt atctgctttg tacactttgg ccttcttggc ttttcactga aacacacaca | 840 |
| catggatgca cactcacttc cacacacaaa cccacaccaa gacagacaca cacacacact | 900 |
| cacacacaaa ctcatgtaca tggtttcata cccacatcca tgcaaacaca catacaaatc | 960 |
| cagaaatacg caccctcaca cccacaaact tgtacacaca cacacgta tacacaccaa | 1020 |
| cacacataca accctggctt ggacaaaagc ttcccgtttt ttcttgtttg aagtggaaat | 1080 |
| ctcccacctt ccatgagatt caatttctcg cccttccccc gctaaaatcc tcctggcccc | 1140 |
| atcatttctt gggtccttc cagacagtgc tgtgtcttta aggaagttga agctgctaaa | 1200 |
| agtgagtgag agagagagaa aaaacacaac ccaaaaaaat ttggcatctc ttccccctc | 1260 |
| aagtttctgg tgtcacttat gaaacacagg tccttgttgc tgcagagaag cagttgtttt | 1320 |
| gctggaagga gggagtgcgc gggctgcccc gggctcctcc ctgccgcctc ctctcagtgg | 1380 |
| atggttccag gcaccctgtc tggggcaggg agggcacagg cctgcacatc gaaggtgggg | 1440 |
| tgggaccagg ctgcccctcg ccccagcatc caagtcctcc cttgggcgcc cgtggccctg | 1500 |
| cagactctca gggctaaggt cctctgttgc tttttggttc caccttagaa gaggctccgc | 1560 |
| ttgactaaga gtagcttgaa ggtaagccag tggggaggag ggctccaggg ccagcggcgg | 1620 |
| gagcgggagg cctgttggac atagggggctg gttccctctt ggtccatccc tgctggtctg | 1680 |
| aggtgcgtgg gacaatccct agcttggagc cgtccagggg gcatctgctt cttccacaac | 1740 |
| ccacaactga ggccccagaa atcccagctg cgtttgggct gagcctctgg cctcacccaa | 1800 |
| gtcagctgag aggtcctggc gggggtttat ttaggcagct gcctggctaa gtttgaacag | 1860 |
| aacaggccac gggtgtgatt ccacagaaaa ggcctggtgt ctgctgcggt catggccgga | 1920 |

```
ggagcgggag agggcgggtg gagtggatgg gggtggtgtg cactgcacaa ggggcctcgt    1980
ctgggccaag gcaaagcata cctatggggg gctccggtgg gagggactgc ggccaggatg    2040
tgggagggca gggggaggtt ctgcaaagtg ctggggagg ggggtggctg gaaaacagat     2100
ttcaagtcat aaagtcagct aggaacaggc cgaggcaggg agaactctcc actcggagga    2160
ggagctgggg tcctcttcca tcccgtcttc atcctgcctg gctgcgtgac ctcgggcaag    2220
tctccgccct tctcttggcc tcagtttctc cttccgtagg atggggggcgg tgggctaggt   2280 ggtgttggga tttagctggg ttatgtggga cagggcctcc tgatgggaaa gagctctggc    2340
tgggcttgtg ggaggaatga gtccctttgg caggttctcg ggatcccctg ggtgacatgc    2400
ctttctctgc aggaggcacc atgcaggagc tgcatctgct ctggtgggcg cttctcctgg    2460
gcctggctca ggcctgccct gagccctgcg actgtgggga aaagtatggc ttccagatcg    2520
ccgactgtgc ctaccgcgac ctagaatccg tgccgcctgg cttcccggcc aatgtgacta    2580
cactgagcct gtcagccaac cggctgcag gcttgccgga gggtgccttc agggaggtgc     2640
ccctgctgca gtcgctgtgg ctggcacaca atgagatccg cacggtggcc gccggagccc    2700
tggcctctct gagccatctc aagagcctgg acctcagcca caatctcatc tctgactttg    2760
cctggagcga cctgcacaac ctcagtgccc tccaattgct caagatggac agcaacgagc    2820
tgaccttcat ccccccgcgac gccttccgca gcctccgtgc tctgcgctcg ctgcaactca    2880
accacaaccg cttgcacaca ttggccgagg gcaccttcac cccgctcacc gcgctgtccc    2940
acctgcagat caacgagaac cccttcgact gcacctgcgg catcgtgtgg ctcaagacat    3000
gggccctgac cacggccgtg tccatcccgg agcaggacaa catcgcctgc acctcacccc    3060
atgtgctcaa gggtacgccg ctgagccgcc tgccgccact gccatgctcg cgcccctcag    3120
tgcagctcag ctaccaaccc agccaggatg gtgccgagct gcggcctggt tttgtgctgg    3180
cactgcactg tgatgtggac gggcagccgg cccctcagct tcactggcac atccagatac    3240
ccagtggcat tgtggagatc accagcccca acgtgggcac tgatgggcgt gccctgcctg    3300
gcacccctgt ggccagctcc cagccgcgct tccaggcctt tgccaatggc agcctgctta    3360
tccccgactt tggcaagctg gaggaaggca cctacagctg cctggccacc aatgagctgg    3420
gcagtgctga gagctcagtg gacgtggcac tggccacgcc cggtgagggt ggtgaggaca    3480
cactggggcg caggttccat ggcaaagcgg ttgagggaaa gggctgctat acggttgaca    3540
acgaggtgca gccatcaggg ccggaggaca atgtggtcat catctacctc agccgtgctg    3600
ggaaccctga ggctgcagtc gcagaagggg tccctgggca gctgccccca ggcctgctcc    3660
tgctgggcca aagcctcctc ctcttcttct tcctcacctc cttctagccc cacccagggc    3720
ttccctaact cctcccttg cccctaccaa tgccccttta agtgctgcag gggtctgggg     3780
ttggcaactc ctgaggcctg catgggtgac ttcacatttt cctacctctc cttctaatct    3840
cttctagagc acctgctatc cccaacttct agacctgctc caaactagtg actaggatag    3900
aatttgatcc cctaactcac tgtctgcggt gctcattgct gctaacagca ttgcctgtgc    3960
tctcctctca ggggcagcat gctaacgggg cgacgtccta                         4000
```

<210> SEQ ID NO 256
<211> LENGTH: 3100
<212> TYPE: DNA
<213> ORGANISM: Homo sapiens
<220> FEATURE:
<223> OTHER INFORMATION: OGHAv1.0 microarray feature identifier
       ha1p_56412 genomic DNA region

```
<400> SEQUENCE: 256
ggaaagaagg cagcaggaag agagaaggaa ggcaaccctc ctgcaaaggg tccagggtgg      60
cggtggtggg ggggacagtg atggcggaag aactcagtgt gctttccaag aggaatgggt     120
aggctgggaa acgggaagga gagtcagaat ttatcattgt ttggtttcac cctagggttt     180
tgaggcaaaa tttatccaga gcaggaaggt ggcaagtggg ctgccacaga atggccccag     240
gggcccgagg gtcagtgatg tgtgggatgg gggcttttag agttgaggag agcactcagt     300
gggcgctggt cttctggaag gtgggggagg ggccgagaaa tgatacggca atactggatg     360
aaaatgggga tctctgcaga agtaggggca cagctcaaca gcctttcccc ttcctctcag     420
tgtcctcgga ccccgcttgg gctgtggagt ggatcgaact tcctcggggt ctctctctat     480
cctctttggg atctgctcga accctccgag gctggagcag gtcctcccgc ccttcctcgg     540
tggacagtca ggacttgcca gaggtgctgg gcccctggtg gtgggggggaa ggaggacgtc     600 atccatataa aggggatctg cagccccccac ccacgcctgg ccagccagct tctggctccc     660
ttttccggcg ggcggaggcg ctatccggcg gcgggccggg aggccgcccc cgtgccggtc     720
tgctctgctc ggcgctgtgc cagcaggcgg agagctcgcg ccttccgcgc tgacgtcagc     780
gcatcccggg ccgtatcccg ggagaccctg ttgcgtggtg atgggttgcc agggagacat     840 acacctttttc tctgggcctg ggccgcagct gcgcggagcg ccgggcacgg atggcggcgg     900
ctgaggggag cgaagcgagg gagggagagc aagctaagaa cacccagca ggtgctcccc     960 cgcctaggcc tggctggagg ctactggcgc caccctgggg gcctgtcag ccaggtaccc    1020 aaggggaggg atcgagggtg ggcctcaggt caaggggcag tgttggctgc ccttgtgagg    1080
gacgggaacg tgatagaaga gagctgggca atgccgggga gggatgtgtg cctccaactt    1140
cattaagtga gggaaacatt tgctggggct tgtcaggagg ccctgagcca ggtacagggt    1200
ggagttagga acttacgtgc atcagactta ggccttgcca tcctgagctc cctcgggaga    1260
cagacaaggg caatgatggg ggcggggtgt gtcagagaaa agaagaggct gtcggctgaa    1320
agcattattt gcaggtgaca cttgagatgg gccttaagtg atggcaagca ttttttcacg    1380
taaggatggc attcttggcc cagaggaaag ctgagttcct tttcctggag gcaggcgggc    1440
tgcttgctga cagggattgg tggagaaggg ttttttgtttt ttgttattta tttttatgta    1500
tttatttatt tgagacggag tttcgctctt gttgcccagg ctggaatgca atggtgcgat    1560
ctcggctcac cgcagcctct gcctctgggg ttcaagcgat tatcctgcct cagcctccag    1620
agtagctggg attacaggca tgcgctgcca cgcccggctg attttgtatt tttagtagag    1680
gcggggtttc accatgttgg ccaggctggt ctccaactcc cgacctcagg tgatccgcct    1740
gcttcggcct cccaaaatgc tgggattaca ggcgtgagcc actgcgcccg gcctgagaag    1800
gggggtttta ttgggcagag gagatcagca gtggattcaa aggaggcttg gaaggaggca    1860
agggtgtcac agagtgggat ccttcaggc ctgggtatga tgcctgcact aacctcactg    1920
gacagtagcg taggctagac aagattttag agatgtgttg tgaccagctg cactccagga    1980
aaactgttta cattatatct tacctcattc atccagcctt tgcatttttg tttgcttgtt    2040
tttgagacag agtctttttc tgtcgcccag gctggagtgc agtggcacaa tcttggctca    2100
ctgcaatctc cgcctcctgg gttcaagcaa ttctcctgcc tcagcctcct gagtagctgg    2160
gataacaggc acccgccacc atgccctgcc cattttttaa attattttta gtggagatgg    2220
ggtttcacca tgttggcctg gctggtctca aactcctgac ctcagatgat ctacccacct    2280 tggcccctttg gcctcccaaa gtgctggaat tacaggcgtg agccaccacg cctggcccag    2340
```

```
cctatgcatt ttttttttt ttttttttt ttgagatgga gtcttgcacc gtagcctaag    2400
ctggagtgca gtggtgcgat ctcggctcac cgcaacctcc gcctcccggg tcctggttca    2460
agcaattttc ttgcctcagc ctcctgagta gctgggatta caggaacgtg ccaccatgcc    2520
cagctaattt ttgtattttt agtagagacg gggtttcacc atgttggcca ggctggtctt    2580
gaactcgtga cctcatgatc cgctcacctc ggcctcccaa agtgctggga ttacaggcat    2640
gagccactga cgcctggcca gcctatgcat ttttaagaaa ttattctgta ttaggtgctg    2700
tgctaaacat tgggcactac agtgaccaaa acagactgaa ttccccaaga gccaaagacc    2760
agtgagggag accaacaaga aacaggaaat gcaaagagag ccattattac tcactatgac    2820
taagggccac aaatggggta cgttgatgga gagtgatttg ttaagagact acagagggag    2880
gacagactac caagaggggg gccaggaaag ctcctctgac gaggtggtat ttcagcccaa    2940
actggaagaa tgagaaagag ctagccagcc atcagaatag tccagaagag atggggagca    3000
ctacactcac tacactttgg cctgagaaaa tagcatggga ttggaggagg ctggggaac     3060 accacttctg ccgacctggg caggaggcat tgagggcttg                          3100
```

<210> SEQ ID NO 257
<211> LENGTH: 2600
<212> TYPE: DNA
<213> ORGANISM: Homo sapiens
<220> FEATURE:
<223> OTHER INFORMATION: OGHAv1.0 microarray feature identifier
      ha1p_18292 genomic DNA region

<400> SEQUENCE: 257

```
caagctccca ggtgatgttg atgctgctgg ttggcatttg agtagcaaag ctgtgccgta      60
tttaaagaat tagccctaac taccaatatg aaaactttac atccctgaat cttcaattac     120
tctgaggtga cactactatt attctggctt cacagtcgag aaggcactga gaagtgaact     180
ttccagagat cacagagctg agatgtggga aggcaggatt caaacttagg ttgactgact     240
gcagggcatt ttcaactgtt tgcctcccaa tattatctca attaataggt aacgagagtt     300
cgaagccggg tccagagcta tcttctgtaa cattcttctg ggtcgagtcc ctgccccgct     360
acggtatgtg cctagggtca acacaagggc tggggaaaga ggaaactgag cctcttttc      420 aacacaacag ggaggacgga gaacagacgg ctcctccggc agacgcgacc cggcccgctc     480
caaacaacgc ttcgggcagg agaaggttct ccgggtggtc cgcagccggg ctggagggt      540 ggggcctacg ctgggaaaag gttccggcg ggtcgtacca acgcgcgcag ggggaagagg      600
tttccgaggc caggacggtg tcgctgccta cgcgctcagt ggcgaggtgg agaaactctt     660
catccaccct cggctacctg ttcgagagcc atggcaccag gagctctcgc gtcccacagc     720
cgactcctaa agactcttcc tccggccccc ctgtcgagtg ggagtccccg gaaatggggg     780 ccggcggta tcgggcaggc ggtggggaga agagtgtcct gtcatttacc aacttcacta     840
cgccccacac agatccaccc gcttatctgc cgccgccgta gccctttacca gttctttggg    900 cggcttctcc tgggtctttc caaacagccc catgacgaac tgaacccgtc ttgccccttc     960
cggctttcag ttccccgcgc ccaggcaggt cacgggcagc cgcctgggcg gggcccgcgg    1020
aaaaggaggt agtcccaacc cccagagtag ggagcggcgg cactagggga tgttgcgcat    1080
gcgccatacg cctgcgcaga atcgagtgag tgggagacta gtcaaaaagg ctgacgtcat    1140
cgcacatgtt ctggtcatgt ctgtgtgggg gagaccacgg attcggtgct tttcgtaagg    1200
tgtagaaatg attgctctga aagatacgaa tttgttggct acaactgctt ctaatacttc    1260 acctaaaacct agatgttgca ccagaagtct ggatctccac gcagacgtgt acacttagca    1320
```

-continued

| | |
|---|---|
| tcactttccc gacagcttca tctttgtgtc cagtaggcaa ctcacaggtg acaaaccaaa | 1380 |
| aataacctct ttttcctccc gccaacccac tcctcccctc tgcttgcacc accatcacct | 1440 |
| ggtcactaaa ccctaggcat cgtcctctct cccctcttac caagtcccaa ccattctaac | 1500 |
| ttcaatatgt ctgaacttca accctcccct ttccatccca actgcggtcg tttttttttca | 1560 |
| ggccatcgcc ctttccagcg tgggcgattc ctgcctagca tttgtccatg tgtgtcccgt | 1620 |
| cctacacgcc acactgaccg tgagcttaat cacactctca aaggaatctg actaaagaga | 1680 |
| actagacaca ttttagcacg gacagttcct gattaggcct atacggtgag ctgatggtta | 1740 |
| ctgtcattaa ctcatccgag gatggtgaag gggaccattt gttacctcag ccccatactc | 1800 |
| ctgtctctgg tggaatcata aaatggttcg gcagctttga aaacattttg acaatttctt | 1860 |
| aaaatgctaa acaaagccag ccttccattc ctagctattt acccaagagg gaaaaaagca | 1920 |
| tatgttctta caaagacttg tacacaaatg ttcatagcag ctctatttgt aatagccata | 1980 |
| aactggaaac aatccaaatg tctatcaaca agtgaatgga taaaccagtc gtgattgatc | 2040 |
| catacgaagg aatagtactg agcaataaaa aagtaaacta ttgataaatg caacagcatg | 2100 |
| gatgaatctc aaaataattc tgccaagtga agaagccag aaccgtatga ttccatttac | 2160 |
| ataacattct ggaaaatgca aactaataca tagtgacaga gagtacatgg gcggttgcta | 2220 |
| gcggatagga gtggggtcag aaagaggcag aaaagaggga ttacaaagag acacgaagtt | 2280 |
| taggggggatg atggataata tcttgattgt gatgatggtt tcacagatgt atacaatatc | 2340 |
| aaaacttacc aggttggaca ctaagtatgt gcgattatt ttatgtccaa tcatacttca | 2400 |
| ataaagttgt ttttaaaaaa gcactgcctg ttcattgtga aaagttaaac cctcattctc | 2460 |
| acttcctcag ggggaaaaggt ctcaaaggat tcacaccaac tattaaatat agtgtgaatc | 2520 |
| ttctgaaacc ttttcctttg gaaaatatac ttttattttt atttatgtat ttgttttttga | 2580 |
| gaccgggtat cactttgtca | 2600 |

<210> SEQ ID NO 258
<211> LENGTH: 2100
<212> TYPE: DNA
<213> ORGANISM: Homo sapiens
<220> FEATURE:
<223> OTHER INFORMATION: OGHAv1.0 microarray feature identifier
      ha1p_12075 genomic DNA region

<400> SEQUENCE: 258

| | |
|---|---|
| gggatacttc aaggagaagt tgactctttg acttcataca tagagagact agaaattccg | 60 |
| atgagaatat acacgctgat gtgggatcag cttcccctgc ttcctcctcc ttggggcact | 120 |
| tgaaacaaga catccatatt cctaacaaca aattcctatt tgagccatct tgagactctc | 180 |
| cacatggacc actattgtgt aagttctcag ataataaaaa tttgagtaag catcaaaatg | 240 |
| tcctatttgt gctcagcaat ggtgatggct tttgaatcaa ggtgaagatc tctttcgtgc | 300 |
| ttctcactgt gccagaagtt acaccacagt gtttgtgtga tctgctgttg tctgttgtct | 360 |
| tattttcccc aagagcttgt aggtttctgg agactaggaa ccttgctgta tgatttctgt | 420 |
| ctccctcccg cagcactgag tatagtgata cgtgtgccaa ggctttgttt ttcagctttta | 480 |
| gagcctccac tgctaagcaa ctttccctct cagagtcgcc aggctgggc atctatccca | 540 |
| ggaaattggc tatttgggat gaatgtgggt ctacctccag gggtatttgt attttggtgg | 600 |
| ggaattcttg aaggcagcaa aatctgtaag ctcctcccca acaaagacta ccgggatgga | 660 |
| ataacagggc accccgccac tttattccca gcagtcacac tacctggcct gtgtgcttca | 720 |

```
ttgacatatt gagtattgtt cactcgggca gaaaaaaata ccacaacctc acagccttct    780
tagtttcctg aaaaaagatc tgtcactttg aatttgctag tttgccaaat gacagctgtt    840
tgcctcccag gcaggctttg ctgtcatcag agacagggat ggagggaaaa taatgccatc    900
atctagggga agggtcttgt gttgatcttc aacatggcta accaaatgga cgatcagcag    960
gcagacacga ggtattttca ttttcactct tatttcaaga gatttgtgat ggtgtttcat   1020
agtctaaaaa taaaggatcc gcccgcagac atttctccct ccactaccct catcatatta   1080
gctgctgcgt tttcctctcc agattttgat tctattattt tttattataa atgaaaggtc   1140
aaggaatact tttcgtattc cataatagga ttggttctgg aagaatcttt gaaaaaaaaa   1200
atacgttcaa gacattgggg ctgggaatag aacggaagca tctcaaaagc atgttttcct   1260
ggttaaggaa agcacacgag aacgtttcac agcggtgctc tgctatcttc tctgtaccccc  1320 tccgccctac gctcatggga gagctcattt ctctccccat cagacactgg gaaatactcc   1380
caaggctctg gcagtctcaa ggctgcaatt cctgagaccg gggactctgt gctgccatct   1440
cgtggcagat ctcagacaca gcaagctggc tgccggaatc ctgtttgaac ttggcttgcg   1500
gcgggagctg tggtttggct caaatcctta tagagctttg ttgccagtca tgttgatttt   1560
taaaaaatgt tttactccct atgcccccct tttagttttt catgttggca cttcatttaa   1620
tgtgcctcca gaggctacat tttgggtttt gatgtgtttg gtcaatgtta agaatcggt    1680 taactatctt cctgaaagaa ggcagtaatg cagacagacg cctttgacag caggtagacc   1740
actggctggc aaccgtagaa agagggacac acgggagact aagaatgaaa gatgcagtaa   1800
ggtttattgc tcttattcat tggttaggtt tttttttttt tttttttag agtattctga    1860 cctttttcctt gagtgtattt ttgctaccat ttctcttgtt tagatctgga gagactcaaa  1920
ctcaagctgg gatttgggga aaagtgtttg aggatgccag tctggctttc agaggcatga   1980
taggcacatc tctgttgata tccaaattgg aacaactttc cttgttacca gaaacagct    2040 ggtgtctgca gaccttccca tggttggcca tgacacaggc ccctggagtt gctctgcttt   2100
```

<210> SEQ ID NO 259
<211> LENGTH: 2400
<212> TYPE: DNA
<213> ORGANISM: Homo sapiens
<220> FEATURE:
<223> OTHER INFORMATION: OGHAv1.0 microarray feature identifier
      ha1p_22519 genomic DNA region

<400> SEQUENCE: 259

```
ctttaaacag cacagatatg caatgaaatt tccattaatc cagaatatac atagtggtta     60
acatgcagtg atttgaaata aaatattatt tgaaaagcta ttttatagc tgcaaaatat    120 tgcattgaag aggctgccac caattatttg tttccatatg agcattttaa aggctgatac   180
acaacatttt aaaaatgtat atgcaccttg agaggcccag gcgtgcagat cacgagatca   240
ggagatcgag accatcctgg ctaacacggt gaaacccgt ctgtactaaa aatacaaaaa    300
attagccagg cgtagtggcg ggcgcctgta gtcccagcta ctcggaggc tgcggcagga    360 gaatcgcttg aacccgggcg gtggaggttg cggtgagccg agatcacgcc attgcactcc   420
agcctgggca acaagagcaa aactccgtct caaaagacaa acaaaaaact atatgaaaaa   480
gtctctcatt attttcacaa gcattaagaa tctcacttaa aaacatggct gggcgcggtg   540
gttcacgcct gtaatcccac cactttgagg gggcgaggca ggcagatcac ttgaggtcag   600
gagttcgaga ccagcctggc caacagggtg aaaccccgtc tctactaaaa atacaaaatt   660
agccggtcgt ggcggcgcgc gcctgtaatc ctaattactc gggaggctga gacaggagaa   720
```

| | | |
|---|---|---|
| ttacttgaac ccaggaggca gaggttgcaa tgagccgaga ttgcaccact gcactccagc | 780 |
| ctgggcaaca agcgcgaaac tctgtcgcaa aaataaata aatacataca tacatacata | 840 |
| caaatattgc caatttgata ggcaaaaata tatgcaaatt atgttttaac aaatattaat | 900 |
| aaagttgaac aatggcccaa tgtaatttgt tacctatctg aaagacatgc acattcaggg | 960 |
| agttacagta cttttttcatg tcttgcagca tcaacaaatt gttttctaaa tgtggaaaaa | 1020 |
| gagacattca gtacaggcta acgtaacgtg ggacagcatg caaagccatg agaagtggga | 1080 |
| aaatgagaga gaatctgggc gtggcttaca gggctgctga agtaagacac acccttcgct | 1140 |
| tcacctgtgg cctcccgcgg cggctgcggc tccttcgcag gaccggtagg gggcgcgcgc | 1200 |
| ggttgagtcc agcaattgcg aggacctccg caggcgcagc ccagcactga cgcctctccg | 1260 |
| ggccgtggct cctcttccc aggccgaaag cggccgggcc ctctgctccg ctgcgccctg | 1320 |
| gcgcggccgc acccactgcg cgtttgtgag ctggccatcg gtcacactgg gatactcgag | 1380 |
| gaggaggcct ggggcctgca ttcaattccc taagagggac ccgcgctggc cgctgcaggc | 1440 |
| gggtggagaa cgggcgtctg agtctttggc tttcgtaccg gaatctcccc gggagatttt | 1500 |
| acaagcccct ccgaatgttc tgattgaatt ggtctggggg ggtcggtccg ggcatctaac | 1560 |
| gagcagccgg gatggagaat tactagtctg gattctggtc ctcagaggtt cactcacgtt | 1620 |
| aatcaacccg agtccatctt ggtgggattg tcttgctccg aggccctccc actgagcttt | 1680 |
| attttcctgc ctgatttcgg ggtccgctaa caggatgaac agcggaccat acaggcacgg | 1740 |
| tgaaaatgac acttggtgac gtggaagacc cagcttgcca cagttgaggc agagctcctc | 1800 |
| agggtctttt gtcttagtta tccccgagct attttttcagg aaccgacagg ctcccccacc | 1860 |
| ccaacaccgg atgaaggcca gcaactggag gccaggaata atcaagcacg ctctcatttc | 1920 |
| aaagaggtga cgattgtgcc cgtgtttaaa agggatgcct gagaccatga ggatttggag | 1980 |
| ttttggaggc ggatctgcct ttggggagtg agcgtagggc cctaagatgt ggttgtgctt | 2040 |
| tgagacagtt cccagggtga tgtgtcccat catccaaaca ttgcaggata agtcaaagtt | 2100 |
| acagaaagac tctagtttac ttccagccta acattaccaa aatacggtat ttgtcagaaa | 2160 |
| acatgtagta tttgtataat ttgagaatgt aattgaagaa cccgatatag agcttttaga | 2220 |
| aaggggaaat agaaaactta aaagaatct tgcttggtat attaatacca acatctaaaa | 2280 |
| tataataaaa ttgaataaac cagtgagttt tatactatga ttgaaataaa atgccactat | 2340 |
| gttcttaaga gtgctagttt aacaggaaat ctccaatgca ttattatcta gactcatctc | 2400 |

<210> SEQ ID NO 260
<211> LENGTH: 2300
<212> TYPE: DNA
<213> ORGANISM: Homo sapiens
<220> FEATURE:
<223> OTHER INFORMATION: OGHAv1.0 microarray feature identifier
    ha1p_29531 genomic DNA region

<400> SEQUENCE: 260

| | | |
|---|---|---|
| aagactgtgc ctcaaacaaa agctttgtat aactgcccct tgtgttcaagg taatattttt | 60 |
| cctcttttca aagaggctgg aaagtggtga agggcatttt cagcaggctc tcctcctgac | 120 |
| agatcttttt ttcctgctac ctacctcgtc tccctttatt gtcccgccta cattcatctc | 180 |
| tttctccagt ttccaattcc aacctggtag cagctacaat ctggattgta tttaagggaa | 240 |
| ttgctttttt tttttttct tgaagagcgg ggaggaaggg taaagtgggg ggaggggcgc | 300 |
| agaagcagta ggaccgacgg caatctccca cctccccaaa tccattttttt cttacctcct | 360 |

-continued

| | |
|---|---|
| ctgacctctc tagcttggaa gaggaaggtc aatgcgaggg ttgttacggt gaaatcccag | 420 |
| agccaccgtt tcgttttcca cctagaggac cacggctcca tctccgagcc ccgcactcac | 480 |
| aactgtgaac tcaacccacg aaattgcgac tgcagaccaa cttcgtcctt tccaaggtat | 540 |
| cgccagggat gtttgctaca cagccattgg ggagggagag ggggaaaaag tcaaagggct | 600 |
| ttttcttcta aatttgatgg tttgcgttct tcgtgtctct agccctttcc tctccctctg | 660 |
| agttggcccc accggccggg accctccggc cgcgaccctc tgatccttcc tctgccgggc | 720 |
| cctgccttca gaatgaaggc agatgagggg cttccaccaa caagctgaga gtactgtgtg | 780 |
| cccctaaagg cttcatgccg tcagtgggct ggacgagtgg ctccgggcag cccctcctc | 840 |
| cgcccactcc cctccctgct cccagctccc cctcccaggg cgaaactgac aagcaggctg | 900 |
| agggtcagac ccaatcacac gactctgggg cggcccaag cccgcccccg cctccctcag | 960 |
| cccaagaatg aggactccga gcaggcccag cccaccaacc accccccatc tccccactcc | 1020 |
| tctcctccct cctcgcctac caaatcccg agaaaaaatg ggaggagtt acggggacg | 1080 |
| cgtgcttggc tccagcactt tgggaatgaa aggaattgca ggagagcccc ggagcacacg | 1140 |
| gagttttcaa ggagcttctg tattcaataa aaacagctac ttgtctactt gcacccgtct | 1200 |
| gttagcctct cgctggtcgg cgggagaggg gaggaggcca gcgcctgatc ggccacaccg | 1260 |
| ctggagtcct gggctggcag cggtaaccttt atccttgtgc aaaaatctgc ttcgtatggc | 1320 |
| agacgtggaa ccagtggact cattgcgctg cctactctga aaagtgtttt tatttttatt | 1380 |
| tttttaaccc aataattaga agaaaggaat gaagatagaa tggagggacc ctagaagtca | 1440 |
| aaacctagag catgtaggga agtcctcttt ggagatctga aactgacagg tttatctctt | 1500 |
| aaacgtttaa attcagcact aggttcattc agtggctttc ctcttaaaag agttgaactg | 1560 |
| tactctgagg gagaaggagg aaaaaattta tgggagctga cattaagagg gtgagtaatt | 1620 |
| taattttcca gctgattctg ttctgatcct ggatgagggg gtactgagga gtgtgtagaa | 1680 |
| aaggcgagga aagcaactag cagaaatctc caagaggctc ggcccacagc tcctcattaa | 1740 |
| gggcctggcc ctggccctca gcctcgggag ccaaaaacgt ggtcactcca cagtgagagt | 1800 |
| aatgaagagg gcaggtttct aaattccctc tctacttaac ccatcctcaa gtaatcctc | 1860 |
| ttacacctgg aatatagatt cccaagtcac ttttttccacg ttaaaatcat tccattctat | 1920 |
| tgactccttt ttgttcgtta ataattccta agatgtttct ctcaaagatt ttctggaaca | 1980 |
| gtgcccatca gggtgccagc atacattagc cactcaatag agatgggttg gatgaatgaa | 2040 |
| cacattttc tgttgacaaa gactagaagc attggccagg gcctactttg agtatttaag | 2100 |
| tcatttaaat gcttaaaggc cctcaactaa gtttactggg tacatatgtt caattctaca | 2160 |
| gctgccacta atctttagga actcagtttt ctattagtca tcaaaatatg cctcatgatc | 2220 |
| tatcagatta catcaaatct cttccatgcag tttaaaattg gaagaaaggt gatcaaagac | 2280 |
| tagattgagc ccttataggg | 2300 |

<210> SEQ ID NO 261
<211> LENGTH: 3400
<212> TYPE: DNA
<213> ORGANISM: Homo sapiens
<220> FEATURE:
<223> OTHER INFORMATION: OGHAv1.0 microarray feature identifier
    ha1p_58853
<400> SEQUENCE: 261

| | |
|---|---|
| agtgcccct ctaattgtct attcttatgt gctgttact gggtcattaa aatcttacaa | 60 |
| ggcctttata gtcattgtaa ttgttgaatt caaggtttgt cccagttgtt tgtacagaag | 120 |

```
tctctcactt tgaaactcag aaacatttcc cctaacatct tgtctaaaag aacctttcaa    180
gcaatgtact gaccaactcc ttgagtgatc tgtggcccct gcaggagtgg gggtagggag    240
cgccatgtcg cacacctgtt gtcaggtgac actgccagca gcatcctgca cactcacctc    300
cccactccac cccaccccca gcgaggctct ttcctgctgg ccttctccac ccggggaagc    360
ctacagcctt ccggagttac cttttaaaaa aagcaaaccc ttcctaccac aaagcaaaca    420
aaaggctgat accgagacaa tcgggagcag cgggggttcc cgtggcccct ctccagccca    480
tccttggacc actccccaac ccggtccccc gcaccagccc ggcttcaatc ccgcgagtag    540
cccccgcctt cccctccctg cagatagcga gccagacgcc tacacctcgg ccccccgggg    600
ctcgggcccg acttattgtg ccggggccgg caactcgcgg gccggcgggg gcctcaccaa    660
gtacaactct gctcacagca gctcccgggt gccaggccc  agactgccta gccagcgccg    720
cggggcctcc tgcggcctcg ggcctggccc gtgagcccgc ccaggaagg  gtcgccaggg    780
taggcgccag caccgctttt ttcccacaaa agcgcccagg gcgggggcagg gggatgcgtt    840
tcgaagagaa gttggtttcc aggtttcttt tttgaacaaa accaaaggga atcccgcgcg    900
gcccgacaag gcctgggagg acgtagtgca gcgcgcgagga cccggcgtgg gccacaccga    960
acccggcggc ccgagcccgg cccgcaccac accggtgcgc gccaggccgg gccgctcccg   1020
ggcacccgcg gccggacccg agcggcgggg acagggagtg cggcaagggg gcccgcgcgg   1080
cacttacgcg gcggctcggt ggcggcggcg gcagctgcaa ggtgtctcgg cctgagccct   1140
cctggccgct cgcgccttt  ctctccgcgc tcctcgctgg cccgcccgcc tcttcgcttc   1200
ccgcccgcgc ggcccgcgct ctcccccctcc gcccggcgcc gctgccgagt gaactggaac   1260
cagtcctcgc ggccggcttc ccacaatgca cagcgcgccg ctcgtcacat cccttcgcgg   1320
ccccgagcgt ccggcctccg cgcccgtgcc gcccggcgcc ccggccttga ccccgggccc   1380
gcgcccctacc cgttgacgcc ggccgctctg cgcccaggca ccagcccgca ccccggacgc   1440
gaggtctgac ccatgacccc ggggacgccc agagcccagt ccttgggaag ggccaggccc   1500
ctggagagga gcttcttcag ggcgcgtccc agactctgcg tctcgagtga acgcctactg   1560
tgtgcctggc tctgagcacg ggactgtcgc tgccacggca tctttaggaa ccttcccact   1620
aacccagtgg gaaggcacaa tggctgttac cagcgatcgc tcttccctcc ccagtcaatg   1680
ccaactcccc cctgccccgc ctcagagacc ccgctgtctt tagatacagg ccaccgccaa   1740
gccctggtct gccccaagat caattactgc gcacccggtt ccctggggt  ccttcagtta   1800
atcctcctca ccccgaagtc tggaacctgc cttgcacatg gaagcggtta gctacttcgc   1860
ttcagcaaaa gttcactttc ggacccaagt tgggaattac taatgtagac agtgattcct   1920
tatcatcaca cacgtttttt aaaaactgcg gacaggccga agaggagga  gccgccacaa   1980
agcccgccac gtcttcctaa attggtttac cgcctgaagg cattggtgcc ccatcccggg   2040
tacttaaatg ggggcctgcc ctctactccc ctccctccaa agtgtggagc cggaagccac   2100
ttctccatcc agctgtgaac taaatttgga taataataca catccctcag ggttgatgtg   2160
aagtttaaag tgccgctact ggggattatg gaggtaatta gagaccccca cccccacccc   2220
ccagtcctca ggctgcgcgg gaatcgcagc ggcagtaacc tccacctcac cgggatgctt   2280
tacaccttac tttaagagtt tgcaaaacaa tgtccaatac ctgccattca tgcattcgtt   2340
aattcgatta agtactgaga acgtattttg tgtcatacat cgatttgggt gctggatatg   2400
aaacagccaa gagaacaggc agaaatctct gccctcctgt agtttgcagt ctcgtggggg   2460
aaagacagac aaacgggaga atgtgtcaga gggtctccat ggggtggaga aaataaggc    2520
```

| | |
|---|---|
| ggagaaggggg aataggaagt gtgagataag agtgaggctc aaatacaaga gaaggcctct | 2580 |
| atgagaaagt aacatttaaa gcctgaagaa attgagggag caagccgtgt ggatgtctgg | 2640 |
| ggaagaactg cgccgagcat gaggaatagc aagtgcaaag gctgggggtag gagtgtgtcc | 2700 |
| aaaatagtca agacagagcg agtgtgaggt tggagtagaa tgggtgaagg ggaaagtaac | 2760 |
| aggagatgaa gctggaaaaa tgatgatgct tatgatgctt ctggtcccaa aacaaagcat | 2820 |
| tatggttcta tgaggatctc ccgaagaaaa gatgtcagga aaggtgcaga gaccctcccc | 2880 |
| cacacaccac attgttgttc catccttctc tgtgcctttg ggcaaggact ctccgttctg | 2940 |
| tagggaccac caggtggaat taaagtctac actcctccaa gagctgatct tggggcggcc | 3000 |
| ccacctccat gccctctac agcgtgccat tctcatagaa cacactagga cctttgtcct | 3060 |
| ctggagctgt tcagtgcagc agctctgacc tcatccttct ccagaagcct ccaccttctc | 3120 |
| tcccctctct cctcctgcgc tttgtgtgtc ctgttcttcc acttcggtga cctgtctcct | 3180 |
| cccctaatct ggctcagaga ggggtaccag ctgctgctgc tgctattgct tcttcttctg | 3240 |
| ttaaaggttt tttatttttt tccaatgaca aagctatgct cattctgaaa acatgaaaaa | 3300 |
| taaaaatgct caaaaaataa aactcactct acattcattg ctaggagaga acagcctgct | 3360 |
| cccattccag ccttttttatc tatatccact taacattaaa | 3400 |

<210> SEQ ID NO 262
<211> LENGTH: 1060
<212> TYPE: DNA
<213> ORGANISM: Homo sapiens
<220> FEATURE:
<223> OTHER INFORMATION: OGHAv1.0 microarray feature identifier
ha1p_35052 genomic DNA region

<400> SEQUENCE: 262

| | |
|---|---|
| cagaagtttt ggccatcgta tgcttgggga cagacctggg caaaagccca cagaggaagt | 60 |
| tgccacaaac acatgatcta ccctcctggc cctgaccgca gggcttttgg gtttggtcca | 120 |
| cagacagagc cctagtgttc tgtttgttac cctgattgat tgatgagagg ttttggggga | 180 |
| gaaaggactt cactttcttt tcttttcttc tttttaacct ttgcctcttc ttctaggaga | 240 |
| acttcgcttt ctacactgat tataatttag acatcttccc agtagggctg aatcctagac | 300 |
| caatctatca atcccagact aatcaggcat ttgcctgggg atatgcatct ttggcatttt | 360 |
| tccaagggtt catcaggatg gagatatccg gtgcaccatg agttctgttt ccttaatcaa | 420 |
| caccgttgta acttgcccat ccagttttgt gacattaatt caaacctgtg ccctagtcct | 480 |
| cttttaggca gcgtatcagt gctggaaagt gcagcaagga taagagggta ctgttctctc | 540 |
| atttctgagg gcgttgtctc gataattaac taacttgata gacttttag tgagtggcag | 600 |
| gtgagatgca aggtactgtg ctaggtgctg tgggggatgt acagacaaac aacacacctc | 660 |
| cctaaggagg taagtaatag ctacttacta ttcactttgc tctttcactg taatgtatcc | 720 |
| tcaagcacag gttttcacta caccatcagg cccagaagta ctagcttatt ttccacagga | 780 |
| ggatttcagt ttgatgcctc tggttatctt gtatagagag gtcttttctt tctttctttt | 840 |
| tttccccctt cttttgcaat cacaaaatct gtcctaccag atgtgcctct cttgcttggg | 900 |
| aacccaatag ttttctttgc agacaacaga cttgaagtca cagagcagca gattgtagaa | 960 |
| gagctacagc ttcgggacct ctgactcttg agctggaaca gcaatagggc tgggttgggg | 1020 |
| gtggggtgga tgtgtctttc aatactgatg tatttcaagg | 1060 |

<210> SEQ ID NO 263
<211> LENGTH: 1900

```
<212> TYPE: DNA
<213> ORGANISM: Homo sapiens
<220> FEATURE:
<223> OTHER INFORMATION: OGHAv1.0 microarray feature identifier
      ha1p_67002 genomic DNA region

<400> SEQUENCE: 263
tggatcaaat attttttaa agggaagata aaagctgtgg tatcttttag ttcacgtcac    60
tttaatcttt gaaaaataaa aacagcctca aatattattg gtaaaataca gatgttgtca   120
aaatataaat agacagacta aattatgcag ttcaggtagc gccctgccga ccctgtctct   180
taaaaaacaa aaaaacgggg tcacctttcc atcccttttc taacggtttg aatctcagga   240
ctgtattcct aggcccctgt tgcttatgct gccctgtggt gcccaggtga gcttttattc   300
tgagattggc tggttggggt atggataaca atcgaaggct ctgttaccgc aggcgtgttt   360
ctgagtcctg ctcccgcccc atgcccgagg gtgcccagac tcaccagctc gggtcgcggc   420
tcgcttcccg gcaggcgccg gcctactggc ggcaggcaca gagcccccag cgtgcggagg   480
cgcgcggcgc agctcctcag catggctccg ggccgcgggg ccgcgcttgc tctagccctg   540
gacggcgcac tctacctccg ccacaagagc gcgcgtgcga gttaacccct ggggtggacg   600
cagggcgggg cttggggagg aggcggtgcg cactactggc ggctggctgg ccggggtgtg   660
aggccggcgg ggtccgggta gggcatcgct gttgagtcta tcttctggtt ccggcctttt   720 cttttccgaag acctcccgct gcggccaaca gccgggccac ttccggggct tctcaaaggc   780
aagaggagcg cggccggagc ggatcccggt tatcgcttgg gccccctcag ccctcagcc    840 ccggaacccg cgcgccgact ggaggctttg cggtcatcct tcccacatga cccagggcgt   900
acgcagtgct ccgtgtcccc aagtagttat ccctccccg gaagactgaa gtccctgggg    960
cgggtaggag cgcacgctag gagtagtatg aataaagtgt tttcttggag gtcatgggca  1020
agtctctgga cagggttgat agtgctgatt tatagagggc agtctgggca caaagagcat  1080
ttatacgatc gaaaagctgc tttccctgcc aacagcccca taccctcccc aggagcgcgc  1140
ttacgcctta aaagactctt tgttatgta aactgacagt taaattaaac gaaggtaatg   1200
gatactaaag gcgtaacagg tattgtaact attttactgt tatcgatgct tttgaggtta  1260
cttacctcgc ttgtattcgt atggtgggaa tactaggcgc ataccttctg agcttcgaat  1320
tcagtaacct cactgggacc ttgaaatcgg actgggttgg agtattccca ttactcagat  1380
aatgcaaatc cgggccatca tacccctta tttttaaatg cttaccagta tgccatagcc    1440
ctagtccatc ctaaggtgaa gactctaatg ggtttttttt gagacagagt ctcgcagaga  1500
tactgctatt gcacttcagc ctgggcaaca tactgatgcc ccatctcaaa aaagcaataa  1560
attaaaaaga aaactcgaat gacctgaatg cattagatat tttgccttga ttcctttccc   1620
atgaacaact ccagcagttt gtcagtaggt aagaacacct agatacattt taagcctaca  1680
ctattaactg ggggaaggtg taacattctg agagaaaggg aattggggag agaaggcaat   1740
gcagttagga ggggcccctt ggaatcctag agctactgaa ccgaagatca ggcataaagg  1800
atggttgttg agattctgta attctaagag gttgtattct gatatctcct aagcacccccc  1860 cccaacctcc cacattccct ttatctcagt tgtcttcctt                         1900

<210> SEQ ID NO 264
<211> LENGTH: 2100
<212> TYPE: DNA
<213> ORGANISM: Homo sapiens
<220> FEATURE:
<223> OTHER INFORMATION: OGHAv1.0 microarray feature identifier
      ha1p_45580 genomic DNA region
```

<400> SEQUENCE: 264

```
ctgagccatc tgcaccctga gtaggctctt gagctgtgac atgagtcagg tggagtagcc      60
accaaggcaa tagcttccct ctggcacccc aaatgcaggc tcacattctc tccagcccag     120
gcagttggat gagggcccgg cagatatctg cgggcccagc aggcgggac cttcccacct      180
ggagaaggca cctccaggct ctaggtctga agtttcccaa actctgtact cctctccatc    240
cagttcactc cagtctcctc cagctgtctt tgagacagca tgcccaggag ataggacaaa     300
attagtacca agactcacct gagtgcccct ggctgaggct gtagagcctt gtccctcag     360
atctcagcat ttgccatggt ggccagagag ctggctgcca ccacgctgag agccaggccg     420
cccctcggac cgcgtcccca cagccagcca atccagatg gagtcataga aggggctgc      480
aggggcgccc agggacgagt ctcagagcag gaccacaggg gccacttctg caggaggacc     540
aggtcaagat gcaacctgtg gcagagtggg ggtctgggcc tggggaccc agaatggggg     600
gtgtgcgcct gggactccct gtccttggtg cctggtcctg ggtagcgatc aggagatgtt    660
ctgaggaggc accggcagct cctctaggta ctgcctgaga tgcgaactgc agctgctctc    720
gccgccagtc cgtataaaat aaagttcttg gagcagttgc ggaggcttct gcaatggggt   780
ctggaatacg ccccctcc tgcggccaat cgtggcatta cagcccgtg tgggaacgcc       840
cgctgggccc agagcagcgc ggtcggcctt ggccttggga ctccaacacc ccagtctaaa     900
ggtcctgctc aaaatacttt ttggaagact tctgggggag tggcagctag acctggctta    960
tgagccacgc aagaaaacca gtcttgtaaa tttatttata gcacagaatt ggcatggctc    1020
aattcattca ccaagcttgg cacagagtta cttcatgtat tttcctggag tcacattcat    1080
cctcagtgga cacggattgg ccacactggg ggtagtcagg aaaatgcccc agggggttcc    1140
acggaactca gcagcagaat cagcgtttct ggctcattaa cgctgcacag gggctggggg    1200
gtgcaggatg aagactagct ggctgtccat agcaattcag tatgggaggg ggacccaggc    1260
acgaataatc ctaaacctga gcatgattgc ttacgtttga aaaggacat ctaggccggg     1320
tgcagtgact cacacctgtg gtcccagcac tttgggaggc tgaggtggga ggattgcttg    1380
agcccaccca caagttcaag accagcctgg gcaacatagt gagaccccat ctctaaaaaa    1440
aaaaaaatc tctttaaagg caatctaacc atatgtgaag ggagctgcta aattcagatt     1500
gaggtggtag tatcaggggc atcagagaaa tcaccataat tgtccaagcc agggtggcag    1560
agttaggcta tgcagatggc ttccagagga cagcacccag aggtaacatt catgaatgca    1620
ttcctgtttg ttggtgaaaa gttcagcctc aagactccag ggtcaggctt cgtacatgaa    1680
aagtgttgc caagactcag ctgtgtcact gcagctgccc gcccacagct gagtcagaaa     1740
cgccgtcctc attctcagtg actgccctgc ctgactgcct aggaagcagc tccaacatca    1800
aactccattt tacagaaaga acaaatgata attgtatcat tatggtaata atcccaggga    1860
gcggaggagg agaaggaaaa gaagacaaca ctttatagca tataccatgt gttttcttata   1920
tattagctca ttgaacctat tcaacaaccc cctgaggcag gtgctgctat tatgctcatt    1980
tacagagaca gagaggaagt gacttgtcca gggtcttgta gccagtaagt ggcagagcta    2040
gtattcaacc ctaggcaatg tgatcctagg gtctatgctc ttaaccctc ccctgtacca     2100
```

<210> SEQ ID NO 265
<211> LENGTH: 2900
<212> TYPE: DNA
<213> ORGANISM: Homo sapiens
<220> FEATURE:
<223> OTHER INFORMATION: OGHAv1.0 microarray feature identifier ha1p_12646 genomic DNA region

<400> SEQUENCE: 265

```
gcggtgcatg gcacatggag ctgacctgaa agaggaaac aaggaatcag catttaggcc      60
ctcacctgct tctcctgccc cttcccagag cctgctaggc acttctcccc gcaactcacc     120
taggagggct agggcctgcc ccctgctttt tggcaggaa ggatgggca cagctcaact       180
tcttcctcat cactgtcctc ttcctcttcc tcgctctcct cctcagaaac atcattgctc     240
atcgtaactg gtggacacac aagcagtaga aggatggggt gttaagacca gaccgtttca    300
caccgcatgc catttcttca cgccgtggtg ttaggcttac agggaccatg acctcccagt    360
gcttatgggc taggtgggaa gaacctcaga ccctaaactg ggtcacaaag agccaaagga    420
gtcttcatta ttggagctgg agaagttggg ccatgttcca tggaggaggt aggcttgagt    480
agacggaaag gagagggcat gtcatgcaca gggcacagcg tggagggcac acagacctgt    540
acagggctgc actgggagat gagggtggga tgggcagga gtgcggagtg ggggaagcct    600
gatgggagag tccactggaa gcaaaggaga gggccctccc ctcttctcac caatctggtg    660
ccgcccagtg atccgcacag ggccagagcc cgacttcagg cggaaggtta caggtggttg    720
gagctggaag tcatccagac tgagctggga ggaagacaag gatgaaggcc tggcccactc    780
ctagcccacc ccacactgta atgagtgcta acgtcctcaa tccctcacc accaccacca    840
ccaccaccaa ggcagagctg gggaactcac catgggttgg caggacagct tgaggttggc    900
cacagggact gcgatctcct gatggtcatg gttccgggcc acaacttcta ccacattaca    960
ctcgtctttg gctccctcgg tgaggcagag ctgggaacgg tacacagggc ctcagggtct   1020
cctcaagtga gggttgacac cacaactaaa ggcatctacc ctagcacctg cccagcctca   1080
gaggtcccgg ttcacctggc caggggagcc gcccatgccg gggggttagg ctgaggatgt   1140
gtctccaagt aaaggggatc cggaggttgg gtagagacct atattgcctg cctgggctta   1200
ttcattaaaa ccccactccc ctgccctca ccatggttag tgccagcacg tgctccgcat    1260
catcctcttc ctctacctta aaggtgaagg agcgggtgtg gccggagagc tcacagcctg   1320
gtagaaataa cagtgagtat gcctgagcgt gtgtacgggg ctgggcagcg ggggatgtca   1380
ccaacccgcc gtcacgtgta accttgggcg gacgggtcat ttacacgtcc acctccgtct   1440
cttctctcag aacacctggg acgctctgcc gtgggcccg cccaacacat ctggggcagg   1500
gatctcgcca ccccctttgg ctgtgcgtgc gaggcccct ctcctgcggg aacagcgaag    1560
cagccctccg cccacaccca cgccttgaaa ccctccgcat tcccgcctca catccctacc   1620
tcttaccgcc ccagtaccac cctcagcctc tcccttcact aataccgaag aaaaaactgt   1680
ccatagtgac cggggccggg accgtaggc ccccgacacc cccggcccgc gttcggctct    1740
cctgactcaa aaacgctaag gcagctgcag taccggcggc catgctgtaa gagccttctt   1800
caaactccgc ccccgacacg cacaaagccg gggaccctcg gccagttccg gccccgccca   1860
ttaaaggaga cgcacagtcc tggaaaagaa aaggcgccga gaccccgcag ccctacccgg   1920
agcccgcagc ttctgctcat attttatcaa gaccgaagag aaaggaagta acatcacaga   1980
agaatggatt tggggtttat gttaacatcc ttgctcattt ccacgaccat gagggtgtcc   2040
acttccccaa gctcctcgct ctgtgtcgga agagtgtctc ccactcttcc aacccagggt   2100
aagctttcgt taaaggagtt atagatataa aaatgtaaac ccttcttact cctcccagca   2160
aaggtggggt tcagggcagt gctttttctgc tacaagcaaa ggaaatgcac tcagattgtc   2220
tttgcctcaa gagagccgag gagccttagg aatttccatc ccaacacgtc tgtcctgtct   2280
```

```
gtcctctcgg ctaagcctct cttaattctt cctgctctaa agacccgca acttgctatg    2340 ccttcactga gacttagctg ctggcacttg ctagcagagg actagttagc tcatgtgtgt    2400
tggctgttcc tggcccaccc acgcttttg agcttttaat tccaaatcat ccaggagtat    2460
ctttgcgccg tggattattt tgtcagttta tgctactcgc gccatctttc gccttttaag    2520
aatcaggcaa actgtgtgct ttctatccta atagatggca aaactcaaac tagaggccct    2580
atttcacatc caggttataa ctgtggcaag agggtggggt ggcttggcta aaaactagtc    2640
tacttttctt agctcttgtc ttaatgaaaa tctggaagtc ttactggtga tggaggtagg    2700
ggagggctgc cttcaagatc caatctctaa cttggaacag ctgtggagag gagagaatac    2760
ctgcttgtag gtgaggcatg aaagaggaga aaagggaggg ggcagacagg aaatagattc    2820
acacaataca acacgacaag cattcacttc aagtttatt ttgcctcttg catggtcttt    2880
tacagttcgt tttctacagg                                                2900
```

US 8,067,168 B2

GENE METHYLATION IN CANCER DIAGNOSIS

CROSS-REFERENCE TO RELATED PATENT APPLICATIONS

The present application claims benefit of priority to U.S. Provisional Patent application No. 60/803,571, filed May 31, 2006, and U.S. Provisional Patent application No. 60/848,543, filed Sep. 28, 2006, each of which are incorporated by reference in their entirety.

BACKGROUND OF THE INVENTION

Human cancer cells typically contain somatically altered genomes, characterized by mutation, amplification, or deletion of critical genes. In addition, the DNA template from human cancer cells often displays somatic changes in DNA methylation. See, e.g., E. R. Fearon, et al, *Cell* 61:759 (1990); P. A. Jones, et al., *Cancer Res.* 46:461 (1986); R. Holliday, *Science* 238:163 (1987); A. De Bustros, et al., *Proc. Natl. Acad. Sci. USA* 85:5693 (1988); P. A. Jones, et al., *Adv. Cancer Res.* 54:1 (1990); S. B. Baylin, et al., *Cancer Cells* 3:383 (1991); M. Makos, et al., *Proc. Natl. Acad Sci. USA* 89:1929 (1992); N. Ohtani-Fujita, et al., *Oncogene* 8:1063 (1993).

DNA methylases transfer methyl groups from the universal methyl donor S-adenosyl methionine to specific sites on the DNA. Several biological functions have been attributed to the methylated bases in DNA. The most established biological function is the protection of the DNA from digestion by cognate restriction enzymes. This restriction modification phenomenon has, so far, been observed only in bacteria.

Mammalian cells, however, possess different methylases that exclusively methylate cytosine residues on the DNA that are 5' neighbors of guanine (CpG). This methylation has been shown by several lines of evidence to play a role in gene activity, cell differentiation, tumorigenesis, X-chromosome inactivation, genomic imprinting and other major biological processes (Razin, A., H., and Riggs, R. D. eds. in *DNA Methylation Biochemistry and Biological Significance*, Springer-Verlag, N.Y., 1984).

In eukaryotic cells, methylation of cytosine residues that are immediately 5' to a guanosine, occurs predominantly in CG poor loci (Bird, A., *Nature* 321:209 (1986)). In contrast, discrete regions of CG dinucleotides called CG islands (CGi) remain unmethylated in normal cells, except during X-chromosome inactivation and parental specific imprinting (Li, et al., *Nature* 366:362 (1993)) where methylation of 5' regulatory regions can lead to transcriptional repression. For example, de novo methylation of the Rb gene has been demonstrated in a small fraction of retinoblastomas (Sakai, et al., *Am. J Hum. Genet.*, 48:880 (1991)), and a more detailed analysis of the VHL gene showed aberrant methylation in a subset of sporadic renal cell carcinomas (Herman, et al., *Proc. Natl. Acad. Sci. U.S.A.*, 91:9700 (1994)). Expression of a tumor suppressor gene can also be abolished by de novo DNA methylation of a normally unmethylated 5' CG island. See, e.g., Issa, et al., *Nature Genet.* 7:536 (1994); Merlo, et al., *Nature Med.* 1:686 (1995); Herman, et al., *Cancer Res.*, 56:722 (1996); Graff, et al., *Cancer Res.*, 55:5195 (1995); Herman, et al., *Cancer Res.* 55:4525 (1995).

Identification of the earliest genetic and epigenetic changes in tumorigenesis is a major focus in molecular cancer research. Diagnostic approaches based on identification of these changes can allow implementation of early detection strategies, tumor staging and novel therapeutic approaches targeting these early changes, leading to more effective cancer treatment. The present invention addresses these and other problems.

BRIEF SUMMARY OF THE INVENTION

The present invention provides methods for determining the methylation status of an individual. In one aspect, the methods comprise:
  obtaining a biological sample from an individual; and
  determining the methylation status of at least one cytosine within a DNA region in a sample from the individual where the DNA region is a SEQ ID NO: selected from the group consisting of 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

In a further aspect, the methods comprise determining the presence or absence of cancer (including but not limited to breast, lung, renal, liver, ovarian, head and neck, thyroid, bladder, cervical, colon, endometrial, esophageal, or prostate cancer or melanoma) in an individual.

In some embodiments, the methods comprise:
  a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
  b) comparing the methylation status of the at least one cytosine to a threshold value for the biomarker, wherein the threshold value distinguishes between individuals with and without cancer, wherein the comparison of the methylation status to the threshold value is predictive of the presence or absence of cancer in the individual.

In some embodiments, the methods comprise:
  a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
  b) comparing the methylation status of the-at least one cytosine to a threshold value for the biomarker, wherein the threshold value distinguishes between individuals with and without breast cancer, wherein the comparison of the methylation status to the threshold value is predictive of the presence or absence of breast cancer in the individual.

In some embodiments, the methods comprise:
  a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;

b) comparing the methylation status of the at least one cytosine to a threshold value for the biomarker, wherein the threshold value distinguishes between individuals with and without lung cancer, wherein the comparison of the methylation status to the threshold value is predictive of the presence or absence of lung cancer in the individual.

In some embodiments, the methods comprise:

a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;

b) comparing the methylation status of the at least one cytosine to a threshold value for the biomarker, wherein the threshold value distinguishes between individuals with and without renal cancer, wherein the comparison of the methylation status to the threshold value is predictive of the presence or absence of renal cancer in the individual.

In some embodiments, the methods comprise:

a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;

b) comparing the methylation status of the at least one cytosine to a threshold value for the biomarker, wherein the threshold value distinguishes between individuals with and without liver cancer, wherein the comparison of the methylation status to the threshold value is predictive of the presence or absence of liver cancer in the individual.

In some embodiments, the methods comprise:

a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;

b) comparing the methylation status of the at least one cytosine to a threshold value for the biomarker, wherein the threshold value distinguishes between individuals with and without ovarian cancer, wherein the comparison of the methylation status to the threshold value is predictive of the presence or absence of ovarian cancer in the individual.

In some embodiments, the methods comprise:

a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;

b) comparing the methylation status of the at least one cytosine to a threshold value for the biomarker, wherein the threshold value distinguishes between individuals with and without head and neck cancer, wherein the comparison of the methylation status to the threshold value is predictive of the presence or absence of head and neck cancer in the individual.

In some embodiments, the methods comprise:

a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;

b) comparing the methylation status of the at least one cytosine to a threshold value for the biomarker, wherein the threshold value distinguishes between individuals with and without thyroid cancer, wherein the comparison of the methylation status to the threshold value is predictive of the presence or absence of thyroid cancer in the individual.

In some embodiments, the methods comprise:

a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;

b) comparing the methylation status of the at least one cytosine to a threshold value for the biomarker, wherein the threshold value distinguishes between individuals with and without bladder cancer, wherein the comparison of the methylation status to the threshold value is predictive of the presence or absence of bladder cancer in the individual.

In some embodiments, the methods comprise:

a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
b) comparing the methylation status of the at least one cytosine to a threshold value for the biomarker, wherein the threshold value distinguishes between individuals with and without cervical cancer, wherein the comparison of the methylation status to the threshold value is predictive of the presence or absence of cervical cancer in the individual.

In some embodiments, the methods comprise:
a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
b) comparing the methylation status of the at least one cytosine to a threshold value for the biomarker, wherein the threshold value distinguishes between individuals with and without colon cancer, wherein the comparison of the methylation status to the threshold value is predictive of the presence or absence of colon cancer in the individual.

In some embodiments, the methods comprise:
a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
b) comparing the methylation status of the at least one cytosine to a threshold value for the biomarker, wherein the threshold value distinguishes between individuals with and without endometrial cancer, wherein the comparison of the methylation status to the threshold value is predictive of the presence or absence of endometrial cancer in the individual.

In some embodiments, the methods comprise:
a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
b) comparing the methylation status of the at least one cytosine to a threshold value for the biomarker, wherein the threshold value distinguishes between individuals with and without esophageal cancer, wherein the comparison of the methylation status to the threshold value is predictive of the presence or absence of esophegeal cancer in the individual.

In some embodiments, the methods comprise:
a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
b) comparing the methylation status of the at least one cytosine to a threshold value for the biomarker, wherein the threshold value distinguishes between individuals with and without colon cancer, wherein the comparison of the methylation status to the threshold value is predictive of the presence or absence of colon cancer in the individual.

In some embodiments, the methods comprise:
a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
b) comparing the methylation status of the at least one cytosine to a threshold value for the biomarker, wherein the threshold value distinguishes between individuals with and without prostate cancer, wherein the comparison of the methylation status to the threshold value is predictive of the presence or absence of prostate cancer in the individual.

In some embodiments, the methods comprise:
a) determining the methylation status of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265;
b) comparing the methylation status of the at least one cytosine to a threshold value for the biomarker, wherein the threshold value distinguishes between individuals with and without melanoma, wherein the comparison of the methylation status to the threshold value is predictive of the presence or absence of melanoma in the individual.

With regard to the embodiments, in some embodiments, the determining step comprises determining the methylation status of at least one cytosine -in the DNA region corresponding to a nucleotide in a biomarker in the DNA region, wherein the biomarker is at least 90%, 91%, 92%, 93%, 94%, 95%, 96%, 97%, 98%, or 99% identical to, or comprises, a sequence selected from the group consisting of SEQ ID NOs:

160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, and 212.

In some embodiments, the determining step comprises determining the methylation status of the DNA region corresponding to a biomarker.

In some embodiments, the sample is from any body fluid, including but not limited to blood serum, blood plasma, fine needle aspirate of the breast, biopsy of the breast, ductal fluid, ductal lavage, feces, urine, sputum, saliva, semen, lavages, biopsy of the lung, bronchial lavage or bronchial brushings. In some embodiments, the sample is from a tumor or polyp. In some embodiments, the sample is a biopsy from lung, kidney, liver, ovarian, head, neck, thyroid, bladder, cervical, colon, endometrial, esophageal, prostate or skin tissue. In some embodiments, the sample is from cell scrapes, washings, or resected tissues.

In some embodiments, the methylation status of at least one cytosine is compared to the methylation status of a control locus. In some embodiments, the control locus is an endogenous control. In some embodiments, the control locus is an exogenous control.

In some embodiments, the determining step comprises determining the methylation status of at least one cytosine in at least two of the DNA regions.

In a further aspect, the invention provides computer implemented methods for determining the presence or absence of cancer (including but not limited to breast, lung, renal, liver, ovarian, head and neck, thyroid, bladder, cervical, colon, endometrial, esophageal, prostate or melanoma) in an individual. In some embodiments, the methods comprise:

receiving, at a host computer, a methylation value representing the methylation status of at least one cytosine within a DNA region in a sample from the individual where the DNA region is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265; and comparing, in the host computer, the methylation value to a threshold value, wherein the threshold value distinguishes between individuals with and without cancer (including but not limited to breast, lung, renal, liver, ovarian, head and neck, thyroid, bladder, cervical, colon, endometrial, esophageal, prostate or melanoma), wherein the comparison of the methylation value to the threshold value is predictive of the presence or absence of cancer (including but not limited to breast, lung, renal, liver, ovarian, head and neck, thyroid, bladder, cervical, colon, endometrial, esophageal, or prostate cancer or melanoma) in the individual.

In some embodiments, the receiving step comprises receiving at least two methylation values, the two methylation values representing the methylation status of at least one cytosine biomarkers from two different DNA regions; and the comparing step comprises comparing the methylation values to one or more threshold value(s) wherein the threshold value distinguishes between individuals with and without cancer (including but not limited to breast, lung, renal, liver, ovarian, head and neck, thyroid, bladder, cervical, colon, endometrial, esophageal, prostate or melanoma), wherein the comparison of the methylation value to the threshold value is predictive of the presence or absence of cancer (including but not limited to breast, lung, renal, liver, ovarian, head and neck, thyroid, bladder, cervical, colon, endometrial, esophageal, or prostate cancer or melanoma) in the individual.

In another aspect, the invention provides computer program products for determining the presence or absence of cancer (including but not limited to breast, lung, renal, liver, ovarian, head and neck, thyroid, bladder, cervical, colon, endometrial, esophageal, or prostate cancer or melanoma) in an individual. In some embodiments, the computer readable products comprise:

a computer readable medium encoded with program code, the program code including:
program code for receiving a methylation value representing the methylation status of at least one cytosine within a DNA region in a sample from the individual where the DNA region is is at least 90%, 91%, 92%, 93%, 94%, 95%, 96%, 97%, 98%, or 99% identical to, or comprises, a sequence selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265; and
program code for comparing the methylation value to a threshold value, wherein the threshold value distinguishes between individuals with and without cancer (including but not limited to breast, lung, renal, liver, ovarian, head and neck, thyroid, bladder, cervical, colon, endometrial, esophageal, or prostate cancer or melanoma), wherein the comparison of the methylation value to the threshold value is predictive of the presence or absence of cancer (including but not limited to breast, lung, renal, liver, ovarian, head and neck, thyroid, bladder, cervical, colon, endometrial, esophageal, or prostate cancer or melanoma) in the individual.

In a further aspect, the invention provides kits for determining the methylation status of at least one biomarker. In some embodiments, the kits comprise:

a pair of polynucleotides capable of specifically amplifying at least a portion of a DNA region where the DNA region is a sequence selected from the group consisting of SEQ ID NOs: of 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265; and
a methylation-dependent or methylation sensitive restriction enzyme and/or sodium bisulfite.

In some embodiments, the pair of polynucleotides are capable of specifically amplifying a biomarker selected from the group consisting of one or more of SEQ ID NOs: 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, and 212.

In some embodiments, the kits comprise at least two pairs of polynucleotides, wherein each pair is capable of specifically amplifying at least a portion of a different DNA region selected from the group consisting of SEQ ID NOs: of 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

In some embodiments, the kits further comprise a detectably labeled polynucleotide probe that specifically detects the amplified biomarker in a real time amplification reaction.

In a further aspect, the invention provides kits for determining the methylation status of at least one biomarker. In some embodiments, the kits comprise:

sodium bisulfite and polynucleotides to quantify the presence of the converted methylated and or the converted unmethylated sequence of at least one cytosine from a DNA region that is selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

In a further aspect, the invention provides kits for determining the methylation status of at least one biomarker. In some embodiments, the kits comprise:

sodium bisulfite, primers and adapters for whole genome amplification, and polynucleotides to quantify the presence of the converted methylated and or the converted unmethylated sequence of at least one cytosine from a DNA region that is selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

In another aspect, the methods provide kits for determining the methylation status of at least one biomarker. In some embodiments, the kits comprise:

a methylation sensing restriction enzymes, primers and adapters for whole genome amplification, and polynucleotides to quantify the number of copies of at least a portion of a DNA region where the DNA region is selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

In a further aspect, the invention provides kits for determining the methylation status of at least one biomarker. In some embodiments, the kits comprise:

a methylation binding moiety and one or more polynucleotides to quantify the number of copies of at least a portion of a DNA region where the DNA region is selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

DEFINITIONS

"Methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was methylated or methylated, respectively.

A "methylation profile" refers to a set of data representing the methylation states of one or more loci within a molecule of DNA from e.g., the genome of an individual or cells or tissues from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus.

"Methylation status" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value." A methylation value can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC (see, e.g., U.S. Pat. No. 5,405,760), McrA, MrrA, and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al, *Nucleic Acids Res.* 22(17):3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

A "threshold value that distinguishes between individuals with and without" a particular disease refers to a value or range of values of a particular measurement that can be used to distinguish between samples from individuals with the disease and samples without the disease. Ideally, there is a threshold value or values that absolutely distinguishes between the two groups (i.e., values from the diseased group are always on one side (e.g., higher) of the threshold value and values from the healthy, non-diseased group are on the other side (e.g., lower) of the threshold value). However, in many instances, threshold values do not absolutely distinguish between diseased and non-diseased samples (for example, when there is some overlap of values generated from diseased and non-diseased samples).

The phrase "corresponding to a nucleotide in a biomarker" refers to a nucleotide in a DNA region that aligns with the same nucleotide (e.g., a cytosine) in a biomarker sequence. Generally, as described herein, biomarker sequences are subsequences of the DNA regions. Sequence comparisons can be performed using any BLAST including BLAST 2.2 algorithm with default parameters, described in Altschul et al., Nuc. Acids Res. 25:3389 3402 (1997) and Altschul et al., *J. Mol. Biol.* 215:403 410 (1990), respectively. Thus for example, a DNA region or biomarker described herein can correspond to a DNA sequence in a human genome even if there is slight variation between the biomarker or DNA region and the particular human genome in question. Such difference can be the result of slight genetic variation between humans.

"Sensitivity" of a given biomarker refers to the percentage of tumor samples that report a DNA methylation value above a threshold value that distinguishes between tumor and non-tumor samples. The percentage is calculated as follows:

$$\text{Sensitivity} = \left[ \frac{\text{(the number of tumor samples above the threshold)}}{\text{(the total number of tumor samples tested)}} \right] \times 100$$

The equation may also be stated as follows:

$$\text{Sensitivity} = \left[ \frac{\text{(the number of true positive samples)}}{\text{(the number of true positive samples)} + \text{(the number of false negative samples)}} \right] \times 100$$

where true positive is defined as a histology-confirmed tumor sample that reports a DNA methylation value above the threshold value (i.e. the range associated with disease), and false negative is defined as a histology-confirmed tumor sample that reports a DNA methylation value below the threshold value (i.e. the range associated with no disease). The value of sensitivity, therefore, reflects the probability that a DNA methylation measurement for a given biomarker obtained from a known diseased sample will be in the range of disease-associated measurements. As defined here, the clinical relevance of the calculated sensitivity value represents an estimation of the probability that a given biomarker would detect the presence of a clinical condition when applied to a patient with that condition.

"Specificity" of a given biomarker refers to the percentage of non-tumor samples that report a DNA methylation value below a threshold value that distinguishes between tumor and non-tumor samples. The percentage is calculated as follows:

$$\text{Specificity} = \left[ \frac{\text{(the number of non-tumor samples below the threshold)}}{\text{(the total number of non-tumor samples tested)}} \right] \times 100$$

The equation may also be stated as follows:

$$\text{Specificity} = \left[ \frac{\text{(the number of true negative samples)}}{\text{(the number of true negative samples)} + \text{(the number of false positive samples)}} \right] \times 100$$

where true negative is defined as a histology-confirmed non-tumor sample that reports a DNA methylation value below the threshold value (i.e. the range associated with no disease), and false positive is defined as a histology-confirmed non-tumor sample that reports DNA methylation value above the threshold value (i.e. the range associated with disease). The value of specificity, therefore, reflects the probability that a DNA methylation measurement for a given biomarker obtained from a known non-diseased sample will be in the range of non-disease associated measurements. As defined here, the clinical relevance of the calculated specificity value represents an estimation of the probability that a given biomarker would detect the absence of a clinical condition when applied to a patient without that condition.

Software for performing BLAST analyses is publicly available through the National Center for Biotechnology Information. This algorithm involves first identifying high scoring sequence pairs (HSPs) by; identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

As used herein, the terms "nucleic acid," "polynucletide" and "oligonucleotide" refer to nucleic acid regions, nucleic acid segments, primers, probes, amplicons and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA.

A nucleic acid, polynucleotide or oligonucleotide can comprise, for example, phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, uracil-5- oxyacetic acidmethylester, 3-(3-amino-3-N-2-carboxypropyl) uracil, (acp3)w, 2,6- diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785.

Furthermore, a nucleic acid, polynucleotide or oligonucleotide can comprise one or more modified sugar moieties including, but not limited to, arabinose, 2-fluoroarabinose, xylulose, and a hexose.

BRIEF DESCRIPTION OF THE DRAWINGS

FIG. 1 illustrates a general overview of the experimental design of differential methylation screening. A graphical representation of the transcription start site and 5' structure of one predicted differentially methylated gene is indicated (A). The bar graph (B) indicates the relative local density of purine-CG sequences within this region. The relative position of the DNA microarray feature that reported differential DNA methylation at this locus is indicated by (C). PCR primers were selected to amplify the region indicated by (D). The vertical bars (E and F) represent the microarray DNA methylation measurement representing all breast tumors (E) and all normal breast samples (F).

FIG. 2 illustrates an example of McrBC-based real-time PCR strategy to monitor DNA methylation status. Panel A shows the untreated/treated PCR replicate 1 for amplification of the GHSR locus in a breast tumor sample. The delta Ct (Treated 1—Untreated 1) is 5.38 cycles. Panel B shows the untreated/treated PCR replicate 2 for amplification of the same locus from the same tumor sample. The delta Ct (Treated 2—Untreated 2) is 5.40 cycles. Panel C shows the untreated/treated PCR replicate 1 for amplification of the GHSR locus in a normal breast sample. The delta Ct (Treated 1—Untreated 1) is 0.18 cycles. Panel D shows the untreated/treated PCR replicate 2 for amplification of the same locus from the same normal sample. The delta Ct (Treated 2—Untreated 2) is 0.03 cycles. Tumor samples produce a change in cycle threshold ("delta Ct") of 1.0 or greater. Normal samples produce a delta Ct of less than 1.0.

FIGS. 3A-B illustrates verification of microarray DNA methylation predictions. Open boxes represent loci that are unmethylated (average delta Ct<1.0), grey boxes represent loci that are methylated (average delta Ct>1 and <2), and black boxes represent loci that are densely methylated (average delta Ct>2).

FIGS. 4A and 4B illustrate validation of DNA methylation differences in biomarkers from independent tumor and normal samples. Boxes are as indicated for FIG. 3.

FIG. 5 illustrates DNA methylation differences in biomarkers from a larger panel of breast tumor, normal breast and normal peripheral blood samples. Boxes are as indicated for FIG. 3.

FIG. 6 illustrates demonstration of threshold adjustment for determining sensitivity and specificity.

FIG. 7 illustrates bisulfite sequencing confirmation of differential DNA methylation.

FIG. 8 illustrates the correlation between qPCR based DNA methylation measurements and DNA methylation occupancies determined by bisulfite sequencing. Primers were designed to amplify approximately 150 bp amplicons within the region of three loci that were analyzed by qPCR as described above. The loci included feature ID halp__39189 (locus number 2), halg__00644 (locus number 3) and halp$_{13}$ 104423 (locus number 12). For each amplicon, products were amplified from three normal breast DNA samples that reported average dCt values <0.5, three normal breast DNA samples that reported average dCt values between 0.5 and 1.0, and three breast tumor DNA samples that reported average dCt values greater than 1.0. Amplicons were purified and cloned using TA cloning kits (Invitrogen). At least 29 independent clones were sequenced per amplicon, per locus. The graph shows the median 5-methylcytosine content for all sequenced clones per amplicon plotted against the average dCt value for that locus in the same DNA sample. The dashed vertical line represents the dCt=1.0 threshold used to indicate a positive qPCR measurement for DNA methylation detection.

FIG. 9 illustrates an example of selection of a potentially differentially methylated region based on an analysis of CpG density (identification of a CG island).

FIG. 10A illustrates the frequency of differential DNA methylation of 16 loci in stage I breast tumors relative to stage II-III breast tumors. The 16 loci include those listed in Table 5.

FIG. 10B illustrates the DNA methylation density of three selected loci relative to tumor stage. The averaged approximate percent depletion of methylated molecules by McrBC was calculated to determine the load of methylated molecules in each sample [1-(1/2^delta Ct (McrBC digested-Mock treated))*100]. Data are plotted (from left to right) for normal breast samples, stage I tumors, stage IIA tumors, stage IIB tumors and stage III tumors.

FIG. 11A illustrates the differential DNA methylation of four selected loci in breast tumor, normal breast tissue and peripheral blood from a cancer-free woman. Each data point represents the averaged delta Ct value for an independent clinical sample.

FIG. 11B illustrates ROC curve analyses of the four loci depicted in FIG. 11A. Sensitivity (percentage of tumor samples scoring above a methylation threshold) and specificity (percentage of non-tumor samples scoring below that same threshold) were calculated for all observed delta Ct values.

FIG. 12 illustrates the analysis of DNA methylation of four selected loci by bisulfite sequencing. Analyzed loci included locus number 2 (A, B), 3 (C, D), 4 (E, F) and 12 (G, H). Bisulfite sequencing was performed. The average number of molecules sequenced for each locus within each sample was 587. The calculated DNA methylation density (number of methylated CpGs divided by the total number of Cpos sequenced) for each sample is plotted versus the qPCR DNA methylation measurement for the same sample (A, C, E, G). In addition, the percent methylation occupancy at each analyzed CpG dinucleotide is shown (B, D, F, H). Analyzed samples included normal breast tissues (open circles), adjacent histology normal breast tissues (filled circles) and breast tumors (filled squares).

FIG. 13 illustrates the correlation between DNA hypermethylation and gene expression. Transcription of GHSR (locus number 2), MGA (locus number 4), and NFX1 (locus number 12) were analyzed by RT-PCR. Serial dilutions of cDNA from normal breast tissue and four breast tumors were used as template as indicated. GAPDH expression was analyzed as an internal control for each sample. The DNA methylation measurement (qPCR) for each locus in each tumor sample is indicated (-average dCt<1.0, +average dCt≧1.0 but <2.0, and ++average dCt≧2.0).

FIG. 14 illustrates the comparison of DNA methylation detection in fine needle aspirate (% POSITIVE FNA) samples relative to unmatched primary breast tumor samples (% POSITIVE TUMOR). Each sample was scored as positive if the average dCt was ≧1.0, as described in Example 3. Analyzed samples included 7 FNA samples and at least 14 primary breast tumor samples.

DETAILED DESCRIPTION OF THE INVENTION

I. Introduction

The present invention is based, in part, on the discovery that sequences in certain DNA regions are methylated in cancer cells, but not normal cells. The inventors have found that methylation within the DNA regions described herein are associated with breast cancer, particularly ductal carcinoma, as well as a number of other cancers.

In view of this discovery, the inventors have recognized that methods for detecting the biomarker sequences and DNA regions comprising the biomarker sequences as well as sequences adjacent to the biomarkers that contain a significant amount of CG subsequences, methylation of the DNA regions, and/or expression of the genes regulated by the DNA regions can be used to detect cancer cells. Detecting cancer cells allows for diagnostic tests that detect disease, assess the risk of contracting disease, determining a predisposition to disease, stage disease, diagnose disease, monitor disease, and/or aid in the selection of treatment for a person with disease.

II. Methylation Biomarkers

In some embodiments, the presence or absence or quantity of methylation of the chromosomal DNA within a DNA region or portion thereof (e.g., at least one cytosine) selected from SEQ ID Nos: 213-265 is detected. Portions of the DNA regions described herein will comprise at least one potential methylation site (i.e., a cytosine) and can in some embodiments generally comprise 2, 3, 4, 5, 10, or more potential methylation sites. In some embodiments, the methylation status of all cytosines within at least 20, 50, 100, 200, 500 or more contiguous base pairs of the DNA region are determined.

In some embodiments, the methylation of more than one DNA region (or portion thereof) is detected. In some embodiments, the methylation status at least one cytosine in 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or 53 of the DNA regions is determined.

In some embodiments of the invention, the methylation of a DNA region or portion thereof is determined and then compared (e.g., normalized) to the methylation of a control locus. Typically the control locus will have a known, relatively constant, methylation status. For example, the control sequence can be previously determined to have no, some, or a high amount of methylation, thereby providing a relative constant value to control for error in detection methods, etc., unrelated to the presence or absence of cancer. In some embodiments, the control locus is endogenous, i.e., is part of the genome of the individual sampled. For example, in mammalian cells, the testes-specific histone 2B gene (hTH2B in human) gene is known to be methylated in all somatic tissues except testes. Alternatively, the control locus can be an exogenous locus, i.e., a DNA sequence spiked into the sample in a known quantity and having a known methylation status.

A DNA region comprises a nucleic acid including one or more methylation sites of interest (e.g., a cytosine, a "microarray feature" as exemplified in FIG. 1C, or an amplicon amplified from select primers as exemplified in FIG. 1D) and flanking nucleic acid sequences (i.e., "wingspan") of up to 4 kilobases (kb) in either or both of the 3' or 5' direction from the amplicon. This range corresponds to the lengths of DNA fragments obtained by randomly shearing the DNA before screening for differential methylation between DNA in two or more samples (e.g., carrying out methods used to initially identify differentially methylated sequences as described in the Examples, below). In some embodiments, the wingspan of the one or more DNA regions is about 0.5 kb, 0.75 kb, 1.0 kb, 1.5 kb, 2.0 kb, 2.5 kb, 3.0 kb, 3.5 kb or 4.0 kb.

In some cases, the DNA region comprises more nucleotides than simply the wingspan of the discovery method because the relevant microarray feature or amplicon reside in a larger region of higher CG density in the chromosome. This range corresponds to identified lengths of nucleic acid sequences having higher CG density (e.g., a "CG island") than flanking nucleic acid sequences (e.g., "local minimum" CG density) (see, for example, FIG. 8). DNA regions having extended sequences of heightened CG density include, for example, sequences 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265 (see, Table 2 and section "SEQUENCE LISTING").

The methylation sites in a DNA region can reside in non-coding transcriptional control sequences (e.g., promoters, enhancers, etc.) or in coding sequences, including introns and exons of the designated genes listed in Tables 1 and 2 and in section "SEQUENCE LISTING." In some embodiments, the methods comprise detecting the methylation status in the promoter regions (e.g., comprising the nucleic acid sequence that is about 1.0 kb, 1.5 kb, 2.0 kb, 2.5 kb, 3.0 kb, 3.5 kb or 4.0 kb 5' from the transcriptional start site through to the transcriptional start site) of one or more of the genes identified in Tables 1 and 2 and in the "SEQUENCE LISTING" section.

The DNA regions of the invention also include naturally occurring variants, including for example, variants occurring in different subject populations and variants arising from single nucleotide polymorphisms (SNPs). Variants include nucleic acid sequences from the same DNA region (e.g., as set forth in Tables 1 and 2 and in the "SEQUENCE LISTING" section) sharing at least 90%, 95%, 98%, 99% sequence identity, i.e., having one or more deletions, additions, substitutions, inverted sequences, etc., relative to the DNA regions described herein.

III. Methods For Determining Methylation

Any method for detecting DNA methylation can be used in the methods of the present invention.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. patent application Ser. Nos. 10/971,986; 11/071,013; and 10/971,339. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. patent application Ser. No. 10/971,986.

Kits for the above methods can include, e.g., one or more of methylation-dependent restriction enzymes, methylation-sensitive restriction enzymes, amplification (e.g., PCR) reagents, probes and/or primers.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). Amplifications may be monitored in "real time."

Additional methods for detecting DNA methylation can involve genomic sequencing before and after treatment of the DNA with bisulfite. See, e.g., Frommer et al., *Proc. Natl. Acad. Sci. USA* 89:1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, *Nucl. Acids Res.* 24:5058-5059 (1996); Xiong & Laird, *Nucleic Acids Res.* 25:2532-2534 (1997).

In some embodiments, a MethyLight assay is used alone or in combination with other methods to detect DNA methylation (see, Eads et al., *Cancer Res.* 59:2302-2306 (1999)). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see, Gonzalgo & Jones, *Nucleic Acids Res.* 25:2529-2531 (1997)). The Ms-SNuPE technique is a quantitative method for assessing methylation differences at specific CpG sites based on bisulfite treatment of DNA, followed by single-nucleotide primer extension (Gonzalgo & Jones, supra). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultra-filtration, affinity column); desulfonation buffer; and DNA recovery components.

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated versus unmethylated DNA. See, Herman et al., *Proc. Natl. Acad. Sci. USA* 93:9821-9826, (1996); U.S. Pat. No. 5,786,146.

Additional methylation detection methods include, but are not limited to, methylated CpG island amplification (see, Toyota et al., Cancer Res. 59:2307-12 (1999)) and those described in, e.g., U.S. Patent Publication 2005/0069879; Rein, et al. *Nucleic Acids Res.* 26 (10): 2255-64 (1998); Olek, et al. *Nat Genet.* 17(3): 275-6 (1997); and PCT Publication No. WO 00/70090.

It is well known that methylation of genomic DNA can affect expression (transcription and/or translation) of nearby gene sequences. Therefore, in some embodiments, the methods include the step of correlating the methylation status of at least one cytosine in a DNA region with the expression of nearby coding sequences, as described in Tables 1 and 2 and in the "SEQUENCE LISTING" section. For example, expression of gene sequences within about 1.0 kb, 1.5 kb, 2.0 kb, 2.5 kb, 3.0 kb, 3.5 kb or 4.0 kb in either the 3' or 5' direction from the cytosine of interest in the DNA region can be detected. Methods for measuring transcription and/or translation of a particular gene sequence are well known in the art. See, for example, Ausubel, *Current Protocols in Molecular Biology,* 1987-2006, John Wiley & Sons; and Sambrook and Russell, *Molecular Cloning: A Laboratory Manual,* 3rd Edition, 2000, Cold Spring Harbor Laboratory Press. In some embodiments, the gene or protein expression of a gene in Tables 1 and 2 and in the "SEQUENCE LISTING" section is compared to a control, for example, the methylation status in the DNA region and/or the expression of a nearby gene sequence; and/or the same gene sequence from a sample from an individual known to be negative for cancer or known to be positive for cancer, or to an expression level that distinguishes between cancer and noncancer states. Such methods, like the methods of detecting methylation described herein, are useful in providing diagnosis, prognosis, etc., of breast cancer.

In some embodiments, the methods further comprise the step of correlating the methylation status and expression of one or more of the gene regions identified in Tables 1 and 2 and in the "SEQUENCE LISTING" section.

IV. Cancer Detection

The present biomarkers and methods can be used in the detection, diagnosis, prognosis, classification, and treatment of a number of types of cancers. A cancer at any stage of progression can be detected, such as primary, metastatic, and recurrent cancers. Information regarding numerous types of cancer can be found, e.g., from the American Cancer Society (available on the worldwide web at cancer.org), or from, e.g., *Harrison's Principles of internal Medicine,* Kaspar, et al., eds., 16th Edition, 2005, McGraw-Hill, Inc. Exemplary cancers that can be detected include, e.g., breast cancers, including ductal carcinoma, as well as lung, renal, liver, ovarian, head and neck, thyroid, bladder, cervical, colon, endometrial, esophageal, or prostate cancer or melanoma.

The present invention provides methods for determining whether or not a mammal (e.g., a human) has cancer, i.e., whether or not a biological sample taken from a mammal contains cancerous cells, estimating the risk or likelihood of a mammal developing cancer, classifying cancer types and stages, and monitoring the efficacy of anti-cancer treatment or selecting the appropriate anti-cancer treatment in a mammal with cancer. Such methods are based on the discovery that cancer cells have a different methylation status than normal cells in the DNA regions described in the invention. Accordingly, by determining whether or not a cell contains differentially methylated sequences in the DNA regions as described herein, it is possible to determine whether or not the cell is cancerous.

In numerous embodiments of the present invention, the presence of methylated nucleotides in the diagnostic biomarker sequences of the invention is detected in a biological sample, thereby detecting the presence or absence of cancerous cells in the mammal from which the biological sample was taken. In some embodiments, the biological sample comprises a tissue sample from a tissue suspected of containing cancerous cells. For example, in an individual suspected of having cancer, breast tissue, lymph tissue, lung tissue, brain tissue, or blood can be evaluated. Alternatively, lung, renal, liver, ovarian, head and neck, thyroid, bladder, cervical, colon, endometrial, esophageal, prostate, or skin tissue can be evaluated. The tissue or cells can be obtained by any method known in the art including, e.g., by surgery, biopsy, phlebotomy, swab, nipple discharge, stool, etc. In other embodiments, a tissue sample known to contain cancerous cells, e.g., from a tumor, will be analyzed for the presence or quantity of methylation at one or more of the diagnostic biomarkers of the invention to determine information about the cancer, e.g., the efficacy of certain treatments, the survival expectancy of the individual, etc. In some embodiments, the methods will be used in conjunction with additional diagnostic methods, e.g., detection of other cancer biomarkers, etc.

The methods of the invention can be used to evaluate individuals known or suspected to have cancer or as a routine clinical test, i.e., in an individual not necessarily suspected to have cancer.

Further, the present methods may be used to assess the efficacy of a course of treatment. For example, the efficacy of an anti-cancer treatment can be assessed by monitoring DNA methylation of the biomarker sequences described herein over time in a mammal having cancer. For example, a reduction or absence of methylation in any of the diagnostic biomarkers of the invention in a biological sample taken from a mammal following a treatment, compared to a level in a sample taken from the mammal before, or earlier in, the treatment, indicates efficacious treatment.

The methods detecting cancer can comprise the detection of one or more other cancer-associated polynucleotide or polypeptides sequences. Accordingly, detection of methylation of any one or more of the diagnostic biomarkers of the invention can be used either alone, or in combination with other biomarkers, for the diagnosis or prognosis of cancer.

The methods of the present invention can be used to determine the optimal course of treatment in a mammal with cancer. For example, the presence of methylated DNA within any of the diagnostic biomarkers of the invention or an increased quantity of methylation within any of the diagnostic biomarkers of the invention can indicate a reduced survival expectancy of a mammal with cancer, thereby indicating a more aggressive treatment for the mammal. In addition, a correlation can be readily established between the presence, absence or quantity of methylation at a diagnostic biomarker, as described herein, and the relative efficacy of one or another anti-cancer agent. Such analyses can be performed, e.g., retrospectively, i.e., by detecting methylation in one or more of the diagnostic genes in samples taken previously from mammals that have subsequently undergone one or more types of anti-cancer therapy, and correlating the known efficacy of the treatment with the presence, absence or levels of methylation of one or more of the diagnostic biomarkers.

In making a diagnosis, prognosis, risk assessment or classification, in monitoring disease, or in determining the most beneficial course of treatment based on the presence or absence of methylation in at least one of the diagnostic biomarkers, the quantity of methylation may be compared to a threshold value that distinguishes between one diagnosis, prognosis, risk assessment, classification, etc., and another. For example, a threshold value can represent the degree of methylation found at a particular DNA region that adequately distinguishes between breast cancer samples and normal breast samples with a desired level of sensitivity and specificity. It is understood that a threshold value will likely vary depending on the assays used to measure methylation, but it is also understood that it is a relatively simple matter to determine a threshold value or range by measuring methylation of a DNA sequence in diseased and normal samples using the particular desired assay and then determining a value that distinguishes at least a majority of the cancer samples from a majority of non-cancer samples. An example of this is shown in FIG. 6 and the accompanying text in the examples. If methylation of two or more DNA regions is detected, two or more different threshold values (one for each DNA region) will often, but not always, be used. Comparisons between a quantity of methylation of a sequence in a sample and a threshold value in any way known in the art. For example, a manual comparison can be made or a computer can compare and analyze the values to detect disease, assess the risk of contracting disease, determining a predisposition to disease, stage disease, diagnose disease, monitor, or aid in the selection of treatment for a person with disease.

In some embodiments, threshold values provide at least a specified sensitivity and specificity for detection of a particular cancer type. In some embodiments, the threshold value allows for at least a 50%, 60%, 70%, or 80% sensitivity and specificity for detection of a specific cancer, e.g., breast, lung, renal, liver, ovarian, head and neck, thyroid, bladder, cervical, colon, endometrial, esophageal, prostate cancer or melanoma. More detail regarding specificity and sensitivity for various cancers can be found in, e.g., Tables 5-6, and 8-20.

In embodiments involving prognosis of cancer (including, for example, the prediction of progression of non-malignant lesions to invasive carcinoma, prediction of metastasis, prediction of disease recurrance or prediction of a response to a particular treatment), in some embodiments, the threshold value is set such that there is at least 10, 20, 30, 40, 50, 60, 70, 80% or more sensitivity and at least 70% specificity with regard to detecting cancer.

In some embodiments, the methods comprise recording a diagnosis, prognosis, risk assessment or classification, based on the methylation status determined from an individual. Any type of recordation is contemplated, including electronic recordation, e.g., by a computer.

V. Kits

This invention also provides kits for the detection and/or quantification of the diagnostic biomarkers of the invention, or expression or methylation thereof using the methods described herein.

For kits for detection of methylation, the kits of the invention can comprise at least one polynucleotide that hybridizes to at least one of the diagnostic biomarker sequences of the invention and at least one reagent for detection of gene methylation. Reagents for detection of methylation include, e.g., sodium bisulfite, polynucleotides designed to hybridize to sequence that is the product of a biomarker sequence of the invention if the biomarker sequence is not methylated (e.g., containing at least one C→U conversion), and/or a methylation-sensitive or methylation-dependent restriction enzyme. The kits can provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides capable of specifically amplifying at least a portion of a DNA region where the DNA region is a sequence selected from the group consisting of SEQ ID NOs: 213, 214, 215, 216, 217, 218, 219, 220, 221, 222, 223, 224,225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265. Optionally, one or more detectably-labeled polypeptide capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotoides) to quantify the presence of the converted methylated and or the converted unmethylated sequence of at least one cytosine from a DNA region that is selected from the group consisting of SEQ ID NOs:213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

In some embodiments, the kits comprise a methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region where the DNA region is selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

In some embodiments, the kits comprise a methylation binding moiety and one or more polynucleotides to quantify the number of copies of at least a portion of a DNA region where the DNA region is selected from the group consisting of SEQ ID NOs: 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265. A methylation binding moiety refers to a molecule (e.g., a polypeptide) that specifically binds to methyl-cytosine. Examples include restriction enzymes or fragments thereof that lack DNA cutting activity but retain the ability to bind methylated DNA, antibodies that specifically bind to methylated DNA, etc.).

VI. Computer-Based Methods

The calculations for the methods described herein can involve computer-based calculations and tools. For example, a methylation value for a DNA region or portion thereof can be compared by a computer to a threshold value, as described herein. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

EXAMPLES

Example 1

Identification of Breast Cancer DNA Methylation Biomarkers

Loci that are differentially methylated in breast tumors relative to matched adjacent histologically normal breast tissue were identified using a DNA microarray-based technology platform (U.S. Pat. No. 7,186,512) that utilizes the methylation-dependent restriction enzyme McrBC. In this discovery phase, 10 infiltrating ductal breast carcinomas (9 Stage II, 1 Stage III) and 10 matched adjacent histologically normal breast tissue samples were analyzed. Purified genomic DNA from each sample (60 µg) was randomly sheared to a range of 1 to 4 kb. The sheared DNA of each sample was then split into four equal portions of 15 µg each. Two portions were digested with McrBC under the following conditions: 15 µg sheared genomic DNA, 1X NEB2 buffer (New England Biolabs), 0.1 mg/mL bovine serum albumin (New England Biolabs), 2 mM GTP (Roche) and 120 units of McrBC enzyme (New England Biolabs) in a total volume of 600 µL at 37° C. for approximately 12 hours. These two portions represent a technical replicate of McrBC digestion (Treated 1 and Treated 2). The remaining two 15 µg portions were mock treated under identical conditions with the exception that 12 µL of sterile 50% glycerol were added instead of McrBC enzyme. These two portions represent a technical replicate of mock treatment (Untreated 1 and Untreated 2). All reactions were treated with 5 µL proteinase K (50 mg/mL) for 1 hour at 50° C., and precipitated with EtOH under standard conditions. Pellets were washed twice with 70% EtOH, dried and resuspended in 30 µL H2O. Samples were then resolved on a 1% low melting point SeaPlaque GTG Agarose gel (Cambridge Bio Sciences). Untreated 1 and Treated 1 portions were resolved side-by-side, as were Untreated 2 and Treated 2 portions. 1 kb DNA sizing ladder was resolved adjacent to each untreated/treated pair to guide accurate gel slice excision. Gels were visualized with long-wave UV, and gel slices including DNA within the modal size range of the untreated fraction (approximately 1-4 kb) were excised with a clean razor blade. DNA was extracted from gel slices using gel extraction kits (Qiagen).

McrBC recognizes a pair of methylated cytosine residues in the context 5'-Pu$^m$C (N$_{40-2000}$) Pu$^m$C-3' (where Pu=A or G, $^m$C=5-methylcytosine, and N=any nucleotide), and cleaves within approximately 30 base-pairs from one of the methylated cytosine residues. Therefore, loci that include high local densities of Pu $^m$C will be cleaved to a greater extent than loci that include low local densities of Pu $^m$C. Since Untreated and Treated portions were resolved by agarose gel electrophoresis, and DNA within the modal size range of the Untreated portions were excised and gel extracted, the Untreated portions represent the entire fragmented genome of the sample while the Treated portions are depleted of DNA fragments including Pu $^m$C. Fractions were analyzed using a duplicated dye swap microarray hybridization paradigm. For example, equal mass (200 ng) of Untreated 1 and Treated 1 fraction DNA were used as template for labeling with Cy3 and Cy5, repectively, and hybridized to a DNA microarray (described below). Equal mass (200 ng) of the same Untreated 1 and Treated 1 fraction DNA were used as template for labeling with Cy5 and Cy3, respectively, and hybridized to a second DNA microarray (these two hybridizations represent a dye swap of Untreated 1/Treated 1 fractions). Equal mass (200 ng) of Untreated 2 and Treated 2 fraction DNA were used as template for labeling with Cy3 and Cy5, respectively, and hybridized to a third DNA microarray. Finally, equal mass (200 ng) of Untreated 2 and Treated 2 fraction DNA were used as template for labeling with Cy5 and Cy3, respectively, and hybridized to a fourth DNA microarray (the final two hybridizations represent a technical replicate of the first dye swap). All 20 DNA samples (10 tumor samples and 10 adjacent normal samples) were analyzed in this way. Therefore, the discovery experiment included a total of 80 microarray hybridizations.

The microarray described in this Example consists of 85,176 features. Each 60 mer oligonucleotide feature is represented by four replicates per microarray slide, yielding a total of 21,294 unique feature probes. The features represent 19,595 randomly selected human transcriptional start sites (TSS) representing 79% of the identified human genes, 1395 GenBank BAC annotated CG islands (CGi), 161 features spanning ~165 kb along the MTAPase/CDKN2A/B locus on chromosome 9, 66 additional features dedicated to cancer gene promoters, and 77 features designed as copy number (HERV, LINEs, SINE) and other controls. Together, the TSS features and CGi features scan more than 9000 UCSC annotated human CG islands.

Following statistical analysis of these datasets, loci that were predicted to be differentially methylated in at least 70% of tumors relative to normal tissues were identified. As described in the Examples below, differential DNA methylation of a collection of 53 loci identified by the microarray discovery experiment described herein was verified within the discovery panel of 10 infiltrating ductal breast carcinomas relative to 10 matched adjacent histologically normal breast samples, as well as validated in larger panels of independent infiltrating ductal breast carcinomas, normal breast samples and normal female peripheral blood samples. Tables 1 and 2 and the "SEQUENCE LISTING" section list the unique microarray feature identifier (Feature name) for each of these 53 loci. Locus number is an arbitrary locus identifier that will be used to identify the loci in the following examples. Of the 53 features, 48 represent sequence within 1 kb of at least one annotated transcribed gene. These are referred to in the table by the Ensembl gene ID, as well as the official gene symbol for each gene (Gene Name). The genomic region in which a given microarray feature can report DNA methylation status is dependent upon the molecular size of the DNA fragments that were labeled for the microarray hybridizations. As described above, DNA in the size range of 1 to 4 kb was purified by agarose gel extraction and used as template for cyanogen dye labeling. Therefore, the genomic region interrogated by each microarray feature is at least 1 kb (i.e., 500 bp upstream and 500 bp downstream of the sequence represented by the microarray feature). Note that 5 features represent loci in which there is no annotated transcribed gene within this 1 kb "wingspan" (Locus numbers 3, 9, 20, 31, and 47). Also note that 8 features represent loci in which more than one annotated transcribed gene falls within wingspan (Locus numbers 21, 26, 27, 29, 35, 38, 39, and 53). DNA methylation at these loci can affect the regulation of any of these neighboring genes, and thus detection of gene expression from neighboring genes is also useful for determining the presence or absence of cancer for numerous types of diagnostic tests.

TABLE 1

Microarray Features Reporting Differential DNA Methylation And Identity Of Annotated Genes Within 1 kb Of Each Feature.

| Featurename | Locus Number | Ensembl Gene ID | Gene Name |
|---|---|---|---|
| ha1g_00681 | 1 | ENSG00000105997 | HOXA3 |
| ha1p_39189 | 2 | ENSG00000121853 | GHSR |
| ha1g_00644 | 3 | N/A | |
| ha1p_81674 | 4 | ENSG00000174197 | MGA |
| ha1p_81149 | 5 | ENSG00000122971 | ACADS |
| ha1p_83841 | 6 | ENSG00000178187 | ZNF454 |

TABLE 1-continued

Microarray Features Reporting Differential DNA Methylation And Identity Of Annotated Genes Within 1 kb Of Each Feature.

| Featurename | Locus Number | Ensembl Gene ID | Gene Name |
|---|---|---|---|
| ha1p__38705 | 7 | ENSG00000163638 | ADAMTS9 |
| ha1p__40164 | 8 | ENSG00000118855 | MFSD1 |
| ha1p__23178 | 9 | | N/A |
| ha1p__46057 | 10 | ENSG00000132640 | BTBD3 |
| ha1p__40959 | 11 | ENSG00000111707 | SUDS3 |
| ha1p__104423 | 12 | ENSG00000008441 | NFIX |
| ha1g__00847 | 13 | ENSG00000116106 | EPHA4 |
| ha1p__08347 | 14 | ENSG00000134802 | SLC43A3 |
| ha1g__02416 | 15 | ENSG00000172238 | ATOH1 |
| ha1p__87540 | 16 | ENSG00000159403 | PREDICTED: similar to Complement C1r subcomponent precursor |
| ha1p__110107 | 17 | ENSG00000122254 | HS3ST2 |
| ha1p__89799 | 18 | ENSG00000163739 | CXCL1 |
| ha1p__45173 | 19 | ENSG00000120915 | EPHX2 |
| ha1p__80771 | 20 | | N/A |
| ha1p__69407 | 21 | ENSG00000180667 | YOD1 |
| | | ENSG00000198878 | O9P1L8_HUMAN |
| ha1p__05406 | 22 | ENSG00000165556 | CDX2 |
| ha1p__80287 | 23 | ENSG00000109113 | RAB34 |
| ha1g__02345 | 24 | ENSG00000122592 | HOXA7 |
| ha1p__36172 | 25 | ENSG00000185070 | FLRT2 |
| ha1p__70459 | 26 | ENSG00000163481 | RNF25 |
| | | ENSG00000163482 | STK36 |
| ha1p__105937 | 27 | ENSG00000161551 | ZNF577 |
| | | ENSG00000198093 | ZNF649 |
| ha1p__89099 | 28 | ENSG00000062485 | CS |
| ha1g__03099 | 29 | ENSG00000066032 | CTNNA2 |
| | | ENSG00000162951 | LRRTM1 |
| ha1p__67625 | 30 | ENSG00000130711 | PRDM12 |
| ha1g__00218 | 31 | | N/A |
| ha1p__12535 | 32 | ENSG00000149090 | RAMP |
| ha1p__105474 | 33 | ENSG00000033627 | ATP6V0A1 |
| ha1p__74707 | 34 | ENSG00000010278 | CD9 |
| ha1p__93325 | 35 | ENSG00000101019 | C20orf44 |
| | | ENSG00000125965 | GDF5 |
| ha1p__101161 | 36 | ENSG00000130176 | CNN1 |
| ha1p__101251 | 37 | ENSG00000142235 | LMTK3 |
| ha1p__69214 | 38 | ENSG00000158927 | C8orf58 |
| | | ENSG00000158941 | KIAA1967 |
| | | ENSG00000183646 | |
| ha1p__88517 | 39 | ENSG00000101412 | E2F1 |
| | | ENSG00000125967 | APBA2BP |
| ha1p__103824 | 40 | ENSG00000167178 | ISLR2 |
| ha1p__108445 | 41 | ENSG00000175287 | PHYHD1 |
| ha1g__02210 | 42 | ENSG00000151615 | POU4F2 |
| ha1p__103872 | 43 | ENSG00000129009 | ISLR |
| ha1p__56412 | 44 | ENSG00000175182 | C3orf40 |
| ha1p__18292 | 45 | ENSG00000115561 | VPS24 |
| ha1p__12075 | 46 | ENSG00000164619 | BMPER |
| ha1p__22519 | 47 | | N/A |
| ha1p__29531 | 48 | ENSG00000060718 | COL11A1 |
| ha1p__58853 | 49 | ENSG00000113648 | H2AFY |
| ha1p__35052 | 50 | ENSG00000111341 | MGP |
| ha1p__67002 | 51 | ENSG00000159445 | THEM4 |
| ha1p__45580 | 52 | ENSG00000168079 | SCARA5 |
| ha1p__12646 | 53 | ENSG00000107833 | NPM3 |
| | | ENSG00000198408 | MGEA5 |

Example 2

Design of Independent DNA Methylation Verification and Validation Assays

PCR primers that interrogated the 53 loci predicted to be differentially methylated between breast tumor and adjacent histologically normal breast tissue were designed. Due to the functional properties of the enzyme, DNA methylation-dependent depletion of DNA fragments by McrBC is capable of monitoring the DNA methylation status of sequences neighboring the genomic sequences represented by the features on the microarray described in Example 1 (wingspan). Since the size of DNA fragments analyzed as described in Example 1 was approximately 1-4 kb, we selected a 1 kb region spanning the sequence represented by the microarray feature as an estimate of the predicted region of differential methylation. For each locus, PCR primers were selected within this approximately 1 kb region flanking the genomic sequence represented on the DNA microarray (approximately 500 bp upstream and 500 bp downstream). Selection of primer sequences was guided by uniqueness of the primer sequence across the genome, as well as the distribution of purine-CG sequences within the 1 kb region. PCR primer pairs were selected to amplify an approximately 400-600 bp sequence within each 1 kb region. For demonstration, an example of one such PCR amplicon design is shown in FIG. 1. A graphical representation of the transcription start site and 5' structure of one predicted differentially methylated gene is indicated (A). The bar graph (B) indicates the relative local density of purine-CG sequences within this region. The relative position of the DNA microarray feature that reported differential DNA methylation at this locus is indicated by (C). PCR primers were selected to amplify the region indicated by (D). The vertical bars (E and F) represent the microarray DNA methylation measurement representing all breast tumors (E) and all normal breast samples (F). For example, this locus is predicted to be hypermethylated in the breast tumors (positive value) relative to the adjacent normal breast samples (negative value). Suitable PCR cycling conditions for the 53 primer pairs were empirically determined, and amplification of a specific PCR amplicon of the correct size was verified. The sequences of the 53 microarray features, primer pairs and amplicons are indicated in Table 2, and in the "SEQUENCE LISTING" section.

TABLE 2

Sequence identification numbers for all sequences described in the application.
See, section "SEQUENCE LISTING" for actual sequences as listed by locus number in the table.

| Locus Number | Feature Name | Feature Seq. | Left Primer | Right Primer | Annealing Temp. | Amplicon Seq. | DNA Region Seq. | Selection Criteria |
|---|---|---|---|---|---|---|---|---|
| 1 | ha1g__00681 | 1 | 54 | 107 | 66 C. | 160 | 213 | CG |
| 2 | ha1g__39189 | 2 | 55 | 108 | 66 C. | 161 | 214 | CG |
| 3 | ha1g__00644 | 3 | 56 | 109 | 66 C. | 162 | 215 | CG |
| 4 | ha1p__81674 | 4 | 57 | 110 | 66 C. | 163 | 216 | CG |
| 5 | ha1p__81149 | 5 | 58 | 111 | 66 C. | 164 | 217 | CG |
| 6 | ha1p__83841 | 6 | 59 | 112 | 66 C. | 165 | 218 | CG |

TABLE 2-continued

Sequence identification numbers for all sequences described in the application.
See, section "SEQUENCE LISTING" for actual sequences as listed by locus number in the table.

| Locus Number | Feature Name | Feature Seq. | Left Primer | Right Primer | Annealing Temp. | Amplicon Seq. | DNA Region Seq. | Selection Criteria |
|---|---|---|---|---|---|---|---|---|
| 7 | ha1p_38705 | 7 | 60 | 113 | 66 C. | 166 | 219 | CG |
| 8 | ha1p_40164 | 8 | 61 | 114 | 66 C. | 167 | 220 | CG |
| 9 | ha1p_23178 | 9 | 62 | 115 | 66 C. | 168 | 221 | CG |
| 10 | ha1p_46057 | 10 | 63 | 116 | 66 C. | 169 | 222 | CG |
| 11 | ha1p_40959 | 11 | 64 | 117 | 66 C. | 170 | 223 | CG |
| 12 | ha1p_104423 | 12 | 65 | 118 | 66 C. | 171 | 224 | CG |
| 13 | ha1g_00847 | 13 | 66 | 119 | 66 C. | 172 | 225 | CG |
| 14 | ha1p_08347 | 14 | 67 | 120 | 66 C. | 173 | 226 | CG |
| 15 | ha1g_02416 | 15 | 68 | 121 | 66 C. | 174 | 227 | CG |
| 16 | ha1p_87540 | 16 | 69 | 122 | 66 C. | 175 | 228 | CG |
| 17 | ha1p_110107 | 17 | 70 | 123 | 66 C. | 176 | 229 | CG |
| 18 | ha1p_89799 | 18 | 71 | 124 | 66 C. | 177 | 230 | CG |
| 19 | ha1p_45173 | 19 | 72 | 125 | 66 C. | 178 | 231 | CG |
| 20 | ha1p_80771 | 20 | 73 | 126 | 66 C. | 179 | 232 | CG |
| 21 | ha1p_69407 | 21 | 74 | 127 | 66 C. | 180 | 233 | CG |
| 22 | ha1p_05406 | 22 | 75 | 128 | 66 C. | 181 | 234 | CG |
| 23 | ha1p_80287 | 23 | 76 | 129 | 66 C. | 182 | 235 | CG |
| 24 | ha1g_02345 | 24 | 77 | 130 | 72 C. | 183 | 236 | CG |
| 25 | ha1p_36172 | 25 | 78 | 131 | 72 C. | 184 | 237 | CG |
| 26 | ha1p_70459 | 26 | 79 | 132 | 66 C. | 185 | 238 | CG |
| 27 | ha1p_105937 | 27 | 80 | 133 | 66 C. | 186 | 239 | CG |
| 28 | ha1p_89099 | 28 | 81 | 134 | 66 C. | 187 | 240 | CG |
| 29 | ha1g_03099 | 29 | 82 | 135 | 66 C. | 188 | 241 | CG |
| 30 | ha1p_67625 | 30 | 83 | 136 | 72 C. | 189 | 242 | CG |
| 31 | ha1g_00218 | 31 | 84 | 137 | 66 C. | 190 | 243 | CG |
| 32 | ha1p_12535 | 32 | 85 | 138 | 66 C. | 191 | 244 | CG |
| 33 | ha1p_105474 | 33 | 86 | 139 | 66 C. | 192 | 245 | 1 kb |
| 34 | ha1p_74707 | 34 | 87 | 140 | 66 C. | 193 | 246 | CG |
| 35 | ha1p_93325 | 35 | 88 | 141 | 66 C. | 194 | 247 | 1 kb |
| 36 | ha1p_101161 | 36 | 89 | 142 | 66 C. | 195 | 248 | 1 kb |
| 37 | ha1p_101251 | 37 | 90 | 143 | 66 C. | 196 | 249 | 1 kb |
| 38 | ha1p_69214 | 38 | 91 | 144 | 66 C. | 197 | 250 | 1 kb |
| 39 | ha1p_88517 | 39 | 92 | 145 | 66 C. | 198 | 251 | CG |
| 40 | ha1p_103824 | 40 | 93 | 146 | 66 C. | 199 | 252 | CG |
| 41 | ha1p_108445 | 41 | 94 | 147 | 72 C. | 200 | 253 | 1 kb |
| 42 | ha1g_02210 | 42 | 95 | 148 | 72 C. | 201 | 254 | CG |
| 43 | ha1p_103872 | 43 | 96 | 149 | 66 C. | 202 | 255 | CG |
| 44 | ha1p_56412 | 44 | 97 | 150 | 72 C. | 203 | 256 | CG |
| 45 | ha1p_18292 | 45 | 98 | 151 | 72 C. | 204 | 257 | CG |
| 46 | ha1p_12075 | 46 | 99 | 152 | 66 C. | 205 | 258 | CG |
| 47 | ha1p_22519 | 47 | 100 | 153 | 66 C. | 206 | 259 | CG |
| 48 | ha1p_29531 | 48 | 101 | 154 | 66 C. | 207 | 260 | CG |
| 49 | ha1p_58853 | 49 | 102 | 155 | 66 C. | 208 | 261 | CG |
| 50 | ha1p_35052 | 50 | 103 | 156 | 66 C. | 209 | 262 | 1 kb |
| 51 | ha1p_67002 | 51 | 104 | 157 | 72 C. | 210 | 263 | CG |
| 52 | ha1p_45580 | 52 | 105 | 158 | 72 C. | 211 | 264 | CG |
| 53 | ha1p_12646 | 53 | 106 | 159 | 66 C. | 212 | 265 | CG |

Example 3

Verification of Microarray DNA Methylation Predictions

Initially, the DNA methylation state of these 53 loci was independently assayed in the 10 infiltrating ductal breast carcinoma samples and the 10 matched adjacent histologically normal samples described above (i.e., the discovery tissue panel used for microarray experiments). DNA methylation was assayed by a quantitative PCR approach utilizing digestion by the McrBC restriction enzyme to monitor DNA methylation status. Genomic DNA purified from each sample was split into two equal portions of 9.6 µg. One 9.6 µg portion (Treated Portion) was digested with McrBC in a total volume of 120 µL including 1X NEB2 buffer (New England Biolabs), 0.1 mg/mL bovine serum albumin (New England Biolabs), 2 mM GTP (Roche) and 80 units of McrBC enzyme (New England Biolabs). The second 9.6 µg portion (Untreated Portion) was treated exactly the same as the Treated Portion, except that 8 µL of sterile 50% glycerol was added instead of McrBC enzyme. Reactions were incubated at 37° C. for approximately 12 hours, followed by incubation at 60° C. for 20 minutes to inactivate McrBC.

The extent of McrBC cleavage at each locus was monitored by quantitative real-time PCR (qPCR). For each assayed locus, qPCR was performed using 20 ng of the Untreated Portion DNA as template and, separately, using 20 ng of the Treated Portion DNA as template. Each reaction was performed in 10 µL total volume including 1X LightCycler 480 SYBR Green I Master mix (Roche) and 625 nM of each primer. Reactions were run in a Roche LightCycler 480 instrument. Optimal annealing temperatures varied depending on the primer pair. Primer sequences (Left Primer; Right Primer) and appropriate annealing temperatures (Annealing Temp.) are shown in Table 2. Cycling conditions were: 95° C. for 5 min.; 45 cycles of 95° C. for 1 min., [annealing temperature, see Table 2] for 30 sec., 72° C. for 1 min., 83° C. for 2 sec. followed by a plate read. Melting curves were calculated under the following conditions: 95° C. for 5 sec., 65° C.

for 1 min., 65° C. to 95° C. at 2.5° C./sec. ramp rate with continuous plate reads. Each Untreated/Treated qPCR reaction pair was performed in duplicate. The difference in the cycle number at which amplification crossed threshold (delta Ct) was calculated for each Untreated/Treated qPCR reaction pair by subtracting the Ct of the Untreated Portion from the Ct of the Treated Portion. Because McrBC-mediated cleavage between the two primers increases the Ct of the Treated Portion, increasing delta Ct values reflect increasing measurements of local DNA methylation densities. The average delta Ct between the two replicate Untreated/Treated qPCR reactions was calculated, as well as the standard deviation between the two delta Ct values.

For demonstration purposes, amplification profiles for one locus (GHSR) in a tumor sample and a normal sample are shown in FIG. 2. Panel A shows the untreated/treated PCR replicate 1 for amplification of the GHSR amplicon in a breast tumor sample. The delta Ct (Treated 1—Untreated 1) is 5.38 cycles. Panel B shows the untreated/treated PCR replicate 2 for amplification of the same amplicon from the same tumor sample. The delta Ct (Treated 2—Untreated 2) is 5.40 cycles. The average delta Ct of the two replicates is 5.39 cycles, representing a ~97% reduction of amplifiable copies in the treated relative to the untreated portions [100%−((1/2^delta Ct)×100)]. The standard deviation of the delta Ct's between the two qPCR replicates is 0.01 cycles. Panel C shows the untreated/treated PCR replicate 1 for amplification of the GHSR amplicon in a normal breast sample. The delta Ct (Treated 1—Untreated 1) is 0.18 cycles. Panel D shows the untreated/treated PCR replicate 2 for amplification of the same amplicon from the same normal sample. The delta Ct (Treated 2—Untreated 2) is 0.03 cycles. The average delta Ct of the two replicates is 0.11 cycles, representing a ~7% reduction of amplifiable copies in the treated relative to the untreated portions. The standard deviation of the delta Ct's between the two qPCR replicates is 0.11 cycles. The average delta Ct of the tumor sample would be scored as a methylated locus. In contrast, the average delta Ct of the normal sample would be scored as a relatively unmethylated locus. An average delta Ct of >1.0 cycle, representing >~50% reduction of amplifiable copies in the treated relative to the untreated portions, was set as the threshold for scoring a sample as positive for DNA methylation. Any average delta Ct measurement with a standard deviation >1.0 cycle in qPCR replicates was excluded as an unreliable measurement (ND in FIG. 3). Finally, any average delta Ct <0 was adjusted to 0.

FIG. 3 shows the results of the DNA methylation measurements for the 53 loci in the 10 tumor samples and 10 normal samples used in the microarray discovery experiment. Open boxes represent loci that are unmethylated (average delta Ct <1.0), grey boxes represent loci that are methylated (average delta Ct >1 and <2), and black boxes represent loci that are densely methylated (average delta Ct >2).

Example 4

Validation of DNA Methylation Changes in Independent Breast Tumor and Normal Breast Samples The differential DNA methylation status of the 53 loci was further validated by analyzing an independent panel of 16 infiltrating ductal breast carcinoma samples (1 Stage I, 4 Stage II, 11 Stage III) and 25 normal breast tissue samples. The normal breast tissues included in this panel were obtained from biopsies unrelated to breast cancer. Each sample was split into two equal portions of 4 µg. One portion was digested with McrBC (Treated Portion) in a total volume of 200 µL including 1X NEB2 buffer (New England Biolabs), 0.1 mg/mL bovine serum albumin (New England Biolabs), 2 mM GTP (Roche) and 32 units McrBC (New England Biolabs). The second portion was mock treated under identical conditions, except that 3.2 µL sterile 50% glycerol was added instead of McrBC enzyme (Untreated Portion). Samples were incubated at 37° C. for approximately 12 hours, followed by incubation at 60° C. to inactivate the McrBC enzyme. qPCR reactions and data analysis were performed as described in Example 3.

The DNA methylation state measurements are summarized in FIG. 4. As described above, each locus was scored as unmethylated (average delta Ct <1.0, open boxes), methylated (average delta Ct >1.0 and <2.0, grey boxes) or densely methylated (average delta Ct >2.0, black boxes). Measurements with a standard deviation between pPCR replicates >1 cycle were not included in the analysis (ND). Table 3 indicates the percent sensitivity and specificity for each locus. Sensitivity reflects the frequency of scoring a known tumor sample as positive for DNA methylation at each locus. Specificity reflects the frequency of scoring a known normal sample as negative for DNA methylation at each locus. As described above, an average delta Ct >1.0 (Treated Portion— Untreated Portion) was used as a threshold to score a sample as positive for DNA methylation at each locus (representing >~50% depletion of amplifiable molecules in the DNA methylation-dependent restricted population relative to the untreated population). Percent sensitivity was calculated as the number of tumor samples with an average delta Ct >1.0 divided by the total number of tumor samples analyzed for that locus (i.e. excluding any measurements with a standard deviation between qPCR replicates >1 cycle)×100. Percent specificity was calculated as (1−(the number of normal samples with an average delta Ct >1.0 divided by the total number of normal samples analyzed for that locus))×100. As shown in Table 3, the 53 loci have sensitivities >13% and specificities >80%. Notably, 33 of the 53 loci have 100% specificity. It is important to point out that the sensitivity and specificity of the differential DNA methylation status of any given locus may be increased by further optimization of the precise local genetic region interrogated by a DNA methylation-sensing assay.

TABLE 3

Sensitivity and specificity of differentially methylated loci in a panel of 25 normal breast and 16 breast tumor samples.

| FEATURE ID | LOCUS NUMBER | SENSITIVITY | SPECIFICITY |
|---|---|---|---|
| ha1g_00681 | 1 | 86% | 100% |
| ha1p_39189 | 2 | 81% | 100% |
| ha1g_00644 | 3 | 79% | 100% |
| ha1p_81674 | 4 | 69% | 100% |
| ha1p_81149 | 5 | 69% | 100% |
| ha1p_83841 | 6 | 69% | 100% |
| ha1p_38705 | 7 | 63% | 100% |
| ha1p_40164 | 8 | 63% | 100% |
| ha1p_23178 | 9 | 63% | 100% |
| ha1p_46057 | 10 | 56% | 100% |
| ha1p_40959 | 11 | 56% | 100% |
| ha1p_104423 | 12 | 50% | 100% |
| ha1g_00847 | 13 | 50% | 100% |
| ha1p_08347 | 14 | 50% | 100% |
| ha1g_02416 | 15 | 44% | 100% |
| ha1p_87540 | 16 | 44% | 100% |
| ha1p_110107 | 17 | 38% | 100% |
| ha1p_89799 | 18 | 31% | 100% |
| ha1p_45173 | 19 | 31% | 100% |
| ha1p_80771 | 20 | 25% | 100% |

TABLE 3-continued

Sensitivity and specificity of differentially methylated loci in a panel of 25 normal breast and 16 breast tumor samples.

| FEATURE ID | LOCUS NUMBER | SENSITIVITY | SPECIFICITY |
|---|---|---|---|
| ha1p__69407 | 21 | 25% | 100% |
| ha1p__05406 | 22 | 25% | 100% |
| ha1p__80287 | 23 | 25% | 100% |
| ha1g__02345 | 24 | 20% | 100% |
| ha1p__36172 | 25 | 20% | 100% |
| ha1p__70459 | 26 | 19% | 100% |
| ha1p__105937 | 27 | 19% | 100% |
| ha1p__89099 | 28 | 19% | 100% |
| ha1g__03099 | 29 | 14% | 100% |
| ha1p__67625 | 30 | 13% | 100% |
| ha1g__00218 | 31 | 13% | 100% |
| ha1p__12535 | 32 | 75% | 96% |
| ha1p__105474 | 33 | 75% | 96% |
| ha1p__74707 | 34 | 69% | 96% |
| ha1p__93325 | 35 | 69% | 96% |
| ha1p__101161 | 36 | 56% | 96% |
| ha1p__101251 | 37 | 87% | 96% |
| ha1p__69214 | 38 | 81% | 96% |
| ha1p__88517 | 39 | 69% | 96% |
| ha1p__103824 | 40 | 17% | 96% |
| ha1p__108445 | 41 | 60% | 95% |
| ha1g__02210 | 42 | 18% | 95% |
| ha1p__103872 | 43 | 94% | 92% |
| ha1p__56412 | 44 | 79% | 92% |
| ha1p__18292 | 45 | 60% | 91% |
| ha1p__12075 | 46 | 31% | 90% |
| ha1p__22519 | 47 | 88% | 88% |
| ha1p__29531 | 48 | 88% | 88% |
| ha1p__58853 | 49 | 50% | 88% |
| ha1p__35052 | 50 | 31% | 88% |
| ha1p__67002 | 51 | 64% | 83% |
| ha1p__45580 | 52 | 40% | 83% |
| ha1p__12646 | 53 | 81% | 80% |

Example 5

Further Validation of Selected DNA Methylation Biomarkers in a Larger Panel of Breast Tumor Samples, Normal Breast Samples, and Normal Female Peripheral Blood Samples A panel of 15 loci were selected for further validation in a panel of 9 additional 5 infiltrating ductal breast carcinoma samples, bringing the total number of tumor samples analyzed to 25 (I Stage II, Stage III). In addition, 25 normal female peripheral blood samples were analyzed. Samples were treated and analyzed as described in Example 4. FIG. 5 shows the results of these analyses, including the 25 normal breast samples described in Example 4. As shown in Table 4, these loci display >17% sensitivity, >92% specificity relative to normal breast tissue, and >92% specificity relative to normal female peripheral blood.

TABLE 4

Sensitivity and specificity of differentially methylated loci in a panel of 25 normal breast and 25 breast tumor samples and 25 normal blood samples.

| FEATURE ID | LOCUS NUMBER | SENSI-TIVITY | SPECIFICITY VS NORMAL BREAST | SPECIFICITY VS BLOOD |
|---|---|---|---|---|
| ha1p__39189 | 2 | 84% | 100% | 96% |
| ha1g__00644 | 3 | 83% | 100% | 100% |
| ha1p__81674 | 4 | 76% | 100% | 95% |
| ha1p__74707 | 34 | 72% | 96% | 100% |
| ha1p__101251 | 37 | 88% | 96% | 92% |
| ha1g__02416 | 15 | 54% | 100% | 100% |
| ha1p__110107 | 17 | 52% | 100% | 100% |
| ha1p__89799 | 18 | 40% | 100% | 100% |
| ha1p__80771 | 20 | 36% | 100% | 100% |
| ha1p__69407 | 21 | 26% | 92% | 96% |
| ha1p__05406 | 22 | 32% | 100% | 100% |
| ha1g__02345 | 24 | 17% | 100% | 100% |
| ha1p__36172 | 25 | 38% | 100% | 100% |
| ha1p__70459 | 26 | 24% | 100% | 96% |
| ha1p__67625 | 30 | 35% | 100% | 100% |

Example 6

Demonstration of a DNA Methylation Measurement Threshold

In the examples above, a threshold for scoring differential methylation (average delta Ct>1.0) was established and indiscriminately applied to all loci. However, the most informative threshold is dependent upon the specific locus in question. This is demonstrated in FIG. 6. The graph shows the average delta Ct (Treated Portion—Untreated Portion) for the analyzed region of the GHSR locus in 25 tumor samples, 25-normal breast samples, and 24 normal female peripheral blood samples. Using an average delta Ct threshold of >1.0 as the criteria for a positive DNA methylation measurement, sensitivity is 84%, specificity relative to normal tissue is 100% and specificity relative to blood is 96% (Table 4). However, an optimal threshold may be set for each individual locus, and this threshold is dependent upon the technology used to detect the differential DNA methylation state. For example, in the GSHR example shown in FIG. 6, a threshold of >1.3 (hatched line in figure) would adjust the specificity relative to blood to 100%.

Example 7

Validation of Selected DNA Methylation Biomarkers in a Panel Including Approximately 100 Breast Tumor Samples And 100 Normal Breast Samples A panel of 16 biomarker loci was further validated in additional breast tumor and normal breast samples. In total, approximately 100 samples were analyzed for each group. The total number of samples analyzed for each biomarker and for each sample category is reported in Table 5.

TABLE 5

Sensitivity and specificity of differentially methylated loci in a panel of approximately 100 breast tumor samples, 100 normal breast samples and 25 normal blood samples.

| Feature ID | Locus Number | No. Positive Tumor | Total Tumor | % Sensitivity | No. Positive Normal Breast | Total Normal Breast | % Specficity (Normal Breast) | No. Positive Normal Blood | Total Normal Blood | % Specficity (Normal Blood) |
|---|---|---|---|---|---|---|---|---|---|---|
| ha1p__39189 | 2 | 87 | 102 | 85% | 1 | 103 | 99% | 1 | 24 | 96% |
| ha1g__00644 | 3 | 74 | 101 | 73% | 1 | 104 | 99% | 0 | 25 | 100% |
| ha1p__81674 | 4 | 71 | 99 | 72% | 10 | 93 | 89% | 1 | 19 | 95% |
| ha1p__101251 | 37 | 67 | 101 | 66% | 4 | 102 | 96% | 2 | 24 | 92% |
| ha1p__74707 | 34 | 55 | 102 | 54% | 1 | 104 | 99% | 0 | 25 | 100% |
| ha1g__02416 | 15 | 41 | 101 | 41% | 1 | 104 | 99% | 0 | 25 | 100% |
| ha1p__67625 | 30 | 36 | 91 | 40% | 1 | 99 | 99% | 0 | 21 | 100% |
| ha1p__69407 | 21 | 37 | 100 | 37% | 6 | 103 | 94% | 1 | 23 | 96% |
| ha1p__104423 | 12 | 36 | 98 | 37% | 0 | 97 | 100% | 1 | 24 | 96% |
| ha1p__36172 | 25 | 34 | 102 | 33% | 0 | 104 | 100% | 0 | 23 | 100% |
| ha1p__89799 | 18 | 27 | 101 | 27% | 0 | 99 | 100% | 0 | 24 | 100% |
| ha1p__80771 | 20 | 27 | 103 | 26% | 0 | 104 | 100% | 0 | 25 | 100% |
| ha1p__70459 | 26 | 26 | 101 | 26% | 0 | 103 | 100% | 1 | 24 | 96% |
| ha1p__110107 | 17 | 24 | 101 | 24% | 0 | 104 | 100% | 0 | 24 | 100% |
| ha1p__05406 | 22 | 23 | 103 | 22% | 0 | 103 | 100% | 0 | 24 | 100% |
| ha1g__02345 | 24 | 17 | 102 | 17% | 0 | 103 | 100% | 0 | 22 | 100% |

No. Positive Tumor: Number of tumor samples that reported avg. dCt ≧ 1.0 (methylated locus).
Total Tumor: Number of tumor samples tested.
% Sensitivity: (No. Positive Tumor/Total Tumor) × 100
No. Positive Normal Breast: Number of normal breast samples that reported avg. dCt ≧ 1.0 (methylated locus).
Total Normal Breast: Number of normal breast samples tested.
% Specificity (Nomral Breast): (1 − (No. Positive Nomral Breast/Total Normal Breast)) × 100
No. Posivite Normal Blood: Number of normal blood samples that reported avg. dCt ≧ 1.0 (methylated locus).
Total Normal Blood: Number of normal blood samples tested.
% Specificity (Normal Blood): (1 − (No. Positive Normal Blood/Total Normal Blood)) × 100

Example 8

Bisulfite Sequencing Confirmation of Differential DNA Methylation

An example of confirmation of differential DNA methylation by bisulfite sequencing is shown in FIG. 7. Primers were designed to amplify a 130 bp amplicon within the 412 bp region of Nuclear Factor 1 X-type analyzed by qPCR (as discussed in the Examples above) from bisulfite converted genomic DNA. Primers sequences lack CpG dinucleotides, and therefore amplify bisulfite converted DNA independently of DNA methylation status. Products were amplified from one tumor sample (positive for DNA methylation) and from one pooled normal female peripheral blood sample. Amplicons were purified and cloned using TA cloning kits (Invitrogen). Eighteen (18) independent clones were sequenced for the tumor sample. Seven (7) independent clones were sequenced for the blood sample. Bisulfite treatment results in conversion of unmethylated cytosines to uracil, but does not convert methylated cytosines. The percent methylation of each CpG dinucleotide within the region was calculated as the number of sequence reads of C at each CpG divided by the total number of sequence reads. FIG. 7A shows the % methylation occupancy for each of the 18 CpG dinucleotides in the tumor sample. FIG. 7B shows the % methylation occupancy for each of the 18 CpG dinucleotides in the normal blood sample. All 18 CpG dinucleotides are methylated in the tumor (occupany ranging from 11% to 89%). However, only one CpG dinucleotide displayed methylation in the normal blood sample (14%).

To provide further confirmation of DNA methylation differences and to justify the qPCR based strategy for high-throughput detection of DNA methylation, three loci were analyzed by bisulfite genomic sequencing. Primers were designed to amplify approximately 150 bp amplicons within the region of three loci that were analyzed by qPCR as described above. The loci included feature ID ha1p__39189 (locus number 2), ha1g__00644 (locus number 3) and ha1p__104423 (locus number 12). Primer sequences lacked CpG dinucleotides, and therefore amplify bisulfite converted DNA independently of DNA methylation status. For each amplicon, products were amplified from three normal breast DNA samples that reported average dCt values <0.5, three normal breast DNA samples that reported average dCt values between 0.5 and 1.0, and three breast tumor DNA samples that reported average dCt values greater than 1.0. Amplicons were purified and cloned using TA cloning kits (Invitrogen). At least 29 independent clones were sequenced per amplicon, per locus. FIG. 8 shows the median 5-methylcytosine content for all sequenced clones per amplicon plotted against the average dCt value for that locus in the same DNA sample. The dashed vertical line represents the dCt=1.0 threshold used to indicate a positive qPCR measurement for DNA methylation detection. These data verify the differential DNA methylation content in tumors relative to normal breast samples. Furthermore, the linear relationship between the qPCR measurement and the 5-methylcytosine content determined by bisulfite sequencing ($R^2$=0.7965) provides justification for the high-throughput qPCR method for DNA methylation detection.

Example 9

Selection of Sequence Identified As Potential Region of Differential DNA Methylation As described in the examples above, the loci identified as differentially methylated were originally discovered based on DNA methylation-dependent microarray analyses. The sequences of the 53 microarray features reporting this differential methylation are indicated in Table 2 and in the "SEQUENCE LISTING" section. Because the "wingspan" of genomic interrogation by each feature is conservatively 1 kb, PCR primers that amplify an amplicon within a 1 kb region surrounding the sequence represented by each microarray feature were selected and used for independent verification and validation experiments. Primer sequences and amplicon sequences are indicated in Table 2 and in the "SEQUENCE LISTING" section. To optimize successful PCR amplification, these amplicons were designed to be less than the entire 1 kb region represented by the wingspan of the microarray feature. However, it should be noted that differential methylation may be detectable anywhere within this sequence window. For each locus, the sequence representing at least this 1 kb region flanking the sequence represented by the microarray feature was selected as the claimed potentially differentially methylated genomic region. These sequences are indicated in Table 2 (DNA Region Sequences) and in the "SEQUENCE LISTING" section. Sequences claimed based on the 1 Kb region flanking the sequence represented by the microarray feature are indicated by "1" kb in Table 2 (Selection Criteria).

In addition, the local CpG density surrounding each region was calculated.

Approximately 10 kb of sequence both upstream and downstream of each feature was 30 extracted from the human genome. For each 20 kb region of the genome, a sliding window of 500 bp moving in 100 bp steps was used to calculate the CG density. CG density was expressed as the ratio of CG dinucleotides per kb. An example is shown in FIG. 9 and illustrates the position of the transcription start site of the GHSR gene relative to the regional CpG density of the surrounding sequence. In this example, methylation anywhere with the ~4 kb peak of CpG density associated with the promoter region of the gene is monitored and is useful in a clinical diagnostic assay. Loci in which the claimed region was determined by analysis of local CpG density are indicated by "CG" in Table 2 (Selection Criteria). As diagrammed in FIG. 9, the claimed sequences were selected based on setting the local minimum of CpG density flanking the sequence represented by the PCR amplicon as the upstream and downstream boundaries.

Example 10

Demonstration that Differential DNA Methylation is Detectable in Early Stage Disease Although fewer Stage I tumors compared to Stage II or III tumors were analyzed (8 of 103 samples), the inclusion of a small number of Stage I tumors allowed a determination of whether the differential methylation events are related to tumor stage. FIG. 10A shows a plot of the frequency of hypermethylation of the 16 loci in the 8 Stage I tumors (i.e. the percentage of Stage I tumors scoring as intermediately to densely methylated) versus the Stage II and III tumors. The relationship between the two sensitivity calculations ($R^2=0.887$; slope=0.9815) indicates that the frequency of hypermethylation of these loci is similar regardless of tumor stage. Therefore, for the majority of loci, the differential methylation events are just as likely to be present in a Stage I tumor as they are in later stage tumors. The proportion of methylated loci in tumors at each stage was then analyzed for three selected loci. The percent depletion by McrBC for each sample in which a given locus scored as methylated was calculated [1−(1/2^delta Ct (McrBC digested−Mock treated))]*100] to provide a measure of the load of methylated molecules within the sample. The mean percent depletion at each tumor stage is shown in FIG. 10B. While there is a trend for increased methylation density at these loci with increasing tumor stage, methylation density of Stage I tumors is not significantly different than Stage II-III tumors, yet is dramatically different than the average of all normal samples. Therefore, differential methylation of these loci is independent of tumor stage in regards to both the frequency and the density of hypermethylation.

Example 11

Receiver-Operator Curve Analysis of Biomarker Sensitivity and Specificity

Receiver-operator characteristic (ROC) analyses were performed for each of the 16 loci described in Table 5 to determine optimal thresholds for calculation of sensitivity and specificity of the differential DNA methylation event. Examples of the primary qPCR data for four selected loci are shown in FIG. 11A. These plots demonstrate the overall discrimination between tumor, normal breast tissue and normal peripheral blood samples. The frequency at which tumor tissues were scored as differentially methylated at these loci was not significantly associated with either age of the cancer patient or estrogen receptor status of the patient's primary tumor. ROC curves for the corresponding four datasets are shown in FIG. 11B. Optimal thresholds were identified as the maximum sum of sensitivity and specificity calculated at each observed delta Ct value. The minimum allowed threshold was set at 0.5 so that calculations could not be based on thresholds within the variability range of the qPCR platform. Results are summarized in Table 6. Sensitivity and specificity calculations based on optimal thresholds are similar to those calculated using a standard delta Ct threshold of 1.0. As hypothesized, the direct global profiling of DNA methylation identified numerous novel DNA methylation-based biomarkers that display substantially improved sensitivity and specificity relative to the vast majority of previously identified differentially methylated genes in breast cancer. In fact, a single differentially methylated biomarker, located in the promoter region of GHSR, was capable of distinguishing IDC from normal and benign breast tissue with sensitivity of 90% and specificity of 96%. Other biomarkers displayed similar specificity, with decreasing sensitivity. Several of these biomarkers were hypermethylated at a higher frequency than the majority of previously reported hypermethylated biomarkers (i.e. 12 of 16 displayed sensitivity between 53% and 90%).

TABLE 6

Breast Cancer Biomarker Validation. Thresholds indicate the optimal average dCt value for distinction between tumor and non-tumor tissues.

| Feature ID | Locus Number | BREAST TUMOR VS. NORMAL BREAST | | | | | BREAST TUMOR VS. NORMAL BLOOD | | |
|---|---|---|---|---|---|---|---|---|---|
| | | Sensitivity | Pos. of Total | Specificity | Neg. of Total | Threshold | Specificity | Neg. of Total | Threshold |
| ha1p__39189 | 2 | 90% | 92 of 102 | 96% | 99 of 103 | 0.64 | 100% | 24 of 24 | 1.22 |
| ha1g__00644 | 3 | 89% | 90 of 101 | 92% | 96 of 104 | 0.555 | 100% | 25 of 25 | 0.695 |
| ha1p__101251 | 37 | 77% | 78 of 101 | 87% | 89 of 102 | 0.755 | 96% | 23 of 24 | 1.06 |

TABLE 6-continued

Breast Cancer Biomarker Validation. Thresholds indicate the optimal average dCt value for distinction between tumor and non-tumor tissues.

| Feature ID | Locus Number | BREAST TUMOR VS. NORMAL BREAST | | | | | BREAST TUMOR VS. NORMAL BLOOD | | |
|---|---|---|---|---|---|---|---|---|---|
| | | Sensitivity | Pos. of Total | Specificity | Neg. of Total | Threshold | Specificity | Neg. of Total | Threshold |
| ha1p__81674 | 4 | 70% | 69 of 99 | 92% | 86 of 93 | 1.11 | 95% | 18 of 19 | 0.935 |
| ha1p__74707 | 34 | 69% | 69 of 100 | 82% | 84 of 103 | 0.615 | 87% | 20 of 23 | 0.63 |
| ha1g__02416 | 15 | 65% | 66 of 102 | 97% | 101 of 104 | 0.705 | 100% | 25 of 25 | 0.535 |
| ha1p__70459 | 26 | 63% | 64 of 101 | 97% | 101 of 104 | 0.525 | 100% | 25 of 25 | 0.57 |
| ha1p__69407 | 21 | 63% | 64 of 101 | 93% | 96 of 103 | 0.5 | 71% | 17 of 24 | 0.55 |
| ha1p__110107 | 17 | 60% | 61 of 101 | 98% | 102 of 104 | 0.51 | 96% | 23 of 24 | 0.51 |
| ha1p__36172 | 25 | 58% | 59 of 102 | 100% | 104 of 104 | 0.515 | 100% | 23 of 23 | 0.515 |
| ha1p__67625 | 30 | 56% | 51 of 91 | 97% | 96 of 99 | 0.545 | 95% | 20 of 21 | 0.545 |
| ha1p__104423 | 12 | 53% | 52 of 98 | 97% | 94 of 97 | 0.61 | 96% | 23 of 24 | 0.855 |
| ha1p__05406 | 22 | 48% | 49 of 103 | 97% | 100 of 103 | 0.51 | 100% | 24 of 24 | 0.51 |
| ha1p__89799 | 18 | 42% | 42 of 101 | 99% | 98 of 99 | 0.545 | 100% | 24 of 24 | 0.71 |
| ha1p__80771 | 20 | 38% | 39 of 103 | 97% | 101 of 104 | 0.5 | 100% | 25 of 25 | 0.72 |
| ha1g__02345 | 24 | 34% | 35 of 102 | 97% | 100 of 103 | 0.535 | 100% | 22 of 22 | 0.535 |

Example 12

In-Depth Analysis of DNA Methylation by Bisulfite Sequencing

To provide an in-depth analysis of DNA methylation states relative to the qPCR-based measurements of methylated DNA load between different tissue types, we selected four loci (Locus Number 2, 3, 4 and 12) for extensive bisulfite sequencing analysis (FIG. 12). For each locus, analyzed regions overlapped those amplified in the qPCR assay. Primer pairs were designed to flank, but not include CpG dinucleotides. For analysis of each locus, we selected tumor samples that scored as intermediately to densely methylated and normal breast samples that scored as sparsely methylated. In addition, we selected three histology normal tumor-adjacent tissue samples. Loci were amplified from bisulfite-modified genomic DNA with primers that included patient-specific sequence tags to identify the tissue sample, and amplicons were pooled and sequenced. The average number of molecules analyzed for each locus in each sample was 587. To provide a general measurement of local DNA methylation density at each locus, the total number of CpG sites sequenced as C (methylated) was divided by the total of number of CpG sites sequenced for each individual sample. This percent methylated CpG value was then plotted against the qPCR methylation measurement for the same tissue sample (FIG. 12A, C, E, G). Methylation load values obtained by bisulfite sequencing and by qPCR displayed a strong correlation for Locus number 2, 12 and 3($R^2$=0.76, 0.87 and 0.78, respectively). While tumor samples displayed higher DNA methylation load at Locus number 4 than normal breast and adjacent histology normal breast samples, the non-tumor tissues displayed higher baseline DNA methylation densities than at the other loci (FIG. 12E). Next, the average occurrence of DNA methylation per CpG site in each tissue type was calculated (FIG. 12B, D, F, H). In general, tumor samples displayed higher variability in methylation per CpG site than non-tumor (i.e., normal) samples (indicated by higher standard deviations for the average percent methylated CpGs). At each locus, the DNA methylation pattern was significantly hypermethylated relative to non-tumor samples. Furthermore, analysis of DNA methylation per CpG site provided an explanation for the higher baseline DNA methylation densities detected at the Locus Number 4 (FIG. 12F). In non-tumor samples, methylation densities at the first three CpG dinucleotides of the analyzed region were greater than 50%, while methylation of the following four CpG dinucleotides fell to lower densities more consistent with the baseline levels of methylation at the other analyzed loci. Interestingly, tumor samples displayed the same general methylation density pattern, but with significantly higher methylation density per CpG across the entire analyzed region. Together, these results confirm the hypermethylated state of these loci in breast cancer and provide an extensive validation of the accuracy of the qPCR-based method used to screen for DNA methylation changes in this study.

Example 13

DNA Hypermethylation is Associated with Decreased Transcription

To address the association between hypermethylation and transcription repression, we performed RT-PCR analyses of Locus Numbers 2, 4 and 12 (FIG. 13). Four breast infiltrating ductal carcinoma samples (>90% neoplastic cellularity) were analyzed for both DNA methylation and transcription of the three genes. DNA methylation was analyzed using the qPCR-based assays described above. For gene expression analyses, RT-PCR was performed using gene-specific primer pairs designed to flank intronic sequences so that the contribution of contaminating genomic DNA could be excluded. Analysis of GAPDH expression was performed as an internal control. Serial dilutions of first-strand cDNA preparations from tumor samples and a normal breast tissue sample were used as templates for PCR. As shown in FIG. 13, expression of Locus Number 2 transcript (GHSR) was undetectable in all four tumor samples, while expression was detected at 1:10 dilution of the normal breast cDNA. Consistent with the high sensitivity of hypermethylation at the GHSR locus (90%), all tumor samples demonstrated intermediate to dense DNA methylation at this locus. Likewise, all tumor samples displayed reduced expression of Locus Number 12 (NFX1) relative to normal breast tissue. Expression was undetectable in three of four tumor samples, whereas expression was detected in one tumor using undiluted cDNA as template. In normal breast tissue, expression was detected at 1:10 dilution of the cDNA. Interestingly, the tumor sample in which NFX1 expression was detected was scored as sparsely methylated by the qPCR-based assay. Methylation of the analyzed region of Locus Number 4 (MGA) was detected in all four tumors.

However, reduced expression of MGA relative to normal breast was demonstrated in two of the four tumor samples.

Example 14

Detection of Tumor-Specific DNA Methylation in Fine Needle Aspirate Specimens

A common procedure to biopsy suspect masses in the breast is to perform fine needle aspiratation (FNA) of the tissue. The procedure involves removal of a small amount of fluid and cellular material from the suspect mass using a fine gauge needle. In addition, random periareolar fine needle aspiration (RPFNA) can be used to sample breast tissue in asymptomatic women to assess the risk of breast cancer development. Both approaches typically involve a cytological based diagnosis. Therefore, applying molecular tests to specimens obtained by these approaches promises to offer significantly improved clinical sensitivity and specificity relative to the current practice. To assess the ability to detect breast tumor-specific DNA methylation of the claimed differentially methylated loci, eight loci with varying frequency of differential DNA methylation in primary breast tissue were analyzed in a panel of 7 FNA specimens taken from women with confirmed infiltrating ductal breast carcinoma. DNA methylation was measured as described in Example 3. These included Locus Number 1, 2, 3, 4, 12, 37, 38 and 43. In FIG. 14, the percent sensitivity for each locus as listed in Tables 3A and 3B (i.e. the percentage of tumors that report and average dCt≧1.0) is plotted against the percentage of unmatched FNA samples that report and average dCt≧1.0. The frequency of DNA methylation detection (i.e. samples that report an average dCt≧1.0) is very similar regardless of whether primary tumor samples or unmatched FNA specimens from confirmed breast cancer patients were analyzed ($R^2$=0.7415, slope=0.817). These results suggest that the DNA methylation biomarkers described herein can be detected in a sample type relevant to molecular diagnostics of breast cancer.

Example 15

Analysis of DNA Methylation in Various Cancer Types

To address the applicability of the claimed DNA methylation biomarkers to cancer types other than breast cancer, all 53 claimed biomarkers were analyzed in panels of lung, renal, liver, ovarian, head and neck, thyroid, bladder, cervical, colon, endometrial, esophageal and prostate tumors. Adjacent histology normal tissues were analyzed as controls. In addition, melanoma tumors were analyzed, although no adjacent normal tissues were available. The number of samples analyzed for each cancer type is provided in Table 7. DNA methylation was measured as described in Example 3. For each locus and each cancer type, the sensitivity and specificity for discriminating between tumor and adjacent normal tissue are reported in Tables 8-20. For melanoma tumors (Table 20), only sensitivity (the frequency of DNA methylation detection (i.e. samples that report an average dCt≧1.0)) is reported due to the unavailability of adjacent normal tissues. For each locus, the optimal threshold for discriminating between tumor and adjacent normal tissue was calculated following ROC curve analyses as described in Example 11. These data demonstrate that particular biomarker loci are applicable to cancer types other than breast cancer.

TABLE 7

Number of Tumor and Adjacent Normal tissues tested for methylation of the 53 biomarker loci.

| Cancer Type | Tumor | Adjacent Normal |
|---|---|---|
| Lung | 10 | 10 |
| Renal | 10 | 10 |
| Liver | 9 | 9 |
| Ovarian | 8 | 8 |
| Head and Neck | 9 | 5 |
| Thyroid | 9 | 9 |
| Bladder | 9 | 9 |
| Cervical | 10 | 9 |
| Colon | 8 | 8 |
| Endometrial | 14 | 9 |
| Esophageal | 9 | 10 |
| Prostate | 9 | 9 |
| Melanoma | 7 | 0 |

TABLE 8

Sensitivity and Specificity of differentially methylated loci in lung tumors relative to adjacent histological normal lung tissue.

| Feature ID | Locus Number | Threshold | Sensitivity | Pos. of Total | Specificity | Neg. of Total |
|---|---|---|---|---|---|---|
| ha1p_105474 | 33 | 1.98 | 80% | 8 of 10 | 100% | 10 of 10 |
| ha1p_39189 | 2 | 1.17 | 70% | 7 of 10 | 100% | 10 of 10 |
| ha1p_23178 | 9 | 3.015 | 70% | 7 of 10 | 100% | 10 of 10 |
| ha1p_89099 | 28 | 1.38 | 70% | 7 of 10 | 100% | 10 of 10 |
| ha1g_00644 | 3 | 1.445 | 60% | 6 of 10 | 100% | 10 of 10 |
| ha1p_40164 | 8 | 1.96 | 60% | 3 of 5 | 100% | 5 of 5 |
| ha1p_81149 | 5 | 2.37 | 50% | 5 of 10 | 100% | 10 of 10 |
| ha1p_08347 | 14 | 1.67 | 50% | 4 of 8 | 100% | 7 of 7 |
| ha1p_12075 | 46 | 2.33 | 43% | 3 of 7 | 100% | 7 of 7 |
| ha1p_40959 | 11 | 2.435 | 40% | 4 of 10 | 100% | 10 of 10 |
| ha1p_36172 | 25 | 0.835 | 40% | 4 of 10 | 100% | 10 of 10 |
| ha1p_56412 | 44 | 3.86 | 40% | 4 of 10 | 100% | 9 of 9 |
| ha1g_03099 | 29 | 0.635 | 30% | 3 of 10 | 100% | 10 of 10 |
| ha1p_67625 | 30 | 0.965 | 30% | 3 of 10 | 100% | 9 of 9 |
| ha1p_93325 | 35 | 2.93 | 30% | 3 of 10 | 100% | 10 of 10 |
| ha1p_103824 | 40 | 0.765 | 30% | 3 of 10 | 100% | 10 of 10 |
| ha1p_69407 | 21 | 2.77 | 29% | 2 of 7 | 100% | 6 of 6 |
| ha1p_81674 | 4 | 2.165 | 25% | 2 of 8 | 100% | 7 of 7 |
| ha1p_80771 | 20 | 1.05 | 20% | 2 of 10 | 100% | 9 of 9 |

TABLE 8-continued

Sensitivity and Specificity of differentially methylated loci in lung tumors relative to adjacent histological normal lung tissue.

| Feature ID | Locus Number | Threshold | Sensitivity | Pos. of Total | Specificity | Neg. of Total |
|---|---|---|---|---|---|---|
| ha1g__00218 | 31 | 0.71 | 10% | 1 of 10 | 100% | 10 of 10 |
| ha1p__45173 | 19 | 1.66 | 100% | 10 of 10 | 90% | 9 of 10 |
| ha1p__83841 | 6 | 1.54 | 90% | 9 of 10 | 90% | 9 of 10 |
| ha1p__46057 | 10 | 0.9 | 90% | 9 of 10 | 90% | 9 of 10 |
| ha1p__105937 | 27 | 1.375 | 80% | 8 of 10 | 90% | 9 of 10 |
| ha1p__69214 | 38 | 3.735 | 78% | 7 of 9 | 90% | 9 of 10 |
| ha1p__18292 | 45 | 2.06 | 60% | 6 of 10 | 90% | 9 of 10 |
| ha1p__12535 | 32 | 2.05 | 50% | 5 of 10 | 90% | 9 of 10 |
| ha1p__67002 | 51 | 2.025 | 50% | 5 of 10 | 90% | 9 of 10 |
| ha1p__87540 | 16 | 0.98 | 80% | 8 of 10 | 89% | 8 of 9 |
| ha1p__108445 | 41 | 1.9 | 40% | 4 of 10 | 89% | 8 of 9 |
| ha1p__88517 | 39 | 1.38 | 50% | 3 of 6 | 83% | 5 of 6 |
| ha1p__29531 | 48 | 1.01 | 90% | 9 of 10 | 80% | 8 of 10 |
| ha1p__58853 | 49 | 1.315 | 80% | 8 of 10 | 80% | 8 of 10 |
| ha1p__103872 | 43 | 2.96 | 70% | 7 of 10 | 80% | 8 of 10 |
| ha1p__89799 | 18 | 0.5 | 63% | 5 of 8 | 80% | 8 of 10 |
| ha1p__104423 | 12 | 0.83 | 40% | 4 of 10 | 80% | 8 of 10 |
| ha1p__80287 | 23 | 0.82 | 40% | 4 of 10 | 80% | 8 of 10 |
| ha1p__74707 | 34 | 0.76 | 78% | 7 of 9 | 78% | 7 of 9 |
| ha1p__38705 | 7 | 0.62 | 63% | 5 of 8 | 78% | 7 of 9 |
| ha1g__00681 | 1 | 1.965 | 56% | 5 of 9 | 78% | 7 of 9 |
| ha1p__35052 | 50 | 1.6 | 70% | 7 of 10 | 70% | 7 of 10 |
| ha1p__45580 | 52 | 3.1 | 70% | 7 of 10 | 70% | 7 of 10 |
| ha1g__02345 | 24 | 0.51 | 67% | 6 of 9 | 67% | 6 of 9 |
| ha1p__05406 | 22 | 0.615 | 71% | 5 of 7 | 63% | 5 of 8 |
| ha1p__22519 | 47 | 1.6 | 100% | 10 of 10 | 60% | 6 of 10 |
| ha1g__02416 | 15 | 0.58 | 90% | 9 of 10 | 60% | 6 of 10 |
| ha1p__101161 | 36 | 0.885 | 80% | 8 of 10 | 60% | 6 of 10 |
| ha1g__00847 | 13 | 0.53 | 63% | 5 of 8 | 60% | 6 of 10 |
| ha1g__02210 | 42 | 0.605 | 60% | 6 of 10 | 60% | 6 of 10 |
| ha1p__70459 | 26 | 0.54 | 100% | 6 of 6 | 56% | 5 of 9 |
| ha1p__12646 | 53 | 5.455 | 78% | 7 of 9 | 56% | 5 of 9 |
| ha1p__101251 | 37 | 1.34 | 100% | 10 of 10 | 40% | 4 of 10 |
| ha1p__110107 | 17 | 0.55 | 86% | 6 of 7 | 40% | 4 of 10 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 9

Sensitivity and Specificity of differentially methylated loci in renal tumors relative to adjacent histological normal kidney tissue.

| Feature ID | Locus Number | Threshold | Sensitivity | Pos. of Total | Specificity | Neg. of Total |
|---|---|---|---|---|---|---|
| ha1p__29531 | 48 | 0.68 | 80% | 8 of 10 | 100% | 10 of 10 |
| ha1p__23178 | 9 | 1.52 | 70% | 7 of 10 | 100% | 10 of 10 |
| ha1p__69407 | 21 | 1.255 | 70% | 7 of 10 | 100% | 10 of 10 |
| ha1p__22519 | 47 | 1.68 | 67% | 6 of 9 | 100% | 10 of 10 |
| ha1g__00644 | 3 | 1.135 | 60% | 6 of 10 | 100% | 10 of 10 |
| ha1p__83841 | 6 | 1.2 | 60% | 6 of 10 | 100% | 9 of 9 |
| ha1p__80771 | 20 | 0.535 | 60% | 6 of 10 | 100% | 10 of 10 |
| ha1p__103872 | 43 | 3.25 | 60% | 6 of 10 | 100% | 10 of 10 |
| ha1p__89099 | 28 | 0.935 | 56% | 5 of 9 | 100% | 9 of 9 |
| ha1p__74707 | 34 | 1.6 | 56% | 5 of 9 | 100% | 10 of 10 |
| ha1g__02416 | 15 | 0.56 | 50% | 5 of 10 | 100% | 9 of 9 |
| ha1p__45173 | 19 | 0.675 | 50% | 5 of 10 | 100% | 10 of 10 |
| ha1p__105937 | 27 | 0.99 | 50% | 5 of 10 | 100% | 10 of 10 |
| ha1p__93325 | 35 | 1.155 | 50% | 5 of 10 | 100% | 10 of 10 |
| ha1p__108445 | 41 | 1.025 | 50% | 5 of 10 | 100% | 10 of 10 |
| ha1p__103824 | 40 | 0.82 | 44% | 4 of 9 | 100% | 10 of 10 |
| ha1p__56412 | 44 | 1.84 | 44% | 4 of 9 | 100% | 10 of 10 |
| ha1p__38705 | 7 | 1.28 | 40% | 4 of 10 | 100% | 9 of 9 |
| ha1p__70459 | 26 | 0.74 | 40% | 4 of 10 | 100% | 9 of 9 |
| ha1p__36172 | 25 | 0.92 | 33% | 3 of 9 | 100% | 10 of 10 |
| ha1g__02345 | 24 | 0.565 | 30% | 3 of 10 | 100% | 10 of 10 |
| ha1p__80287 | 23 | 1.135 | 22% | 2 of 9 | 100% | 10 of 10 |
| ha1g__03099 | 29 | 0.555 | 20% | 2 of 10 | 100% | 10 of 10 |
| ha1p__58853 | 49 | 1.195 | 11% | 1 of 9 | 100% | 10 of 10 |

TABLE 9-continued

Sensitivity and Specificity of differentially methylated loci in renal tumors relative to adjacent histological normal kidney tissue.

| Feature ID | Locus Number | Threshold | Sensitivity | Pos. of Total | Specificity | Neg. of Total |
| --- | --- | --- | --- | --- | --- | --- |
| ha1p__08347 | 14 | 2.65 | 100% | 9 of 9 | 90% | 9 of 10 |
| ha1p__46057 | 10 | 1.325 | 80% | 8 of 10 | 90% | 9 of 10 |
| ha1g__00681 | 1 | 1.905 | 60% | 6 of 10 | 90% | 9 of 10 |
| ha1p__18292 | 45 | 1.09 | 60% | 6 of 10 | 90% | 9 of 10 |
| ha1p__87540 | 16 | 0.925 | 40% | 4 of 10 | 90% | 9 of 10 |
| ha1p__89799 | 18 | 0.605 | 40% | 4 of 10 | 90% | 9 of 10 |
| ha1p__05406 | 22 | 0.52 | 40% | 4 of 10 | 90% | 9 of 10 |
| ha1g__00218 | 31 | 0.505 | 20% | 2 of 10 | 90% | 9 of 10 |
| ha1p__39189 | 2 | 1.03 | 80% | 8 of 10 | 89% | 8 of 9 |
| ha1p__67625 | 30 | 0.79 | 60% | 6 of 10 | 89% | 8 of 9 |
| ha1p__88517 | 39 | 1.98 | 50% | 5 of 10 | 89% | 8 of 9 |
| ha1p__35052 | 50 | 1.495 | 100% | 10 of 10 | 80% | 8 of 10 |
| ha1p__40164 | 8 | 0.825 | 90% | 9 of 10 | 80% | 8 of 10 |
| ha1p__67002 | 51 | 1.565 | 90% | 9 of 10 | 80% | 8 of 10 |
| ha1p__40959 | 11 | 0.88 | 80% | 8 of 10 | 80% | 8 of 10 |
| ha1p__12535 | 32 | 0.93 | 70% | 7 of 10 | 80% | 8 of 10 |
| ha1p__12646 | 53 | 4.23 | 60% | 6 of 10 | 80% | 8 of 10 |
| ha1p__110107 | 17 | 0.53 | 56% | 5 of 9 | 80% | 8 of 10 |
| ha1p__101161 | 36 | 0.93 | 40% | 4 of 10 | 80% | 8 of 10 |
| ha1g__02210 | 42 | 0.52 | 33% | 3 of 9 | 80% | 8 of 10 |
| ha1g__00847 | 13 | 0.7 | 56% | 5 of 9 | 78% | 7 of 9 |
| ha1p__81674 | 4 | 1.365 | 89% | 8 of 9 | 67% | 6 of 9 |
| ha1p__12075 | 46 | 1.66 | 89% | 8 of 9 | 56% | 5 of 9 |
| ha1p__45580 | 52 | 2.1 | 100% | 10 of 10 | 50% | 5 of 10 |
| ha1p__81149 | 5 | 0.875 | 90% | 9 of 10 | 50% | 5 of 10 |
| ha1p__105474 | 33 | 1.035 | 70% | 7 of 10 | 50% | 5 of 10 |
| ha1p__101251 | 37 | 1 | 70% | 7 of 10 | 50% | 5 of 10 |
| ha1p__104423 | 12 | 0.68 | 80% | 8 of 10 | 40% | 4 of 10 |
| ha1p__69214 | 38 | 1.085 | 100% | 10 of 10 | 33% | 3 of 9 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 10

Sensitivity and Specificity of differentially methylated loci in liver tumors relative to adjacent histological normal liver tissue.

| Feature ID | Locus Number | Threshold | Sensitivity | Pos. of Total | Specificity | Neg. of Total |
| --- | --- | --- | --- | --- | --- | --- |
| ha1p__89799 | 18 | 3.01 | 67% | 6 of 9 | 100% | 9 of 9 |
| ha1p__81674 | 4 | 1.66 | 56% | 5 of 9 | 100% | 9 of 9 |
| ha1p__56412 | 44 | 1.94 | 56% | 5 of 9 | 100% | 9 of 9 |
| ha1p__67002 | 51 | 1.825 | 50% | 4 of 8 | 100% | 9 of 9 |
| ha1p__81149 | 5 | 1.39 | 38% | 3 of 8 | 100% | 9 of 9 |
| ha1p__83841 | 6 | 1.305 | 38% | 3 of 8 | 100% | 9 of 9 |
| ha1p__74707 | 34 | 1.335 | 38% | 3 of 8 | 100% | 8 of 8 |
| ha1p__80771 | 20 | 0.87 | 33% | 3 of 9 | 100% | 9 of 9 |
| ha1p__70459 | 26 | 2.785 | 33% | 3 of 9 | 100% | 9 of 9 |
| ha1p__89099 | 28 | 2.715 | 33% | 3 of 9 | 100% | 8 of 8 |
| ha1p__12535 | 32 | 2.1 | 33% | 3 of 9 | 100% | 9 of 9 |
| ha1p__39189 | 2 | 4.805 | 25% | 2 of 8 | 100% | 9 of 9 |
| ha1g__00218 | 31 | 0.775 | 22% | 2 of 9 | 100% | 9 of 9 |
| ha1p__12646 | 53 | 3.49 | 17% | 1 of 6 | 100% | 7 of 7 |
| ha1g__00847 | 13 | 0.86 | 78% | 7 of 9 | 89% | 8 of 9 |
| ha1p__05406 | 22 | 1.465 | 78% | 7 of 9 | 89% | 8 of 9 |
| ha1p__105474 | 33 | 1.55 | 78% | 7 of 9 | 89% | 8 of 9 |
| ha1p__69407 | 21 | 3.06 | 67% | 6 of 9 | 89% | 8 of 9 |
| ha1g__02416 | 15 | 0.94 | 50% | 4 of 8 | 89% | 8 of 9 |
| ha1p__40164 | 8 | 1.91 | 44% | 4 of 9 | 89% | 8 of 9 |
| ha1p__101251 | 37 | 1.195 | 44% | 4 of 9 | 89% | 8 of 9 |
| ha1p__110107 | 17 | 1.955 | 38% | 3 of 8 | 89% | 8 of 9 |
| ha1p__105937 | 27 | 1.585 | 38% | 3 of 8 | 89% | 8 of 9 |
| ha1p__18292 | 45 | 2.51 | 63% | 5 of 8 | 88% | 7 of 8 |
| ha1p__35052 | 50 | 6 | 89% | 8 of 9 | 78% | 7 of 9 |
| ha1p__67625 | 30 | 1.97 | 83% | 5 of 6 | 78% | 7 of 9 |
| ha1p__23178 | 9 | 2.655 | 78% | 7 of 9 | 78% | 7 of 9 |
| ha1p__93325 | 35 | 4.85 | 78% | 7 of 9 | 78% | 7 of 9 |
| ha1g__00681 | 1 | 0.615 | 75% | 6 of 8 | 78% | 7 of 9 |

TABLE 10-continued

Sensitivity and Specificity of differentially methylated loci in liver tumors relative to adjacent histological normal liver tissue.

| Feature ID | Locus Number | Threshold | Sensitivity | Pos. of Total | Specificity | Neg. of Total |
|---|---|---|---|---|---|---|
| ha1p__22519 | 47 | 1.975 | 71% | 5 of 7 | 78% | 7 of 9 |
| ha1p__38705 | 7 | 2.51 | 67% | 6 of 9 | 78% | 7 of 9 |
| ha1p__08347 | 14 | 1.08 | 67% | 6 of 9 | 78% | 7 of 9 |
| ha1p__101161 | 36 | 1.07 | 67% | 6 of 9 | 78% | 7 of 9 |
| ha1p__69214 | 38 | 3.31 | 67% | 6 of 9 | 78% | 7 of 9 |
| ha1g__02345 | 24 | 0.695 | 63% | 5 of 8 | 78% | 7 of 9 |
| ha1p__87540 | 16 | 1.45 | 56% | 5 of 9 | 78% | 7 of 9 |
| ha1p__45173 | 19 | 4.58 | 56% | 5 of 9 | 78% | 7 of 9 |
| ha1p__88517 | 39 | 1.86 | 44% | 4 of 9 | 78% | 7 of 9 |
| ha1g__00644 | 3 | 0.545 | 22% | 2 of 9 | 78% | 7 of 9 |
| ha1p__103824 | 40 | 1.045 | 75% | 6 of 8 | 75% | 6 of 8 |
| ha1p__108445 | 41 | 1.595 | 67% | 4 of 6 | 75% | 6 of 8 |
| ha1p__45580 | 52 | 2.055 | 63% | 5 of 8 | 75% | 6 of 8 |
| ha1p__80287 | 23 | 3.75 | 83% | 5 of 6 | 71% | 5 of 7 |
| ha1p__46057 | 10 | 1.685 | 67% | 6 of 9 | 67% | 6 of 9 |
| ha1p__36172 | 25 | 2.95 | 67% | 6 of 9 | 67% | 6 of 9 |
| ha1g__02210 | 42 | 0.52 | 67% | 6 of 9 | 67% | 6 of 9 |
| ha1p__12075 | 46 | 1.725 | 67% | 6 of 9 | 67% | 6 of 9 |
| ha1p__29531 | 48 | 3.385 | 67% | 6 of 9 | 67% | 6 of 9 |
| ha1p__58853 | 49 | 1.905 | 63% | 5 of 8 | 67% | 6 of 9 |
| ha1p__103872 | 43 | 1.02 | 56% | 5 of 9 | 67% | 6 of 9 |
| ha1g__03099 | 29 | 0.68 | 67% | 6 of 9 | 56% | 5 of 9 |
| ha1p__104423 | 12 | 0.845 | 100% | 7 of 7 | 43% | 3 of 7 |
| ha1p__40959 | 11 | 3.51 | 75% | 6 of 8 | 33% | 3 of 9 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 11

Sensitivity and Specificity of differentially methylated loci in ovarian tumors relative to adjacent histological normal ovary tissue.

| Feature ID | Locus Number | Threshold | Sensitivity | Pos. of Total | Specificity | Neg. of Total |
|---|---|---|---|---|---|---|
| ha1g__00644 | 3 | 0.535 | 100% | 7 of 7 | 100% | 8 of 8 |
| ha1p__46057 | 10 | 0.6 | 100% | 8 of 8 | 100% | 8 of 8 |
| ha1p__81674 | 4 | 1.47 | 88% | 7 of 8 | 100% | 8 of 8 |
| ha1p__81149 | 5 | 1.335 | 88% | 7 of 8 | 100% | 8 of 8 |
| ha1g__00847 | 13 | 0.69 | 88% | 7 of 8 | 100% | 8 of 8 |
| ha1p__12535 | 32 | 0.695 | 88% | 7 of 8 | 100% | 8 of 8 |
| ha1p__69214 | 38 | 1.06 | 88% | 7 of 8 | 100% | 7 of 7 |
| ha1p__22519 | 47 | 1.395 | 88% | 7 of 8 | 100% | 8 of 8 |
| ha1p__12646 | 53 | 0.88 | 88% | 7 of 8 | 100% | 8 of 8 |
| ha1p__38705 | 7 | 0.65 | 80% | 4 of 5 | 100% | 5 of 5 |
| ha1g__00681 | 1 | 1.01 | 75% | 6 of 8 | 100% | 8 of 8 |
| ha1p__39189 | 2 | 0.97 | 75% | 6 of 8 | 100% | 8 of 8 |
| ha1p__83841 | 6 | 0.83 | 75% | 6 of 8 | 100% | 7 of 7 |
| ha1p__23178 | 9 | 0.655 | 75% | 6 of 8 | 100% | 8 of 8 |
| ha1p__08347 | 14 | 1.165 | 75% | 6 of 8 | 100% | 8 of 8 |
| ha1p__45173 | 19 | 0.74 | 75% | 6 of 8 | 100% | 8 of 8 |
| ha1p__105474 | 33 | 1.115 | 75% | 6 of 8 | 100% | 8 of 8 |
| ha1p__101161 | 36 | 0.53 | 75% | 6 of 8 | 100% | 8 of 8 |
| ha1p__103872 | 43 | 0.77 | 75% | 6 of 8 | 100% | 8 of 8 |
| ha1p__104423 | 12 | 0.54 | 63% | 5 of 8 | 100% | 8 of 8 |
| ha1g__02416 | 15 | 0.665 | 63% | 5 of 8 | 100% | 8 of 8 |
| ha1p__05406 | 22 | 0.92 | 63% | 5 of 8 | 100% | 8 of 8 |
| ha1p__89099 | 28 | 0.575 | 63% | 5 of 8 | 100% | 8 of 8 |
| ha1p__103824 | 40 | 0.635 | 63% | 5 of 8 | 100% | 8 of 8 |
| ha1p__12075 | 46 | 0.87 | 63% | 5 of 8 | 100% | 8 of 8 |
| ha1p__18292 | 45 | 1.335 | 57% | 4 of 7 | 100% | 8 of 8 |
| ha1p__110107 | 17 | 0.7 | 50% | 3 of 6 | 100% | 8 of 8 |
| ha1p__67625 | 30 | 1.105 | 50% | 4 of 8 | 100% | 8 of 8 |
| ha1p__93325 | 35 | 0.505 | 50% | 4 of 8 | 100% | 8 of 8 |
| ha1p__56412 | 44 | 1.63 | 50% | 4 of 8 | 100% | 7 of 7 |
| ha1p__58853 | 49 | 1.215 | 50% | 4 of 8 | 100% | 8 of 8 |
| ha1p__45580 | 52 | 1.6 | 50% | 4 of 8 | 100% | 8 of 8 |
| ha1p__87540 | 16 | 0.715 | 43% | 3 of 7 | 100% | 8 of 8 |
| ha1p__89799 | 18 | 0.865 | 43% | 3 of 7 | 100% | 7 of 7 |

TABLE 11-continued

Sensitivity and Specificity of differentially methylated loci in ovarian tumors relative to adjacent histological normal ovary tissue.

| Feature ID | Locus Number | Threshold | Sensitivity | Pos. of Total | Specificity | Neg. of Total |
|---|---|---|---|---|---|---|
| ha1p__36172 | 25 | 1.235 | 38% | 3 of 8 | 100% | 8 of 8 |
| ha1p__105937 | 27 | 0.81 | 38% | 3 of 8 | 100% | 8 of 8 |
| ha1g__03099 | 29 | 0.6 | 38% | 3 of 8 | 100% | 8 of 8 |
| ha1p__74707 | 34 | 0.665 | 38% | 3 of 8 | 100% | 8 of 8 |
| ha1p__80771 | 20 | 0.505 | 25% | 2 of 8 | 100% | 8 of 8 |
| ha1g__00218 | 31 | 0.59 | 25% | 2 of 8 | 100% | 8 of 8 |
| ha1p__80287 | 23 | 0.675 | 13% | 1 of 8 | 100% | 8 of 8 |
| ha1p__40959 | 11 | 0.515 | 88% | 7 of 8 | 88% | 7 of 8 |
| ha1p__69407 | 21 | 1.335 | 75% | 6 of 8 | 88% | 7 of 8 |
| ha1p__29531 | 48 | 0.865 | 75% | 6 of 8 | 88% | 7 of 8 |
| ha1p__40164 | 8 | 0.625 | 63% | 5 of 8 | 88% | 7 of 8 |
| ha1p__108445 | 41 | 0.56 | 63% | 5 of 8 | 88% | 7 of 8 |
| ha1p__70459 | 26 | 0.605 | 50% | 4 of 8 | 88% | 7 of 8 |
| ha1p__35052 | 50 | 1.63 | 43% | 3 of 7 | 88% | 7 of 8 |
| ha1g__02210 | 42 | 0.715 | 38% | 3 of 8 | 88% | 7 of 8 |
| ha1g__02345 | 24 | 0.525 | 38% | 3 of 8 | 86% | 6 of 7 |
| ha1p__101251 | 37 | 1.045 | 88% | 7 of 8 | 75% | 6 of 8 |
| ha1p__67002 | 51 | 1.175 | 63% | 5 of 8 | 75% | 6 of 8 |
| ha1p__88517 | 39 | 0.59 | 43% | 3 of 7 | 75% | 6 of 8 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 12

Sensitivity and Specificity of differentially methylated loci in head and neck tumors relative to adjacent histological normal head and neck tissue.

| Feature ID | Locus Number | Threshold | Sensitivity | Pos. of Total | Specificity | Neg. of Total |
|---|---|---|---|---|---|---|
| ha1p__108445 | 41 | 2.695 | 89% | 8 of 9 | 100% | 5 of 5 |
| ha1p__39189 | 2 | 1.035 | 78% | 7 of 9 | 100% | 5 of 5 |
| ha1p__45173 | 19 | 1.195 | 78% | 7 of 9 | 100% | 5 of 5 |
| ha1p__08347 | 14 | 0.94 | 67% | 6 of 9 | 100% | 5 of 5 |
| ha1p__105474 | 33 | 2.15 | 67% | 6 of 9 | 100% | 5 of 5 |
| ha1p__12075 | 46 | 0.795 | 67% | 4 of 6 | 100% | 4 of 4 |
| ha1p__12646 | 53 | 2.28 | 67% | 6 of 9 | 100% | 5 of 5 |
| ha1p__67625 | 30 | 0.505 | 63% | 5 of 8 | 100% | 5 of 5 |
| ha1p__35052 | 50 | 1.575 | 63% | 5 of 8 | 100% | 5 of 5 |
| ha1p__23178 | 9 | 1.715 | 56% | 5 of 9 | 100% | 5 of 5 |
| ha1p__74707 | 34 | 0.76 | 56% | 5 of 9 | 100% | 5 of 5 |
| ha1p__103872 | 43 | 2.535 | 56% | 5 of 9 | 100% | 5 of 5 |
| ha1p__18292 | 45 | 1.725 | 56% | 5 of 9 | 100% | 4 of 4 |
| ha1p__22519 | 47 | 2.27 | 56% | 5 of 9 | 100% | 5 of 5 |
| ha1p__83841 | 6 | 1.69 | 50% | 4 of 8 | 100% | 5 of 5 |
| ha1p__81149 | 5 | 2.98 | 44% | 4 of 9 | 100% | 5 of 5 |
| ha1p__93325 | 35 | 2.145 | 44% | 4 of 9 | 100% | 5 of 5 |
| ha1g__02210 | 42 | 1.11 | 38% | 3 of 8 | 100% | 5 of 5 |
| ha1p__58853 | 49 | 2.815 | 38% | 3 of 8 | 100% | 5 of 5 |
| ha1p__40959 | 11 | 1.42 | 33% | 3 of 9 | 100% | 5 of 5 |
| ha1p__05406 | 22 | 0.685 | 33% | 3 of 9 | 100% | 4 of 4 |
| ha1g__02345 | 24 | 0.54 | 33% | 3 of 9 | 100% | 5 of 5 |
| ha1p__29531 | 48 | 1.465 | 33% | 3 of 9 | 100% | 5 of 5 |
| ha1p__40164 | 8 | 1.63 | 22% | 2 of 9 | 100% | 5 of 5 |
| ha1p__110107 | 17 | 0.62 | 22% | 2 of 9 | 100% | 5 of 5 |
| ha1g__03099 | 29 | 0.68 | 22% | 2 of 9 | 100% | 4 of 4 |
| ha1p__80287 | 23 | 1.625 | 13% | 1 of 8 | 100% | 5 of 5 |
| ha1p__36172 | 25 | 0.73 | 11% | 1 of 9 | 100% | 5 of 5 |
| ha1p__56412 | 44 | 1.53 | 89% | 8 of 9 | 80% | 4 of 5 |
| ha1p__38705 | 7 | 0.855 | 75% | 6 of 8 | 80% | 4 of 5 |
| ha1p__105937 | 27 | 0.545 | 67% | 6 of 9 | 80% | 4 of 5 |
| ha1p__45580 | 52 | 1.315 | 67% | 6 of 9 | 80% | 4 of 5 |
| ha1p__87540 | 16 | 0.865 | 63% | 5 of 8 | 80% | 4 of 5 |
| ha1p__46057 | 10 | 1.18 | 56% | 5 of 9 | 80% | 4 of 5 |
| ha1p__104423 | 12 | 0.675 | 56% | 5 of 9 | 80% | 4 of 5 |
| ha1g__00847 | 13 | 1.125 | 56% | 5 of 9 | 80% | 4 of 5 |
| ha1p__70459 | 26 | 0.555 | 56% | 5 of 9 | 80% | 4 of 5 |
| ha1p__101161 | 36 | 0.765 | 44% | 4 of 9 | 80% | 4 of 5 |
| ha1p__67002 | 51 | 1.67 | 44% | 4 of 9 | 80% | 4 of 5 |

TABLE 12-continued

Sensitivity and Specificity of differentially methylated loci in head and neck tumors relative to adjacent histological normal head and neck tissue.

| Feature ID | Locus Number | Threshold | Sensitivity | Pos. of Total | Specificity | Neg. of Total |
|---|---|---|---|---|---|---|
| ha1g__02416 | 15 | 0.71 | 38% | 3 of 8 | 80% | 4 of 5 |
| ha1p__103824 | 40 | 0.525 | 33% | 3 of 9 | 80% | 4 of 5 |
| ha1p__89799 | 18 | 0.69 | 22% | 2 of 9 | 80% | 4 of 5 |
| ha1p__80771 | 20 | 0.86 | 11% | 1 of 9 | 80% | 4 of 5 |
| ha1p__81674 | 4 | 1.15 | 78% | 7 of 9 | 75% | 3 of 4 |
| ha1p__69407 | 21 | 1.315 | 67% | 6 of 9 | 75% | 3 of 4 |
| ha1p__89099 | 28 | 0.59 | 67% | 6 of 9 | 75% | 3 of 4 |
| ha1p__88517 | 39 | 0.985 | 86% | 6 of 7 | 67% | 2 of 3 |
| ha1g__00644 | 3 | 0.52 | 89% | 8 of 9 | 60% | 3 of 5 |
| ha1p__12535 | 32 | 0.95 | 78% | 7 of 9 | 60% | 3 of 5 |
| ha1p__69214 | 38 | 1.39 | 78% | 7 of 9 | 60% | 3 of 5 |
| ha1g__00681 | 1 | 1.045 | 89% | 8 of 9 | 40% | 2 of 5 |
| ha1p__101251 | 37 | 0.78 | 67% | 6 of 9 | 40% | 2 of 5 |
| ha1g__00218 | 31 | — | — | — | — | — |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 13

Sensitivity and Specificity of differentially methylated loci in thyroid tumors relative to adjacent histological normal thyroid tissue.

| Feature ID | Locus Number | Threshold | Sensitivity | Pos. of Total | Specificity | Neg. of Total |
|---|---|---|---|---|---|---|
| ha1g__02345 | 24 | 1.02 | 86% | 6 of 7 | 100% | 8 of 8 |
| ha1g__02210 | 42 | 0.745 | 80% | 4 of 5 | 100% | 5 of 5 |
| ha1p__05406 | 22 | 0.63 | 57% | 4 of 7 | 100% | 9 of 9 |
| ha1p__88517 | 39 | 1.815 | 50% | 4 of 8 | 100% | 5 of 5 |
| ha1p__56412 | 44 | 2.98 | 50% | 4 of 8 | 100% | 9 of 9 |
| ha1p__45580 | 52 | 3.76 | 44% | 4 of 9 | 100% | 9 of 9 |
| ha1g__02416 | 15 | 0.57 | 43% | 3 of 7 | 100% | 9 of 9 |
| ha1p__36172 | 25 | 0.515 | 38% | 3 of 8 | 100% | 9 of 9 |
| ha1g__00218 | 31 | 0.655 | 33% | 3 of 9 | 100% | 9 of 9 |
| ha1p__105937 | 27 | 1.055 | 22% | 2 of 9 | 100% | 9 of 9 |
| ha1g__00847 | 13 | 1.35 | 11% | 1 of 9 | 100% | 9 of 9 |
| ha1p__80771 | 20 | 1.305 | 11% | 1 of 9 | 100% | 9 of 9 |
| ha1p__80287 | 23 | 1.635 | 11% | 1 of 9 | 100% | 9 of 9 |
| ha1g__03099 | 29 | 0.76 | 11% | 1 of 9 | 100% | 9 of 9 |
| ha1p__108445 | 41 | 0.665 | 88% | 7 of 8 | 89% | 8 of 9 |
| ha1p__89099 | 28 | 1.25 | 78% | 7 of 9 | 89% | 8 of 9 |
| ha1p__29531 | 48 | 0.825 | 78% | 7 of 9 | 89% | 8 of 9 |
| ha1p__67002 | 51 | 1.65 | 71% | 5 of 7 | 89% | 8 of 9 |
| ha1p__39189 | 2 | 0.85 | 67% | 6 of 9 | 89% | 8 of 9 |
| ha1g__00644 | 3 | 0.62 | 67% | 6 of 9 | 89% | 8 of 9 |
| ha1p__22519 | 47 | 2.2 | 67% | 6 of 9 | 89% | 8 of 9 |
| ha1p__38705 | 7 | 1.575 | 63% | 5 of 8 | 89% | 8 of 9 |
| ha1p__89799 | 18 | 0.775 | 56% | 5 of 9 | 89% | 8 of 9 |
| ha1p__74707 | 34 | 0.62 | 56% | 5 of 9 | 89% | 8 of 9 |
| ha1p__93325 | 35 | 0.935 | 56% | 5 of 9 | 89% | 8 of 9 |
| ha1p__23178 | 9 | 0.77 | 44% | 4 of 9 | 89% | 8 of 9 |
| ha1p__110107 | 17 | 0.545 | 38% | 3 of 8 | 89% | 8 of 9 |
| ha1p__101161 | 36 | 1.11 | 33% | 3 of 9 | 89% | 8 of 9 |
| ha1p__103824 | 40 | 0.57 | 33% | 3 of 9 | 89% | 8 of 9 |
| ha1p__12646 | 53 | 4.84 | 33% | 3 of 9 | 89% | 8 of 9 |
| ha1p__81674 | 4 | 1.43 | 75% | 6 of 8 | 88% | 7 of 8 |
| ha1p__67625 | 30 | 0.57 | 50% | 3 of 6 | 88% | 7 of 8 |
| ha1p__69407 | 21 | 2.045 | 33% | 3 of 9 | 88% | 7 of 8 |
| ha1g__00681 | 1 | 0.93 | 89% | 8 of 9 | 78% | 7 of 9 |
| ha1p__83841 | 6 | 0.67 | 78% | 7 of 9 | 78% | 7 of 9 |
| ha1p__46057 | 10 | 1.735 | 78% | 7 of 9 | 78% | 7 of 9 |
| ha1p__40959 | 11 | 0.86 | 78% | 7 of 9 | 78% | 7 of 9 |
| ha1p__45173 | 19 | 0.96 | 78% | 7 of 9 | 78% | 7 of 9 |
| ha1p__101251 | 37 | 1.74 | 78% | 7 of 9 | 78% | 7 of 9 |
| ha1p__58853 | 49 | 0.97 | 78% | 7 of 9 | 78% | 7 of 9 |
| ha1p__103872 | 43 | 0.83 | 67% | 6 of 9 | 78% | 7 of 9 |
| ha1p__12535 | 32 | 1.325 | 89% | 8 of 9 | 67% | 6 of 9 |
| ha1p__12075 | 46 | 2.32 | 67% | 6 of 9 | 67% | 6 of 9 |
| ha1p__104423 | 12 | 1.07 | 56% | 5 of 9 | 67% | 6 of 9 |

TABLE 13-continued

Sensitivity and Specificity of differentially methylated loci in thyroid tumors relative to adjacent histological normal thyroid tissue.

| Feature ID | Locus Number | Threshold | Sensitivity | Pos. of Total | Specificity | Neg. of Total |
|---|---|---|---|---|---|---|
| ha1p__105474 | 33 | 2.395 | 56% | 5 of 9 | 67% | 6 of 9 |
| ha1p__08347 | 14 | 1.255 | 100% | 9 of 9 | 56% | 5 of 9 |
| ha1p__69214 | 38 | 2.315 | 100% | 9 of 9 | 56% | 5 of 9 |
| ha1p__18292 | 45 | 0.885 | 100% | 8 of 8 | 56% | 5 of 9 |
| ha1p__81149 | 5 | 1.305 | 89% | 8 of 9 | 56% | 5 of 9 |
| ha1p__40164 | 8 | 0.51 | 78% | 7 of 9 | 56% | 5 of 9 |
| ha1p__87540 | 16 | 1.105 | 67% | 6 of 9 | 56% | 5 of 9 |
| ha1p__35052 | 50 | 0.825 | 89% | 8 of 9 | 44% | 4 of 9 |
| ha1p__70459 | 26 | 0.58 | 88% | 7 of 8 | 43% | 3 of 7 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 14

Sensitivity and Specificity of differentially methylated loci in bladder tumors relative to adjacent histological normal bladder tissue.

| Feature ID | Locus Number | Threshold | Sensitivity | Pos. of Total | Specificity | Neg. of Total |
|---|---|---|---|---|---|---|
| ha1g__00681 | 1 | 0.865 | 100% | 9 of 9 | 100% | 8 of 8 |
| ha1g__00644 | 3 | 1.245 | 100% | 9 of 9 | 100% | 9 of 9 |
| ha1p__81674 | 4 | 1.895 | 100% | 5 of 5 | 100% | 6 of 6 |
| ha1p__46057 | 10 | 1.255 | 100% | 9 of 9 | 100% | 9 of 9 |
| ha1p__45173 | 19 | 1.39 | 100% | 8 of 8 | 100% | 9 of 9 |
| ha1g__00847 | 13 | 2.315 | 89% | 8 of 9 | 100% | 8 of 8 |
| ha1p__105937 | 27 | 0.89 | 89% | 8 of 9 | 100% | 9 of 9 |
| ha1g__03099 | 29 | 1.155 | 89% | 8 of 9 | 100% | 7 of 7 |
| ha1p__12535 | 32 | 0.745 | 89% | 8 of 9 | 100% | 8 of 8 |
| ha1p__105474 | 33 | 0.96 | 89% | 8 of 9 | 100% | 9 of 9 |
| ha1p__101161 | 36 | 1.185 | 89% | 8 of 9 | 100% | 9 of 9 |
| ha1p__69214 | 38 | 2.12 | 89% | 8 of 9 | 100% | 9 of 9 |
| ha1p__103872 | 43 | 1.045 | 89% | 8 of 9 | 100% | 9 of 9 |
| ha1p__38705 | 7 | 0.54 | 88% | 7 of 8 | 100% | 9 of 9 |
| ha1p__18292 | 45 | 2.025 | 88% | 7 of 8 | 100% | 8 of 8 |
| ha1p__104423 | 12 | 1.54 | 78% | 7 of 9 | 100% | 9 of 9 |
| ha1p__08347 | 14 | 2.225 | 78% | 7 of 9 | 100% | 8 of 8 |
| ha1p__110107 | 17 | 0.995 | 78% | 7 of 9 | 100% | 9 of 9 |
| ha1p__70459 | 26 | 2.27 | 78% | 7 of 9 | 100% | 9 of 9 |
| ha1p__74707 | 34 | 1.24 | 78% | 7 of 9 | 100% | 9 of 9 |
| ha1p__101251 | 37 | 1.655 | 78% | 7 of 9 | 100% | 9 of 9 |
| ha1p__88517 | 39 | 3.035 | 78% | 7 of 9 | 100% | 9 of 9 |
| ha1p__29531 | 48 | 0.625 | 78% | 7 of 9 | 100% | 9 of 9 |
| ha1p__39189 | 2 | 0.525 | 75% | 6 of 8 | 100% | 6 of 6 |
| ha1p__40164 | 8 | 1.815 | 67% | 4 of 6 | 100% | 8 of 8 |
| ha1g__02416 | 15 | 2.01 | 67% | 6 of 9 | 100% | 8 of 8 |
| ha1p__40959 | 11 | 0.54 | 56% | 5 of 9 | 100% | 7 of 7 |
| ha1p__93325 | 35 | 1.845 | 56% | 5 of 9 | 100% | 9 of 9 |
| ha1p__22519 | 47 | 1.265 | 56% | 5 of 9 | 100% | 9 of 9 |
| ha1p__23178 | 9 | 1.66 | 50% | 4 of 8 | 100% | 9 of 9 |
| ha1g__02345 | 24 | 0.665 | 44% | 4 of 9 | 100% | 8 of 8 |
| ha1p__45580 | 52 | 1.22 | 22% | 2 of 9 | 100% | 8 of 8 |
| ha1p__56412 | 44 | 1.725 | 100% | 8 of 8 | 89% | 8 of 9 |
| ha1p__58853 | 49 | 1.125 | 100% | 9 of 9 | 89% | 8 of 9 |
| ha1p__83841 | 6 | 0.8 | 89% | 8 of 9 | 89% | 8 of 9 |
| ha1p__80771 | 20 | 0.67 | 89% | 8 of 9 | 89% | 8 of 9 |
| ha1p__89099 | 28 | 1.08 | 89% | 8 of 9 | 89% | 8 of 9 |
| ha1p__103824 | 40 | 0.575 | 89% | 8 of 9 | 89% | 8 of 9 |
| ha1p__12075 | 46 | 0.705 | 88% | 7 of 8 | 89% | 8 of 9 |
| ha1p__80287 | 23 | 0.595 | 78% | 7 of 9 | 89% | 8 of 9 |
| ha1p__36172 | 25 | 0.63 | 75% | 6 of 8 | 89% | 8 of 9 |
| ha1p__67625 | 30 | 0.765 | 75% | 6 of 8 | 89% | 8 of 9 |
| ha1p__05406 | 22 | 2.03 | 56% | 5 of 9 | 89% | 8 of 9 |
| ha1p__67002 | 51 | 2.215 | 56% | 5 of 9 | 89% | 8 of 9 |
| ha1p__87540 | 16 | 1.395 | 89% | 8 of 9 | 88% | 7 of 8 |
| ha1p__35052 | 50 | 0.65 | 56% | 5 of 9 | 88% | 7 of 8 |
| ha1p__89799 | 18 | 1.05 | 89% | 8 of 9 | 78% | 7 of 9 |
| ha1g__00218 | 31 | 0.83 | 89% | 8 of 9 | 78% | 7 of 9 |
| ha1p__12646 | 53 | 0.79 | 78% | 7 of 9 | 78% | 7 of 9 |

TABLE 14-continued

Sensitivity and Specificity of differentially methylated loci in bladder tumors relative to adjacent histological normal bladder tissue.

| Feature ID | Locus Number | Threshold | Sensitivity | Pos. of Total | Specificity | Neg. of Total |
|---|---|---|---|---|---|---|
| ha1g_02210 | 42 | 1.145 | 60% | 3 of 5 | 78% | 7 of 9 |
| ha1p_108445 | 41 | 1.99 | 100% | 9 of 9 | 75% | 6 of 8 |
| ha1p_81149 | 5 | 0.615 | 100% | 8 of 8 | 67% | 6 of 9 |
| ha1p_69407 | 21 | 1.185 | 100% | 9 of 9 | 67% | 6 of 9 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 15

Sensitivity and Specificity of differentially methylated loci in cervical tumors relative to adjacent histological normal cervical tissue.

| Feature ID | Locus Number | Threshold | Sensitivity | Pos. of Total | Specificity | Neg. of Total |
|---|---|---|---|---|---|---|
| ha1p_83841 | 6 | 0.905 | 100% | 9 of 9 | 100% | 8 of 8 |
| ha1p_23178 | 9 | 1 | 100% | 9 of 9 | 100% | 9 of 9 |
| ha1p_74707 | 34 | 0.61 | 100% | 9 of 9 | 100% | 9 of 9 |
| ha1p_108445 | 41 | 0.995 | 100% | 10 of 10 | 100% | 9 of 9 |
| ha1p_40959 | 11 | 1.49 | 90% | 9 of 10 | 100% | 8 of 8 |
| ha1g_00847 | 13 | 1.01 | 90% | 9 of 10 | 100% | 9 of 9 |
| ha1p_69214 | 38 | 0.515 | 90% | 9 of 10 | 100% | 8 of 8 |
| ha1g_00644 | 3 | 0.725 | 89% | 8 of 9 | 100% | 9 of 9 |
| ha1p_40164 | 8 | 0.655 | 89% | 8 of 9 | 100% | 9 of 9 |
| ha1p_103872 | 43 | 0.785 | 89% | 8 of 9 | 100% | 9 of 9 |
| ha1p_110107 | 17 | 0.775 | 88% | 7 of 8 | 100% | 7 of 7 |
| ha1p_39189 | 2 | 0.59 | 80% | 8 of 10 | 100% | 9 of 9 |
| ha1p_46057 | 10 | 0.89 | 80% | 8 of 10 | 100% | 9 of 9 |
| ha1p_45173 | 19 | 0.53 | 80% | 8 of 10 | 100% | 9 of 9 |
| ha1p_58853 | 49 | 1.215 | 80% | 8 of 10 | 100% | 9 of 9 |
| ha1p_88517 | 39 | 0.635 | 78% | 7 of 9 | 100% | 9 of 9 |
| ha1p_80771 | 20 | 0.52 | 70% | 7 of 10 | 100% | 9 of 9 |
| ha1p_105937 | 27 | 0.64 | 70% | 7 of 10 | 100% | 9 of 9 |
| ha1p_101161 | 36 | 0.57 | 70% | 7 of 10 | 100% | 9 of 9 |
| ha1g_02416 | 15 | 0.545 | 60% | 6 of 10 | 100% | 8 of 8 |
| ha1p_103824 | 40 | 0.515 | 60% | 6 of 10 | 100% | 8 of 8 |
| ha1p_38705 | 7 | 0.59 | 56% | 5 of 9 | 100% | 7 of 7 |
| ha1g_02345 | 24 | 0.56 | 56% | 5 of 9 | 100% | 8 of 8 |
| ha1p_104423 | 12 | 0.515 | 50% | 5 of 10 | 100% | 9 of 9 |
| ha1p_36172 | 25 | 0.77 | 50% | 5 of 10 | 100% | 9 of 9 |
| ha1p_70459 | 26 | 1.27 | 50% | 5 of 10 | 100% | 9 of 9 |
| ha1p_05406 | 22 | 0.73 | 44% | 4 of 9 | 100% | 8 of 8 |
| ha1p_87540 | 16 | 0.73 | 40% | 4 of 10 | 100% | 8 of 8 |
| ha1p_89799 | 18 | 0.63 | 38% | 3 of 8 | 100% | 9 of 9 |
| ha1p_08347 | 14 | 1.745 | 33% | 3 of 9 | 100% | 9 of 9 |
| ha1g_03099 | 29 | 0.5 | 33% | 3 of 9 | 100% | 8 of 8 |
| ha1p_89099 | 28 | 0.8 | 30% | 3 of 10 | 100% | 9 of 9 |
| ha1p_67625 | 30 | 0.91 | 22% | 2 of 9 | 100% | 8 of 8 |
| ha1p_80287 | 23 | 0.865 | 20% | 2 of 10 | 100% | 9 of 9 |
| ha1g_00218 | 31 | 0.705 | 10% | 1 of 10 | 100% | 8 of 8 |
| ha1p_12535 | 32 | 0.585 | 100% | 10 of 10 | 89% | 8 of 9 |
| ha1p_93325 | 35 | 0.595 | 90% | 9 of 10 | 89% | 8 of 9 |
| ha1p_29531 | 48 | 1.05 | 80% | 8 of 10 | 89% | 8 of 9 |
| ha1p_101251 | 37 | 1.635 | 70% | 7 of 10 | 89% | 8 of 9 |
| ha1p_81674 | 4 | 0.975 | 50% | 4 of 8 | 89% | 8 of 9 |
| ha1p_67002 | 51 | 2.055 | 50% | 5 of 10 | 89% | 8 of 9 |
| ha1g_02210 | 42 | 0.845 | 38% | 3 of 8 | 89% | 8 of 9 |
| ha1p_45580 | 52 | 1.765 | 67% | 6 of 9 | 88% | 7 of 8 |
| ha1p_12075 | 46 | 0.59 | 78% | 7 of 9 | 83% | 5 of 6 |
| ha1p_81149 | 5 | 1.11 | 100% | 9 of 9 | 78% | 7 of 9 |
| ha1p_105474 | 33 | 0.525 | 100% | 10 of 10 | 78% | 7 of 9 |
| ha1p_22519 | 47 | 1.2 | 100% | 10 of 10 | 78% | 7 of 9 |
| ha1p_12646 | 53 | 2.385 | 100% | 10 of 10 | 78% | 7 of 9 |
| ha1p_18292 | 45 | 1.195 | 70% | 7 of 10 | 75% | 6 of 8 |
| ha1p_56412 | 44 | 0.59 | 90% | 9 of 10 | 67% | 6 of 9 |
| ha1g_00681 | 1 | 0.58 | 89% | 8 of 9 | 67% | 6 of 9 |
| ha1p_35052 | 50 | 1.135 | 80% | 8 of 10 | 56% | 5 of 9 |
| ha1p_69407 | 21 | 0.665 | 90% | 9 of 10 | 44% | 4 of 9 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 16

Sensitivity and Specificity of differentially methylated loci in colon tumors relative to adjacent histological normal colon tissue.

| Feature ID | Locus Number | Threshold | Sensitivity | Pos. of Total | Specificity | Neg. of Total |
|---|---|---|---|---|---|---|
| ha1p_56412 | 44 | 1.855 | 88% | 7 of 8 | 100% | 8 of 8 |
| ha1g_00644 | 3 | 1.46 | 86% | 6 of 7 | 100% | 8 of 8 |
| ha1p_40959 | 11 | 2.16 | 71% | 5 of 7 | 100% | 6 of 6 |
| ha1p_23178 | 9 | 1.805 | 63% | 5 of 8 | 100% | 8 of 8 |
| ha1p_105937 | 27 | 1.425 | 63% | 5 of 8 | 100% | 8 of 8 |
| ha1g_03099 | 29 | 0.63 | 63% | 5 of 8 | 100% | 8 of 8 |
| ha1p_74707 | 34 | 2.08 | 63% | 5 of 8 | 100% | 8 of 8 |
| ha1p_101161 | 36 | 0.65 | 63% | 5 of 8 | 100% | 8 of 8 |
| ha1p_103824 | 40 | 0.605 | 63% | 5 of 8 | 100% | 8 of 8 |
| ha1g_02210 | 42 | 0.82 | 63% | 5 of 8 | 100% | 8 of 8 |
| ha1p_81674 | 4 | 4.63 | 50% | 3 of 6 | 100% | 8 of 8 |
| ha1p_83841 | 6 | 2.175 | 50% | 4 of 8 | 100% | 7 of 7 |
| ha1p_80771 | 20 | 1.31 | 50% | 4 of 8 | 100% | 8 of 8 |
| ha1p_101251 | 37 | 1.29 | 50% | 3 of 6 | 100% | 8 of 8 |
| ha1p_103872 | 43 | 2.36 | 50% | 4 of 8 | 100% | 8 of 8 |
| ha1p_67002 | 51 | 1.57 | 50% | 4 of 8 | 100% | 8 of 8 |
| ha1p_104423 | 12 | 0.575 | 43% | 3 of 7 | 100% | 8 of 8 |
| ha1p_81149 | 5 | 2.82 | 38% | 3 of 8 | 100% | 8 of 8 |
| ha1g_02345 | 24 | 0.58 | 38% | 3 of 8 | 100% | 8 of 8 |
| ha1g_00218 | 31 | 1.745 | 38% | 3 of 8 | 100% | 8 of 8 |
| ha1p_67625 | 30 | 0.515 | 25% | 2 of 8 | 100% | 8 of 8 |
| ha1p_105474 | 33 | 1.99 | 100% | 8 of 8 | 88% | 7 of 8 |
| ha1p_18292 | 45 | 1.545 | 100% | 8 of 8 | 88% | 7 of 8 |
| ha1g_00681 | 1 | 0.705 | 88% | 7 of 8 | 88% | 7 of 8 |
| ha1p_108445 | 41 | 2.175 | 88% | 7 of 8 | 88% | 7 of 8 |
| ha1p_88517 | 39 | 1.645 | 86% | 6 of 7 | 88% | 7 of 8 |
| ha1p_45173 | 19 | 1.145 | 75% | 6 of 8 | 88% | 7 of 8 |
| ha1p_89099 | 28 | 2.22 | 75% | 6 of 8 | 88% | 7 of 8 |
| ha1p_58853 | 49 | 1.85 | 75% | 6 of 8 | 88% | 7 of 8 |
| ha1p_80287 | 23 | 1.485 | 63% | 5 of 8 | 88% | 7 of 8 |
| ha1p_29531 | 48 | 1.3 | 63% | 5 of 8 | 88% | 7 of 8 |
| ha1p_87540 | 16 | 1.52 | 86% | 6 of 7 | 86% | 6 of 7 |
| ha1p_12535 | 32 | 0.93 | 75% | 6 of 8 | 86% | 6 of 7 |
| ha1p_38705 | 7 | 1.01 | 50% | 3 of 6 | 86% | 6 of 7 |

TABLE 16-continued

Sensitivity and Specificity of differentially methylated loci in colon tumors relative to adjacent histological normal colon tissue.

| Feature ID | Locus Number | Threshold | Sensitivity | Pos. of Total | Specificity | Neg. of Total |
|---|---|---|---|---|---|---|
| ha1p_110107 | 17 | 0.74 | 100% | 8 of 8 | 75% | 6 of 8 |
| ha1p_36172 | 25 | 0.53 | 100% | 8 of 8 | 75% | 6 of 8 |
| ha1g_00847 | 13 | 2.085 | 88% | 7 of 8 | 75% | 6 of 8 |
| ha1p_69214 | 38 | 2.085 | 88% | 7 of 8 | 75% | 6 of 8 |
| ha1p_89799 | 18 | 1.295 | 75% | 6 of 8 | 75% | 6 of 8 |
| ha1g_02416 | 15 | 1.295 | 63% | 5 of 8 | 75% | 6 of 8 |
| ha1p_08347 | 14 | 1.415 | 88% | 7 of 8 | 71% | 5 of 7 |
| ha1p_39189 | 2 | 0.575 | 86% | 6 of 7 | 71% | 5 of 7 |
| ha1p_46057 | 10 | 1.06 | 100% | 8 of 8 | 63% | 5 of 8 |
| ha1p_93325 | 35 | 1.07 | 100% | 8 of 8 | 63% | 5 of 8 |
| ha1p_40164 | 8 | 0.815 | 75% | 6 of 8 | 63% | 5 of 8 |
| ha1p_70459 | 26 | 1.21 | 75% | 6 of 8 | 63% | 5 of 8 |
| ha1p_12075 | 46 | 0.935 | 75% | 6 of 8 | 63% | 5 of 8 |
| ha1p_22519 | 47 | 1.15 | 50% | 4 of 8 | 63% | 5 of 8 |
| ha1p_05406 | 22 | 1.64 | 75% | 6 of 8 | 57% | 4 of 7 |
| ha1p_12646 | 53 | 2.16 | 67% | 4 of 6 | 50% | 4 of 8 |
| ha1p_69407 | 21 | 0.565 | 100% | 8 of 8 | 38% | 3 of 8 |
| ha1p_35052 | 50 | 0.565 | 100% | 8 of 8 | 38% | 3 of 8 |
| ha1p_45580 | 52 | 1.505 | 100% | 8 of 8 | 38% | 3 of 8 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 17

Sensitivity and Specificity of differentially methylated loci in endometrial tumors relative to adjacent histological normal endometrial tissue.

| Feature ID | Locus Number | Threshold | Sensitivity | Pos. of Total | Specificity | Neg. of Total |
|---|---|---|---|---|---|---|
| ha1p_39189 | 2 | 0.75 | 93% | 13 of 14 | 100% | 9 of 9 |
| ha1g_00644 | 3 | 0.91 | 93% | 13 of 14 | 100% | 9 of 9 |
| ha1p_83841 | 6 | 1.07 | 93% | 13 of 14 | 100% | 9 of 9 |
| ha1p_103872 | 43 | 0.75 | 93% | 13 of 14 | 100% | 9 of 9 |
| ha1p_56412 | 44 | 0.685 | 93% | 13 of 14 | 100% | 8 of 8 |
| ha1p_12646 | 53 | 2.175 | 93% | 13 of 14 | 100% | 9 of 9 |
| ha1p_40959 | 11 | 0.945 | 86% | 12 of 14 | 100% | 3 of 3 |
| ha1p_58853 | 49 | 0.51 | 86% | 12 of 14 | 100% | 8 of 8 |
| ha1p_12535 | 32 | 1.025 | 83% | 10 of 12 | 100% | 9 of 9 |
| ha1p_18292 | 45 | 1.32 | 83% | 10 of 12 | 100% | 8 of 8 |
| ha1p_46057 | 10 | 0.935 | 79% | 11 of 14 | 100% | 9 of 9 |
| ha1p_45173 | 19 | 0.6 | 79% | 11 of 14 | 100% | 9 of 9 |
| ha1p_105474 | 33 | 0.555 | 79% | 11 of 14 | 100% | 9 of 9 |
| ha1p_101251 | 37 | 1.28 | 79% | 11 of 14 | 100% | 9 of 9 |
| ha1p_22519 | 47 | 2.2 | 79% | 11 of 14 | 100% | 9 of 9 |
| ha1p_29531 | 48 | 0.82 | 79% | 11 of 14 | 100% | 9 of 9 |
| ha1p_87540 | 16 | 0.56 | 77% | 10 of 13 | 100% | 9 of 9 |
| ha1g_02210 | 42 | 0.665 | 75% | 6 of 8 | 100% | 6 of 6 |
| ha1g_00681 | 1 | 1.145 | 71% | 10 of 14 | 100% | 9 of 9 |
| ha1p_23178 | 9 | 0.795 | 71% | 10 of 14 | 100% | 9 of 9 |
| ha1p_110107 | 17 | 0.91 | 71% | 5 of 7 | 100% | 9 of 9 |
| ha1p_105937 | 27 | 0.525 | 71% | 10 of 14 | 100% | 9 of 9 |
| ha1p_101161 | 36 | 0.55 | 71% | 10 of 14 | 100% | 9 of 9 |
| ha1p_69214 | 38 | 0.555 | 71% | 10 of 14 | 100% | 9 of 9 |
| ha1p_88517 | 39 | 0.855 | 69% | 9 of 13 | 100% | 8 of 8 |
| ha1p_108445 | 41 | 0.805 | 67% | 8 of 12 | 100% | 8 of 8 |
| ha1p_38705 | 7 | 1.085 | 64% | 9 of 14 | 100% | 9 of 9 |
| ha1p_40164 | 8 | 0.785 | 64% | 9 of 14 | 100% | 9 of 9 |
| ha1p_104423 | 12 | 0.705 | 64% | 9 of 14 | 100% | 9 of 9 |
| ha1p_89099 | 28 | 0.565 | 64% | 9 of 14 | 100% | 8 of 8 |
| ha1p_05406 | 22 | 0.53 | 50% | 7 of 14 | 100% | 9 of 9 |
| ha1p_67002 | 51 | 2.02 | 46% | 6 of 13 | 100% | 8 of 8 |
| ha1p_36172 | 25 | 0.56 | 43% | 6 of 14 | 100% | 8 of 8 |
| ha1g_03099 | 29 | 0.64 | 43% | 6 of 14 | 100% | 9 of 9 |
| ha1p_74707 | 34 | 1.885 | 43% | 6 of 14 | 100% | 9 of 9 |
| ha1p_35052 | 50 | 1.63 | 43% | 6 of 14 | 100% | 9 of 9 |

TABLE 17-continued

Sensitivity and Specificity of differentially methylated loci in endometrial tumors relative to adjacent histological normal endometrial tissue.

| Feature ID | Locus Number | Threshold | Sensitivity | Pos. of Total | Specificity | Neg. of Total |
|---|---|---|---|---|---|---|
| ha1p_45580 | 52 | 1.435 | 43% | 6 of 14 | 100% | 8 of 8 |
| ha1g_02345 | 24 | 0.6 | 36% | 5 of 14 | 100% | 8 of 8 |
| ha1p_67625 | 30 | 0.56 | 31% | 4 of 13 | 100% | 8 of 8 |
| ha1p_80287 | 23 | 0.51 | 21% | 3 of 14 | 100% | 9 of 9 |
| ha1g_00218 | 31 | 0.535 | 21% | 3 of 14 | 100% | 9 of 9 |
| ha1p_103824 | 40 | 0.645 | 21% | 3 of 14 | 100% | 9 of 9 |
| ha1p_81149 | 5 | 1.165 | 86% | 12 of 14 | 89% | 8 of 9 |
| ha1p_81674 | 4 | 0.875 | 82% | 9 of 11 | 89% | 8 of 9 |
| ha1g_00847 | 13 | 1.11 | 79% | 11 of 14 | 89% | 8 of 9 |
| ha1p_69407 | 21 | 1.59 | 79% | 11 of 14 | 89% | 8 of 9 |
| ha1p_93325 | 35 | 0.795 | 77% | 10 of 13 | 89% | 8 of 9 |
| ha1p_70459 | 26 | 0.655 | 71% | 10 of 14 | 89% | 8 of 9 |
| ha1p_80771 | 20 | 0.58 | 64% | 9 of 14 | 89% | 8 of 9 |
| ha1p_08347 | 14 | 1.86 | 57% | 8 of 14 | 89% | 8 of 9 |
| ha1g_02416 | 15 | 0.61 | 50% | 7 of 14 | 89% | 8 of 9 |
| ha1p_89799 | 18 | 0.52 | 62% | 8 of 13 | 88% | 7 of 8 |
| ha1p_12075 | 46 | 0.915 | 85% | 11 of 13 | 78% | 7 of 9 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 18

Sensitivity and Specificity of differentially methylated loci in esophageal tumors relative to adjacent histological normal esophageal tissue.

| Feature ID | Locus Number | Threshold | Sensitivity | Pos. of Total | Specificity | Neg. of Total |
|---|---|---|---|---|---|---|
| ha1p_110107 | 17 | 0.515 | 67% | 6 of 9 | 100% | 9 of 9 |
| ha1p_38705 | 7 | 2.58 | 43% | 3 of 7 | 100% | 9 of 9 |
| ha1p_87540 | 16 | 1.21 | 33% | 3 of 9 | 100% | 9 of 9 |
| ha1p_67625 | 30 | 0.665 | 33% | 3 of 9 | 100% | 9 of 9 |
| ha1p_103824 | 40 | 0.72 | 13% | 1 of 8 | 100% | 10 of 10 |
| ha1p_05406 | 22 | 0.71 | 11% | 1 of 9 | 100% | 10 of 10 |
| ha1g_03099 | 29 | 0.6 | 11% | 1 of 9 | 100% | 10 of 10 |
| ha1p_39189 | 2 | 1.165 | 89% | 8 of 9 | 90% | 9 of 10 |
| ha1p_29531 | 48 | 1.27 | 78% | 7 of 9 | 90% | 9 of 10 |
| ha1g_02416 | 15 | 0.65 | 38% | 3 of 8 | 90% | 9 of 10 |
| ha1p_80771 | 20 | 0.675 | 22% | 2 of 9 | 90% | 9 of 10 |
| ha1p_45173 | 19 | 0.985 | 100% | 9 of 9 | 89% | 8 of 9 |
| ha1p_88517 | 39 | 1.14 | 100% | 8 of 8 | 89% | 8 of 9 |
| ha1p_89799 | 18 | 0.53 | 14% | 1 of 7 | 89% | 8 of 9 |
| ha1p_40959 | 11 | 1.52 | 78% | 7 of 9 | 88% | 7 of 8 |
| ha1g_02210 | 42 | 0.905 | 33% | 3 of 9 | 88% | 7 of 8 |
| ha1p_23178 | 9 | 1.645 | 100% | 9 of 9 | 80% | 8 of 10 |
| ha1p_46057 | 10 | 0.92 | 100% | 9 of 9 | 80% | 8 of 10 |
| ha1p_104423 | 12 | 0.65 | 100% | 9 of 9 | 80% | 8 of 10 |
| ha1p_08347 | 14 | 0.75 | 100% | 9 of 9 | 80% | 8 of 10 |
| ha1p_108445 | 41 | 1.715 | 100% | 9 of 9 | 80% | 8 of 10 |
| ha1p_105937 | 27 | 0.855 | 89% | 8 of 9 | 80% | 8 of 10 |
| ha1p_105474 | 33 | 1.655 | 89% | 8 of 9 | 80% | 8 of 10 |
| ha1p_101161 | 36 | 0.785 | 89% | 8 of 9 | 80% | 8 of 10 |
| ha1p_22519 | 47 | 1.77 | 89% | 8 of 9 | 80% | 8 of 10 |
| ha1p_81149 | 5 | 2.02 | 78% | 7 of 9 | 80% | 8 of 10 |
| ha1g_00644 | 3 | 0.905 | 75% | 6 of 8 | 80% | 8 of 10 |
| ha1p_56412 | 44 | 0.74 | 67% | 6 of 9 | 80% | 8 of 10 |
| ha1p_74707 | 34 | 1.035 | 56% | 5 of 9 | 80% | 8 of 10 |
| ha1p_80287 | 23 | 0.62 | 22% | 2 of 9 | 80% | 8 of 10 |
| ha1p_36172 | 25 | 0.6 | 22% | 2 of 9 | 80% | 8 of 10 |
| ha1p_67002 | 51 | 1.925 | 78% | 7 of 9 | 78% | 7 of 9 |
| ha1p_89099 | 28 | 0.6 | 56% | 5 of 9 | 78% | 7 of 9 |
| ha1p_18292 | 45 | 1.18 | 89% | 8 of 9 | 75% | 6 of 8 |
| ha1p_58853 | 49 | 1.105 | 100% | 9 of 9 | 70% | 7 of 10 |
| ha1p_83841 | 6 | 1.125 | 89% | 8 of 9 | 70% | 7 of 10 |
| ha1p_12535 | 32 | 0.78 | 89% | 8 of 9 | 70% | 7 of 10 |

TABLE 18-continued

Sensitivity and Specificity of differentially methylated loci in esophageal tumors relative to adjacent histological normal esophageal tissue.

| Feature ID | Locus Number | Threshold | Sensitivity | Pos. of Total | Specificity | Neg. of Total |
|---|---|---|---|---|---|---|
| ha1p_101251 | 37 | 1.025 | 78% | 7 of 9 | 70% | 7 of 10 |
| ha1g_00847 | 13 | 0.825 | 100% | 9 of 9 | 67% | 6 of 9 |
| ha1p_69407 | 21 | 1.005 | 100% | 9 of 9 | 60% | 6 of 10 |
| ha1p_93325 | 35 | 0.93 | 89% | 8 of 9 | 60% | 6 of 10 |
| ha1g_00681 | 1 | 0.52 | 67% | 6 of 9 | 60% | 6 of 10 |
| ha1p_70459 | 26 | 0.515 | 100% | 9 of 9 | 56% | 5 of 9 |
| ha1p_40164 | 8 | 0.645 | 56% | 5 of 9 | 56% | 5 of 9 |
| ha1p_69214 | 38 | 0.73 | 100% | 9 of 9 | 50% | 5 of 10 |
| ha1p_103872 | 43 | 1.5 | 100% | 9 of 9 | 50% | 5 of 10 |
| ha1p_81674 | 4 | 0.645 | 75% | 6 of 8 | 44% | 4 of 9 |
| ha1p_12075 | 46 | 1.02 | 100% | 7 of 7 | 40% | 4 of 10 |
| ha1p_45580 | 52 | 0.73 | 100% | 9 of 9 | 40% | 4 of 10 |
| ha1p_35052 | 50 | 1.84 | 100% | 9 of 9 | 30% | 3 of 10 |
| ha1p_12646 | 53 | 1.085 | 100% | 9 of 9 | 30% | 3 of 10 |
| ha1g_02345 | 24 | 0.83 | 89% | 8 of 9 | 10% | 1 of 10 |
| ha1g_00218 | 31 | — | — | — | — | — |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 19

Sensitivity and Specificity of differentially methylated loci in prostate tumors relative to adjacent histological normal prostate tissue.

| Feature ID | Locus Number | Threshold | Sensitivity | Pos. of Total | Specificity | Neg. of Total |
|---|---|---|---|---|---|---|
| ha1p_38705 | 7 | 0.595 | 78% | 7 of 9 | 100% | 9 of 9 |
| ha1p_36172 | 25 | 1 | 67% | 6 of 9 | 100% | 9 of 9 |
| ha1p_56412 | 44 | 1.63 | 67% | 6 of 9 | 100% | 9 of 9 |
| ha1p_45580 | 52 | 1.785 | 67% | 6 of 9 | 100% | 9 of 9 |
| ha1p_12646 | 53 | 3.13 | 67% | 6 of 9 | 100% | 9 of 9 |
| ha1p_67002 | 51 | 2.05 | 56% | 5 of 9 | 100% | 9 of 9 |
| ha1g_02416 | 15 | 0.845 | 44% | 4 of 9 | 100% | 9 of 9 |
| ha1p_103824 | 40 | 0.59 | 22% | 2 of 9 | 100% | 9 of 9 |
| ha1p_104423 | 12 | 0.655 | 11% | 1 of 9 | 100% | 9 of 9 |
| ha1p_45173 | 19 | 0.53 | 11% | 1 of 9 | 100% | 9 of 9 |
| ha1g_03099 | 29 | 2.165 | 11% | 1 of 9 | 100% | 8 of 8 |
| ha1p_89799 | 18 | 0.51 | 75% | 6 of 8 | 89% | 8 of 9 |
| ha1g_02210 | 42 | 0.715 | 75% | 6 of 8 | 89% | 8 of 9 |
| ha1p_46057 | 10 | 0.605 | 67% | 6 of 9 | 89% | 8 of 9 |
| ha1p_108445 | 41 | 0.83 | 67% | 6 of 9 | 89% | 8 of 9 |
| ha1p_80287 | 23 | 0.545 | 63% | 5 of 8 | 89% | 8 of 9 |
| ha1p_87540 | 16 | 0.54 | 56% | 5 of 9 | 89% | 8 of 9 |
| ha1p_74707 | 34 | 1.425 | 56% | 5 of 9 | 89% | 8 of 9 |
| ha1p_18292 | 45 | 1.5 | 56% | 5 of 9 | 89% | 8 of 9 |
| ha1p_35052 | 50 | 0.73 | 56% | 5 of 9 | 89% | 8 of 9 |
| ha1g_02345 | 24 | 0.635 | 44% | 4 of 9 | 89% | 8 of 9 |
| ha1p_88517 | 39 | 0.885 | 44% | 4 of 9 | 89% | 8 of 9 |
| ha1p_12075 | 46 | 1.15 | 44% | 4 of 9 | 89% | 8 of 9 |
| ha1p_69407 | 21 | 0.75 | 38% | 3 of 8 | 89% | 8 of 9 |
| ha1p_80771 | 20 | 0.585 | 33% | 3 of 9 | 89% | 8 of 9 |
| ha1p_05406 | 22 | 0.745 | 33% | 3 of 9 | 89% | 8 of 9 |
| ha1p_70459 | 26 | 0.615 | 33% | 3 of 9 | 89% | 8 of 9 |
| ha1g_00218 | 31 | 0.675 | 11% | 1 of 9 | 89% | 8 of 9 |
| ha1p_69214 | 38 | 1.175 | 88% | 7 of 8 | 88% | 7 of 8 |
| ha1p_67625 | 30 | 0.53 | 33% | 3 of 9 | 88% | 7 of 8 |
| ha1p_110107 | 17 | 1.15 | 0% | 0 of 8 | 88% | 7 of 8 |
| ha1p_105937 | 27 | 0.545 | 100% | 9 of 9 | 78% | 7 of 9 |
| ha1p_103872 | 43 | 1.64 | 100% | 9 of 9 | 78% | 7 of 9 |
| ha1p_22519 | 47 | 1.38 | 100% | 9 of 9 | 78% | 7 of 9 |
| ha1p_29531 | 48 | 0.77 | 100% | 9 of 9 | 78% | 7 of 9 |
| ha1p_83841 | 6 | 0.515 | 89% | 8 of 9 | 78% | 7 of 9 |
| ha1p_105474 | 33 | 1.35 | 89% | 8 of 9 | 78% | 7 of 9 |
| ha1p_101161 | 36 | 0.875 | 89% | 8 of 9 | 78% | 7 of 9 |
| ha1g_00644 | 3 | 0.56 | 88% | 7 of 8 | 78% | 7 of 9 |
| ha1p_39189 | 2 | 0.53 | 78% | 7 of 9 | 78% | 7 of 9 |
| ha1p_81149 | 5 | 1.17 | 78% | 7 of 9 | 78% | 7 of 9 |
| ha1p_08347 | 14 | 1.405 | 67% | 6 of 9 | 78% | 7 of 9 |
| ha1p_12535 | 32 | 1.19 | 67% | 6 of 9 | 78% | 7 of 9 |
| ha1p_40164 | 8 | 0.7 | 63% | 5 of 8 | 78% | 7 of 9 |
| ha1p_23178 | 9 | 1.575 | 56% | 5 of 9 | 78% | 7 of 9 |
| ha1p_89099 | 28 | 0.5 | 56% | 5 of 9 | 78% | 7 of 9 |
| ha1p_40959 | 11 | 0.745 | 100% | 8 of 8 | 67% | 6 of 9 |
| ha1p_93325 | 35 | 0.535 | 100% | 9 of 9 | 67% | 6 of 9 |
| ha1p_101251 | 37 | 1.27 | 100% | 8 of 8 | 67% | 6 of 9 |
| ha1p_81674 | 4 | 1.245 | 78% | 7 of 9 | 67% | 6 of 9 |
| ha1g_00847 | 13 | 0.63 | 78% | 7 of 9 | 67% | 6 of 9 |
| ha1g_00681 | 1 | 0.55 | 50% | 4 of 8 | 67% | 6 of 9 |
| ha1p_58853 | 49 | 0.835 | 100% | 9 of 9 | 22% | 2 of 9 |

Threshold: Average dCt value established by ROC curve analysis as optimal threshold for distinguishing tumor and adjacent normal tissues.
Sensitivity: % of positive (i.e. methylation score above Threshold) tumors.
Pos. of Total: Number of positive tumors relative to the total number of tumors analyzed.
Specificity: % of negative (i.e. methylation score below Threshold) adjacent normal samples.
Neg. of Total: Number of negative adjacent normal samples relative to the total number of adjacent normal samples analyzed.

TABLE 20

Frequency of methylation of each locus in melanoma tumors.

| Feature ID | Locus Number | Sensitivity | Pos. of Total |
|---|---|---|---|
| ha1p_81149 | 5 | 100% | 7 of 7 |
| ha1p_38705 | 7 | 100% | 5 of 5 |
| ha1p_23178 | 9 | 100% | 7 of 7 |
| ha1p_45173 | 19 | 100% | 6 of 6 |
| ha1p_12535 | 32 | 100% | 7 of 7 |
| ha1p_69214 | 38 | 100% | 7 of 7 |
| ha1p_108445 | 41 | 100% | 7 of 7 |
| ha1p_45580 | 52 | 100% | 7 of 7 |
| ha1p_12646 | 53 | 100% | 7 of 7 |
| ha1g_00644 | 3 | 86% | 6 of 7 |
| ha1p_46057 | 10 | 86% | 6 of 7 |
| ha1p_40959 | 11 | 86% | 6 of 7 |
| ha1p_104423 | 12 | 86% | 6 of 7 |
| ha1p_105474 | 33 | 86% | 6 of 7 |
| ha1p_93325 | 35 | 86% | 6 of 7 |
| ha1p_103872 | 43 | 86% | 6 of 7 |
| ha1p_56412 | 44 | 86% | 6 of 7 |
| ha1p_18292 | 45 | 86% | 6 of 7 |
| ha1p_22519 | 47 | 86% | 6 of 7 |
| ha1p_29531 | 48 | 86% | 6 of 7 |
| ha1p_58853 | 49 | 86% | 6 of 7 |
| ha1p_35052 | 50 | 86% | 6 of 7 |
| ha1p_67002 | 51 | 86% | 6 of 7 |
| ha1p_81674 | 4 | 83% | 5 of 6 |
| ha1p_69407 | 21 | 83% | 5 of 6 |
| ha1p_12075 | 46 | 80% | 4 of 5 |
| ha1g_00681 | 1 | 71% | 5 of 7 |
| ha1p_39189 | 2 | 71% | 5 of 7 |
| ha1p_83841 | 6 | 71% | 5 of 7 |
| ha1p_40164 | 8 | 71% | 5 of 7 |
| ha1g_00847 | 13 | 71% | 5 of 7 |
| ha1p_87540 | 16 | 57% | 4 of 7 |
| ha1p_101251 | 37 | 57% | 4 of 7 |
| ha1p_88517 | 39 | 57% | 4 of 7 |
| ha1p_08347 | 14 | 50% | 3 of 6 |
| ha1p_05406 | 22 | 43% | 3 of 7 |
| ha1p_105937 | 27 | 43% | 3 of 7 |
| ha1p_89099 | 28 | 43% | 3 of 7 |
| ha1g_02210 | 42 | 43% | 3 of 7 |
| ha1p_89799 | 18 | 40% | 2 of 5 |
| ha1p_80287 | 23 | 29% | 2 of 7 |
| ha1p_36172 | 25 | 29% | 2 of 7 |
| ha1p_70459 | 26 | 29% | 2 of 7 |
| ha1g_03099 | 29 | 29% | 2 of 7 |

TABLE 20-continued

Frequency of methylation of each locus in melanoma tumors.

| Feature ID | Locus Number | Sensitivity | Pos. of Total |
|---|---|---|---|
| ha1p__101161 | 36 | 29% | 2 of 7 |
| ha1p__110107 | 17 | 14% | 1 of 7 |
| ha1p__80771 | 20 | 14% | 1 of 7 |
| ha1p__67625 | 30 | 14% | 1 of 7 |
| ha1p__74707 | 34 | 14% | 1 of 7 |
| ha1g__02416 | 15 | 0% | 0 of 7 |
| ha1g__02345 | 24 | 0% | 0 of 7 |
| ha1g__00218 | 31 | 0% | 0 of 7 |
| ha1p__103824 | 40 | 0% | 0 of 7 |

Sensitivity: % of positive (i.e. methylation score above 1.0) tumors.
Pos. of Total: Number of positive tumors relative to the total number of tumors analyzed.
Note that adjacent histology normal or normal skin samples were not available for analysis.
Threshold for a positive methylation score was set at an average dCt of 1.0.

Although the invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, Genbank sequences, patents, and patent applications cited in this specification are herein incorporated by reference as if each was specifically and individually indicated to be incorporated by reference.

What is claimed is:

1. A method for determining an increased likelihood of cancer in a human individual, the method comprising:
   a) detecting, in a sample from said individual, the methylation density of SEQ ID NO: 214, or a sequence that is at least 90% identical to SEQ ID NO: 214 in the Growth Hormone Secretagogue Receptor (GHSR) gene; and
   b) comparing the methylation density to a threshold value, wherein the threshold value distinguishes between individuals with and without cancer, wherein an increased methylation density in SEQ ID NO: 214, or a sequence that is at least 90% identical to SEQ ID NO: 214, compared to a non-cancer control population, is indicative of the presence of cancer in the individual.

2. The method of claim 1, wherein the methylation density of SEQ ID NO:214 is detected.

3. The method of claim 1, wherein the detecting comprises detecting the methylation density of SEQ ID NO: 161, or a sequence that is at least 90% identical to SEQ ID NO: 161.

4. The method of claim 1, wherein the sample is from blood serum, blood plasma, fine needle aspirate of the breast, biopsy of the breast, ductal fluid, or ductal lavage.

5. The method of claim 1, wherein the methylation density of SEQ ID NO: 214, or a sequence that is at least 90% identical to SEQ ID NO: 214, is compared to a methylation value of a control locus.

6. The method of claim 5, wherein the control locus is an endogenous control.

7. The method of claim 5, wherein the control locus is an exogenous control.

8. The method of claim 1, further comprising detecting methylation density within at least one additional DNA region.

9. The method of claim 1, wherein the detecting comprises contacting DNA from the sample with a restriction enzyme.

10. The method of claim 1, wherein the detecting comprises contacting DNA from the sample with sodium bisulfite.

11. The method of claim 8, wherein said at least one additional DNA region is selected from the group consisting of: SEQ ID NOs: 213, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, and 265.

12. The method of claim 1, wherein the comparing is performed on a computer.

13. The method of claim 1, wherein the cancer is breast cancer.

14. The method of claim 1, wherein the cancer is selected from the group consisting of: lung cancer, renal cancer, liver cancer, ovarian cancer, head and neck cancer, thyroid cancer, bladder cancer, cervical cancer, colon cancer, endometrial cancer, esophageal cancer, prostate cancer and melanoma.

* * * * *